(12) United States Patent
Takaku et al.

(10) Patent No.: US 9,608,207 B2
(45) Date of Patent: Mar. 28, 2017

(54) ORGANIC ELECTROLUMINESCENCE ELEMENT

(75) Inventors: Koji Takaku, Kanagawa (JP); Tetsu Kitamura, Kanagawa (JP); Toru Watanabe, Kanagawa (JP); Yasunori Yonekuta, Kanagawa (JP)

(73) Assignee: UDC Ireland Limited, Dublin (IE)

( * ) Notice: Subject to any disclaimer, the term of this patent is extended or adjusted under 35 U.S.C. 154(b) by 491 days.

(21) Appl. No.: 14/110,630

(22) PCT Filed: Apr. 11, 2012

(86) PCT No.: PCT/JP2012/059871
§ 371 (c)(1),
(2), (4) Date: Feb. 7, 2014

(87) PCT Pub. No.: WO2012/141197
PCT Pub. Date: Oct. 18, 2012

(65) Prior Publication Data
US 2014/0299851 A1 Oct. 9, 2014

(30) Foreign Application Priority Data

Apr. 12, 2011 (JP) .................................. 2011-087857
Apr. 10, 2012 (JP) .................................. 2012-089049

(51) Int. Cl.
*H01L 51/00* (2006.01)
*C07C 13/62* (2006.01)
(Continued)

(52) U.S. Cl.
CPC ........ *H01L 51/0067* (2013.01); *C07B 59/001* (2013.01); *C07C 13/62* (2013.01);
(Continued)

(58) Field of Classification Search
None
See application file for complete search history.

(56) References Cited

U.S. PATENT DOCUMENTS

| 6,852,429 | B1 | 2/2005 | Li et al. |
| 7,233,019 | B2 | 6/2007 | Ionkin et al. |
| 2008/0242871 | A1* | 10/2008 | Kawakami ........... C07D 209/86 548/440 |

FOREIGN PATENT DOCUMENTS

| DE | 102008035413 | 2/2010 |
| JP | S60-057347 | 4/1985 |

(Continued)

*Primary Examiner* — Nathan T Leong
(74) *Attorney, Agent, or Firm* — Riverside Law LLP

(57) ABSTRACT

An organic electroluminescence element that uses a compound expressed by the following general formula has low inter-molecular interaction and high orientation during vapor deposition, and by using compounds that are resistant to aggregation, luminous efficiency is high, and there is little change in chromaticity accompanying drive deterioration (either $V^1$ or $W^1$ and either $V^2$ or $W^2$ form rings, the rings formed by $V^1$ and $V^2$ are six-membered rings, and the rings formed by $W^1$ and $W^2$ are five-membered rings; $A^2$ to $A^4$ and $A^6$ to $A^8$ represent $CR^Z$ or N, and $R^Z$ represents a hydrogen atom or a substituent; and $R^2$, $R^3$, $R^7$, and $R^8$ represent a (Continued)

hydrogen atom, an alkyl group, an aryl group, a heteroaryl group, a fluorine atom, a hydrogen atom [sic], or a deuterium atom.).

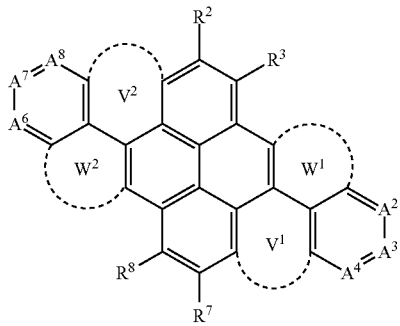

30 Claims, 1 Drawing Sheet

(51) Int. Cl.
| | |
|---|---|
| C07C 25/22 | (2006.01) |
| C07D 213/74 | (2006.01) |
| C07D 239/22 | (2006.01) |
| C07D 295/04 | (2006.01) |
| C07D 307/77 | (2006.01) |
| C07D 333/50 | (2006.01) |
| C07D 333/78 | (2006.01) |
| C07D 487/06 | (2006.01) |
| C07D 493/06 | (2006.01) |
| C07D 495/06 | (2006.01) |
| C09K 11/06 | (2006.01) |
| C07C 211/61 | (2006.01) |
| C07B 59/00 | (2006.01) |
| C07F 7/08 | (2006.01) |
| H01L 51/50 | (2006.01) |
| C07C 33/26 | (2006.01) |
| C09B 57/00 | (2006.01) |
| C09B 1/00 | (2006.01) |

(52) U.S. Cl.
CPC .............. *C07C 25/22* (2013.01); *C07C 33/26* (2013.01); *C07C 211/61* (2013.01); *C07D 213/74* (2013.01); *C07D 239/22* (2013.01); *C07D 295/04* (2013.01); *C07D 307/77* (2013.01); *C07D 333/50* (2013.01); *C07D 333/78* (2013.01); *C07D 487/06* (2013.01); *C07D 493/06* (2013.01); *C07D 495/06* (2013.01); *C07F 7/0807* (2013.01); *C09B 1/00* (2013.01); *C09B 57/00* (2013.01); *C09B 57/001* (2013.01); *C09K 11/06* (2013.01); *H01L 51/006* (2013.01); *H01L 51/0056* (2013.01); *H01L 51/0058* (2013.01); *H01L 51/0061* (2013.01); *H01L 51/0071* (2013.01); *H01L 51/0072* (2013.01); *H01L 51/0073* (2013.01); *H01L 51/0074* (2013.01); *H01L 51/0094* (2013.01); *H01L 51/50* (2013.01); *C07B 2200/05* (2013.01); *C07C 2103/54* (2013.01); *C09K 2211/1011* (2013.01); *C09K 2211/1022* (2013.01); *C09K 2211/1033* (2013.01); *C09K 2211/1044* (2013.01); *C09K 2211/1088* (2013.01); *C09K 2211/1092* (2013.01); *C09K 2211/1096* (2013.01); *H01L 51/5012* (2013.01)

(56) References Cited

FOREIGN PATENT DOCUMENTS

| | | | |
|---|---|---|---|
| JP | 2001102173 | | 4/2001 |
| JP | 2003347058 | | 12/2003 |
| JP | 200715961 | | 1/2007 |
| JP | 2007169581 | | 7/2007 |
| JP | 2007191603 | | 8/2007 |
| JP | 2008-181687 | | 8/2008 |
| JP | 2009182033 | | 8/2009 |
| JP | 2010-034458 | | 2/2010 |
| JP | 2010034458 | * | 2/2010 |
| JP | 2010111620 | | 5/2010 |
| JP | 2010-520617 | | 6/2010 |
| JP | 2010-160189 | | 7/2010 |
| KR | 10-2010-0112903 | | 11/2010 |

* cited by examiner

ORGANIC ELECTROLUMINESCENCE ELEMENT

CROSS-REFERENCE TO RELATED APPLICATIONS

The present U.S. patent application is a U.S. National Stage Entry of international application number PCT/JP2012/059871, filed 11 Apr. 2012, which international application claims priority benefit from Japanese Patent Application Nos. 2012-089049, filed 10 Apr. 2012, and 2011-087857, filed 12 Apr. 2011, all of which are incorporated herein by reference in their entireties.

TECHNICAL FIELD

The present invention relates to an organic electroluminescence element, a compound used therein, and a material used for an organic electroluminescence element. Furthermore, the present invention also relates to a light-emitting device, display device, or illumination device which uses the aforementioned organic electroluminescence element.

BACKGROUND ART

Organic electroluminescence elements (hereinafter also referred to as "elements" or "organic EL elements") emit light at high brightness and at a low drive voltage and have therefore been the subject of active research and development. An organic electroluminescence element has an organic layer between a pair of electrodes. Electrons injected from the cathode and holes injected from the anode are rebound at the organic layer, and the energy of the excitons thus produced is utilized to emit light. Organic electroluminescence elements can be provided as elements having a variety of emission wavelengths, and are expected to find use in a wide range of applications because they have high response speed and are relatively thin and lightweight. In particular, the development of an organic electroluminescence element with high color purity and high luminous efficiency is important in applications to full-color displays and so on, and various research and development results have been reported up to now.

For example, Patent Document 1 describes an organic electroluminescence element in which a wide range of condensed compounds are used. Included therein is a working example of an organic electroluminescence element using a compound in which a five-membered ring is condensed to a pyrene skeleton. It is stated that blue emission is realized at good luminous efficiency and that a long service life is achieved.

Moreover, Patent Documents 2 and 3 also describe an organic electroluminescence element using similar compounds, in which a five-membered ring is condensed to a pyrene skeleton. In these patent documents as well, it is stated that blue emission is realized at good luminous efficiency and that a long service life is achieved.

In addition to these, there are several other reports of development results for organic electroluminescence elements using a compound having a pyrene skeleton (see Patent Documents 4 to 8, for example).

RELATED ART DOCUMENTS

Patent Documents

Patent Document 1: DE 102008035413
Patent Document 2: Japanese Laid-Open Patent Application 2010-111620
Patent Document 3: Korean Laid-Open Patent Application 10-2010-0112903
Patent Document 4: Japanese Laid-Open Patent Application 2007-191603
Patent Document 5: Japanese Laid-Open Patent Application 2007-169581
Patent Document 6: Japanese Laid-Open Patent Application 2007-15961
Patent Document 7: Specification of U.S. Pat. No. 6,852,429
Patent Document 8: Specification of U.S. Pat. No. 7,233,019

SUMMARY OF THE INVENTION

Problems to be Solved by the Invention

However, investigation by the present inventors has revealed that there is still room for improvement in the luminous efficiency of the organic electroluminescence elements described in the aforementioned Patent Documents 1 and 2. Furthermore, it also became clear that when these organic electroluminescence elements are used continuously for an extended period of time, drive deterioration in which emission intensity decreases is accompanied by a change in chromaticity. Moreover, some conventional pyrene-based compounds have such a strong inter-molecular interaction that they are not suited to vapor deposition, and the degree of orientation in vapor deposition is not high, either. In addition, pyrene-based compounds are generally prone to forming aggregates, so a problem has been that the organic electroluminescence element tends to result in aggregate emission (excimer emission).

Means for Solving the Problems

In view of this, the present inventors conducted diligent investigation aimed at providing an organic electroluminescence element which had high luminous efficiency and with which there was little change in chromaticity accompanying drive deterioration, by using a compound that has low inter-molecular interaction, has good orientation in vapor deposition, and is resistant to aggregation. As a result, they arrived at the present invention described below upon discovering that the aforementioned problems could be solved by using a pyrene derivative having a specific structure.

(1) An organic electroluminescence element having a substrate, a pair of electrodes that is disposed on this substrate and that includes an anode and a cathode, and an organic layer disposed between these electrodes, wherein the aforementioned organic layer contains a compound expressed by General Formula $1^1$ below:

[1]Translator's note: In the Japanese original document, the labeling number for each of the general formulas is indicated in parentheses, but we have omitted the parentheses in the translation to avoid confusion with other parenthetical notations.

[First Chemical Formula]

General Formula 1

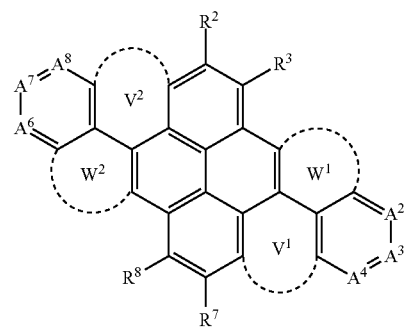

(In the formula, either $V^1$ or $W^1$ forms a ring, either $V^2$ or $W^2$ also forms a ring, the ring formed by $V^1$ and $V^2$ is a six-membered ring, and the ring formed by $W^1$ and $W^2$ is a five-membered ring; $A^2$ to $A^4$ and $A^6$ to $A^8$ represent each independently $CR^Z$ (two adjacent $CR^Z$ [groups] may together form a five- or six-membered ring) or N, and $R^Z$ represents a hydrogen atom or a substituent; and $R^2$, $R^3$, $R^7$, and $R^8$ represent each independently a hydrogen atom, an alkyl group, an aryl group, a heteroaryl group, a fluorine atom, a hydrogen atom [sic][2], or a deuterium atom.)

[2]Translator's note: The term "hydrogen atom" is erroneously repeated in this list in the original. The same error appears many times in paragraph [0007], in the Claims section, and in the Abstract section, and we have marked the second occurrence of the term "hydrogen atom" in the same list with "[sic]" each time in the translation, but no further note will be given. Incidentally, in the remaining portions of the Japanese original document, this error seems to be corrected by deleting the first occurrence of the term "hydrogen atom" in the same list.

(2) The organic electroluminescence element according to (1) is preferably such that the compound expressed by General Formula 1 above is expressed by General Formula 2 below:

[Second Chemical Formula]

General Formula 2

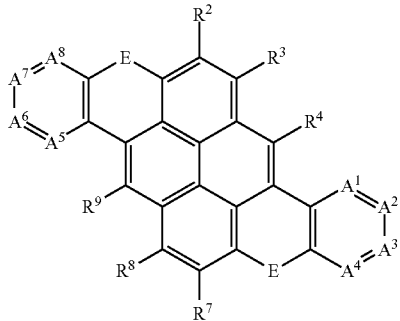

(In the formula, $A^1$ to $A^8$ represent $CR^Z$ or N, and $R^Z$ represents a hydrogen atom or a substituent; E represents $CR^xR^y$, $SiR^aR^b$, S, or O; $R^x$ and $R^y$ represent each independently an alkyl group, an aryl group, or a silyl group; $R^a$ and $R^b$ represent each independently an alkyl group or an aryl group; and $R^2$ to $R^4$ and $R^7$ to $R^9$ represent each independently a hydrogen atom, an alkyl group, an aryl group, a heteroaryl group, a fluorine atom, a hydrogen atom [sic], or a deuterium atom.)

(3) The organic electroluminescence element according to (1) is preferably such that the compound expressed by General Formula 1 above is expressed by General Formula 3 below:

[Third Chemical Formula]

General Formula 3

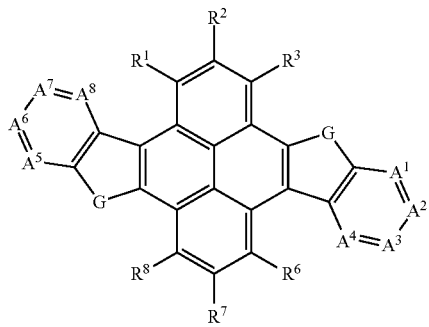

(In the formula, $A^1$ to $A^8$ represent $CR^Z$ or N, and $R^Z$ represents a hydrogen atom or a substituent; G represents $CR^xR^y$, $SiR^aR^b$, $NR^c$, S, or O; $R^x$ and $R^y$ represent each independently an alkyl group, an aryl group, or a silyl group; $R^a$, $R^b$, and $R^c$ represent each independently an alkyl group or an aryl group; and $R^1$ to $R^3$ and $R^6$ to $R^8$ represent each independently a hydrogen atom, an alkyl group, an aryl group, a heteroaryl group, a fluorine atom, a hydrogen atom [sic], or a deuterium atom.)

(4) The organic electroluminescence element according to (2) is preferably such that the compound expressed by General Formula 2 above is expressed by General Formula 4 below:

[Fourth Chemical Formula]

General Formula 4

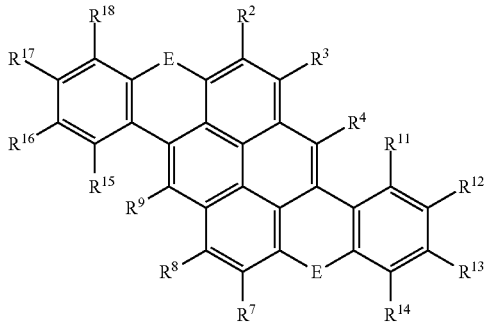

(In the formula, E represents $CR^xR^y$, $SiR^aR^b$, S, or O; $R^x$ and $R^y$ represent each independently an alkyl group, an aryl group, or a silyl group; $R^a$ and $R^b$ represent each independently an alkyl group or an aryl group; $R^2$ to $R^4$ and $R^7$ to $R^9$ represent each independently an alkyl group, an aryl group, a heteroaryl group, a fluorine atom, a hydrogen atom, or a deuterium atom; $R^{11}$ to $R^{18}$ represent each independently a hydrogen atom, an alkyl group, an alkoxy group, an alkylthio group, an aryl group, a heteroaryl group, an arylthio group, a fluorine atom, a hydrogen atom [sic], a deuterium atom, a cyano group, or an amino group; and [each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.)

(5) The organic electroluminescence element according to (4) is preferably such that in General Formula 4 above, one of $R^{12}$ to $R^{14}$ and $R^{16}$ to $R^{18}$ is $NR^{19}R^{20}$ ($R^{19}$ and $R^{20}$ represent each independently an alkyl group or an aryl group, and these may bond to each other to form a ring).

(6) The organic electroluminescence element according to (3) is preferably such that the compound expressed by General Formula 3 above is expressed by General Formula 5 below:

[Fifth Chemical Formula]

General Formula 5

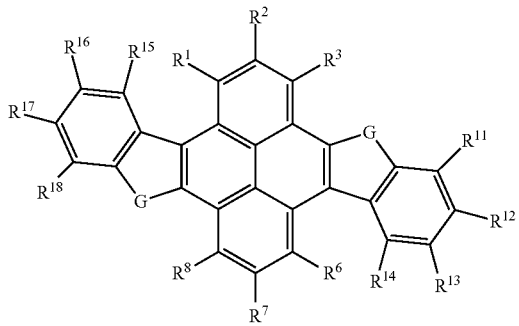

(In the formula, G represents $CR^xR^y$, $SiR^aR^b$, $NR^c$, S, or O; $R^x$ and $R^y$ represent each independently an alkyl group, an aryl group, or a silyl group; $R^a$, $R^b$, and $R^c$ represent each independently an alkyl group or an aryl group; $R^1$ to $R^3$ and $R^6$ to $R^8$ represent each independently an alkyl group, an aryl group, a heteroaryl group, a fluorine atom, a hydrogen atom, or a deuterium atom; $R^{11}$ to $R^{18}$ represent each independently a hydrogen atom, an alkyl group, an alkoxy group, an alkylthio group, an aryl group, a heteroaryl group, an arylthio group, a fluorine atom, a hydrogen atom [sic], a deuterium atom, a cyano group, or an amino group; and [each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.)

(7) The organic electroluminescence element according to (6) is preferably such that in General Formula 5 above, one of $R^{11}$ to $R^{13}$ and $R^{16}$ to $R^{18}$ is $NR^{19}R^{20}$ ($R^{19}$ and $R^{20}$ represent each independently an alkyl group or an aryl group, and these may bond to each other to form a ring).

(8) The organic electroluminescence element according to (6) or (7) is preferably such that in General Formula 5 above, G is $CR^xR^y$ ($R^x$ and $R^y$ represent each independently an alkyl group, an aryl group, or a silyl group), S, or O.

(9) The organic electroluminescence element according to (4) or (5) is preferably such that the compound expressed by General Formula 4 above is expressed by General Formula 6 below:

[Sixth Chemical Formula]

General Formula 6

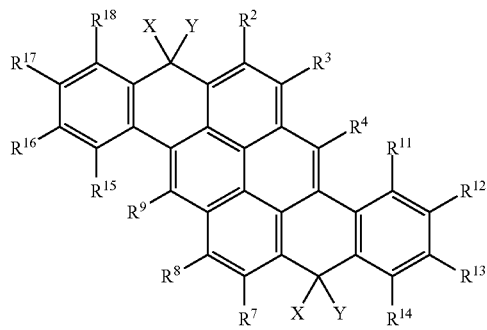

(In the formula, X and Y represent each independently an alkyl group, an aryl group, or a silyl group; $R^2$ to $R^4$ and $R^7$ to $R^9$ represent each independently an alkyl group, an aryl group, a heteroaryl group, a fluorine atom, a hydrogen atom, or a deuterium atom; $R^{11}$ to $R^{18}$ represent each independently a hydrogen atom, an alkyl group, an alkoxy group, an alkylthio group, an aryl group, a heteroaryl group, an arylthio group, a fluorine atom, a hydrogen atom [sic], a deuterium atom, a cyano group, or an amino group; and [each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.)

(10) The organic electroluminescence element according to (9) is preferably such that in General Formula 6 above, one of $R^{12}$ to $R^{14}$ and $R^{16}$ to $R^{18}$ is $NR^{19}R^{20}$ ($R^{19}$ and $R^{20}$ represent each independently an alkyl group or an aryl group, and these may bond to each other to form a ring).

(11) The organic electroluminescence element according to (9) or (10) is preferably such that in General Formula 6 above, $R^{13}$ and/or $R^{17}$ is $NR^{19}R^{20}$ ($R^{19}$ and $R^{20}$ represent each independently an alkyl group or an aryl group, and these may bond to each other to form a ring).

(12) The organic electroluminescence element according to any one of (6) to (8) is preferably such that the compound expressed by General Formula 5 above is expressed by General Formula 7 below:

[Seventh Chemical Formula]

General Formula 7

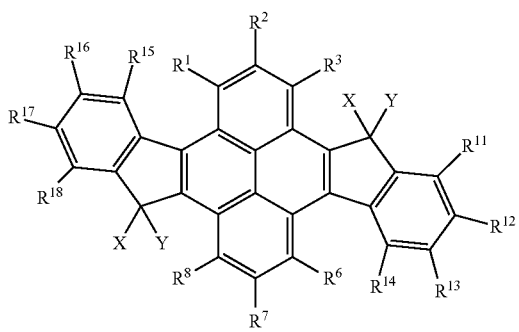

(In the formula, X and Y represent each independently an alkyl group, an aryl group, or a silyl group; $R^1$ to $R^3$ and $R^6$ to $R^8$ represent each independently an alkyl group, an aryl group, a heteroaryl group, a fluorine atom, a hydrogen atom, or a deuterium atom; $R^{11}$ to $R^{18}$ represent each independently a hydrogen atom, an alkyl group, an alkoxy group, an alkylthio group, an aryl group, a heteroaryl group, an arylthio group, a fluorine atom, a hydrogen atom [sic], a deuterium atom, a cyano group, or an amino group; and [each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.)

(13) The organic electroluminescence element according to (12) is preferably such that in General Formula 7 above, one of $R^{11}$ to $R^{13}$ and $R^{16}$ to $R^{18}$ is $NR^{19}R^{20}$ ($R^{19}$ and $R^{20}$ represent each independently an alkyl group or an aryl group, and these may bond to each other to form a ring).

(14) The organic electroluminescence element according to (12) or (13) is preferably such that in General Formula 7 above, $R^{12}$ and/or $R^{17}$ is $NR^{19}R^{20}$ ($R^{19}$ and $R^{20}$ represent each independently an alkyl group or an aryl group, and these may bond to each other to form a ring).

(15) The organic electroluminescence element according to any one of (1) to (14) is preferably such that the compound expressed by General Formula 1 above includes in its molecule a group containing an alkyl group, a silyl group, or a fluorine atom.

(16) The organic electroluminescence element according to any one of (1) to (15) is preferably such that the molecular weight of the compound expressed by General Formula 1 above is 1000 or less.

(17) The organic electroluminescence element according to any one of (1) to (16) is preferably such that at least one organic layer that contains the compound expressed by General Formula 1 above is a light-emitting layer.

(18) The organic electroluminescence element according to (17) is preferably such that the compound expressed by General Formula 1 above is a light-emitting material.

(19) The organic electroluminescence element according to (17) or (18) is preferably such that the aforementioned light-emitting layer includes an anthracene-based host material.

(20) The organic electroluminescence element according to (19) is preferably such that the aforementioned anthracene-based host material is expressed by General Formula An-1 below:

[Eighth Chemical Formula]

General Formula An-1

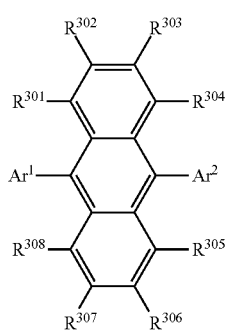

(In General Formula An-1, $Ar^1$ and $Ar^2$ represent each independently an aryl group or a heteroaryl group; $R^{301}$ to $R^{308}$ represent each independently a hydrogen atom or a substituent; and [each pair of] $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may bond to each other to form a ring.)

(21) The organic electroluminescence element according to (20) is preferably such that the compound expressed by General Formula An-1 above is a compound expressed by General Formula An-2 below:

[Ninth Chemical Formula]

General Formula An-2

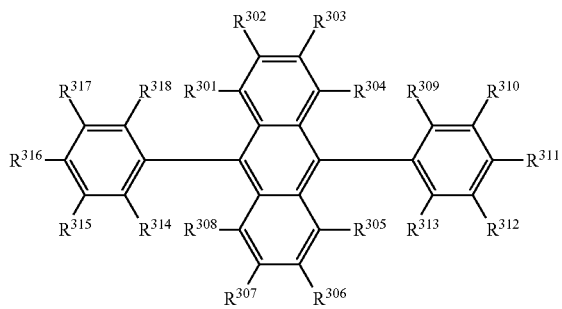

(In General Formula An-2, $R^{301}$ to $R^{318}$ represent each independently a hydrogen atom or a substituent; and [each pair of] $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ may bond to each other to form a ring.)

(22) The organic electroluminescence element according to any one of (17) to (21) is preferably such that the aforementioned light-emitting layer is formed by a vacuum vapor deposition process.

(23) The organic electroluminescence element according to any one of (17) to (21) is preferably such that the aforementioned light-emitting layer is formed by a wet process.

(24) A light-emitting device, display device, or illumination device which makes use of the organic electroluminescence element according to any one of (1) to (23).

(25) A material for an organic electroluminescence element expressed by General Formula 1 below:

[Tenth Chemical Formula]

General Formula 1

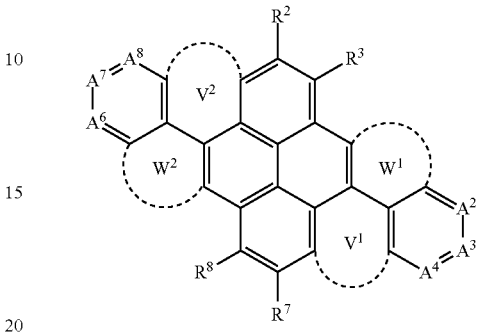

(In the formula, either $V^1$ or $W^1$ forms a ring, either $V^2$ or $W^2$ also forms a ring, the ring formed by $V^1$ and $V^2$ is a six-membered ring, and the ring formed by $W^1$ and $W^2$ is a five-membered ring; $A^2$ to $A^4$ and $A^6$ to $A^8$ represent each independently $CR^Z$ (two adjacent $CR^Z$ [groups] may together form a five- or six-membered ring) or N, and $R^Z$ represents a hydrogen atom or a substituent; and $R^2$, $R^3$, $R^7$, and $R^8$ represent each independently a hydrogen atom, an alkyl group, an aryl group, a heteroaryl group, a fluorine atom, a hydrogen atom [sic], or a deuterium atom.)

(26) The material for an organic electroluminescence element according to (25) is preferably expressed by General Formula 2 below:

[Eleventh Chemical Formula]

General Formula 2

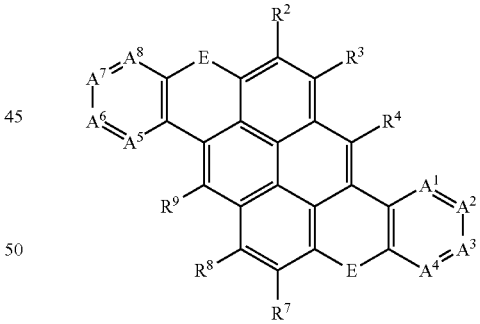

(In the formula, $A^1$ to $A^8$ represent $CR^Z$ or N, and $R^Z$ represents a hydrogen atom or a substituent; E represents $CR^xR^y$, $SiR^aR^b$, S, or O; $R^x$ and $R^y$ represent each independently an alkyl group, an aryl group, or a silyl group; $R^a$ and $R^b$ represent each independently an alkyl group or an aryl group; and $R^2$ to $R^4$ and $R^7$ to $R^9$ represent each independently a hydrogen atom, an alkyl group, an aryl group, a heteroaryl group, a fluorine atom, a hydrogen atom [sic], or a deuterium atom.)

(27) The material for an organic electroluminescence element according to (25) is preferably expressed by General Formula 3 below:

[Twelfth Chemical Formula]

General Formula 3

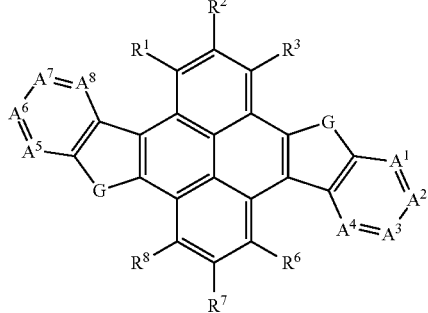

(In the formula, $A^1$ to $A^8$ represent $CR^Z$ or N, and $R^Z$ represents a hydrogen atom or a substituent; G represents $CR^xR^y$, $SiR^aR^b$, $NR^c$, S, or O; $R^x$ and $R^y$ represent each independently an alkyl group, an aryl group, or a silyl group; $R^a$, $R^b$, and $R^c$ represent each independently an alkyl group or an aryl group; and $R^1$ to $R^3$ and $R^6$ to $R^8$ represent each independently a hydrogen atom, an alkyl group, an aryl group, a heteroaryl group, a fluorine atom, a hydrogen atom [sic], or a deuterium atom.)

(28) The material for an organic electroluminescence element according to (25) is preferably expressed by General Formula 6 below:

[Thirteenth Chemical Formula]

General Formula 6

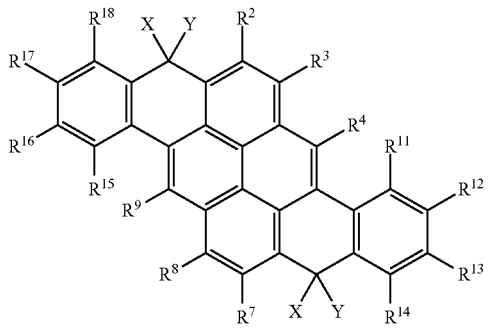

(In the formula, X and Y represent each independently an alkyl group, an aryl group, or a silyl group; $R^2$ to $R^4$ and $R^7$ to $R^9$ represent each independently an alkyl group, an aryl group, a heteroaryl group, a fluorine atom, a hydrogen atom, or a deuterium atom; $R^{11}$ to $R^{18}$ represent each independently a hydrogen atom, an alkyl group, an alkoxy group, an alkylthio group, an aryl group, a heteroaryl group, an arylthio group, a fluorine atom, a hydrogen atom [sic], a deuterium atom, a cyano group, or an amino group; and [each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.)

(29) The material for an organic electroluminescence element according to (25) is preferably expressed by General Formula 7 below:

[Fourteenth Chemical Formula]

General Formula 7

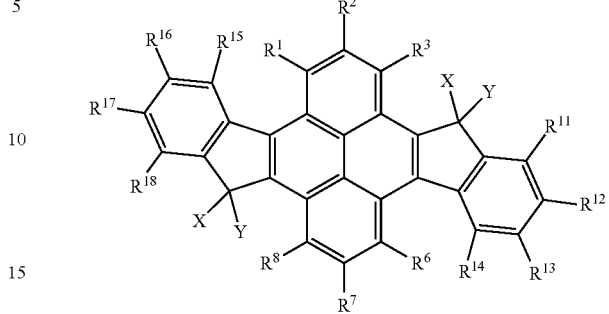

(In the formula, X and Y represent each independently an alkyl group, an aryl group, or a silyl group; $R^1$ to $R^3$ and $R^6$ to $R^8$ represent each independently an alkyl group, an aryl group, a heteroaryl group, a fluorine atom, a hydrogen atom, or a deuterium atom; $R^{11}$ to $R^{18}$ represent each independently a hydrogen atom, an alkyl group, an alkoxy group, an alkylthio group, an aryl group, a heteroaryl group, an arylthio group, a fluorine atom, a hydrogen atom [sic], a deuterium atom, a cyano group, or an amino group; and [each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.)

(30) A compound expressed by General Formula 1 below:

[Fifteenth Chemical Formula]

General Formula 1

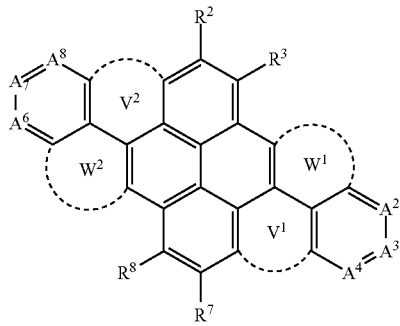

(In the formula, either $V^1$ or $W^1$ forms a ring, either $V^2$ or $W^2$ also forms a ring, the ring formed by $V^1$ and $V^2$ is a six-membered ring, and the ring formed by $W^1$ and $W^2$ is a five-membered ring; $A^2$ to $A^4$ and $A^6$ to $A^8$ represent each independently $CR^Z$ (two adjacent $CR^Z$ [groups] may together form a five- or six-membered ring) or N, and $R^Z$ represents a hydrogen atom or a substituent; and $R^2$, $R^3$, $R^7$, and $R^8$ represent each independently a hydrogen atom, an alkyl group, an aryl group, a heteroaryl group, a fluorine atom, a hydrogen atom [sic], or a deuterium atom.)

Effects of the Invention

The organic electroluminescence element of the present invention has the advantageous effect of having high luminous efficiency and little change in chromaticity accompanying drive deterioration. Furthermore, the compound of the present invention has the advantageous characteristics of low inter-molecular interaction, resulting in good orientation in vapor deposition and resistance to aggregation, so the use of the compound of the present invention makes it possible to easily manufacture an excellent organic electroluminescence element. Moreover, the light-emitting device, display device, and illumination device of the present invention have the advantageous effect of low power consumption and resistance to change in chromaticity over extended usage.

DETAILED DESCRIPTION OF EMBODIMENTS

Figure 1:
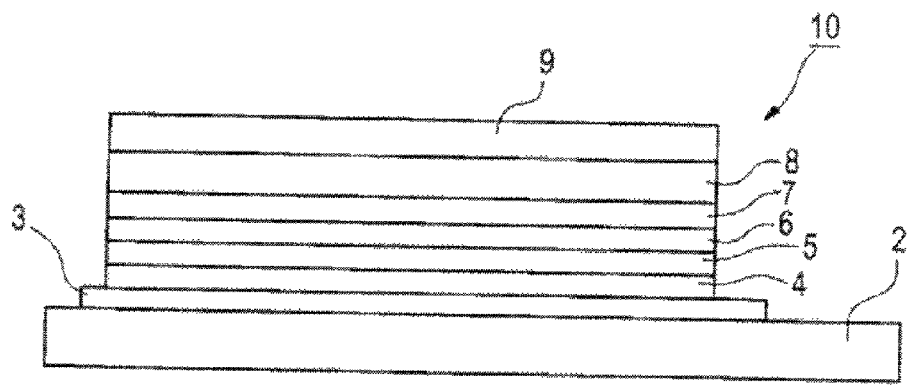
FIG. 1 is a schematic diagram illustrating one example of the configuration of the organic electroluminescence element according to the present invention.

The content of the present invention will be described in detail below. The description of the constituent elements mentioned below may be based on typical embodiments and concrete examples of the present invention, but the present invention is in no way limited to such embodiments or concrete examples. Note that the range of numerical values expressed with the use of [the phrase] "from . . . to . . . " in this Specification means a range which is such that the numerical values given are included as the minimum value and maximum value[, respectively].

Compound Expressed by General Formula 1

The organic electroluminescence element of the present invention is characterized in that the organic layer constituting the organic electroluminescence element contains a compound expressed by General Formula 1 below:

[Sixteenth Chemical Formula]

General Formula 1

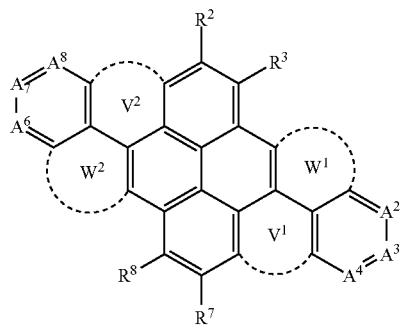

In General Formula 1, either $V^1$ or $W^1$ forms a ring, either $V^2$ or $W^2$ also forms a ring, the ring formed by $V^1$ and $V^2$ is a six-membered ring, and the ring formed by $W^1$ and $W^2$ is a five-membered ring. $A^2$ to $A^4$ and $A^6$ to $A^8$ represent each independently $CR^Z$ (two adjacent $CR^Z$ [groups] may together form a five- or six-membered ring) or N, and $R^Z$ represents a hydrogen atom or a substituent. $R^2$, $R^3$, $R^7$, and $R^8$ represent each independently an alkyl group, an aryl group, a heteroaryl group, a fluorine atom, a hydrogen atom, or a deuterium atom.

When a conventional condensed compound is used to produce an organic electroluminescence element, continued use over an extended period leads to a drop in emission intensity, and this drive deterioration ends up resulting in a change in chromaticity. Conceivable causes of such a change in chromaticity accompanying drive deterioration include a change in the emission location (and the attendant optical interference) due to a change in the element charge balance, the formation of aggregates between pyrene rings due to heat generation or the like accompanying drive, the production of light-emitting components due to deterioration of the chemical reaction of the host material or the light-emitting material through element drive, and so forth. Accordingly, in order to prevent the change in chromaticity that accompanies drive deterioration, it is necessary to provide a material in which all these things are less likely to occur. The compound expressed by General Formula 1 in the present invention is stable with respect to holes (oxidation) and electrons (reduction), has good charge injection and transport properties, is resistant to the formation of aggregates between pyrene rings, and is also resistant to deterioration of the chemical reaction due to element drive. Therefore, the change in chromaticity that accompanies drive deterioration is also less likely to occur.

Pyrene-based compounds have a property such that they tend to produce aggregate emission (excimer emission) of longer wavelength than a monomer emission. Therefore, merely condensing a pyrene ring and an aryl substituent tends to invite a decrease in color purity because aggregate emission occurs. However, the condensed compound expressed by General Formula 1 in the present invention has a characteristic feature of good aggregation suppression capability. Accordingly, the compound expressed by General Formula 1 in the present invention allows a light-emitting layer to be formed by itself, without the use of a host material.

The compound expressed by General Formula 1 in the present invention has less inter-molecular interaction than similar compounds having the same molecular weight, so sublimation properties are better. Accordingly, vapor deposition can be performed at a relatively low temperature, and there is an advantage in that an organic electroluminescence element can be manufactured while preventing pyrolysis of the compound. In addition, it is also possible to save time and energy during vapor deposition. Thus, if the compound expressed by General Formula 1 is used, an organic electroluminescence element can be manufactured efficiently and at high yield.

Furthermore, the compound expressed by General Formula 1 in the present invention also has an advantage in that its molecular symmetry is higher than that of similar compounds, so it can be oriented better. Therefore, an organic electroluminescence element in which the compound expressed by General Formula 1 is used also has the benefit of high light extraction efficiency.

As was described above, an advantageous characteristic of the compound expressed by General Formula 1 in the present invention is that its inter-molecular interaction is low, so orientation is better in vapor deposition, and aggregation is less likely to occur. Therefore, with the use of the compound of the present invention, it is possible to easily manufacture an excellent organic electroluminescence element. Moreover, an organic electroluminescence element manufactured using the compound expressed by General Formula 1 in the present invention exhibits superior performance in terms of high luminous efficiency and little change in chromaticity accompanying drive deterioration.

The compound expressed by General Formula 1 will be described in detail below.

In the present invention, when the term "substituent" is used, that substituent may be further substituted. For example, when "alkyl group" is referred to in the present invention, it encompasses alkyl groups that have been substituted with a fluorine atom (such as a trifluoromethyl group), alkyl groups that have been substituted with an aryl group (such as a triphenylmethyl group), and so forth, and when the term "$C_1$ to $C_6$ alkyl group" is used, this indicates that the carbon number is from 1 to 6 for the entire group, including one that has been substituted.

In General Formula 1, either $V^1$ or $W^1$ forms a ring. When $V^1$ forms a ring, that ring is a six-membered ring, and when $W^1$ forms a ring, that ring is a five-membered ring. In General Formula 1, furthermore, either $V^2$ or $W^2$ also forms a ring. When $V^2$ forms a ring, that ring is a six-membered ring, and when $W^2$ forms a ring, that ring is a five-membered ring.

When $V^1$ or $V^2$ forms a six-membered ring, a linking group E that links the portion represented by a dotted line in General Formula 1 is preferably $CR^xR^y$, $SiR^aR^b$, S, or O. Here, $R^x$ and $R^y$ represent each independently an alkyl group, an aryl group, or a silyl group. $R^a$ and $R^b$ represent each independently an alkyl group or an aryl group.

When $W^1$ or $W^2$ forms a five-membered ring, a linking group G that links the portion represented by a dotted line in General Formula 1 is preferably $CR^xR^y$, $SiR^aR^b$, $NR^c$, S, or O. Here, $R^x$ and $R^y$ represent each independently an alkyl group, an aryl group, or a silyl group. $R^a$, $R^b$, and $R^c$ represent each independently an alkyl group or an aryl group.

Although no particular theory holds sway, employing a structure that satisfies such conditions makes it possible to appropriately suppress the inter-molecular interaction of the compound.

In General Formula 1, $A^2$ to $A^4$ and $A^6$ to $A^8$ represent each independently $CR^Z$ or N. Here, $R^Z$ represents a hydrogen atom or a substituent. In addition, two adjacent $CR^Z$ [groups] may together form a five- or six-membered ring. The five- or six-membered ring that is formed may be an aryl ring such as a benzene ring or may be a hetero ring. When a hetero ring is formed, a heteroaryl ring may be formed, or a non-aromatic hetero ring may be formed. Examples of the hetero atoms constituting the ring when a hetero ring is formed include N, S, and O. The number of hetero atoms constituting the ring is preferably from one to three and more preferably one or two. In concrete terms, a pyridine ring, a pyrazine ring, a pyridazine ring, a pyrimidine ring, an imidazole ring, an oxazole ring, a thiazole ring, a pyrazole ring, a thiophene ring, a furan ring, and the like can be cited as examples. The five- or six-membered ring that is formed may have a substituent, and examples of substituents on a carbon atom include the Substituent Group A (described later), while examples of substituents on a nitrogen atom include the Substituent Group B (described later).

In General Formula 1, $R^2$, $R^3$, $R^7$, and $R^8$ represent each independently an alkyl group, an aryl group, a heteroaryl group, a fluorine atom, a hydrogen atom, or a deuterium atom. Each [pair of] $R^2$ and $R^3$, and $R^7$ and $R^8$ will not form a ring together.

The "alkyl groups" in the description of the present invention may be in the form of a straight-chain, branched, or cyclic and are alkyl groups generally with a carbon number of 1 to 30, preferably with a carbon number of 1 to 20, more preferably with a carbon number of 1 to 10, even more preferably with a carbon number of 1 to 6, and most preferably with a carbon number of 1 to 4. Examples include a methyl group, ethyl group, n-propyl group, isopropyl group, n-butyl group, isobutyl group, sec-butyl group, t-butyl group, n-pentyl group, isopentyl group, neopentyl group, n-hexyl group, n-octyl group, n-decyl group, n-hexadecyl group, cyclopropyl group, cyclopentyl group, and cyclohexyl group, with a methyl group, ethyl group, n-propyl group, n-butyl group, t-butyl group, cyclopentyl group, and cyclohexyl group being preferable, and a methyl group, t-butyl group, cyclopentyl group, and cyclohexyl group, for example, can be favorably employed. The alkyl groups may further have a substituent. The substituents of the Substituent Group A (described later) can be cited as examples.

The "silyl groups" in the description of the present invention are preferably substituted, and the substituent is preferably an alkyl group or an aryl group. If the silyl groups are substituted with an alkyl group or an aryl group, it is more preferable if all of the hydrogen atoms are substituted with an alkyl group or an aryl group, forming a trialkylsilyl group or a triarylsilyl group, and it is even more favorable to form a trimethylsilyl group or a triphenylsilyl group.

The "heteroaryl group" in the description of the present invention is preferably a five- or six-membered heterocycle containing a nitrogen atom. Examples of the aforementioned five- or six-membered heterocycle containing a nitrogen atom include a pyridine ring, a pyrimidine ring, a pyrazine ring, a triazine ring, an imidazole ring, a pyrazole ring, an oxazole ring, a thiazole ring, a triazole ring, an oxadiazole ring, and a thiadiazole ring. Of these, it is more preferably a pyridine ring, a pyrazine ring, an imidazole ring, or a pyrazole ring, with a pyridine ring, an imidazole ring, or a pyrazine ring being especially favorable, a pyridine ring or an imidazole ring being even more favorable, and a pyridine ring being most favorable.

The "aryl group" in the description of the present invention is preferably with a carbon number of 6 to 30, more preferably with a carbon number of 6 to 20, and especially preferably with a carbon number of 6 to 12; examples include a phenyl group, a naphthyl group, and an anthranil group. The aryl group may be either a monocyclic aryl group or an aryl group having a condensed ring, and if it is a monocyclic aryl group, a phenyl group is preferable, and if it is an aryl group having a condensed ring, a naphthylene group is preferable.

The aryl group or heteroaryl group may be further substituted with [one of] the substituents listed in the Substituent Group A (described below), or the like. For example, it may be substituted with an alkyl group, an aryl group, a heteroaryl group, a fluorine atom, or a silyl group.

Of the "substituents" [mentioned] in the description of the present invention, [the substituents in] the Substituent Group A below can be cited as [examples of] a substituent on a carbon atom and a substituent on a silicon atom.

<<Substituent Group A>>

Examples [of Substituent Group A] include alkyl groups (preferably with a carbon number of 1 to 30, more preferably with a carbon number of 1 to 20, and especially preferably with a carbon number of 1 to 10, such as a methyl, ethyl, isopropyl, t-butyl, n-octyl, n-decyl, n-hexadecyl, cyclopropyl, cyclopentyl, and cyclohexyl); alkenyl groups (preferably with a carbon number of 2 to 30, more preferably with a carbon number of 2 to 20, and especially preferably with a carbon number of 2 to 10, such as a vinyl, allyl, 2-butenyl, and 3-pentenyl); alkynyl groups (preferably with a carbon number of 2 to 30, more preferably with a carbon number of 2 to 20, and especially preferably with a carbon number of 2 to 10, such as propargyl and 3-pentynyl); aryl groups (preferably with a carbon number of 6 to 30, more preferably with a carbon number of 6 to 20, and especially preferably with a carbon number of 6 to 12, such as phenyl, p-methylphenyl, naphthyl, and anthranil); amino groups (preferably with a carbon number of 0 to 30, more preferably with a carbon number of 0 to 20, and especially preferably with a carbon number of 0 to 10, such as amino, methylamino, dimethylamino, diethylamino, dibenzylamino, diphenylamino, and ditolylamino); alkoxy groups (preferably with a carbon number of 1 to 30, more preferably with a carbon number of 1 to 20, and especially preferably with a carbon number of 1 to 10, such as methoxy, ethoxy, butoxy, and 2-ethylhexyloxy); aryloxy groups (preferably with a carbon number of 6 to 30, more preferably with a carbon number of 6 to 20, and especially preferably with a carbon number of 6 to 12, such as phenyloxy, 1-naphthyloxy, and 2-naphthyloxy); heterocyclic oxy groups (preferably with a carbon number of 1 to 30, more preferably with a carbon number of 1 to 20, and especially preferably with a carbon number of 1 to 12, such as pyridyloxy, pyrazyloxy, pyrimidyloxy, and quinolyloxy); acyl groups (preferably with a carbon number of 2 to 30, more preferably with a carbon number of 2 to 20, and especially preferably with a carbon number of 2 to 12, such as acetyl, benzoyl, formyl, and pivaloyl); alkoxycarbonyl groups (preferably with a carbon number of 2 to 30, more preferably with a carbon number of 2 to 20, and especially preferably with a carbon number of 2 to 12, such as methoxycarbonyl and ethoxycarbonyl); aryloxycarbonyl groups (preferably with a carbon number of 7 to 30, more preferably with a carbon number of 7 to 20, and especially preferably with a carbon number of 7 to 12, such as phenyloxycarbonyl); acyloxy groups (preferably with a carbon number of 2 to 30, more preferably with a carbon number of 2 to 20, and especially preferably with a carbon number of 2 to 10, such as acetoxy and benzoyloxy); acylamino groups (preferably with a carbon number of 2 to 30, more preferably with a carbon number of 2 to 20, and especially preferably with a carbon number of 2 to 10, such as acetylamino and benzoylamino); alkoxycarbonylamino groups (preferably with a carbon number of 2 to 30, more preferably with a carbon number of 2 to 20, and especially preferably with a carbon number of 2 to 12, such as methoxycarbonylamino); aryloxycarbonylamino groups (preferably with a carbon number of 7 to 30, more preferably with a carbon number of 7 to 20, and especially preferably with a carbon number of 7 to 12, such as phenyloxycarbonylamino); sulfonyl amino groups (preferably with a carbon number of 1 to 30, more preferably with a carbon number of 1 to 20, and especially preferably with a carbon number of 1 to 12, such as methanesulfonyl amino and benzenesulfonyl amino); sulfamoyl groups (preferably with a carbon number of 0 to 30, more preferably with a carbon number of 0 to 20, and especially preferably with a carbon number of 0 to 12, such as sulfamoyl, methylsulfamoyl, dimethylsulfamoyl, and phenylsulfamoyl); carbamoyl groups (preferably with a carbon number of 1 to 30, more preferably with a carbon number of 1 to 20, and especially preferably with a carbon number of 1 to 12, such as carbamoyl, methylcarbamoyl, diethylcarbamoyl, and phenylcarbamoyl); alkylthio groups (preferably with a carbon number of 1 to 30, more preferably with a carbon number of 1 to 20, and especially preferably with a carbon number of 1 to 12, such as methylthio and ethylthio); arylthio groups (preferably with a carbon number of 6 to 30, more preferably with a carbon number of 6 to 20, and especially preferably with a carbon number of 6 to 12, such as phenylthio); heterocyclic thio groups (preferably with a carbon number of 1 to 30, more preferably with a carbon number of 1 to 20, and especially preferably with a carbon number of 1 to 12, such as pyridylthio, 2-benzimizolylthio, 2-benzoxazolylthio, and 2-benzothiazolylthio); sulfonyl groups (preferably with a carbon number of 1 to 30, more preferably with a carbon number of 1 to 20, and especially preferably with a carbon number of 1 to 12, such as mesyl and tosyl); sulfinyl groups (preferably with a carbon number of 1 to 30, more preferably with a carbon number of 1 to 20, and especially preferably with a carbon number of 1 to 12, such as methanesulfinyl and benzenesulfinyl); ureido groups (preferably with a carbon number of 1 to 30, more preferably with a carbon number of 1 to 20, and especially preferably with a carbon number of 1 to 12, such as ureido, methylureido, and phenylureido); phosphoric amide groups (preferably with a carbon number of 1 to 30, more preferably with a carbon number of 1 to 20, and especially preferably with a carbon number of 1 to 12, such as diethylphosphoramide and phenylphosphoramide); a hydroxy group; a mercapto group; halogen atoms (such as a fluorine atom, chlorine atom, bromine atom, and iodine atom); a cyano group; a sulfo group; a carboxyl group; a nitro group; a hydroxamic acid group; a sulfino group; a hydrazino group; an imino group; heterocyclic groups (also including aromatic heterocyclic groups, preferably with a carbon number of 1 to 30 and more preferably with a carbon number of 1 to 12, with examples of the hetero atom including a nitrogen atom, an oxygen atom, a sulfur atom, a phosphorus atom, a silicon atom, a selenium atom, and a tellurium atom, and with concrete examples including pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, selenophenyl, tellurophenyl, piperidyl, piperidino, morpholino, pyrrolidyl, pyrrolidino, benzoxazolyl, benzimidazolyl, benzothiazolyl, a carbazolyl group, azepinyl group, and silolyl group); silyl groups (preferably with a carbon number of 3 to 40, more preferably with a carbon number of 3 to 30, and especially preferably with a carbon number of 3 to 24, such as trimethylsilyl and triphenylsilyl); silyloxy groups (preferably with a carbon number of 3 to 40, more preferably with a carbon number of 3 to 30, and especially preferably with a carbon number of 3 to 24, such as trimethylsilyloxy and triphenylsilyloxy); and phosphoryl groups (such as a diphenylphosphoryl group and a dimethylphosphoryl group). These substituents may be further substituted, and examples of the further substituent include groups selected from the Substituent Group A described above. In addition, the substituents that have been substituted with a substituent may be further substituted, and examples of the further substituents include groups selected from the Substituent Group A described above. Furthermore, the substituents that substitute for substituents that substitute for substituents may be further substituted, and examples of the further substituents include groups selected from the aforementioned Substituent Group A.

Of the "substituents" [mentioned] in the description of the present invention, [the substituents in] the Substituent Group B below can be cited as [examples of] a substituent on a nitrogen atom.

<<Substituent Group B>>

Examples [of Substituent Group B] include alkyl groups (preferably with a carbon number of 1 to 30, more preferably with a carbon number of 1 to 20, and especially preferably with a carbon number of 1 to 10, such as a methyl, ethyl, isopropyl, t-butyl, n-octyl, n-decyl, n-hexadecyl, cyclopropyl, cyclopentyl, and cyclohexyl); alkenyl groups (preferably with a carbon number of 2 to 30, more preferably with a carbon number of 2 to 20, and especially preferably with a carbon number of 2 to 10, such as a vinyl, allyl, 2-butenyl, and 3-pentenyl); alkynyl groups (preferably with a carbon number of 2 to 30, more preferably with a carbon number of 2 to 20, and especially preferably with a carbon number of 2 to 10, such as propargyl and 3-pentynyl); aryl groups (preferably with a carbon number of 6 to 30, more preferably with a carbon number of 6 to 20, and especially preferably with a carbon number of 6 to 12, such as phenyl, p-methylphenyl, naphthyl, and anthranil); heterocyclic groups (also including aromatic heterocyclic groups, preferably with a carbon number of 1 to 30 and more preferably with a carbon number of 1 to 12, with examples of the hetero atom including a nitrogen atom, an oxygen atom, a sulfur atom, a phosphorus atom, and a silicon atom, and with concrete examples including pyridyl, pyrazinyl, pyrimidyl, pyridazinyl, pyrrolyl, pyrazolyl, triazolyl, imidazolyl, oxazolyl, thiazolyl, isoxazolyl, isothiazolyl, quinolyl, furyl, thienyl, piperidyl, piperidino, morpholino, pyrrolidyl, pyrrolidino, benzoxazolyl, benzimidazolyl, benzothiazolyl, a carbazolyl group, azepinyl group, and silolyl group). These substituents may be further substituted, and examples of the further substituent include groups selected from the Substituent Group B described above. Moreover, the substituents that have been substituted with a substituent may be further substituted, and examples of the further substituents include groups selected from the Substituent Group B described above. In addition, the substituents that substitute for substituents that substitute for substituents may be further substituted, and examples of the further substituents include groups selected from the aforementioned Substituent Group B.

The compound expressed by General Formula 1 is preferably a compound expressed by General Formula 2 below:

[Seventeenth Chemical Formula]

General Formula 2

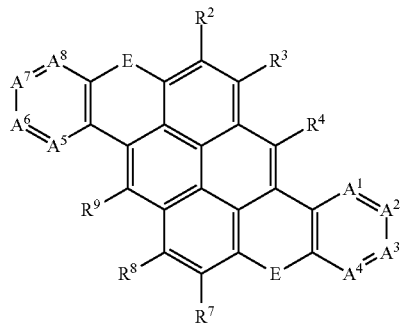

In General Formula 2, $A^1$ to $A^8$ represent $CR^Z$ or N, and $R^Z$ represents a hydrogen atom or a substituent. E represents $CR^xR^y$, $SiR^aR^b$, S, or O. $R^x$ and $R^y$ represent each independently an alkyl group, an aryl group, or a silyl group. $R^a$ and $R^b$ represent each independently an alkyl group or an aryl group. $R^2$ to $R^4$ and $R^7$ to $R^9$ represent each independently an alkyl group, an aryl group, a heteroaryl group, a fluorine atom, a hydrogen atom, or a deuterium atom. For the description and preferred ranges of the various atoms and substituents in General Formula 2, reference can be made to the corresponding description and preferred ranges in General Formula 1.

The compound expressed by General Formula 1 is also preferably a compound expressed by General Formula 3 below:

[Eighteenth Chemical Formula]

General Formula 3

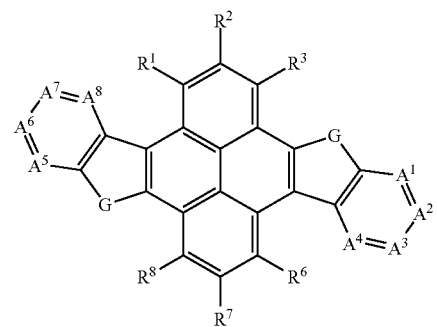

In General Formula 3, $A^1$ to $A^8$ represent $CR^Z$ or N, and $R^Z$ represents a hydrogen atom or a substituent. G represents $CR^xR^y$, $SiR^aR^b$, $NR^c$, S, or O. $R^x$ and $R^y$ represent each independently an alkyl group, an aryl group, or a silyl group. $R^a$, $R^b$, and $R^c$ represent each independently an alkyl group or an aryl group. $R^1$ to $R^3$ and $R^6$ to $R^8$ represent each independently an alkyl group, an aryl group, a heteroaryl group, a fluorine atom, a hydrogen atom, or a deuterium atom. For the description and preferred ranges of the various atoms and substituents in General Formula 3, reference can be made to the corresponding description and preferred ranges in General Formula 1.

Of these, from the standpoint of sublimation properties, G in General Formula 3 above is preferably $CR^xR^y$ ($R^x$ and $R^y$ represent each independently an alkyl group, an aryl group, or a silyl group), S, or O and more preferably $CR^xR^y$.

The compound expressed by General Formula 3 above yields the unexpected effect of improved sublimation properties by making the condensation position the 4 and 5 positions or the 9 and 10 positions on a pyrene skeleton. Although no particular theory holds sway, a pyrene compound condensed at the 4 and 5 positions and the 9 and 10 positions is such that elements with high bulk and/or electrical negativity come to positions closer to the center of the pyrene skeleton than a pyrene compound that is also condensed at the 2 and 7 positions. Accordingly, this is believed to be linked to suitably decreasing inter-molecular interaction and improving sublimation properties. Therefore, this effect is more pronounced with a condensed group $CR^xR^y$.

The compound expressed by General Formula 3 above also yields the additional effect of enhancing orientation because of improved molecular symmetry, which also improves light extraction efficiency.

The compound expressed by General Formula 2 is more preferably a compound expressed by General Formula 4 below:

[Nineteenth Chemical Formula]

General Formula 4

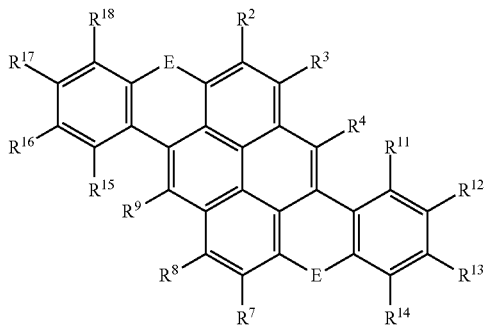

In General Formula 4, E represents $CR^xR^y$, $SiR^aR^b$, S, or O. $R^x$ and $R^y$ represent each independently an alkyl group, an aryl group, or a silyl group. $R^a$ and $R^b$ represent each independently an alkyl group or an aryl group. $R^2$ to $R^4$ and $R^7$ to $R^9$ represent each independently an alkyl group, an aryl group, a heteroaryl group, a fluorine atom, a hydrogen atom, or a deuterium atom. $R^{11}$ to $R^{18}$ represent each independently an alkyl group, an alkoxy group, an alkylthio group, an aryl group, a heteroaryl group, an arylthio group, a fluorine atom, a hydrogen atom, a deuterium atom, a cyano group, or an amino group. [Each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring. For the description and preferred ranges of the various atoms and substituents in General Formula 4, reference can be made to the corresponding description and preferred ranges in General Formula 1.

Of these, one of $R^{12}$ to $R^{14}$ and $R^{16}$ to $R^{18}$ in General Formula 4 above is preferably $NR^{19}R^{20}$ ($R^{19}$ and $R^{20}$ represent each independently an alkyl group or an aryl group, and these may bond to each other to form a ring) from the standpoint of raising luminous efficiency, and it is more preferable for $R^{13}$ and/or $R^{17}$ to be $NR^{19}R^{20}$. It is more preferable if $R^{19}$ and $R^{20}$ are each independently an aryl group, especially preferably a $C_6$ to $C_{10}$ aryl group, and even more especially preferably a phenyl group or 2-naphthyl group. $R^{19}$ and $R^{20}$ may further have a substituent, and the further substituent is preferably an alkyl group, an aryl group, or a fluorine atom, with a $C_1$ to $C_5$ alkyl group, a phenyl group, or a fluorine atom being more favorable, and a methyl group being especially favorable. The number of further substituents when $R^{19}$ and $R^{20}$ have a further substituent is preferably from one to three per $R^{19}$ and $R^{20}$, with one or two being more preferable, and one being especially preferable.

The compound expressed by General Formula 3 is more preferably a compound expressed by General Formula 5 below:

[Twentieth Chemical Formula]

General Formula 5

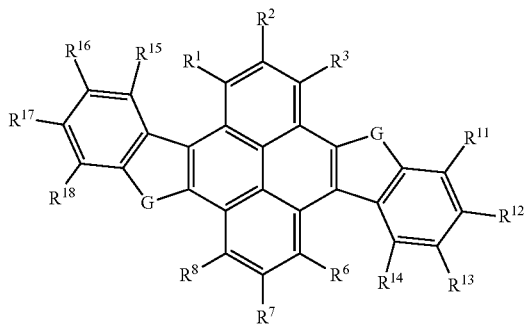

In General Formula 5, G represents $CR^xR^y$, $SiR^aR^b$, $NR^c$, S, or O. $R^x$ and $R^y$ represent each independently an alkyl group, an aryl group, or a silyl group. $R^a$, $R^b$, and $R^c$ represent each independently an alkyl group or an aryl group. $R^1$ to $R^3$ and $R^6$ to $R^8$ represent each independently an alkyl group, an aryl group, a heteroaryl group, a fluorine atom, a hydrogen atom, or a deuterium atom. $R^{11}$ to $R^{18}$ represent each independently an alkyl group, an alkoxy group, an alkylthio group, an aryl group, a heteroaryl group, an arylthio group, a fluorine atom, a hydrogen atom, a deuterium atom, a cyano group, or an amino group, and [each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring. For the description and preferred ranges of G in General Formula 5 above, reference can be made to the description and preferred ranges of G in General Formula 3.

The compound expressed by General Formula 4 is more preferably a compound expressed by General Formula 6 below:

[Twenty-First Chemical Formula]

General Formula 6

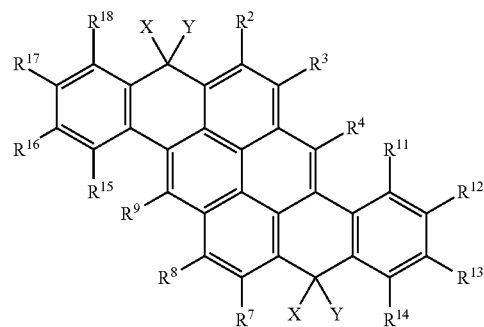

In General Formula 6, X and Y represent each independently an alkyl group, an aryl group, or a silyl group. $R^2$ to $R^4$ and $R^7$ to $R^9$ represent each independently an alkyl group, an aryl group, a heteroaryl group, a fluorine atom, a hydrogen atom, or a deuterium atom. $R^{11}$ to $R^{18}$ represent each independently an alkyl group, an alkoxy group, an alkylthio group, an aryl group, a heteroaryl group, an arylthio group, a fluorine atom, a hydrogen atom, a deuterium atom, a cyano group, or an amino group, and [each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring. For the description and preferred ranges of the various atoms and substituents in General Formula 6, reference can be made to the corresponding description and preferred ranges in General Formula 1.

Of these, one of $R^{12}$ to $R^{14}$ and $R^{16}$ to $R^{18}$ in General Formula 6 above is preferably $NR^{19}R^{20}$ ($R^{19}$ and $R^{20}$ represent each independently an alkyl group or an aryl group, and these may bond to each other to form a ring). For the description and preferred ranges of $R^{19}$ and $R^{20}$ in General Formula 6 above, reference can be made to the description and preferred ranges of $R^{19}$ and $R^{20}$ in General Formula 4.

The compound expressed by General Formula 5 is more preferably a compound expressed by General Formula 7 below:

[Twenty-Second Chemical Formula]

General Formula 7

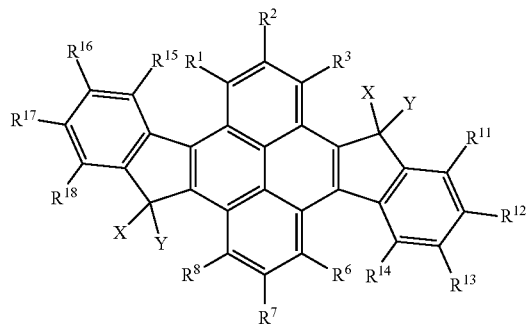

In General Formula 7, X and Y represent each independently an alkyl group, an aryl group, or a silyl group. $R^1$ to $R^3$ and $R^6$ to $R^8$ represent each independently an alkyl group, an aryl group, a heteroaryl group, a fluorine atom, a hydrogen atom, or a deuterium atom. $R^{11}$ to $R^{18}$ represent each independently an alkyl group, an alkoxy group, an alkylthio group, an aryl group, a heteroaryl group, an arylthio group, a fluorine atom, a hydrogen atom, a deuterium atom, a cyano group, or an amino group, and [each pair of] $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring. For the description and preferred ranges of the various atoms and substituents in General Formula 6 [sic][3], reference can be made to the corresponding description and preferred ranges in General Formula 1.

[3]Translator's note: apparent error in the original: "General Formula 6" should be "General Formula 7."

Of these, one of $R^{11}$ to $R^{13}$ and $R^{16}$ to $R^{18}$ in General Formula 7 above is preferably $NR^{19}R^{20}$ ($R^{19}$ and $R^{20}$ represent each independently an alkyl group or an aryl group, and these may bond to each other to form a ring), and it is more preferable for $R^{12}$ and/or $R^{17}$ to be $NR^{19}R^{20}$. For the description and preferred ranges of $R^{19}$ and $R^{20}$ in General Formula 7 above, reference can be made to the description and preferred ranges of $R^{19}$ and $R^{20}$ in General Formula 5.

When a compound expressed by General Formula 1 is used as a light-emitting material, the maximum emission wavelength of the organic electroluminescence element is usually from 390 to 500 nm, preferably from 410 to 480 nm, and more preferably from 430 to 460 nm. In the present invention, [a compound that is] employed as the compound expressed by General Formula 1 is preferably a compound expressed by General Formulas 2 to 7, [more] preferably a compound expressed by General Formulas 4 to 7, and even more preferably a compound expressed by General Formula 6 or 7, and this is favorable because the maximum emission wavelength of the organic electroluminescence element will be about 430 to 460 nm, and blue emission of particularly high color purity can be obtained.

The compound expressed by General Formula 1 preferably has a molecular weight of 1000 or less, more preferably 900 or less, and even more preferably 800 or less. Lowering the molecular weight allows the sublimation temperature to be lowered, so pyrolysis of the compound in vapor deposition can be prevented. Furthermore, this makes it possible to shorten the vapor deposition time and to suppress energy required for vapor deposition.

Concrete examples of the compound expressed by General Formula 1 will be given below, but it should not be construed that the compounds expressed by General Formula 1 that can be used in the present invention are limited to or by these concrete examples:

[Twenty-Third Chemical Formula]

compound 1

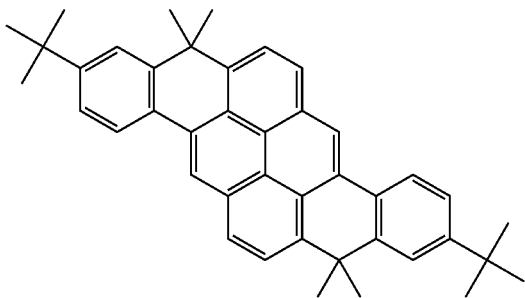

compound 2

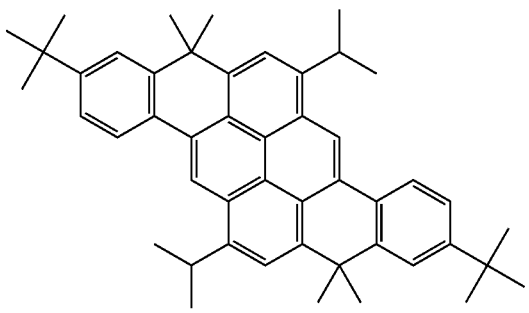

compound 3

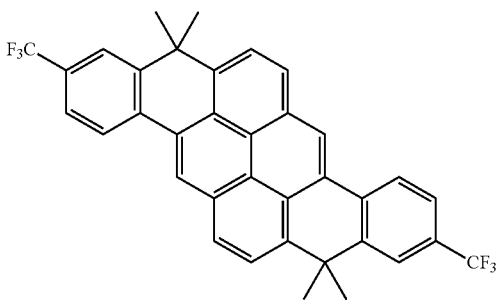

compound 4

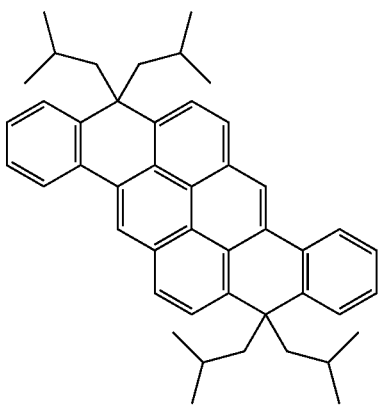

-continued
compound 5
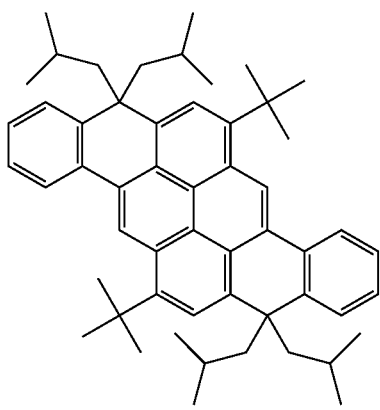
compound 6
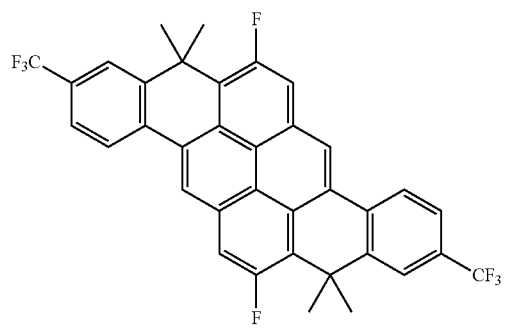
compound 7
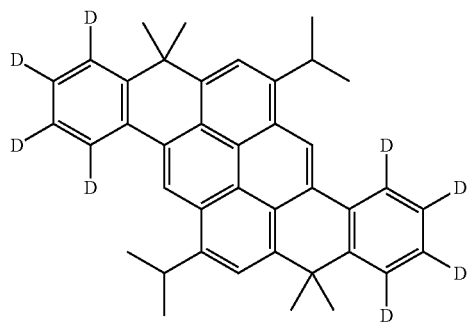
compound 8
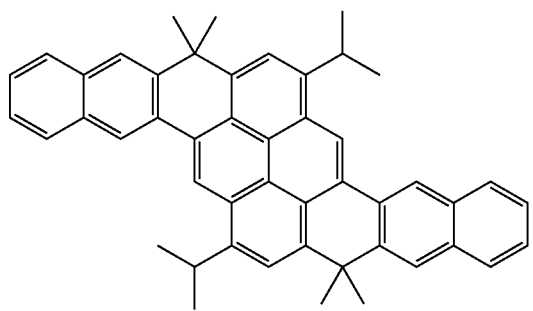
compound 9
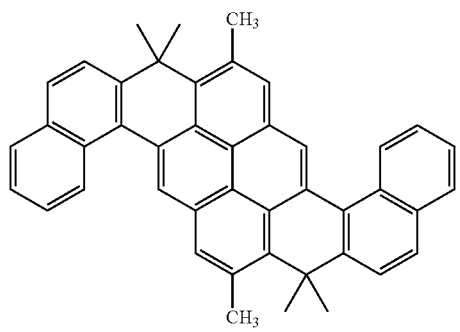
compound 10
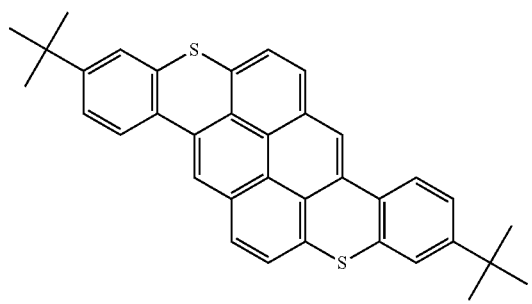
compound 11
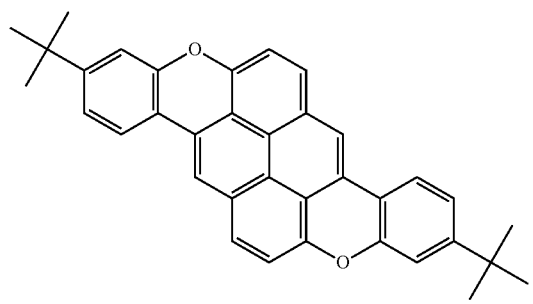
compound 12
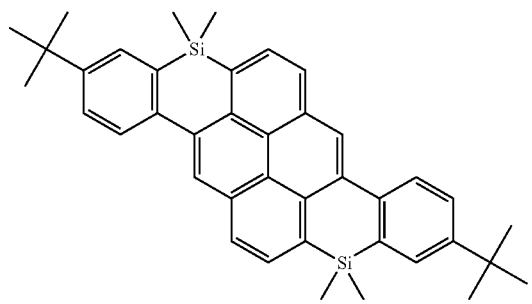

compound 13
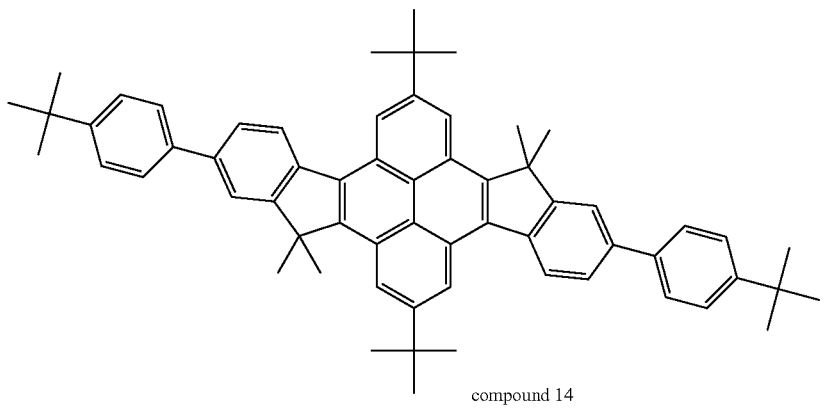
compound 14
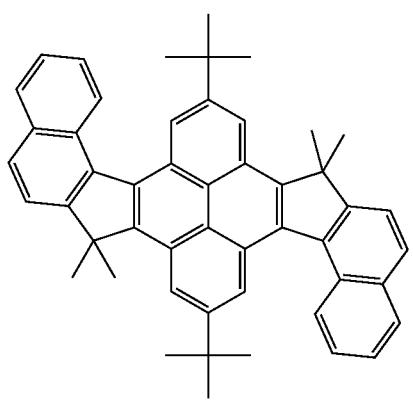
compound 15
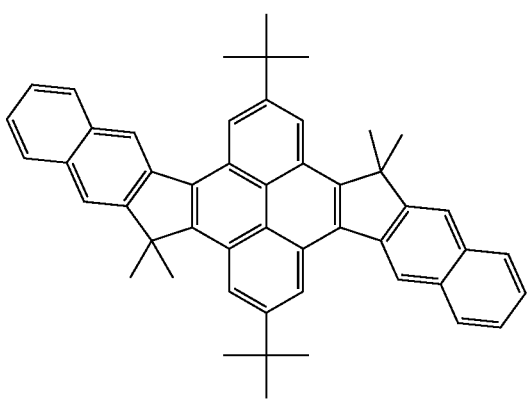
compound 16
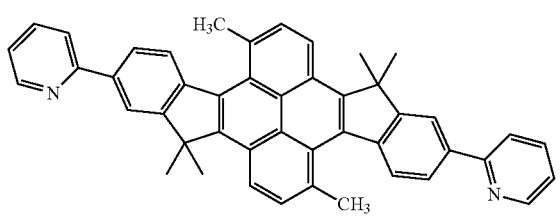
compound 17
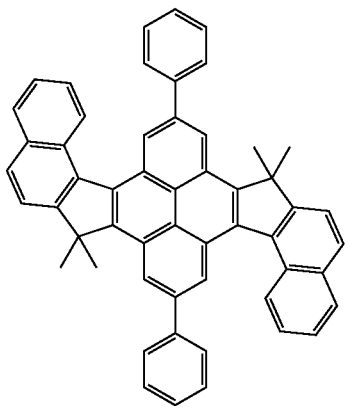
compound 18
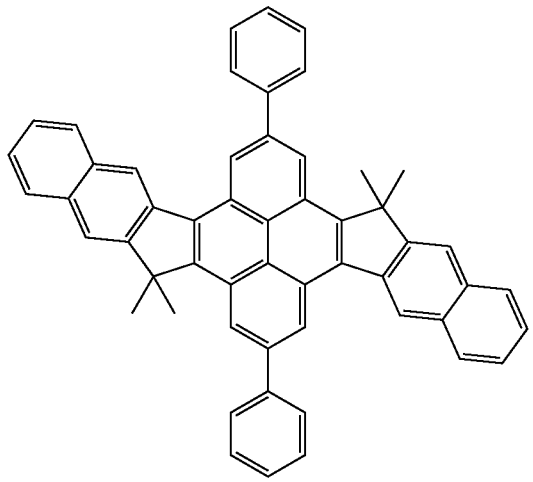

[Twenty-Fourth Chemical Formula]
compound 19
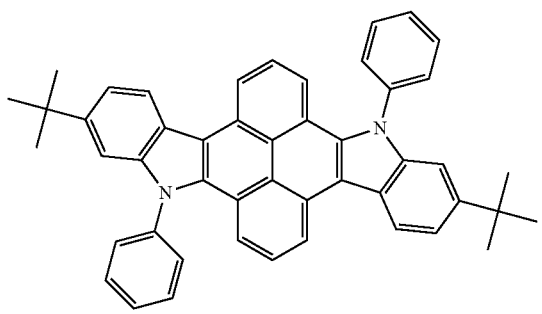
compound 20
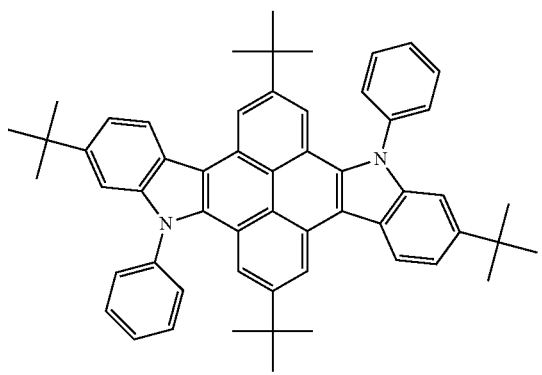
compound 21
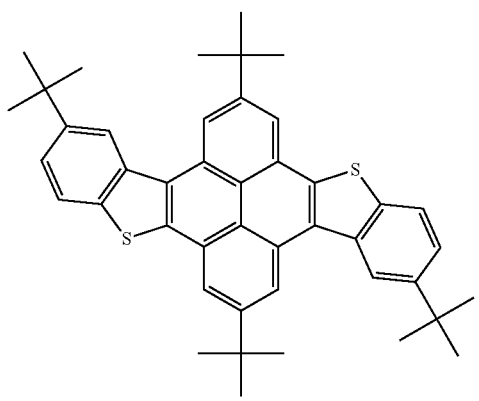
compound 22
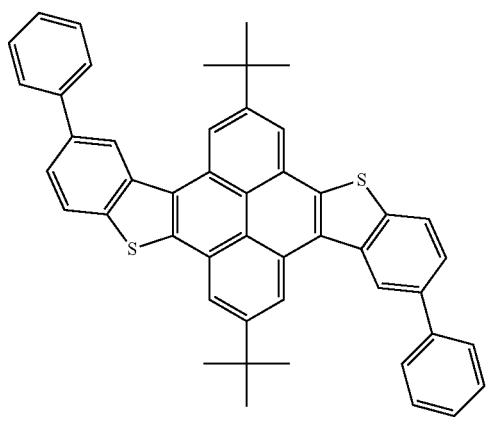
compound 23
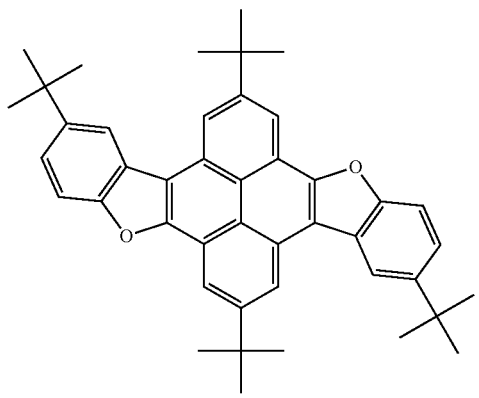
compound 24
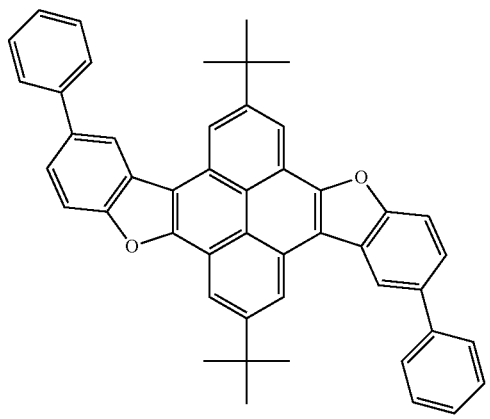
compound 25
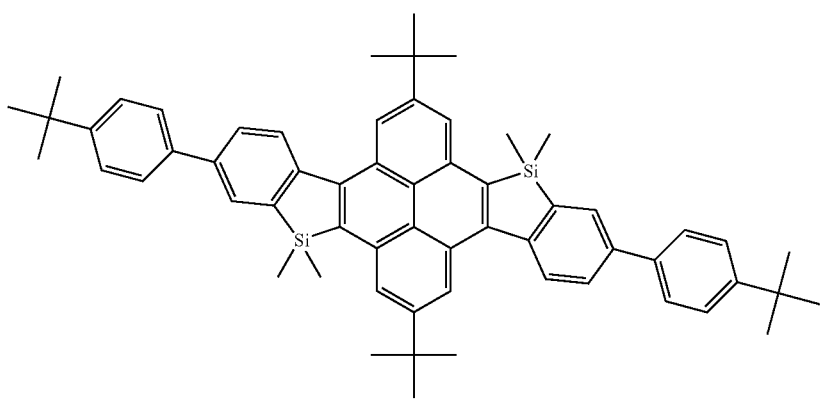

-continued
compound 26
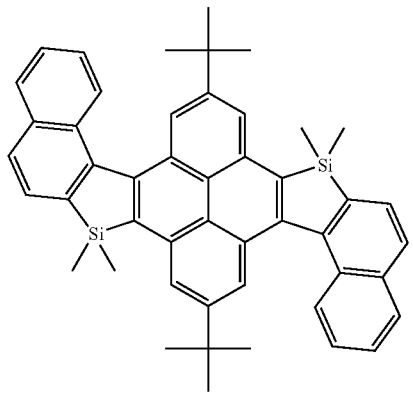
compound 27
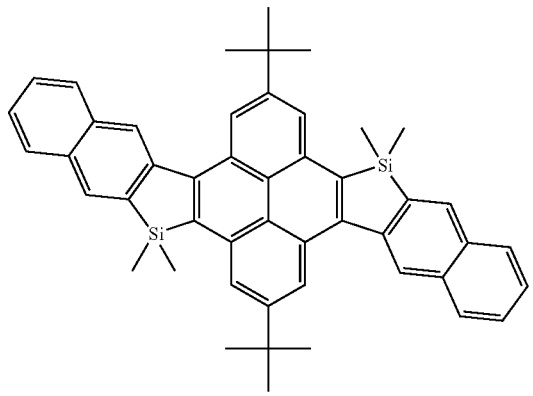
compound 28
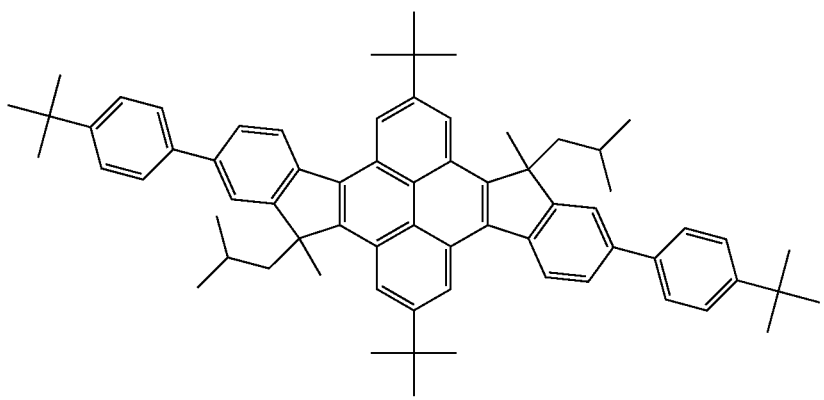
compound 29
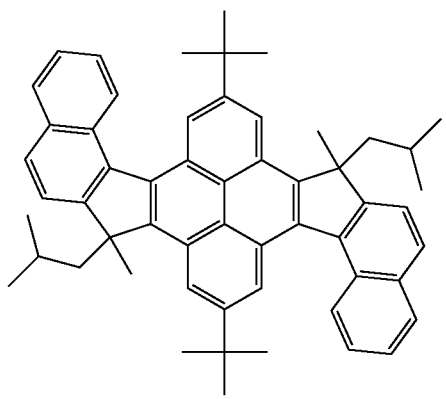
compound 30
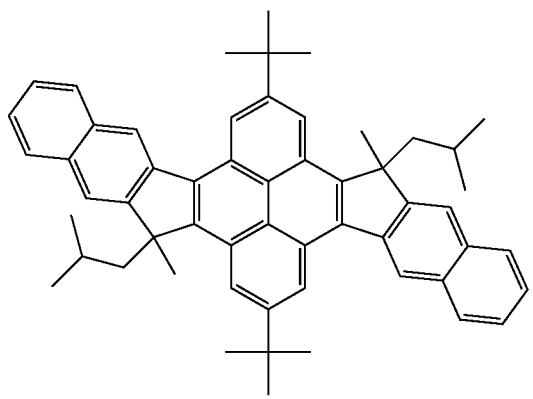
compound 31
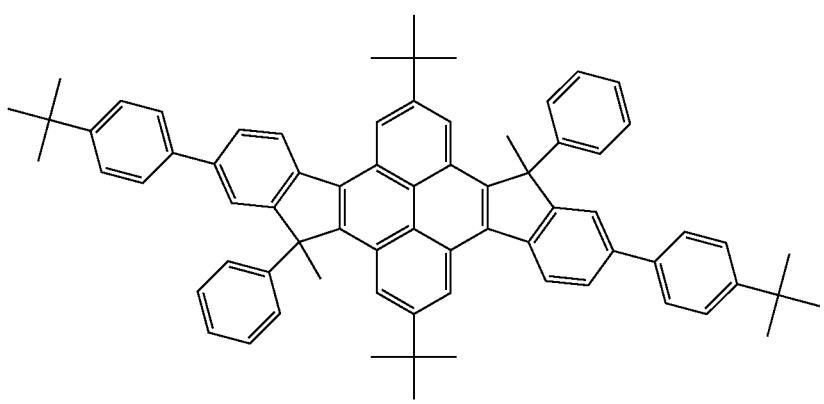

-continued
compound 32
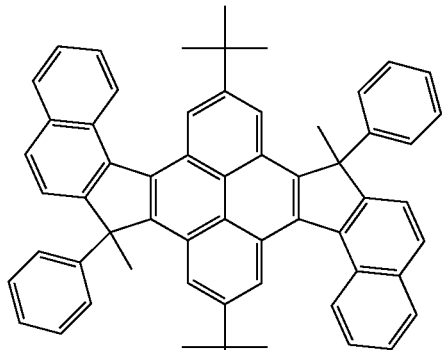
[Twenty-Fifth Chemical Formula]
compound 34
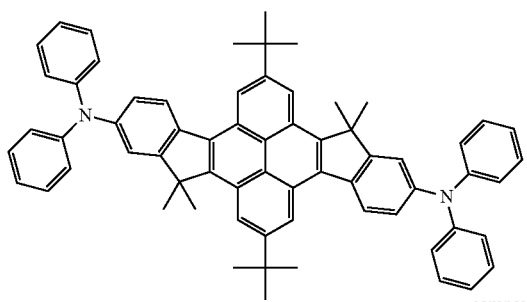
compound 36
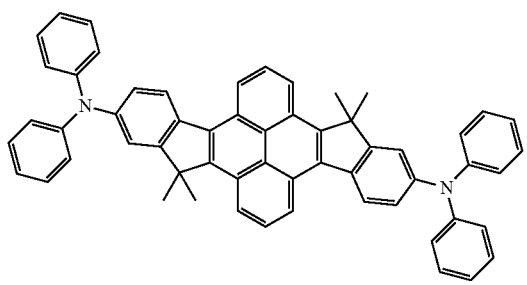
compound 39
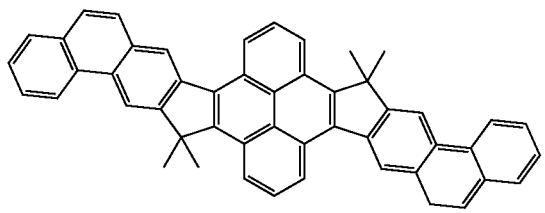
compound 33
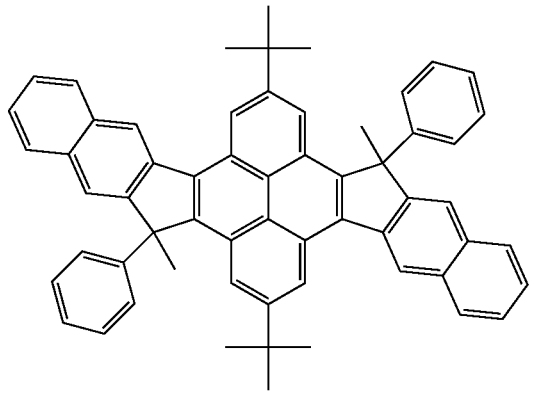
compound 35
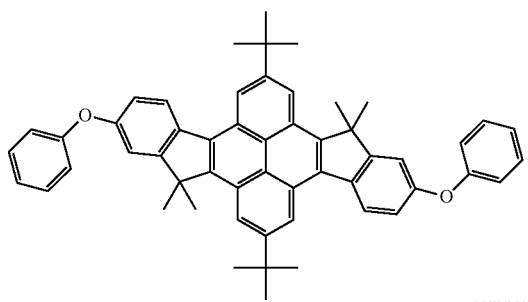
compound 37
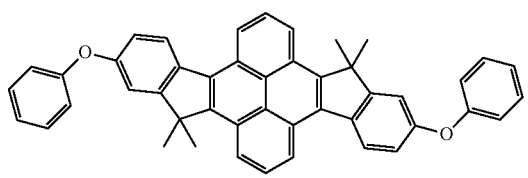
compound 38
compound 40
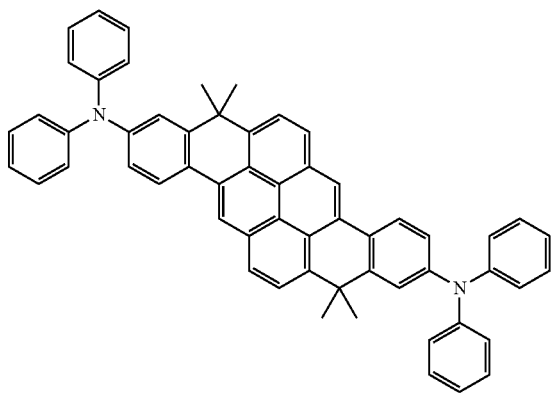

-continued
compound 41
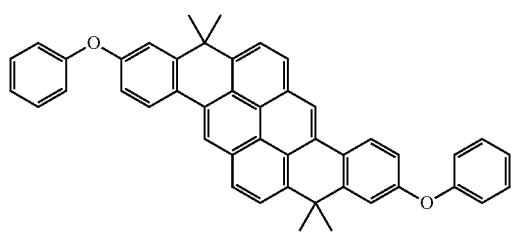
compound 42
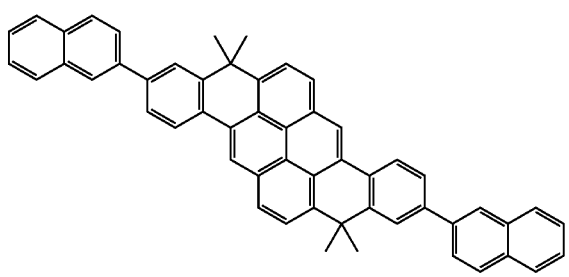
compound 43
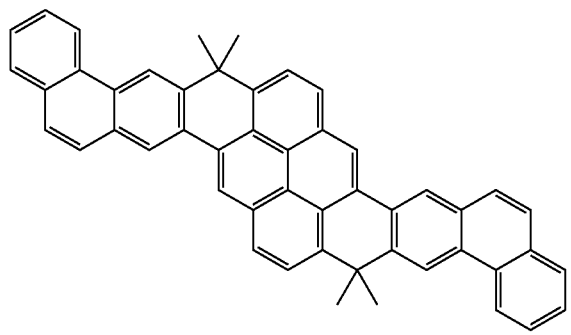
[Twenty-Sixth Chemical Formula]
compound 44
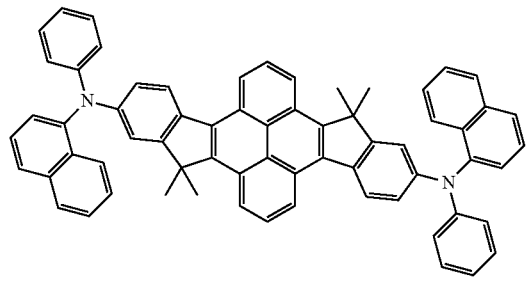
compound 45
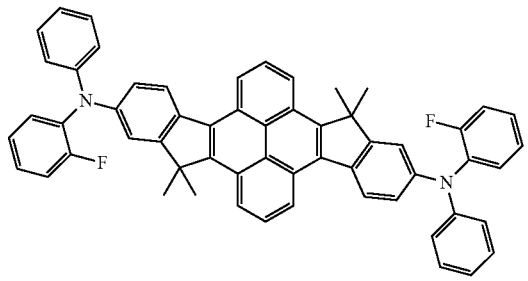
compound 46
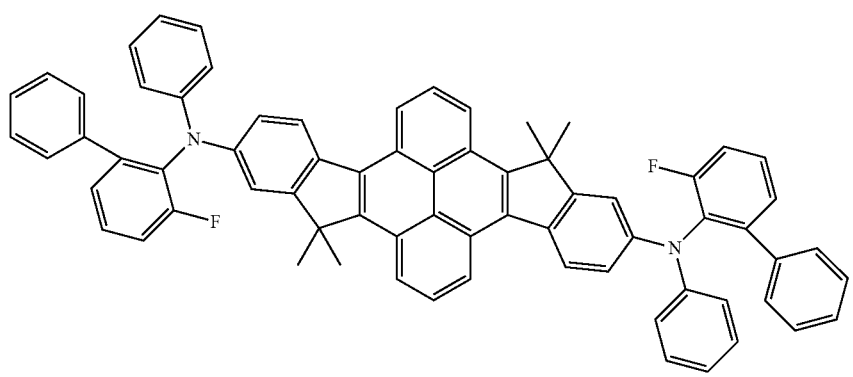

compound 47
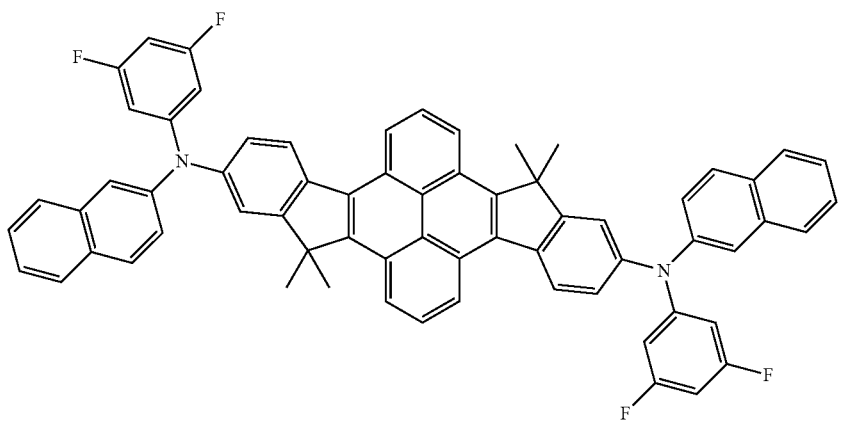
compound 48
compound 49
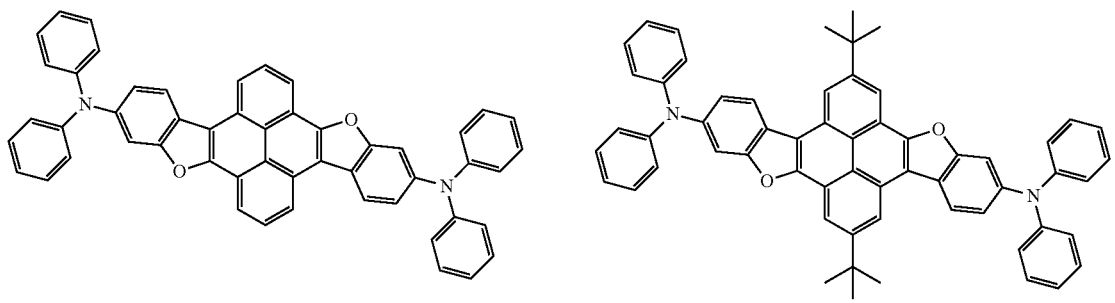
compound 50
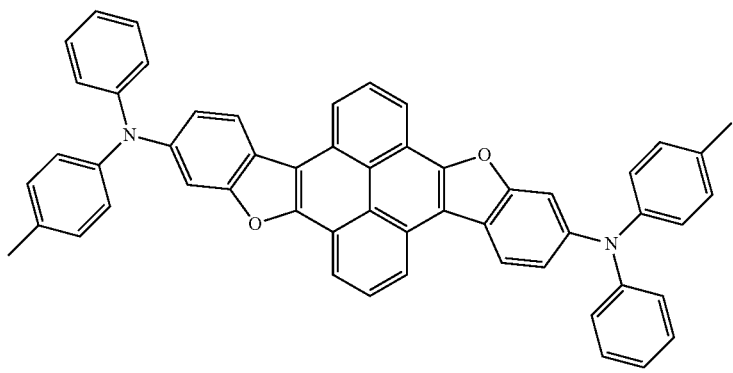
compound 51
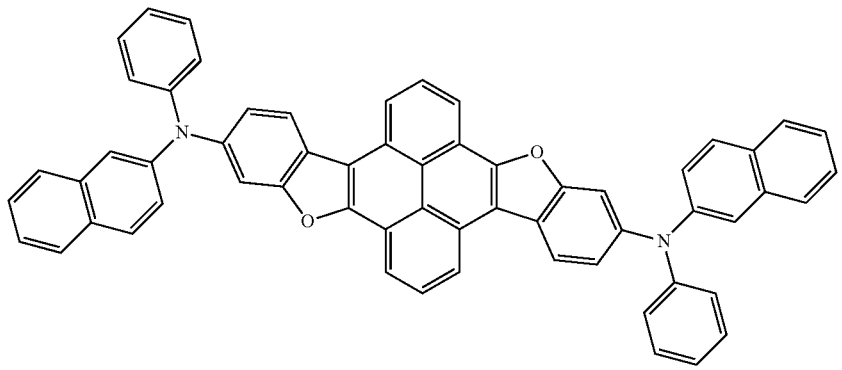

-continued
compound 52
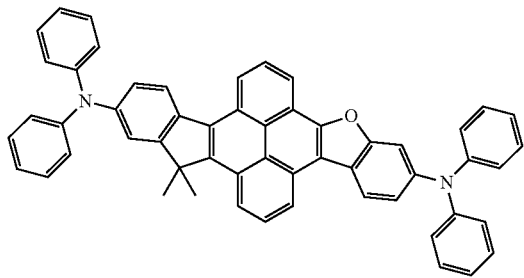
compound 53
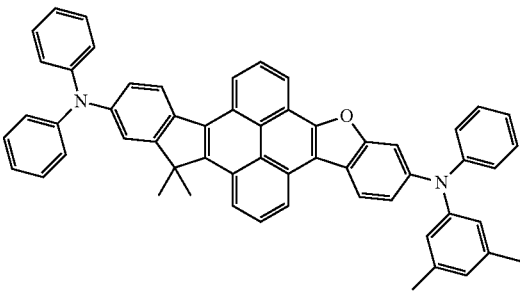
[Twenty-Seventh Chemical Formula]
compound 54
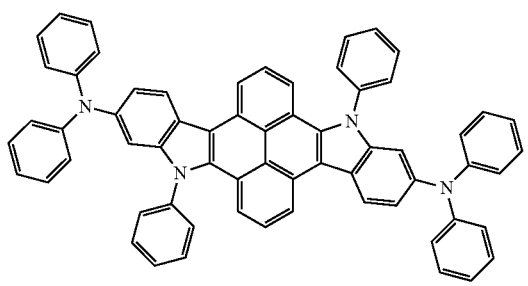
compound 55
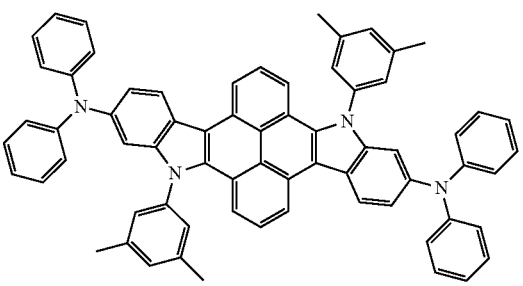
compound 56
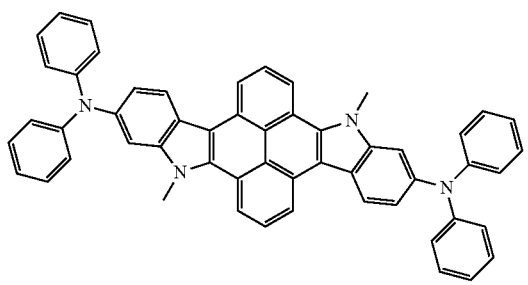
compound 57
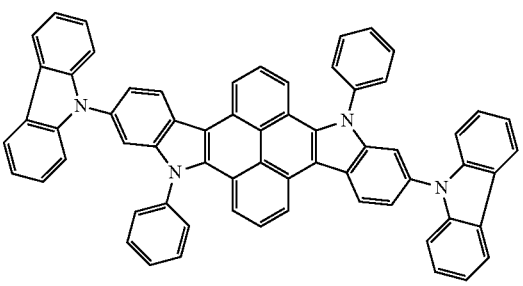
compound 58
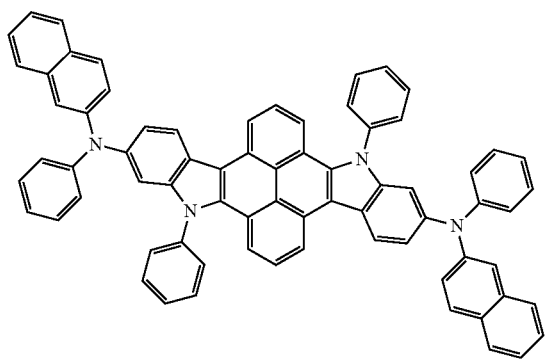
compound 59
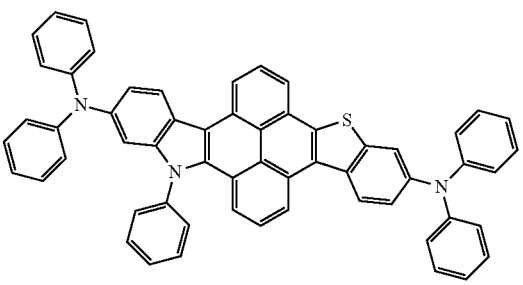
compound 60
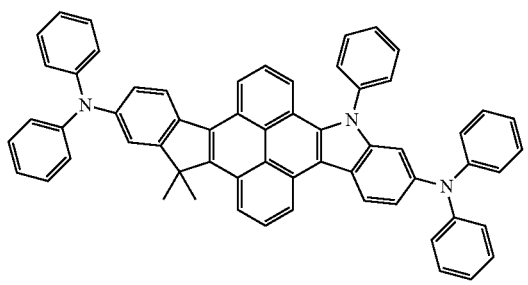
compound 61
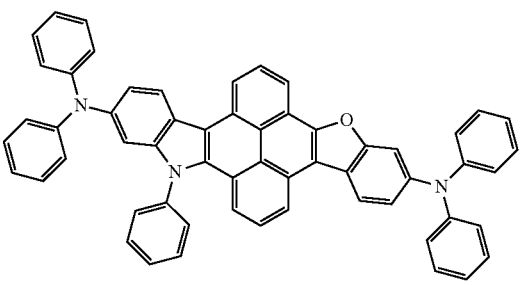

-continued
compound 62
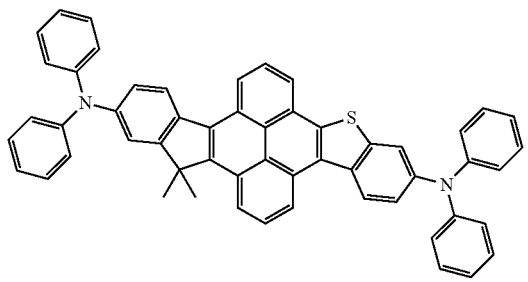
compound 63
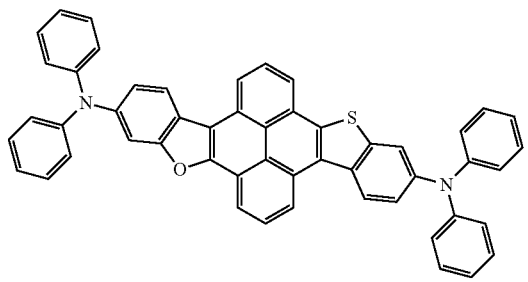
[Twenty-Eighth Chemical Formula]
compound 64
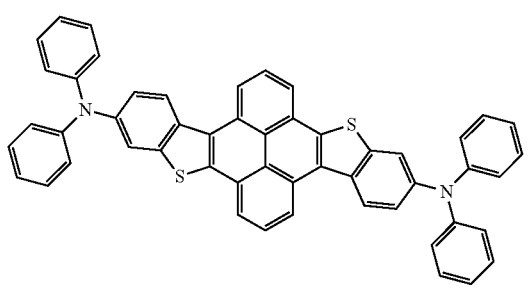
compound 65
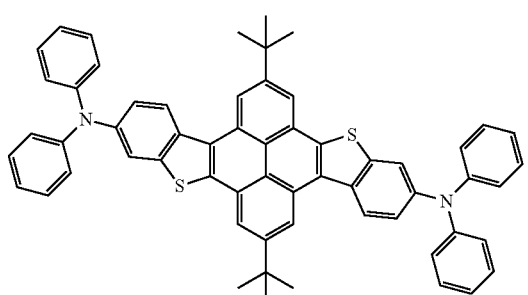
compound 66
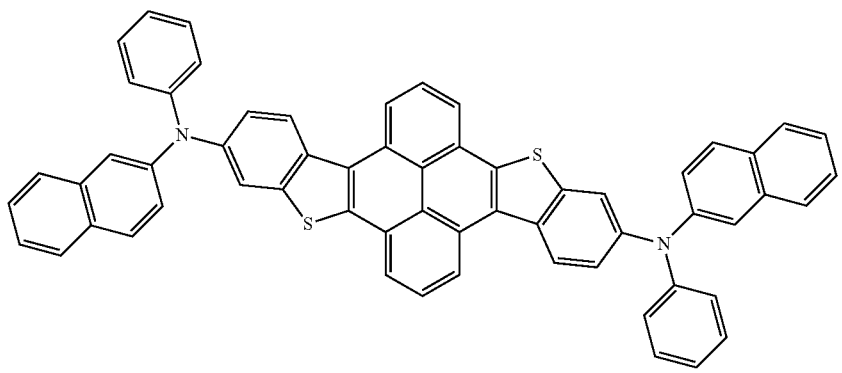
compound 67
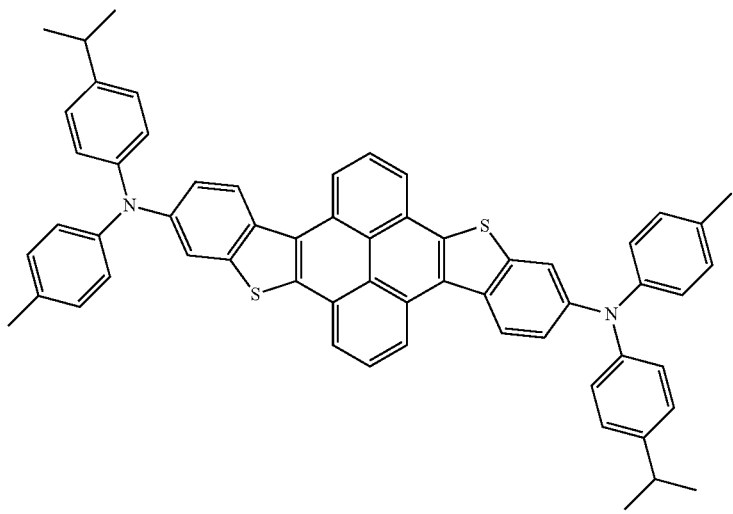

-continued
compound 68
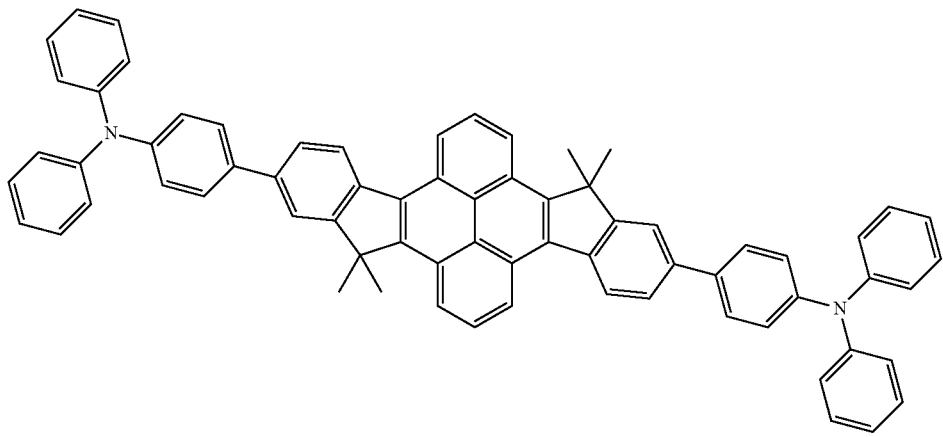
compound 69
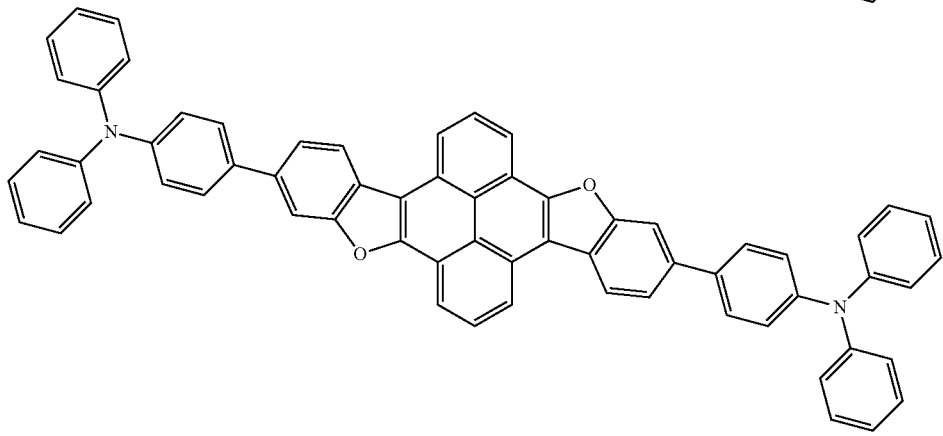
compound 70
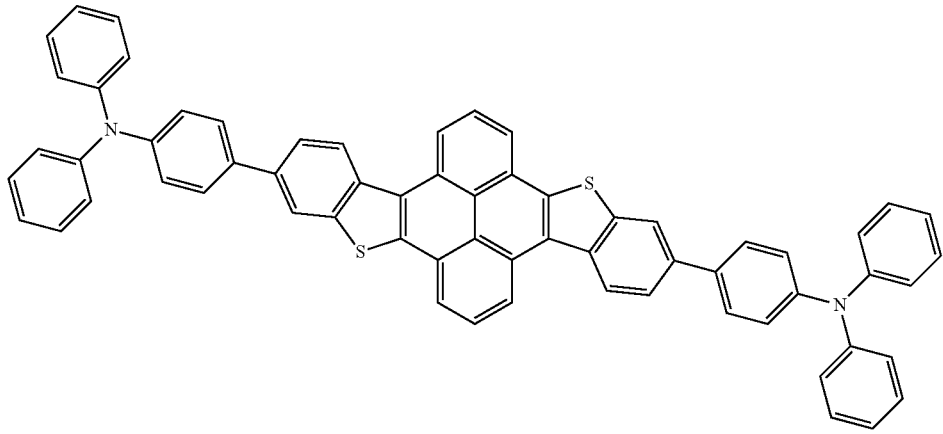
compound 71
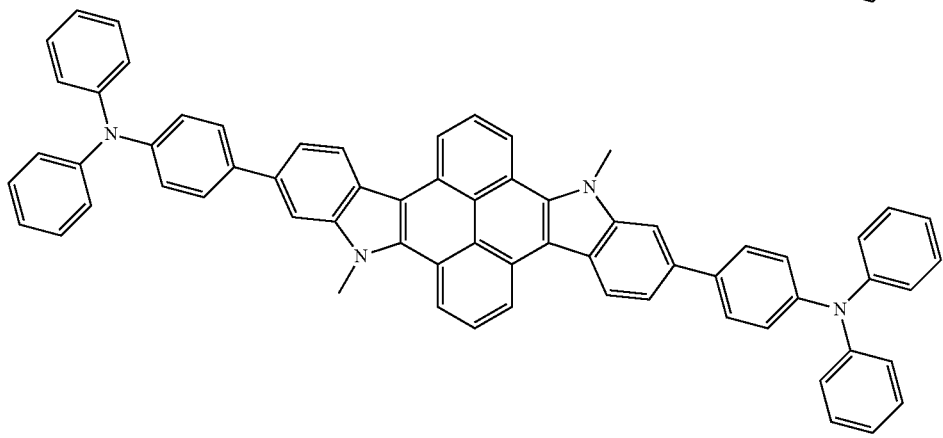

compound 72
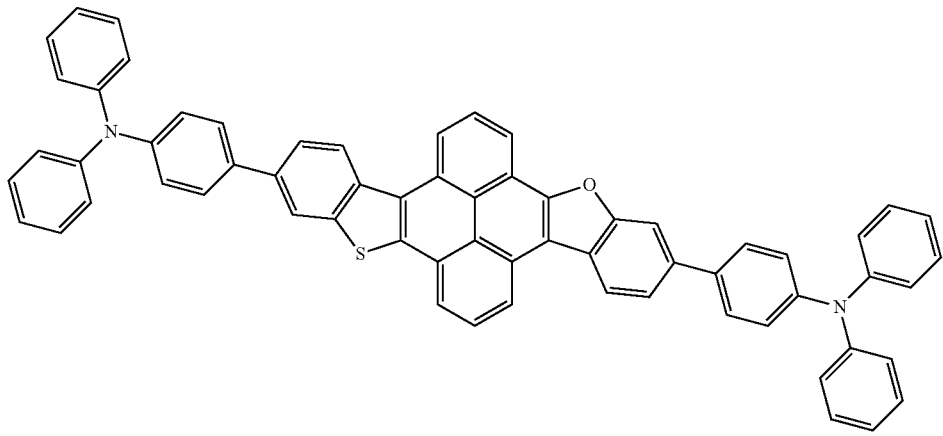
compound 73
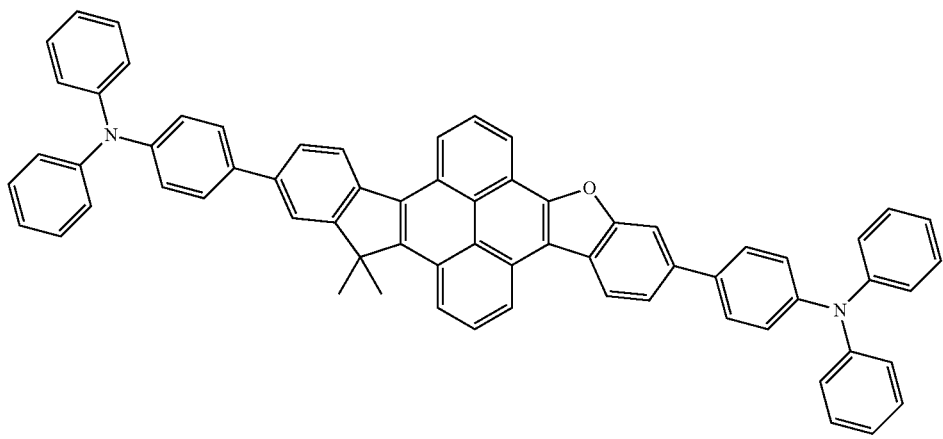
[Twenty-Ninth Chemical Formula]
compound 74
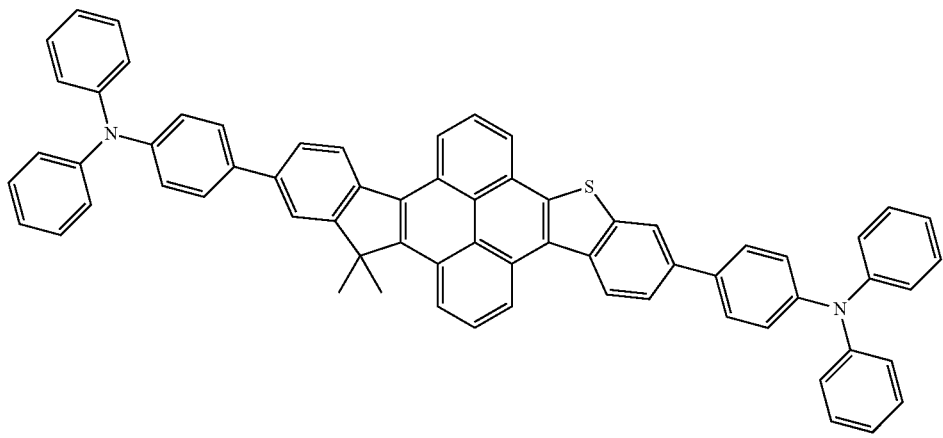

compound 75
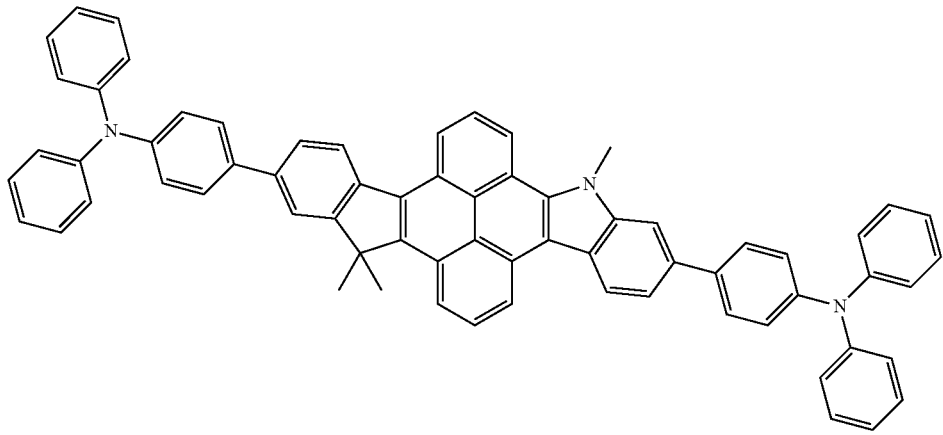
compound 76
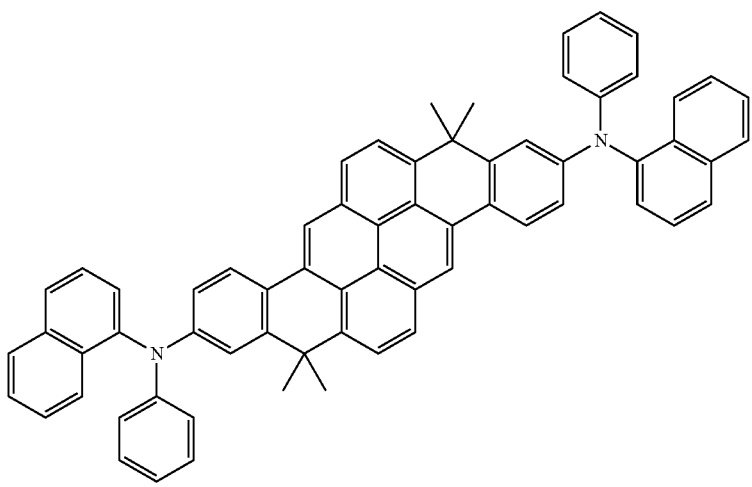
compound 77
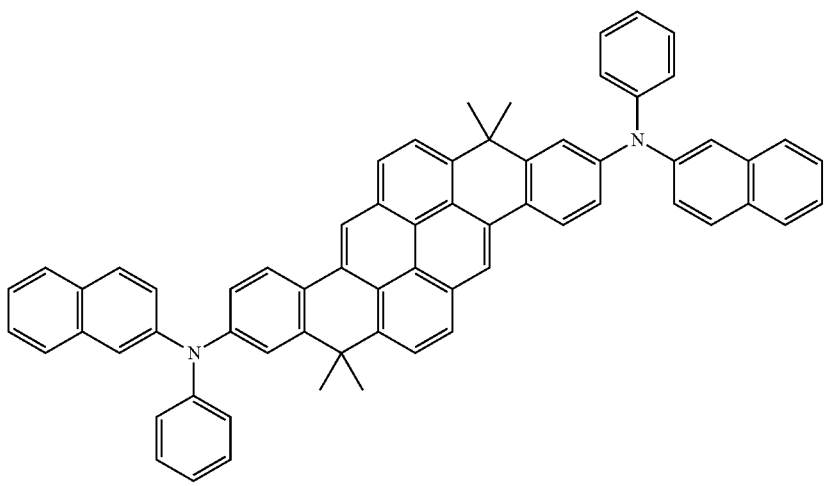

compound 78
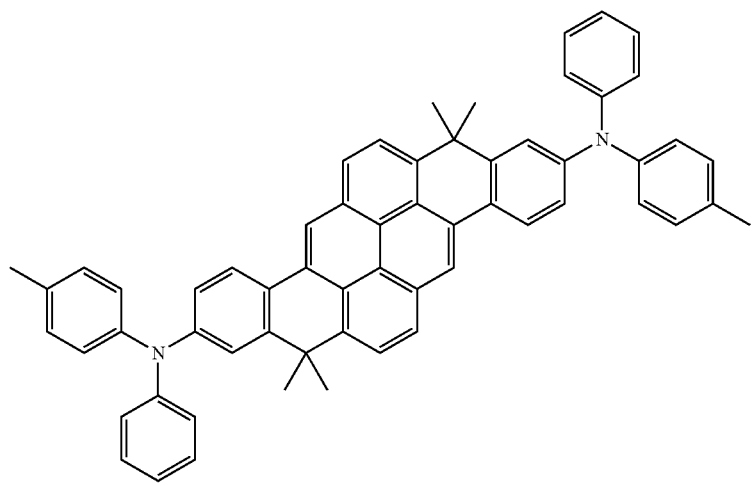
compound 79
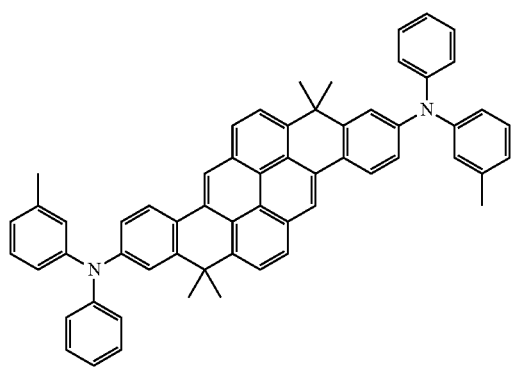
compound 80
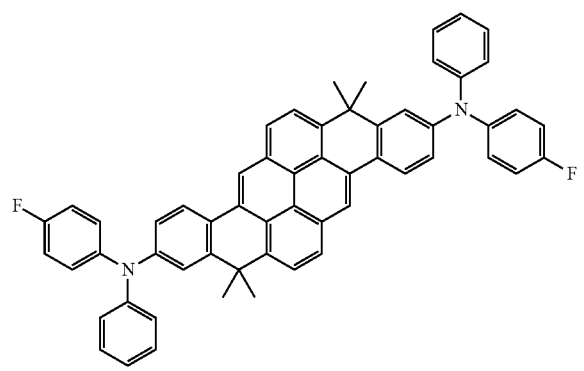
compound 81
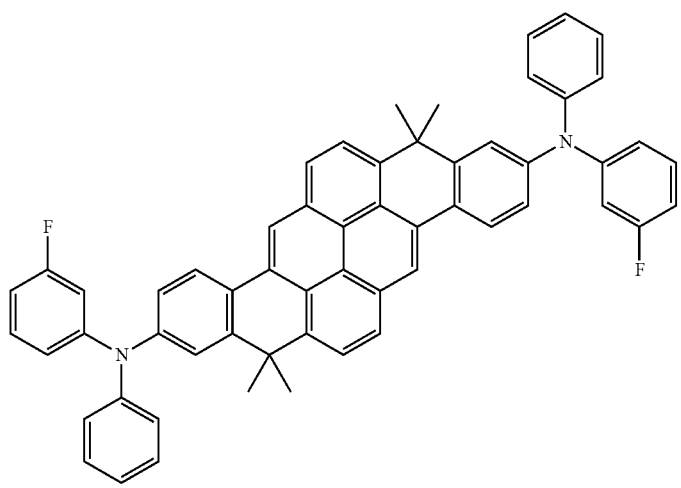

-continued
compound 82
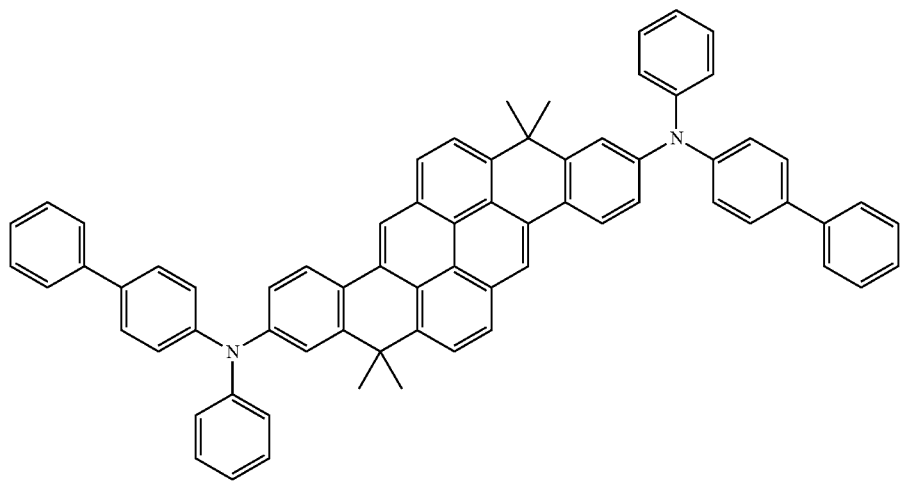
compound 83
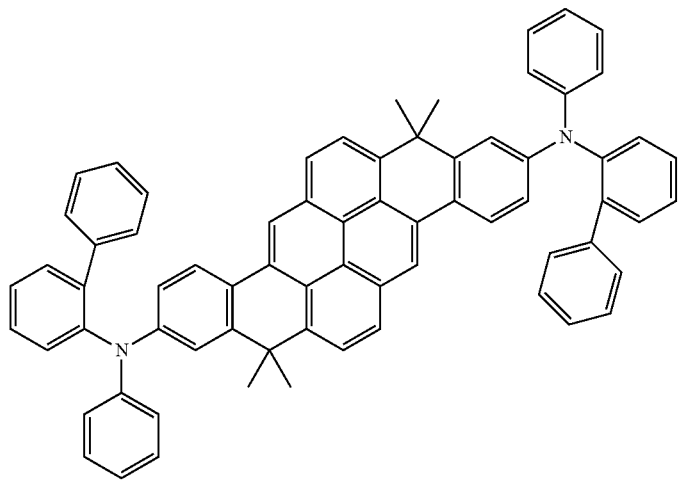
[Thirtieth Chemical Formula]
compound 84
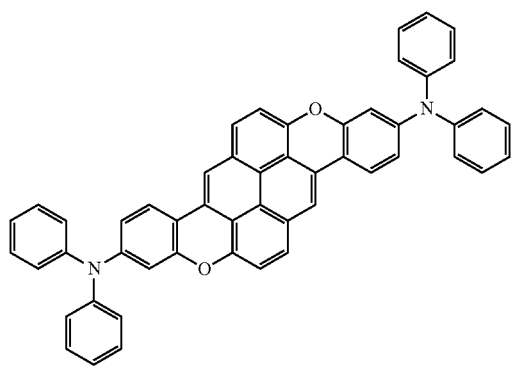
compound 85
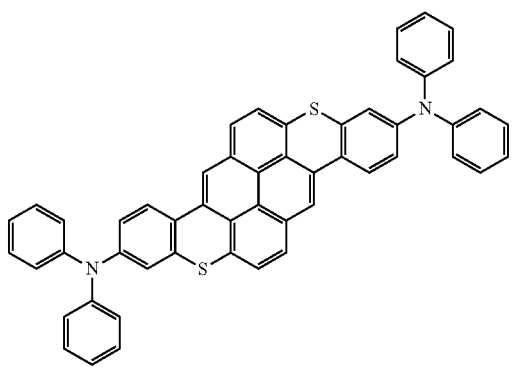

-continued
compound 86
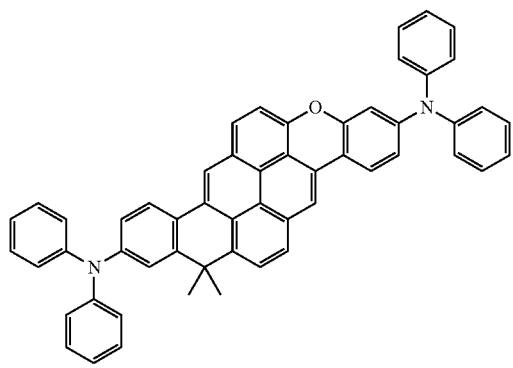
compound 87
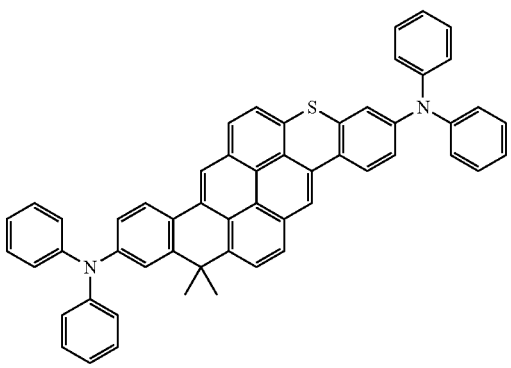
compound 88
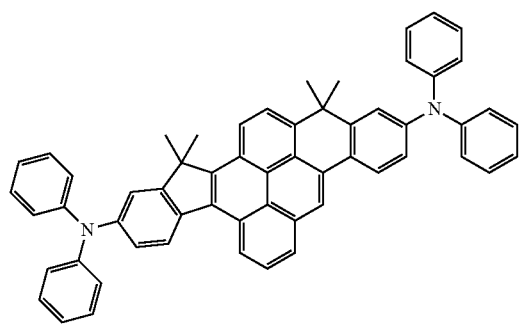
compound 89
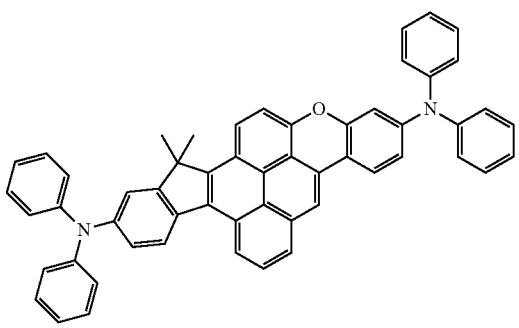
compound 90
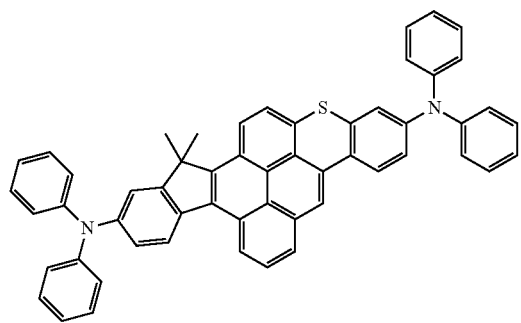
compound 91
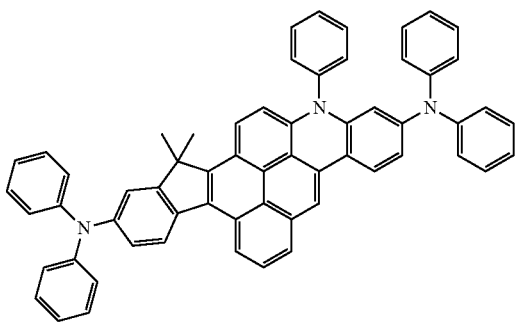
compound 92
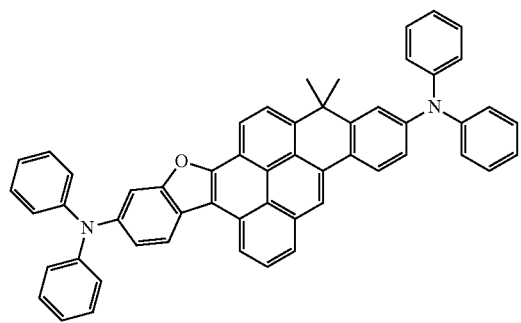
compound 93
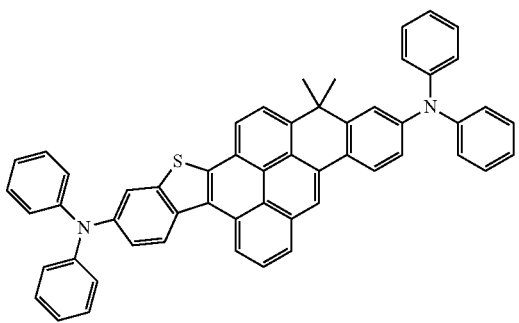

-continued
[Thirty-First Chemical Formula]
compound 94
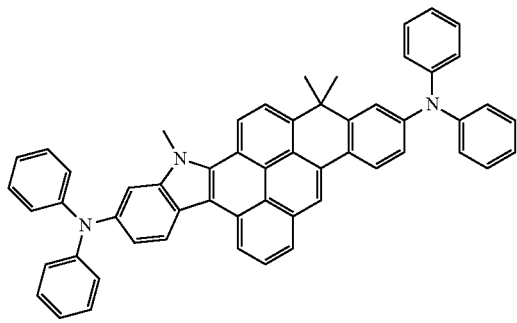
compound 95
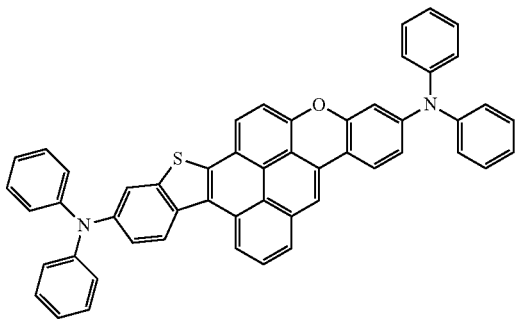
compound 96
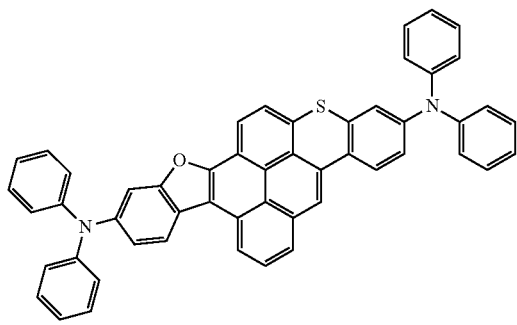
compound 97
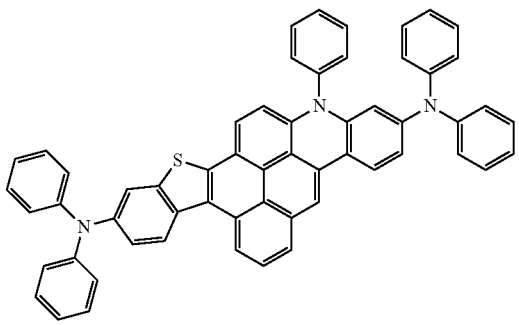
compound 98
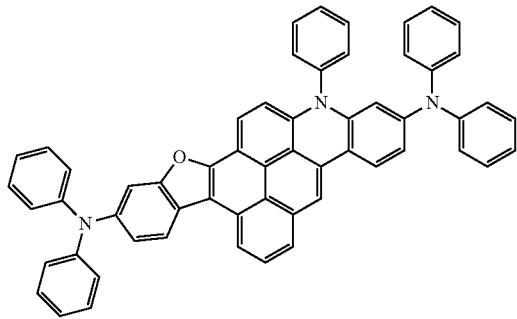
compound 99
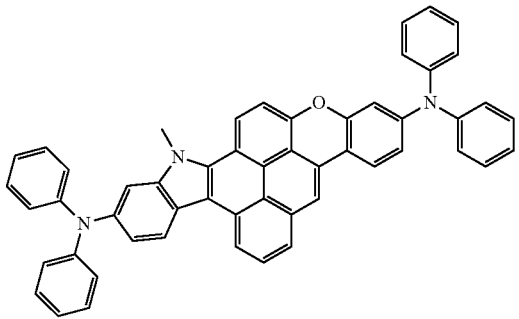
compound 100
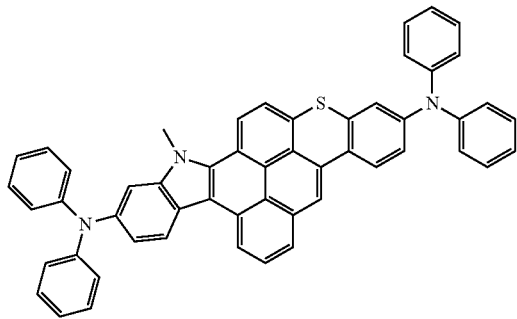
compound 101
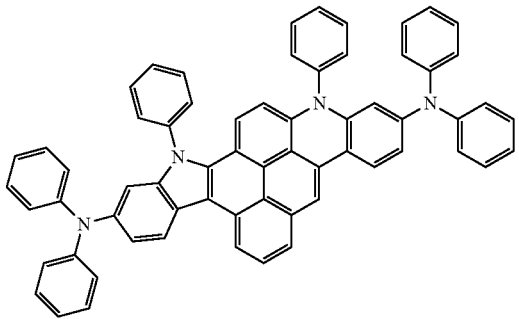

compound 102
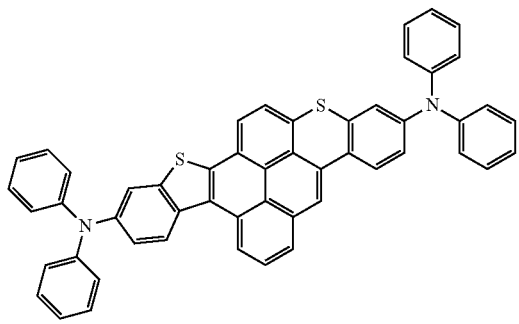
compound 103
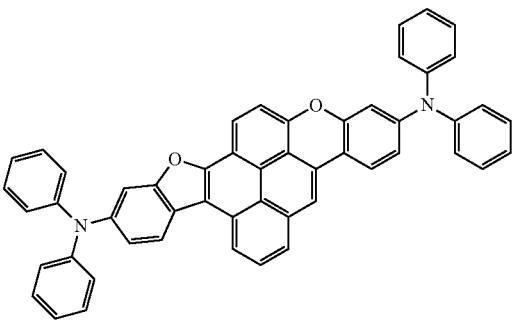
[Thirty-Second Chemical Formula]
compound 104
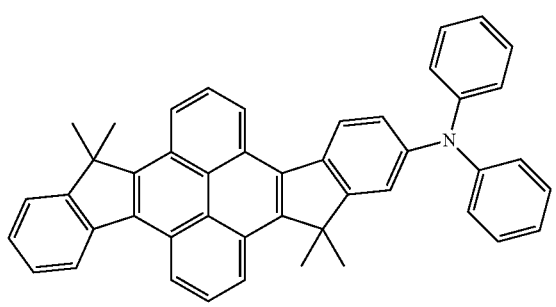
compound 105
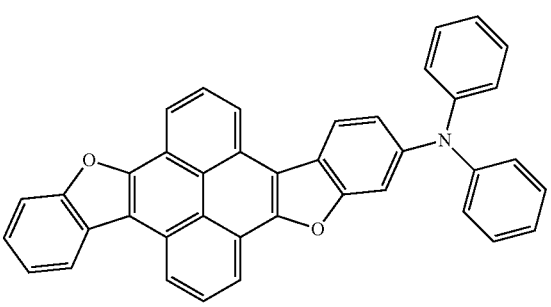
compound 106
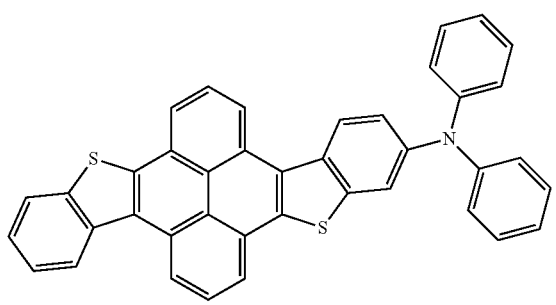
compound 107
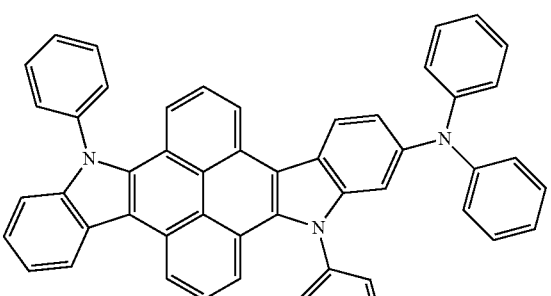
compound 108
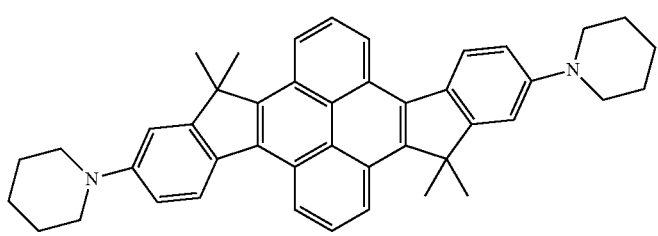
compound 109
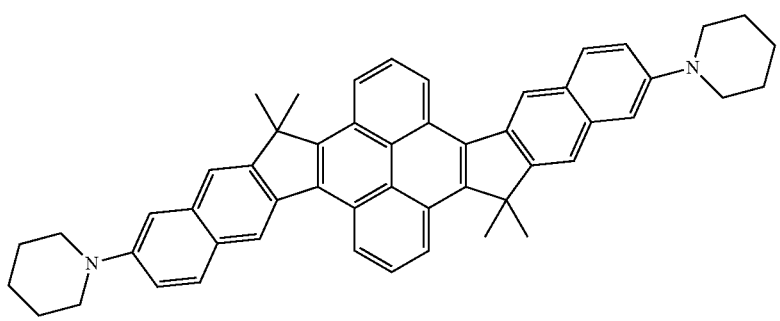

-continued
compound 110
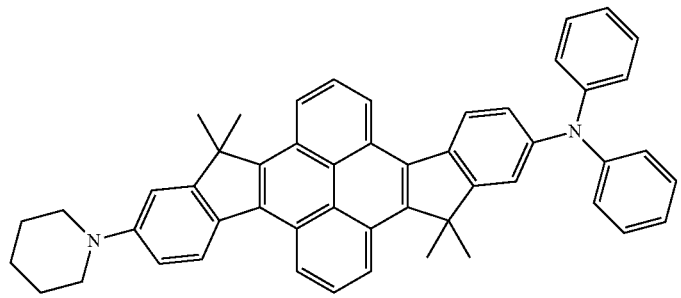
compound 111
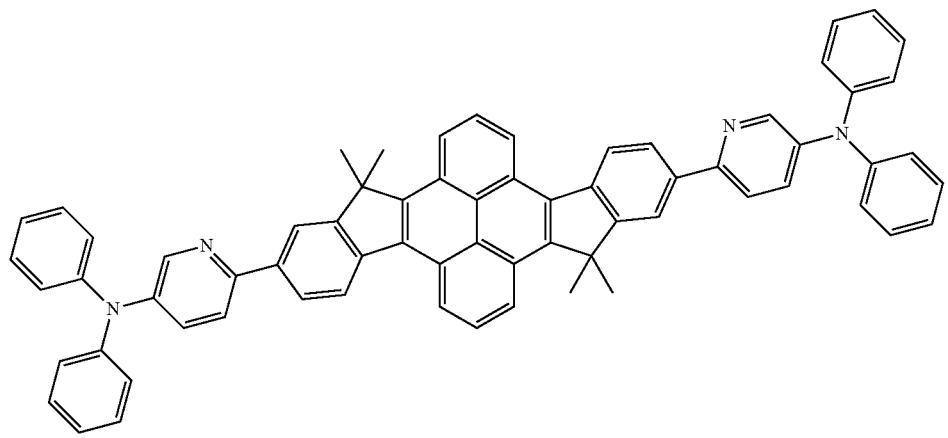
compound 112
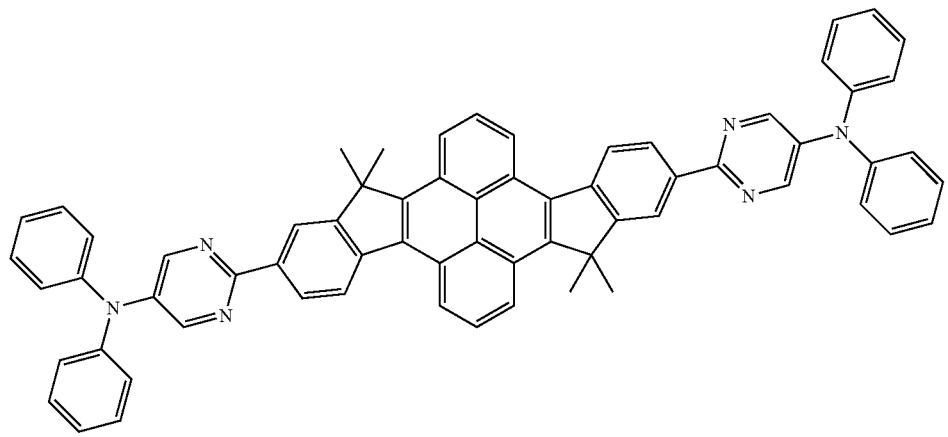
compound 113
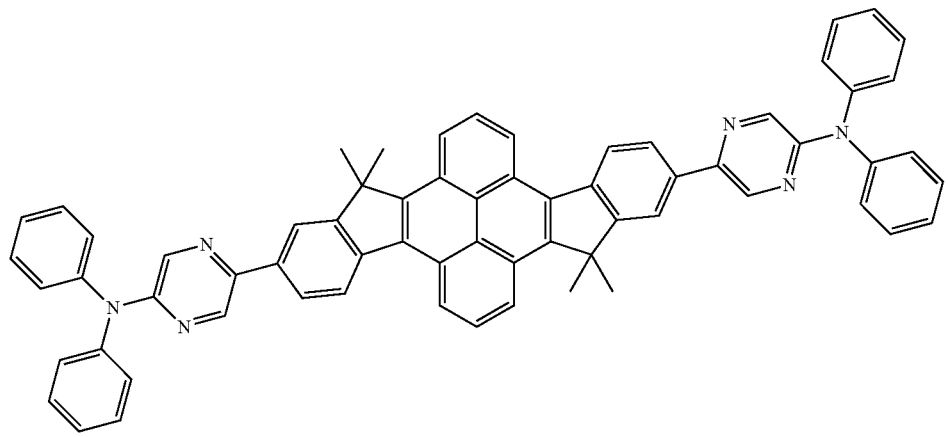

[Thirty-Third Chemical Formula]
compound 114
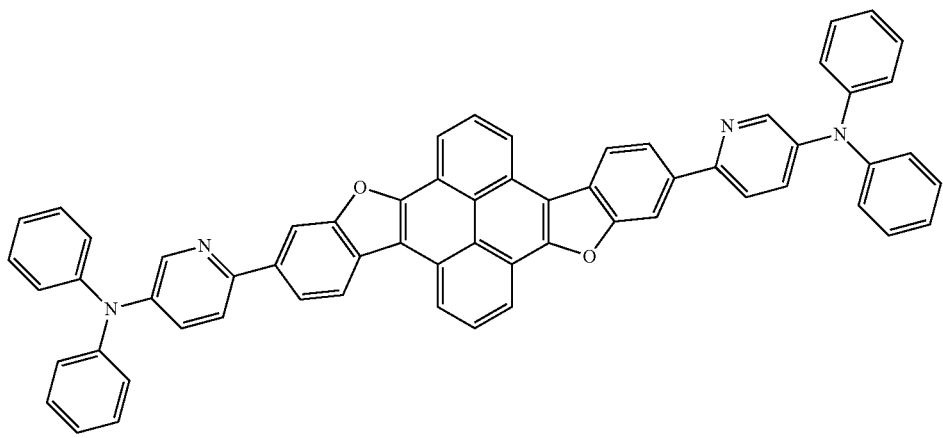
compound 115
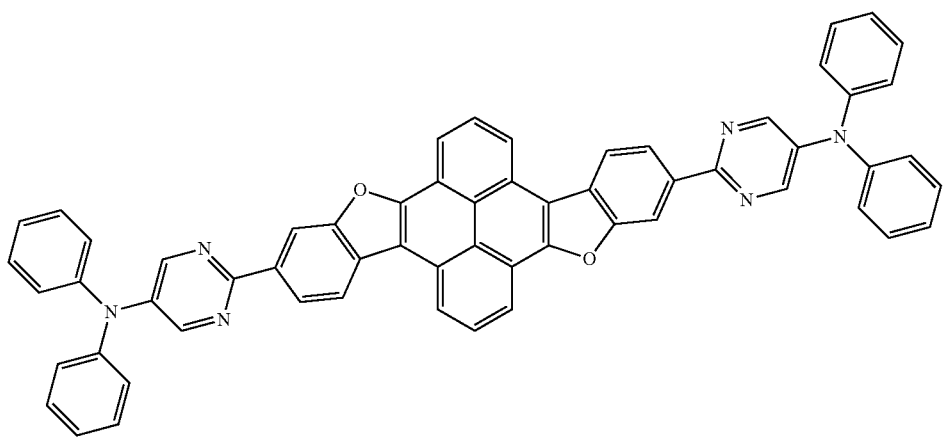
compound 116
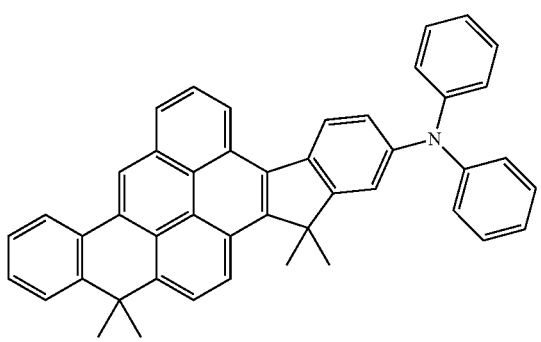
compound 117
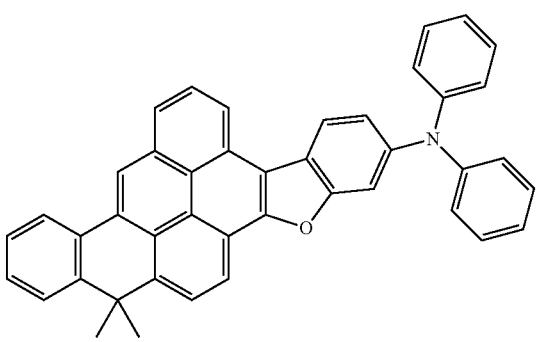
compound 118
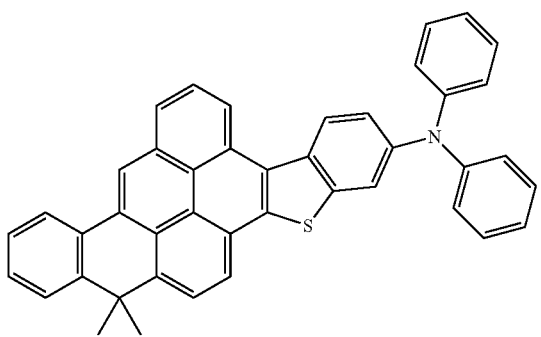
compound 119
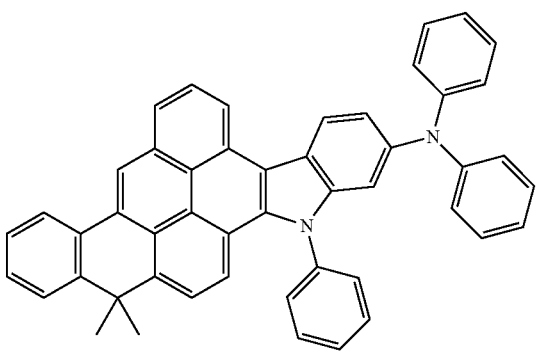

-continued
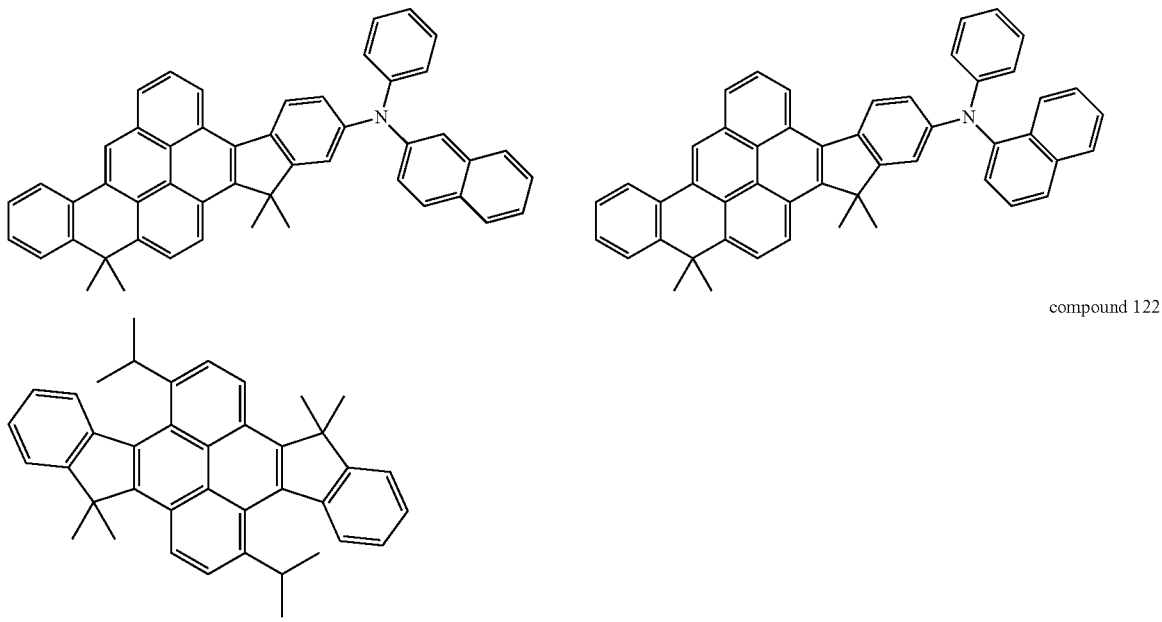
compound 120
compound 121
compound 122
The compounds expressed by General Formula 1 above can be synthesized by the methods described in Japanese Laid-Open Patent Application 2010-111620 or the like, or by combining other publicly known reactions. Moreover, they can be synthesized by the following scheme, for example:
[Thirty-Fourth Chemical Formula]
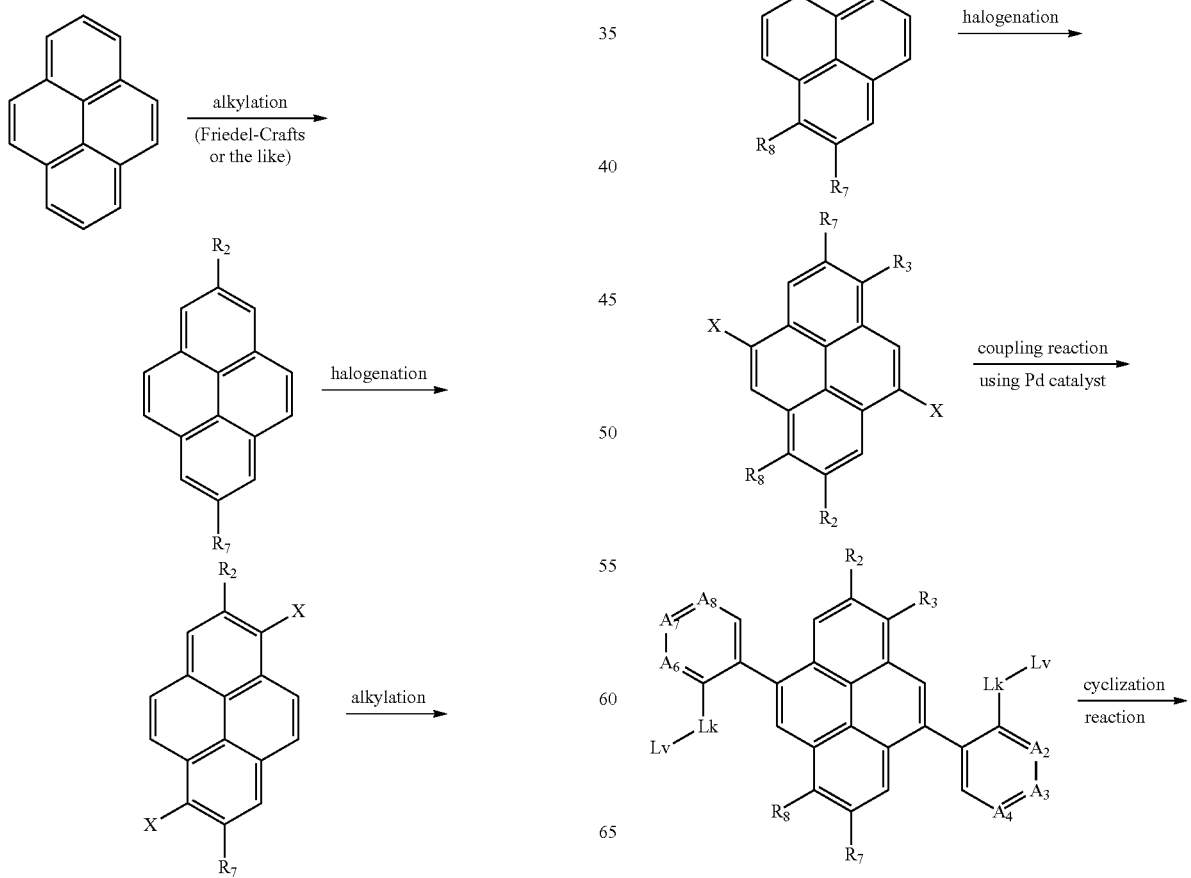
-continued -continued

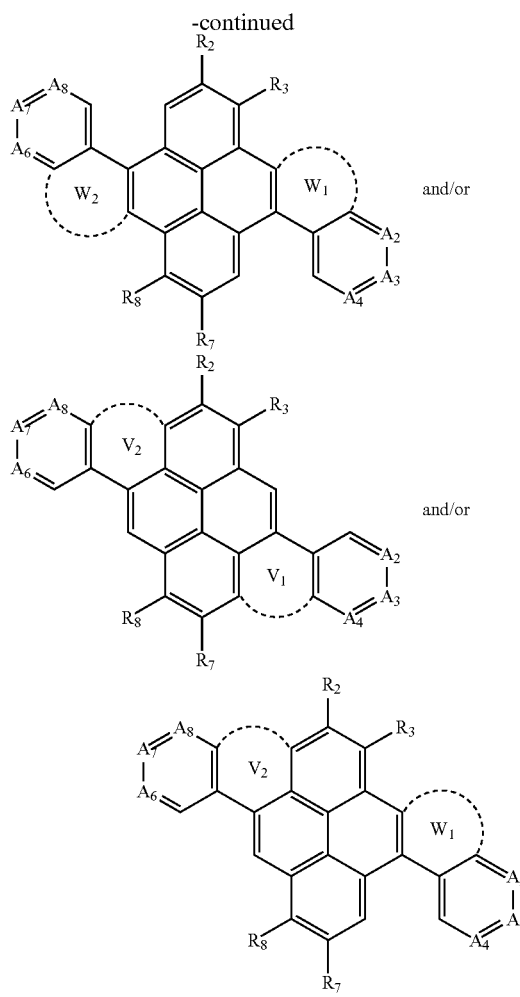

and/or and/or

After synthesis, it is preferable for purification by column chromatography, recrystallization, or the like to be performed, followed by sublimation purification. Sublimation purification not only allows organic impurities to be separated, but also allows inorganic salts, residual solvents, and the like to be effectively removed.

Organic Electroluminescence Element

The organic electroluminescence element of the present invention has a substrate, a pair of electrodes that are disposed on this substrate and that include an anode and a cathode, and an organic layer disposed between these electrodes, and is characterized in that the aforementioned organic layer includes a compound expressed by General Formula 1.

There are no particular restrictions on the configuration of the organic electroluminescence element of the present invention. FIG. 1 shows one example of the configuration of the organic electroluminescence element of the present invention. The organic electroluminescence element 10 of FIG. 1 has, on a substrate 2, organic layers between a pair of electrodes (an anode 3 and a cathode 9).

The element configuration, substrate, cathode, and anode of the organic electroluminescence element are discussed in detail in Japanese Laid-Open Patent Application 2008-270736, for example, and what is discussed in this publication can be applied to the present invention.

Preferred modes of the organic electroluminescence element of the present invention will be described in detail below in the order of the substrate, electrodes, organic layers, protective layer, sealing container, drive method, emission wavelength, and applications.

<Substrate>

The organic electroluminescence element of the present invention has a substrate.

The substrate used in the present invention is preferably a substrate that will not scatter or attenuate light emitted from the organic layers. In the case of an organic material, one with excellent heat resistance, dimensional stability, solvent resistance, electrical insulation properties, and workability is preferable.

<Electrodes>

The organic electroluminescence element of the present invention has a pair of electrodes that are disposed on the aforementioned substrate and that include an anode and a cathode.

For the quality of the light-emitting element, it is preferable for at least one of the electrodes constituting the pair of electrodes (the anode and/or cathode) to be transparent or semitransparent.

(Anode)

In general, there are no particular restrictions on the shape, structure, size, and so forth of the anode as long as it functions as an electrode that supplies holes to the organic layers, and one can be suitably selected from publicly known electrode materials depending on the purpose and application of the light-emitting element. As was described above, the anode is usually provided as a transparent anode.

(Cathode)

In general, there are no particular restrictions on the shape, structure, size, and so forth of the cathode as long as it functions as an electrode that injects electrons into the organic layers, and one can be suitably selected from publicly known electrode materials depending on the purpose and application of the light-emitting element.

<Organic Layers>

The organic electroluminescence element of the present invention has organic layers disposed between the aforementioned electrodes and is characterized in that the aforementioned organic layers include a compound expressed by General Formula 1.

There are no particular restrictions on the aforementioned organic layers, which can be suitably selected according to the purpose and application of the organic electroluminescence element, but [the organic layers] are preferably formed over the aforementioned transparent electrode(s) or the aforementioned semi-transparent electrode(s). In this case, the organic layers are formed on the entire surface or one face of the aforementioned transparent electrode(s) or the aforementioned semi-transparent electrode(s).

There are no particular restrictions on the shape, size, thickness, and so forth of the organic layers, which can be suitably selected according to the purpose.

The configuration of the organic layers, a method for forming the organic layers, preferred modes of various layers configuring the organic layers, and the materials used in the various layers in the organic electroluminescence element of the present invention will be described in order below.

(Configuration of Organic Layers)

In the organic electroluminescence element of the present invention, the aforementioned organic layers preferably include a charge transport layer. The aforementioned term "charge transport layer" refers to a layer in which charge movement occurs when voltage is applied to the organic electroluminescence element. Concrete examples include a hole injection layer, a hole transport layer, an electron blocking layer, a light-emitting layer, a hole blocking layer, an electron transport layer, or an electron injection layer. If the aforementioned charge transport layer is a hole injection layer, a hole transport layer, an electron blocking layer, or a light-emitting layer, it is possible to manufacture a low-cost and high-efficiency organic electroluminescence element.

The compound expressed by General Formula 1 above may be contained in any of the organic layers between the cathode and the anode of the organic electroluminescence element.

Examples of organic layers that may contain the compound expressed by General Formula 1 above include the light-emitting layer, a hole injection layer, a hole transport layer, an electron transport layer, an electron injection layer, an exciton blocking layer, and a charge blocking layer (a hole blocking layer, an electron blocking layer, etc.), with the light-emitting layer, an exciton blocking layer, a charge blocking layer, an electron transport layer, or an electron injection layer being preferable, and the light-emitting layer, an exciton blocking layer, a charge blocking layer, or an electron transport layer being more preferable, and the light-emitting layer being even more preferable.

When the compound expressed by General Formula 1 above is contained in the light-emitting layer, the compound expressed by General Formula 1 is preferably contained in an amount of 0.1 to 100 wt %, more preferably 1 to 95 wt %, and even more preferably 2 to 95 wt %, with respect to the total weight of the light-emitting layer.

When the compound expressed by General Formula 1 above is contained in an organic layer other than the light-emitting layer, the compound expressed by General Formula 1 is preferably contained in an amount of 70 to 100 wt % and more preferably 85 to 100 wt % with respect to the total weight of the organic layer.

(Organic Layer Formation Method)

Each of the organic layers of the organic electroluminescence element of the present invention can be favorably formed by vapor deposition, sputtering, or another such dry film formation method, or by transfer, printing, spin coating, bar coating, or another such wet film formation method (solution coating method) as well.

In the organic electroluminescence element of the present invention, the organic layers disposed between the aforementioned pair of electrodes preferably [include] at least one layer that is formed by vapor deposition of a composition containing the compound expressed by General Formula 1 above.

(Light-Emitting Layer)

When an electric field is applied, the light-emitting layer accepts holes from the anode, the hole injection layer, or the hole transport layer, accepts electrons from the cathode, the electron injection layer, or the electron transport layer, and has the function of emitting light by providing a site for the rebinding of holes and electrons. However, the aforementioned light-emitting layer in the present invention is not necessarily limited to emission of light by such a mechanism.

The aforementioned light-emitting layer in the organic electroluminescence element of the present invention may be constituted solely from the aforementioned light-emitting material or may also be made up of a mixed layer of a host material and the aforementioned light-emitting material. With regard to the types of the aforementioned light-emitting material, there may be just one type or two or more types. The aforementioned host material is preferably a charge transport material. With regard to [the types of] the aforementioned host material, there may be just one type or two or more types. Examples include a mixed configuration of an electron transporting host material and a hole transporting host material. Furthermore, a material which does not have a charge transporting property and does not emit light may also be included in the aforementioned light-emitting layer.

Moreover, the light-emitting layer may be a single layer or a multilayer of two or more layers, and the same light-emitting material or host material may be included in each layer, or different materials may be included in each layer. When there are a plurality of light-emitting layers, each light-emitting layer may also emit light of a different color.

There are no particular restrictions on the thickness of the light-emitting layer, but in general, it is preferably from 2 to 500 nm, and from the standpoint of external quantum efficiency, it is more preferably from 3 to 200 nm and even more preferably from 5 to 100 nm.

A preferred mode of the organic electroluminescence element of the present invention is that the aforementioned light-emitting layer contains the compound expressed by General Formula 1 above, and a more preferred mode is that the compound expressed by General Formula 1 above is used as the light-emitting material of the aforementioned light-emitting layer. Here, in this Specification, the host material refers to a compound that mainly handles the injection and transport of charges in the light-emitting layer, and also a compound that substantially does not emit light itself [The phrase] "substantially does not emit light" here means that the amount of light emitted from this compound that substantially does not emit light is preferably no more than 5% of the total amount of light emitted by the entire element, more preferably no more than 3%, and even more preferably no more than 1%. The compound expressed by General Formula 1 above may also be used as the host material of the light-emitting layer.

(Light-Emitting Material)

With the organic electroluminescence element of the present invention, a compound expressed by General Formula 1 above is preferably used as the light-emitting material, but even in this case as well, a light-emitting material other than the compound expressed by General Formula 1 above can be used in combination. In the organic electroluminescence element of the present invention, furthermore, another light-emitting material different from the compound expressed by General Formula 1 above is used in the light-emitting layer even when the compound expressed by General Formula 1 above is used as the host material of the light-emitting layer or when it is used for an organic layer other than the light-emitting layer.

The light-emitting material that can be used in the present invention may be a phosphorescent material, a fluorescent material, or the like. Moreover, the light-emitting layer in the present invention can contain two or more types of light-emitting material in order to improve color purity or expand the emission wavelength band.

The fluorescent materials and phosphorescent materials that can be used in the organic electroluminescence element of the present invention are discussed at length, for example, in paragraph numbers [0100] to [0164] of Japanese Laid-Open Patent Application 2008-270736 and paragraph numbers [0088] to [0090] of Japanese Laid-Open Patent Application 2007-266458, and what is discussed in these publications can be applied to the present invention.

Examples of phosphorescent materials that can be used in the present invention include the phosphorescent compounds or the like described in patent documents such as the Specification of U.S. Pat. No. 6,303,238, the Specification of U.S. Pat. No. 6,097,147, WO 00/57676, WO 00/70655, WO 01/08230, WO 01/39234, WO 01/41512, WO 02/02714, WO 02/15645, WO 02/44189, WO 05/19373, Japanese Laid-Open Patent Applications 2001-247859, 2002-302671, 2002-117978, 2003-133074, 2002-235076, 2003-123982, and 2002-170684, European Laid-Open Patent Application 1211257, and Japanese Laid-Open Patent Applications 2002-226495, 2002-234894, 2001-247859, 2001-298470, 2002-173674, 2002-203678, 2002-203679, 2004-357791, 2006-256999, 2007-19462, 2007-84635, and 2007-96259. Of these, examples of more preferable light-emitting materials include iridium complexes, platinum complexes, copper complexes, rhenium complexes, tungsten complexes, rhodium complexes, ruthenium complexes, palladium complexes, osmium complexes, europium complexes, terbium complexes, gadolinium complexes, dysprosium complexes, cerium complexes, and other such phosphorescent metal complex compounds. Especially preferable are iridium complexes, platinum complexes, and rhenium complexes, and of these, iridium complexes, platinum complexes, and rhenium complexes that include at least one coordination from among a metal-carbon bond, a metal-nitrogen bond, a metal-oxygen bond, and a metal-sulfur bond are preferred. In addition, from the standpoints of luminous efficiency, drive durability, chromaticity, and so forth, iridium complexes and platinum complexes are especially favorable, with iridium complexes being most favorable.

There are no particular restrictions on the type of fluorescent material that can be used in the present invention, but examples include benzoxazole, benzimidazole, benzothiazole, styryl benzene, polyphenyl, diphenyl butadiene, tetraphenyl butadiene, naphthalimide, coumarin, pyran, perinone, oxadiazole, aldazine, pyralizine, cyclopentadiene, bisstyryl anthracene, quinacridone, pyrrolopyridine, thiadiazolopyridine, cyclopentadiene, styrylamine, condensed polycyclic aromatic compounds (such as anthracene, phenanthroline, pyrene, perylene, rubrene, and pentacene), a variety of metal complexes typified by metal complexes of 8-quinolinol, pyrromethene complexes, and rare earth complexes, polymer compounds such as polythiophene, polyphenylene, and polyphenylene vinylene, organosilanes, and derivatives of these.

Besides these, it is also possible to use the compounds described in [0082] of Japanese Laid-Open Patent Application 2010-111620 as the light-emitting material.

The light-emitting layer in the organic electroluminescence element of the present invention may be configured from only a light-emitting material or may be made up of a mixed layer of a host material and a light-emitting material. The type of the light-emitting material may be just one type or two or more types. The host material is preferably a charge transport material. There may be just one kind of host material, or two or more kinds may be used, and examples include a mixture of an electron transporting host material and a hole transporting host material. Furthermore, a material which does not have a charge transporting property and does not emit light may be included in the light-emitting layer.

Moreover, the light-emitting layer may be a single layer or a multilayer of two or more layers, and the same light-emitting material or host material may be contained in each layer, or a different material may be contained in each layer. When there are a plurality of light-emitting layers, each of the light-emitting layers may also emit light of a different color.

(Host Material)

The host material is a compound that mainly handles the injection and transport of charges in the light-emitting layer, and is also a compound that substantially does not emit light itself [The phrase] "substantially does not emit light" here means that the amount of light emitted from this compound that substantially does not emit light is preferably no more than 5% of the total amount of light emitted by the entire element, more preferably no more than 3%, and even more preferably no more than 1%.

The following compounds are examples of host materials that can be used in the organic electroluminescence element of the present invention:

These examples include pyrrole, indole, carbazole, azaindole, azacarbazole, triazole, oxazole, oxadiazole, pyrazole, imidazole, thiophene, benzothiophene, dibenzothiophene, furan, benzofuran, dibenzofuran, polyarylalkane, pyrazoline, pyrazolone, phenylenediamine, arylamine, amino-substituted chalcone, styrylanthracene, fluorenone, hydrazone, stilbene, silazane, aromatic tertiary amine compounds, styrylamine compounds, porphyrin-based compounds, condensed ring aromatic hydrocarbon compounds (such as fluorene, naphthalene, phenanthrene, and triphenylene), polysilane-based compounds, poly(N-vinylcarbazole), aniline copolymers, conductive macromolecular oligomers such as thiophene oligomers and polythiophene, organosilanes, carbon films, pyridine, pyrimidine, triazine, imidazole, pyrazole, triazole, oxazole, oxadiazole [sic]$^4$, fluorenone, anthraquinodimethane, anthrone, diphenylquinone, thiopyran dioxide, carbodiimide, fluorenylidenemethane, distyrylpyrazine, fluorine-substituted aromatic compounds, heterocyclic tetracarboxylic acid anhydrides such as naphthalene [and] perylene, phthalocyanine, and a variety of metal complexes typified by metal complexes of an 8-quinolinol derivative, metal phthalocyanine, and metal complexes having benzoxazole or benzothiazole as a ligand, and derivatives of these (which may have a substituent or a condensed ring). Besides these, the compounds described in [0081] and [0083] of Japanese Laid-Open Patent Application 2010-111620 can also be used.

$^4$Translator's note: "imidazole," "pyrazole," "triazole," "oxazole," and "oxadiazole" repeatedly appear in this list in the original.

Of these, carbazole, dibenzothiophene, dibenzofuran, arylamine, condensed ring aromatic hydrocarbon compounds, and metal complexes are preferable, and anthracene-based compounds are stable and are therefore especially preferable. The compounds described in WO 2010/134350 can be suitably used as the anthracene-based compounds, and examples include compounds H-1 and H-2 (mentioned later).

The organic electroluminescence element of the present invention preferably contains a compound expressed by General Formula An-1 below as the host material:

[Thirty-Fifth Chemical Formula]

General Formula An-1

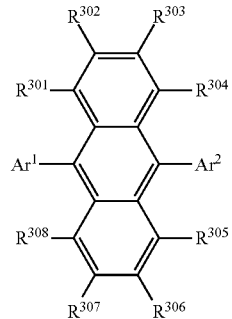

In General Formula An-1 above, Ar$^1$ and Ar$^2$ represent each independently an aryl group or a heteroaryl group, and $R^{301}$ to $R^{308}$ represent each independently a hydrogen atom or a substituent. [Each pair of] $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may bond to each other to form a ring.

In General Formula An-1, the aryl groups represented by $Ar^1$ and $Ar^2$ are [each] preferably a $C_6$ to $C_{36}$ aryl group, more preferably a $C_6$ to $C_{18}$ aryl group, and especially preferably a $C_6$ to $C_{14}$ aryl group, with a phenyl group or a naphthyl group being even more especially favorable.

The heteroaryl groups represented by $Ar^1$ and $Ar^2$ are [each] preferably a heteroaryl group with 5 to 20 ring members and more preferably a heteroaryl group with 5 to 13 ring members. The hetero atoms included in the heteroaryl groups represented by $Ar^1$ and $Ar^2$ are preferably nitrogen atoms, oxygen atoms, and sulfur atoms and more preferably nitrogen atoms. The number of hetero atoms included in the heteroaryl groups represented by $Ar^1$ and $Ar^2$ is preferably from one to three, more preferably one or two, and especially preferably one. It is especially favorable for the heteroaryl groups represented by $Ar^1$ and $Ar^2$ to be pyridyl groups, carbazolyl groups, dibenzofuryl groups, or dibenzothiophenyl groups.

$Ar^1$ and $Ar^2$ are [each] preferably a phenyl group, a naphthyl group, a pyridyl group, a carbazolyl group, a dibenzofuryl group, a dibenzothiophenyl group, or a group that is a combination of these. Of these, it is more preferable for $Ar^1$ and $Ar^2$ [each] to be a phenyl group or a naphthyl group, and it is especially preferable for $Ar^1$ and/or $Ar^2$ to be a substituted or unsubstituted phenyl group.

$Ar^1$ and $Ar^2$ may have a further substituent, and examples of this substituent include an aryl group, a heteroaryl group, a fluorine atom, an alkyl group (preferably $C_1$ to $C_4$), an alkenyl group, a silyl group, and a cyano group.

In General Formula An-1, examples of substituents represented by $R^{301}$ to $R^{308}$ include an aryl group, a heteroaryl group, a fluorine atom, an alkyl group, a silyl group, a cyano group, and a group that is a combination of these, and preferable [examples] include a phenyl group, a naphthyl group, a pyridyl group, a carbazolyl group, a dibenzofuryl group, a dibenzothiophenyl group, a fluorine atom, an alkyl group, a silyl group, a cyano group, and a group that is a combination of these, with a phenyl group, a naphthyl group, or a $C_1$ to $C_5$ alkyl group (especially preferably tert-butyl group) being more favorable.

In General Formula An-1, $R^{301}$ to $R^{308}$ may further have a substituent, and examples of this substituent include an aryl group, a heteroaryl group, and an alkyl group, with an aryl group and a heteroaryl group being preferable and a $C_6$ to $C_{18}$ aryl group being more preferable.

In General Formula An-1, the number of substituents included in $R^{301}$ to $R^{308}$ is preferably from zero to four, more preferably zero or two, and especially preferably zero or one, with zero being even more especially preferable.

In General Formula An-1, the position of the substituents included in $R^{301}$ to $R^{308}$ is preferably on $R^{302}$, $R^{303}$, $R^{306}$, or $R^{307}$ and more preferably on either $R^{302}$ or $R^{303}$, or on either $R^{306}$ or $R^{307}$.

In General Formula An-1, [each pair of] $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may bond to each other to form a ring, but it is preferable if these do not bond to each other to form a ring.

The compound expressed by General Formula An-1 above is preferably a compound expressed by General Formula An-2 below:

[Thirty-Sixth Chemical Formula]

General Formula An-2

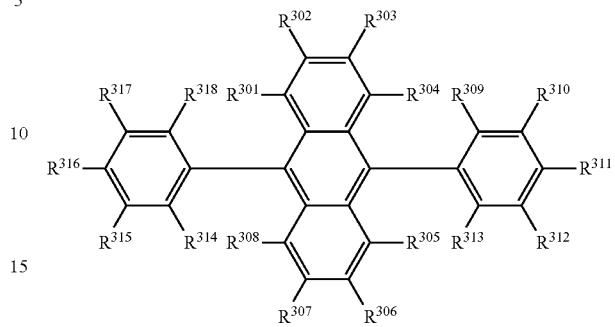

In General Formula An-2 above, $R^{301}$ to $R^{318}$ represent each independently a hydrogen atom or a substituent. [Each pair of] $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ may bond to each other to form a ring.

The preferred ranges of $R^{301}$ to $R^{308}$ in General Formula An-2 are the same as the preferred ranges of $R^{301}$ to $R^{308}$ in General Formula An-1 above.

Examples of the substituents represented by $R^{309}$ to $R^{318}$ in General Formula An-2 include an aryl group, a heteroaryl group, a fluorine atom, an alkyl group, a silyl group, a cyano group, and a group that is a combination of these, preferably a $C_6$ to $C_{18}$ aryl group, a heteroaryl group with 5 to 20 ring members, a fluorine atom, an alkyl group, an alkenyl group, a silyl group, a cyano group, and a group that is a combination of these, and more preferably a phenyl group, a naphthyl group, a pyridyl group, a carbazolyl group, a dibenzofuryl group, a dibenzothiophenyl group, a fluorine atom, an alkyl group, an alkenyl group, a silyl group, a cyano group, and a group that is a combination of these, with a phenyl group, a naphthyl group, or a carbazolyl group being especially preferable.

In General Formula An-1 [sic][5], $R^{309}$ to $R^{318}$ may further have a substituent, and examples of this substituent include an aryl group, an alkyl group, and a fluorine atom. These substituents may bond to each other to form a ring.

[5] Translator's note: apparent error in the original; "General Formula An-1" should be "General Formula An-2," and the same error appears several times below.

In General Formula An-1 [sic], the number of substituents included in $R^{309}$ to $R^{318}$ is preferably from zero to four, more preferably zero or two, and especially preferably zero or one, with zero being even more especially preferable.

In General Formula An-1 [sic], there are no particular restrictions on the position of the substituents included in $R^{309}$ to $R^{318}$, but if there is a substituent, it is preferably on $R^{311}$ and/or $R^{316}$.

In General Formula An-1 [sic], [each pair of] $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$ and $R^{318}$ may bond to each other to form a ring. The ring thus formed is preferably a five- or six-membered ring, with a five-membered ring being more preferable.

With the organic electroluminescence element of the present invention, it is preferable to use a compound expressed by any of General Formulas 1 to 7 above and a compound expressed by either of General Formulas An-1 and An-2 above in combination in the aforementioned light-emitting layer.

Concrete examples of the compound expressed by General Formula An-1 above will be given below, but it should not be construed that the compounds expressed by General Formula An-1 that can be used in the present invention are limited to or by these concrete examples:

[Thirty-Seventh Chemical Formula]

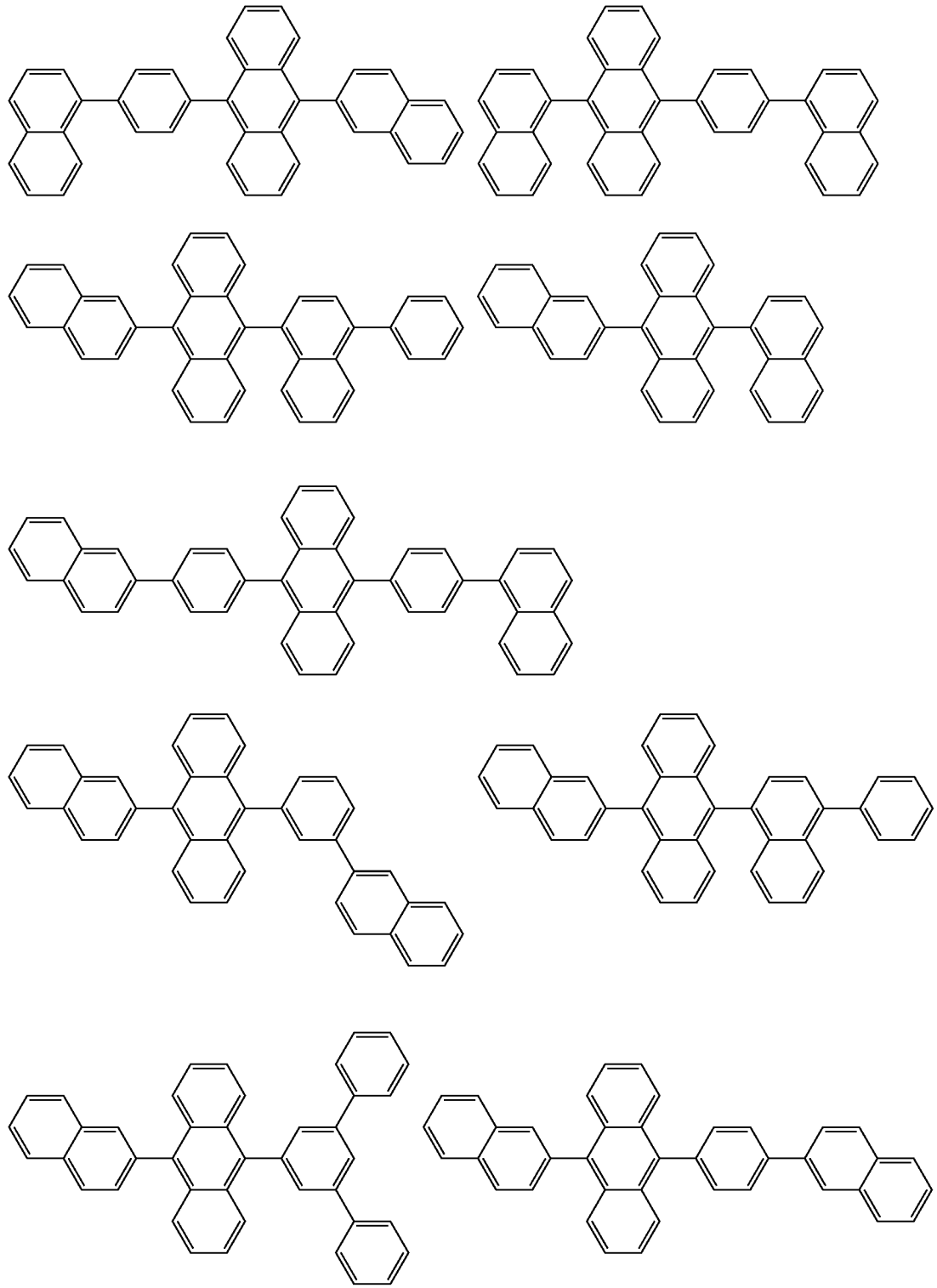

-continued
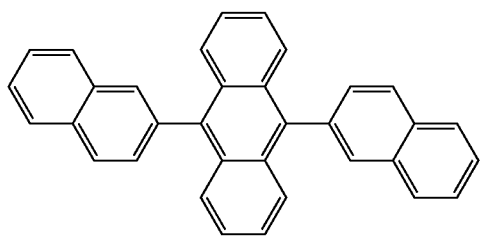
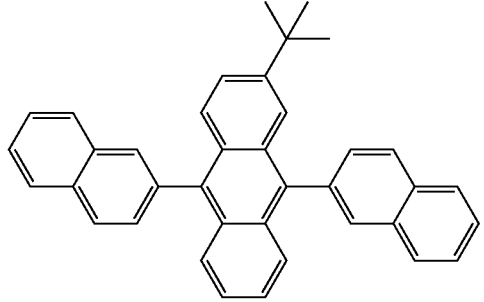
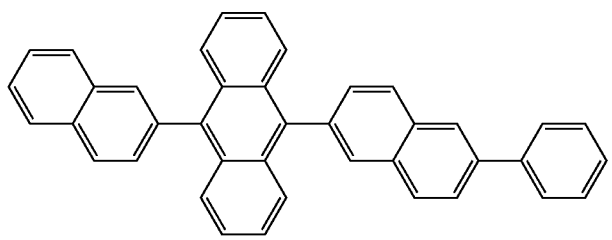
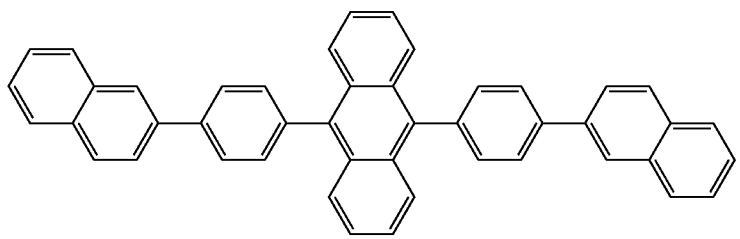
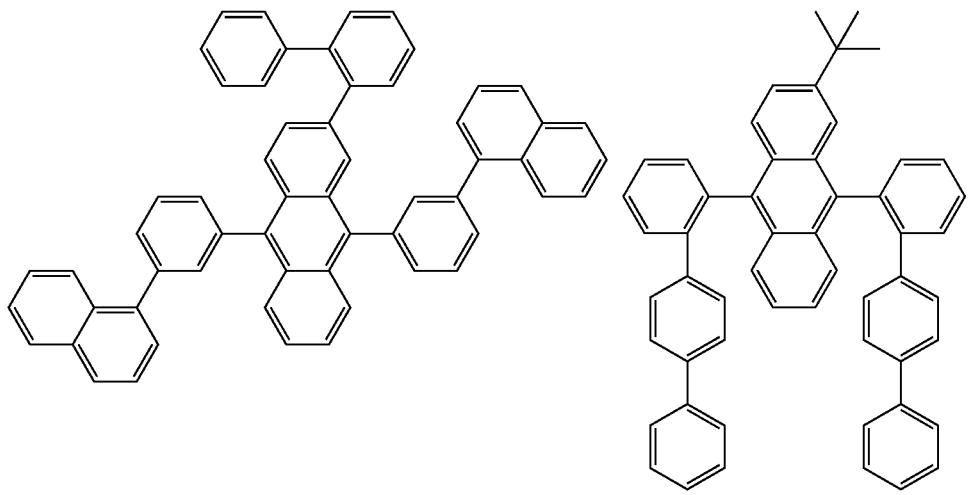
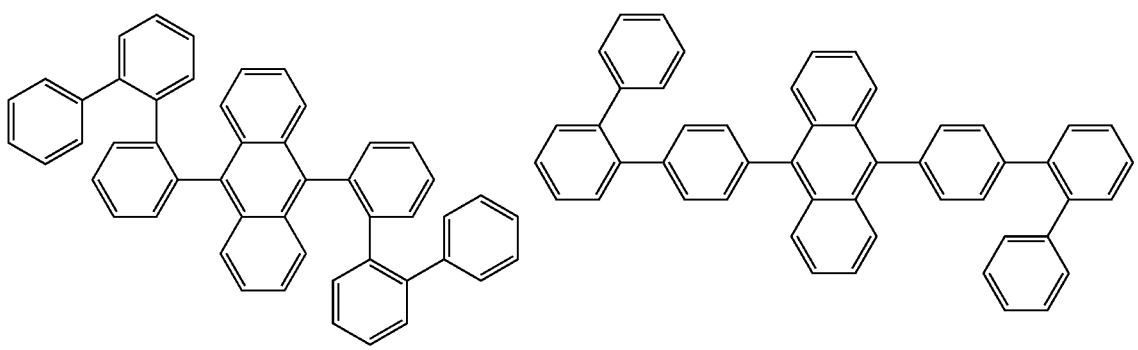

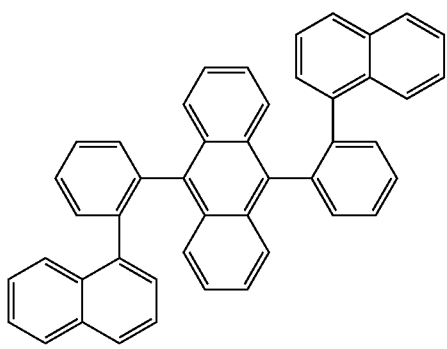
[Thirty-Eighth Chemical Formula]
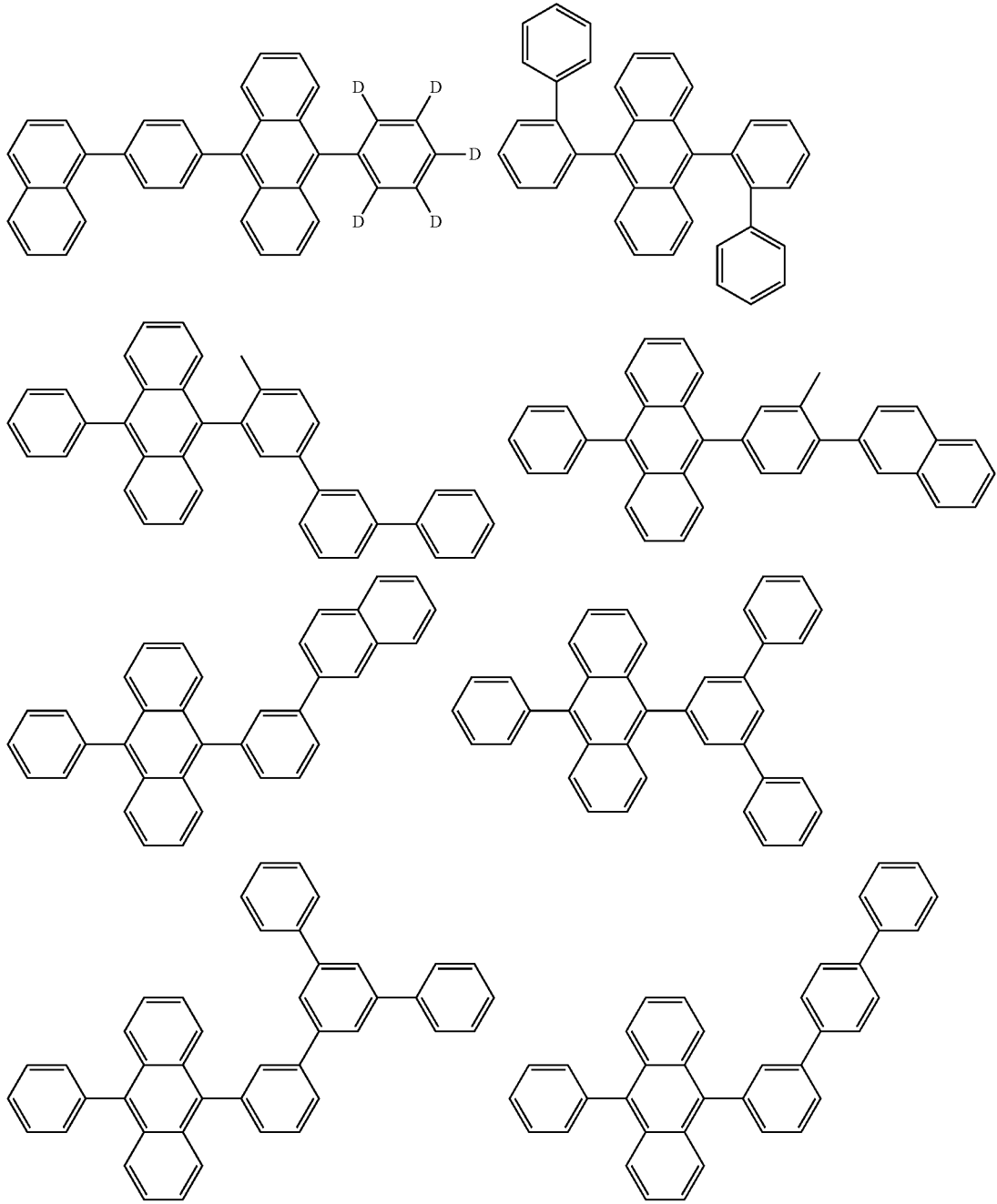

-continued
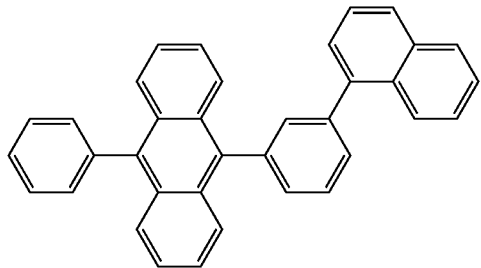
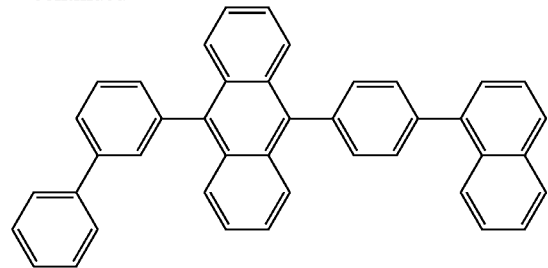
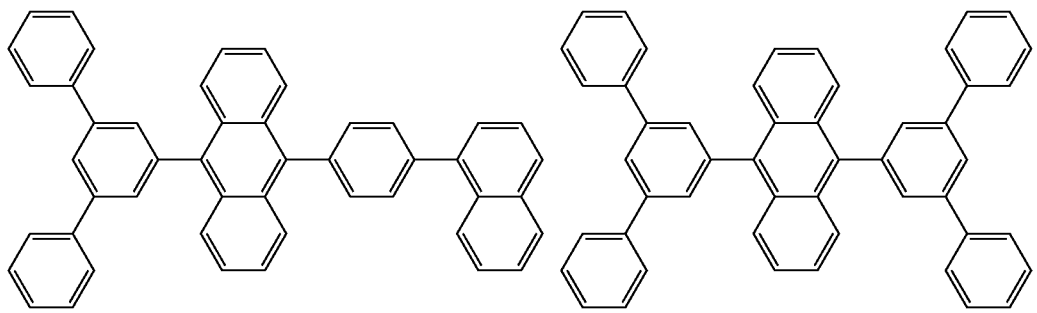
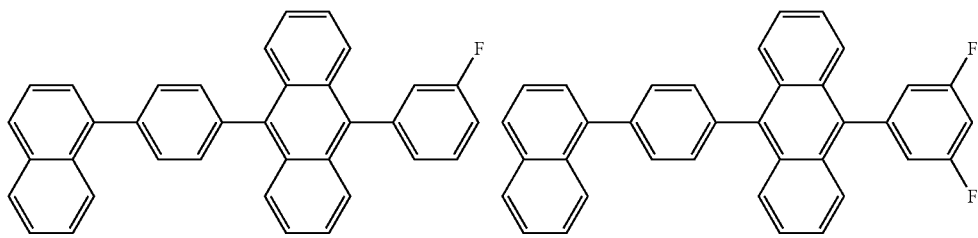
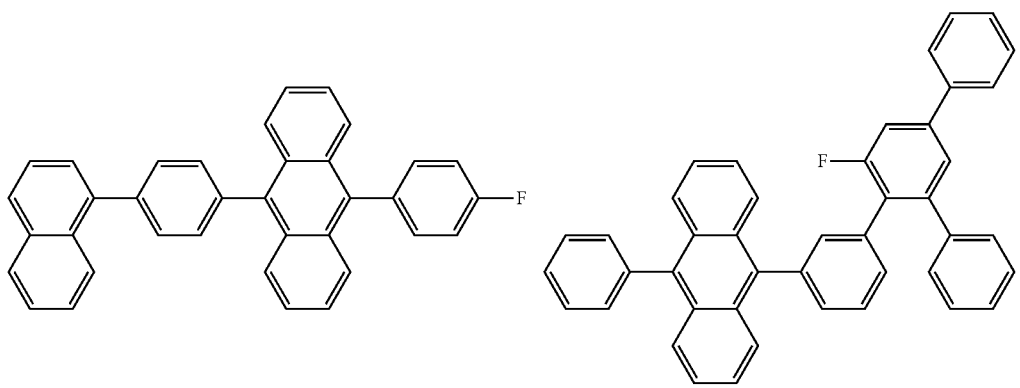
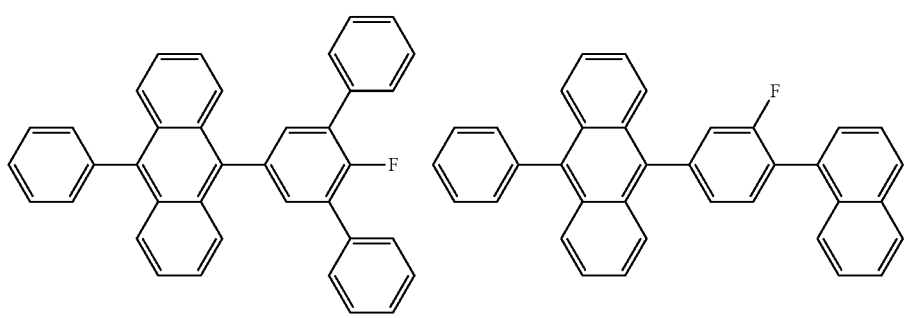

[Thirty-Ninth Chemical Formula]
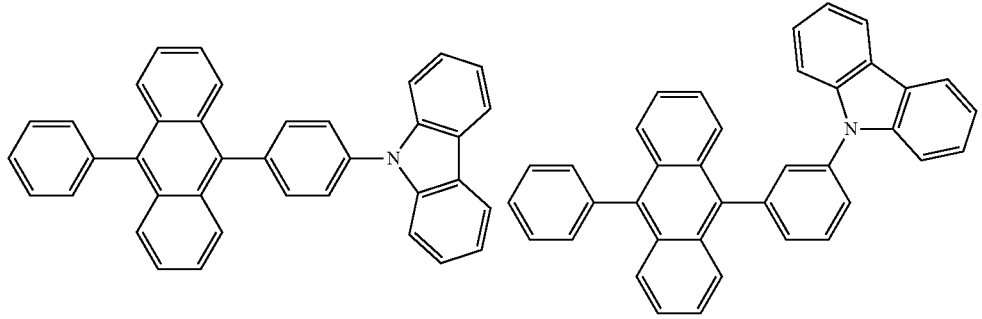
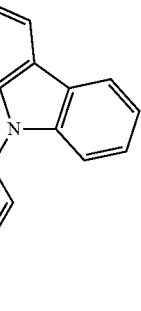
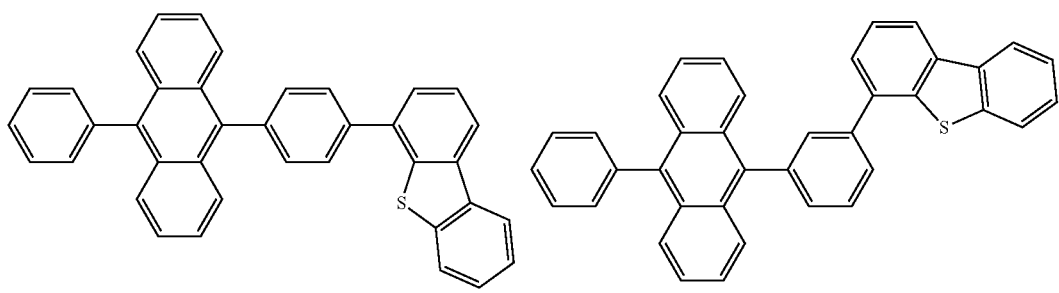
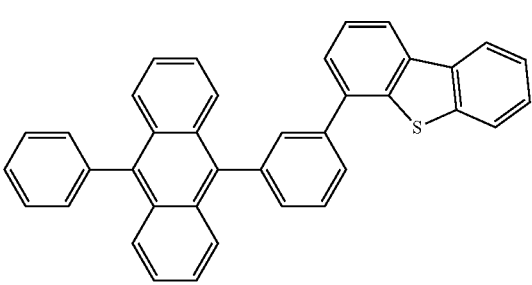
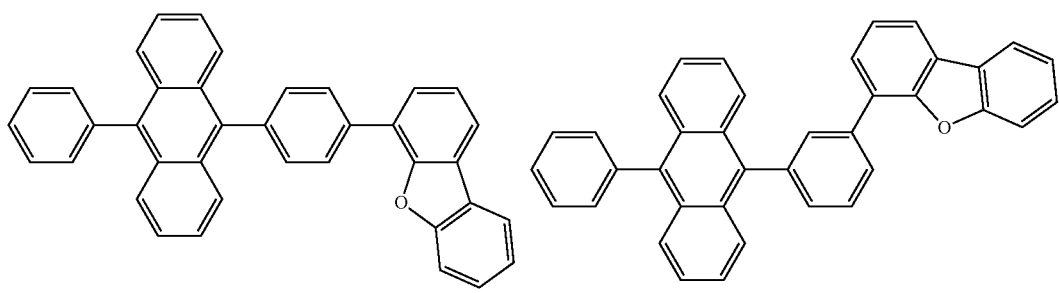
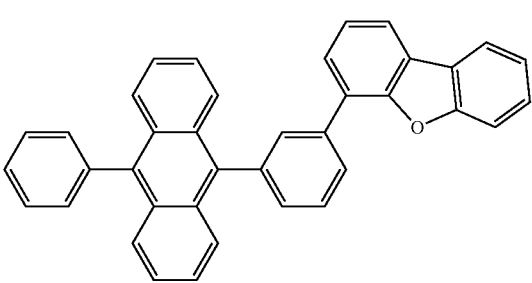
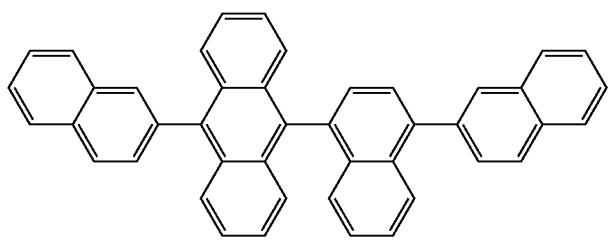
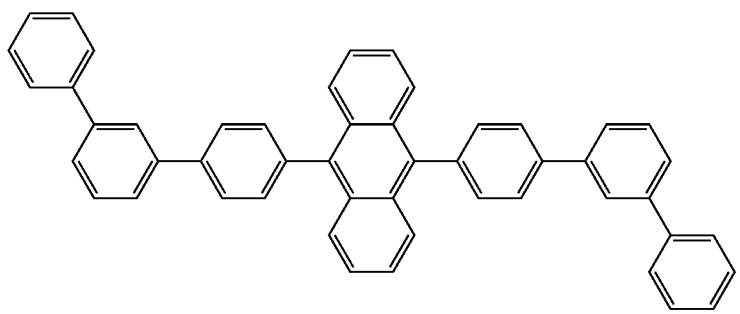

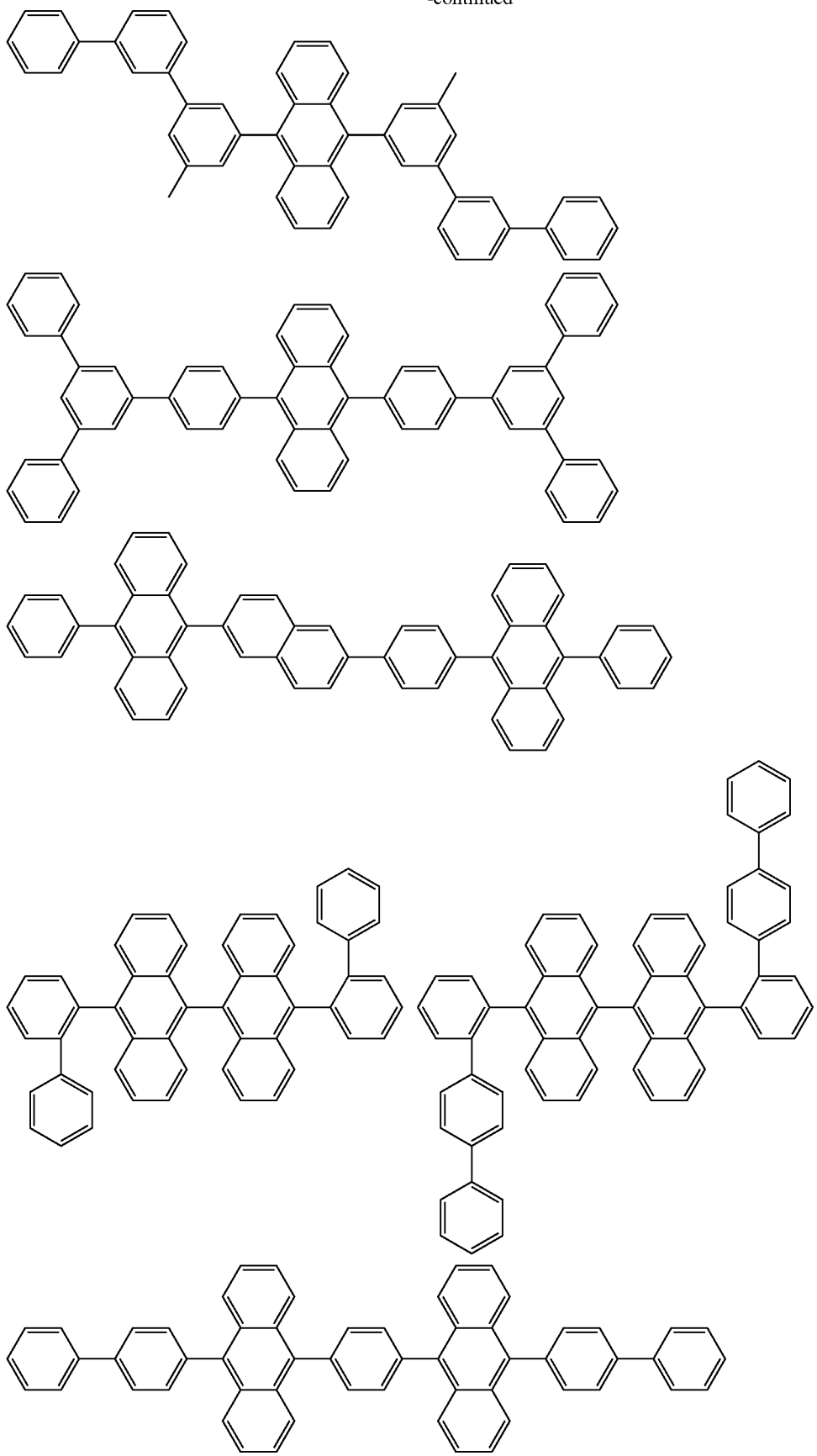

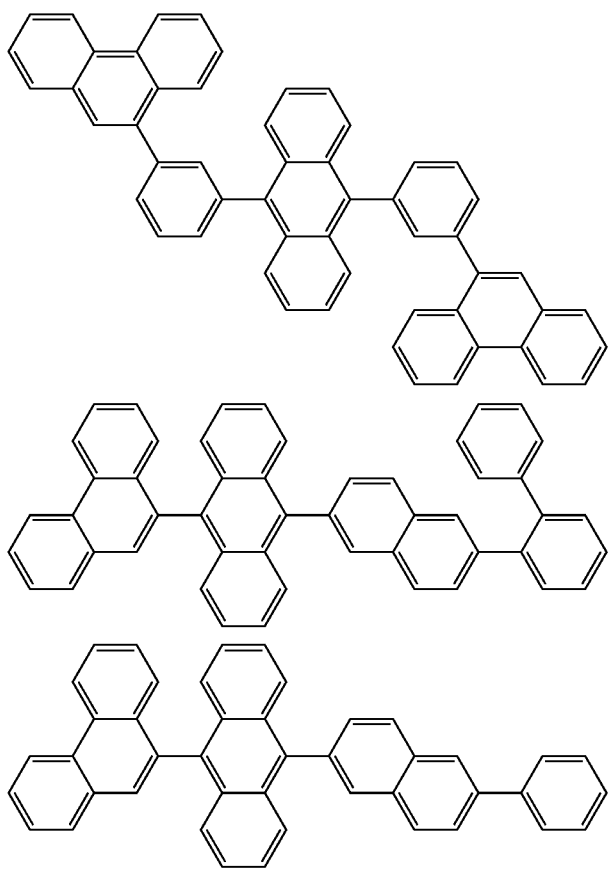
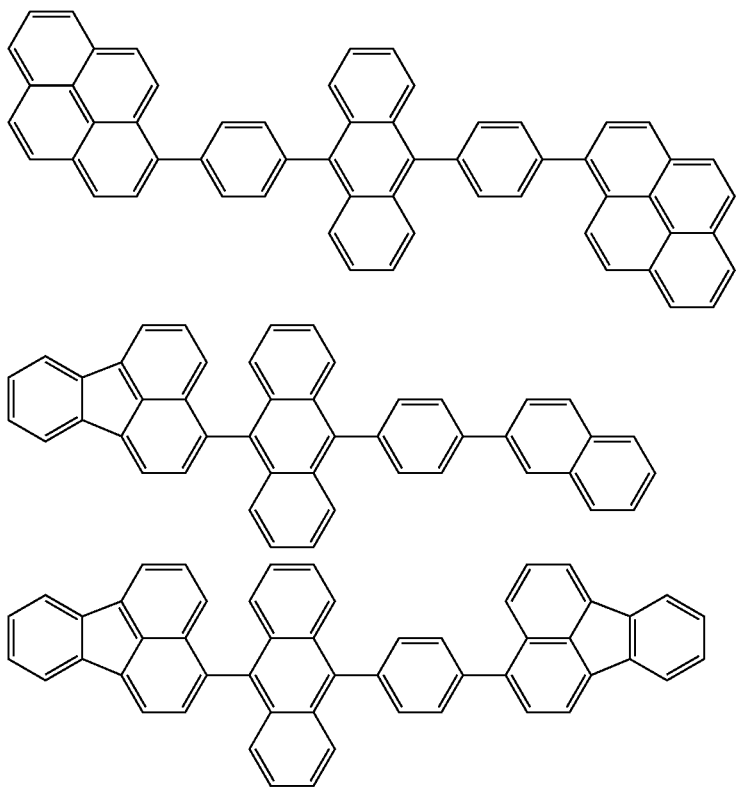
[Fortieth Chemical Formula]

85
-continued
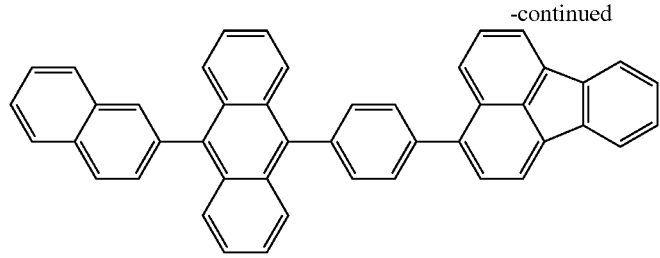
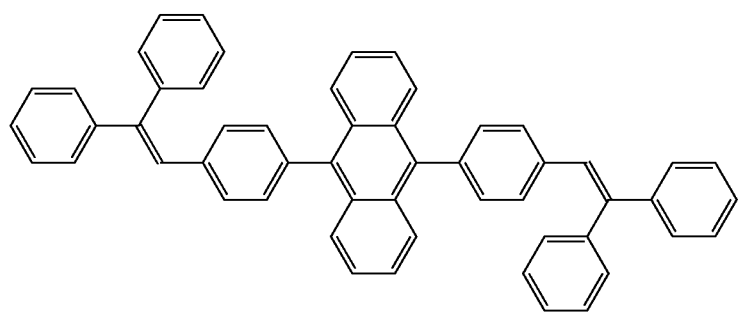
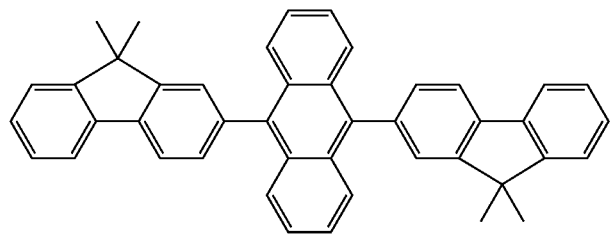
86
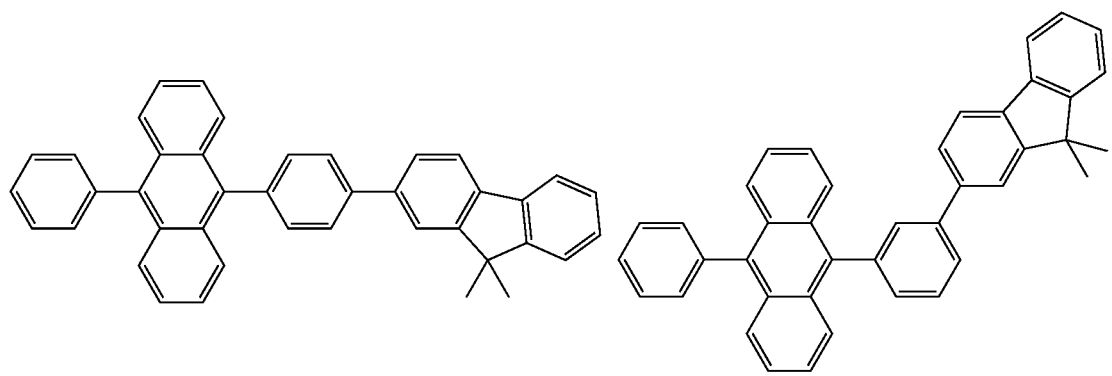

-continued
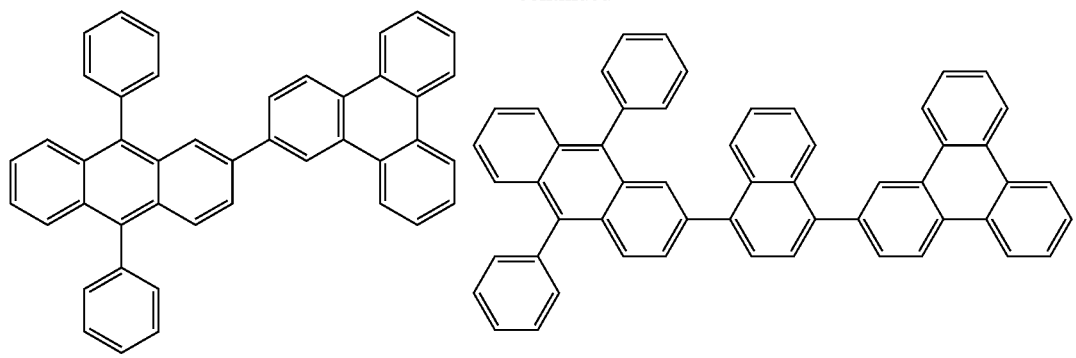
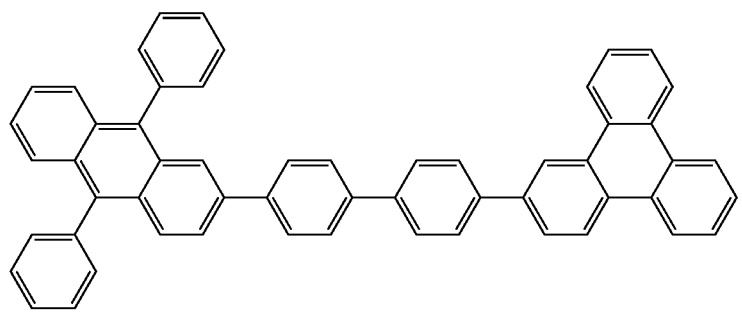
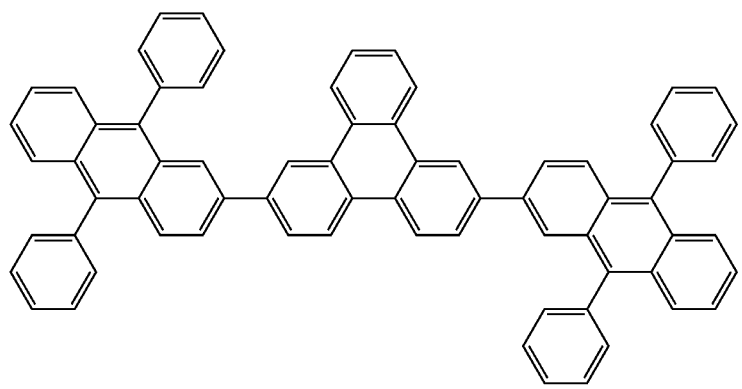
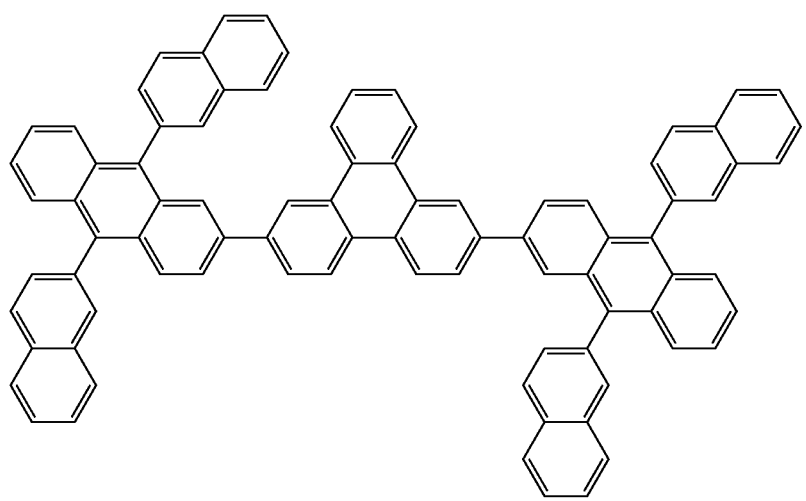

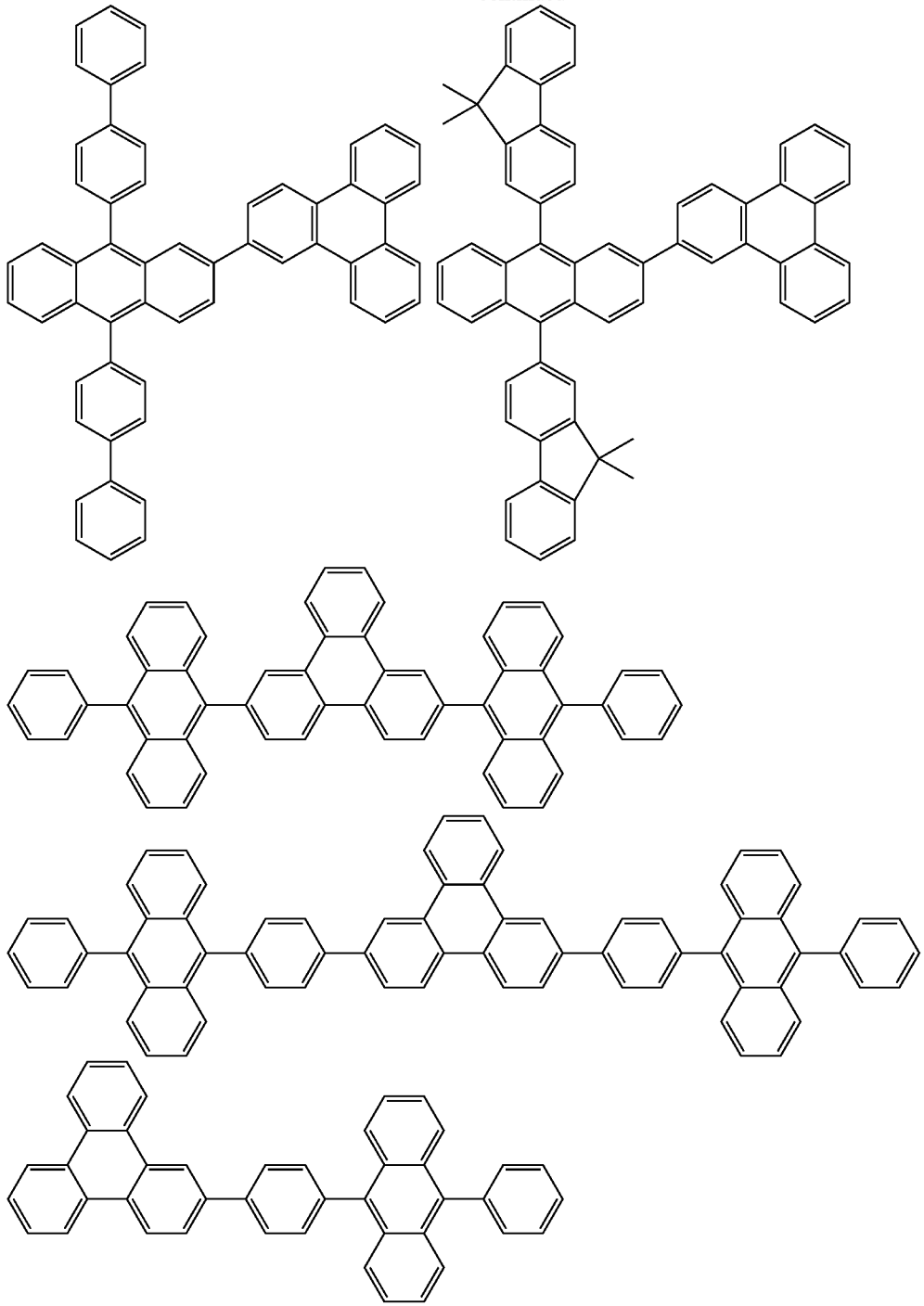

The host material that can be used in the light-emitting layer of the organic electroluminescence element of the present invention may be either a hole transporting host material or an electron transporting host material.

In the light-emitting layer, from the standpoints of color purity, luminous efficiency, and drive durability, it is preferable for the lowest excited singlet energy ($S_1$ energy) of the aforementioned host material in a film state to be higher than the $S_1$ energy of the aforementioned light-emitting material. The $S_1$ of the host material is preferably higher than the $S_1$ of the light-emitting material by at least 0.1 eV, more preferably higher by at least 0.2 eV, and even more preferably higher by at least 0.3 eV.

If the $S_1$ of the host material in a film state is lower than the $S_1$ of the light-emitting material, emission of light is quenched, so the host material needs to have a higher $S_1$ than the light-emitting material. Moreover, even when the $S_1$ of the host material is higher than that of the light-emitting material, if the difference in the $S_1$ [values] between the two is small, reverse energy movement from the light-emitting material to the host material will occur in places, and this can lead to lower efficiency or a decrease in durability. Accordingly, the host material needs to have a sufficiently high $S_1$ as well as good chemical stability and carrier injection and transport properties.

In addition, there are no particular restrictions on the amount in which the host compound is contained in the light-emitting layer of the organic electroluminescence element of the present invention, but from the standpoints of luminous efficiency and drive voltage, it is preferably from 15 to 95 wt % with respect to the weight of all the compounds forming the light-emitting layer. If the light-emitting layer includes a plurality of types of host compound including a compound expressed by General Formula 1, then the compound expressed by General Formula 1 is preferably contained in the total host compound in an amount of at least 50 wt % and no more than 99 wt %.

(Other Layers)

The organic electroluminescence element of the present invention may have other layers besides the aforementioned light-emitting layer.

Examples of other organic layers other than the aforementioned light-emitting layer that may be included in the aforementioned organic layers include a hole injection layer, a hole transport layer, a blocking layer (hole blocking layer, exciton blocking layer, etc.), and an electron transport layer. The following are concrete examples of the layer configuration, but the present invention is in no way limited to these configurations:

anode/hole transport layer/light-emitting layer/electron transport layer/cathode anode/hole transport layer/light-emitting layer/blocking layer/electron transport layer/cathode anode/hole transport layer/light-emitting layer/blocking layer/electron transport layer/electron injection layer/cathode anode/hole injection layer/hole transport layer/light-emitting layer/blocking layer/electron transport layer/cathode anode/hole injection layer/hole transport layer/light-emitting layer/electron transport layer/electron injection layer/cathode anode/hole injection layer/hole transport layer/light-emitting layer/blocking layer/electron transport layer/electron injection layer/cathode anode/hole injection layer/hole transport layer/blocking layer/light-emitting layer/blocking layer/electron transport layer/electron injection layer/cathode The organic electroluminescence element of the present invention preferably includes at least one organic layer preferably disposed between the aforementioned anode and the aforementioned light-emitting layer (A). From the anode side, a hole injection layer, a hole transport layer, and an electron blocking layer can be cited as examples of organic layers preferably disposed between the aforementioned anode and the aforementioned light-emitting layer of (A) above.

The organic electroluminescence element of the present invention preferably includes at least one organic layer preferably disposed between the aforementioned cathode and the aforementioned light-emitting layer (B). From the cathode side, an electron injection layer, an electron transport layer, and a hole blocking layer can be cited as examples of organic layers preferably disposed between the aforementioned cathode and the aforementioned light-emitting layer of (B) above.

In concrete terms, one example of a preferred mode of the organic electroluminescence element of the present invention is the mode described in FIG. 1, being a mode in which a hole injection layer 4, a hole transport layer 5, a light-emitting layer 6, a hole blocking layer 7, and an electron transport layer 8 are laminated in this order from the side of the anode 3 as the aforementioned organic layers.

These layers other than the aforementioned light-emitting layer that may be included in the organic electroluminescence element of the present invention will be described below.

(A) Organic Layers Preferably Disposed between the Anode and the Aforementioned Light-Emitting Layer First, (A) organic layers preferably disposed between the aforementioned anode and the aforementioned light-emitting layer will be described.

(A-1) Hole Injection Layer and Hole Transport Layer

The hole injection layer and the hole transport layer are layers having the function of accepting holes from the anode or the anode side and transporting them to the cathode side.

The light-emitting element of the present invention preferably includes at least one organic layer between the light-emitting layer and the anode, and this organic layer preferably contains at least one type of compound out of the compounds expressed by General Formulas Sa-1, Sb-1, and Sc-1 below:

[Forty-First Chemical Formula]

General Formula Sa-1

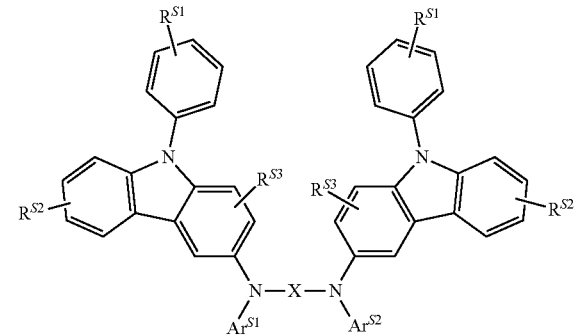

(In the formula, X represents a substituted or unsubstituted $C_1$ to $C_{30}$ alkylene group, a substituted or unsubstituted $C_2$ to $C_{30}$ alkenylene group, a substituted or unsubstituted $C_6$ to $C_{30}$ arylene group, a substituted or unsubstituted $C_2$ to $C_{30}$ heteroarylene group, a substituted or unsubstituted $C_2$ to $C_{30}$ heterocyclic group, or a group that is a combination of these. $R^{S1}$, $R^{S2}$, and $R^{S3}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S1}$, $R^{S2}$, and $R^{S3}$ [groups] may bond to each other to form a saturated or unsaturated carbon ring. $Ar^{S1}$ and $Ar^{S2}$ represent each independently a substituted or unsubstituted $C_6$ to $C_{30}$ aryl group or a substituted or unsubstituted $C_2$ to $C_{30}$ heteroaryl group.)

[Forty-Second Chemical Formula]

General Formula Sb-1

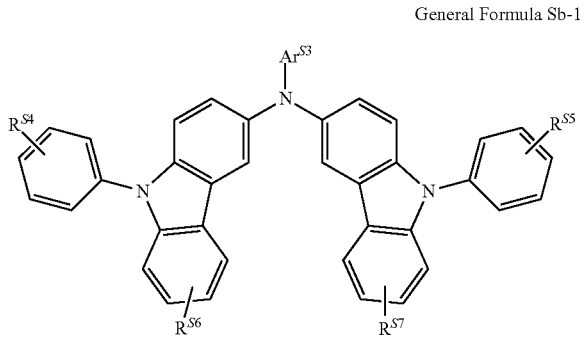

(In the formula, $R^{S4}$, $R^{S6}$, $R^{S6}$, and $R^{S7}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S4}$, $R^{S5}$, $R^{S6}$, and $R^{S7}$ [groups] may bond to each other to form a saturated or unsaturated carbon ring. $Ar^{S3}$ represents a substituted or unsubstituted $C_6$ to $C_{30}$ aryl group or a substituted or unsubstituted $C_2$ to $C_{30}$ heteroaryl group.)

[Forty-Third Chemical Formula]

General Formula Sc-1

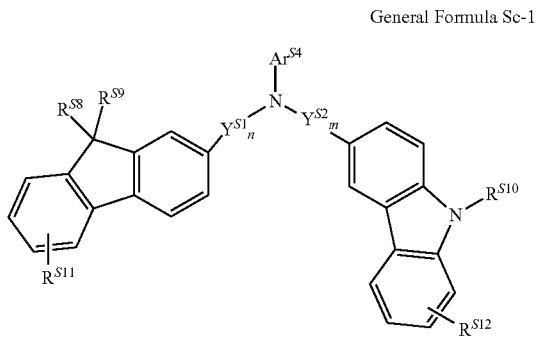

(In the formula, $R^{S8}$ and $R^{S9}$ represent each independently a hydrogen atom, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S10}$ represents a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S11}$ and $R^{S12}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S11}$ and $R^{S12}$ [groups] may bond to each other to form a saturated or unsaturated carbon ring. $Ar^{S4}$ represents a substituted or unsubstituted $C_6$ to $C_{30}$ aryl group or a substituted or unsubstituted $C_2$ to $C_{30}$ heteroaryl group. $Y^{S1}$ and $Y^{S2}$ represent each independently a substituted or unsubstituted $C_1$ to $C_{30}$ alkylene group or a substituted or unsubstituted $C_6$ to $C_{30}$ arylene group. n and m represent each independently an integer from 0 to 5.)

General Formula Sa-1 above will now be described.

In General Formula Sa-1 above, X represents a substituted or unsubstituted $C_1$ to $C_{30}$ alkylene group, a substituted or unsubstituted $C_2$ to $C_{30}$ alkenylene group, a substituted or unsubstituted $C_6$ to $C_{30}$ arylene group, a substituted or unsubstituted $C_2$ to $C_{30}$ heteroarylene group, a substituted or unsubstituted $C_2$ to $C_{30}$ heterocyclic group, or a group that is a combination of these. X is preferably a substituted or unsubstituted $C_6$ to $C_{30}$ arylene group, more preferably a substituted or unsubstituted phenylene, a substituted or unsubstituted biphenylene, and a substituted or unsubstituted naphthylene, and even more preferably a substituted or unsubstituted biphenylene.

$R^{S1}$, $R^{S2}$, and $R^{S3}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S1}$, $R^{S2}$, and $R^{S3}$ [groups] may bond to each other to form a saturated or unsaturated carbon ring. Examples of the aforementioned saturated or unsaturated carbon ring include naphthalene, azulene, anthracene, fluorene, and phenalene. $R^{S1}$, $R^{S2}$, and $R^{S3}$ are preferably a hydrogen atom, a substituted or unsubstituted $C_1$ to $C_{30}$ alkyl group, a substituted or unsubstituted $C_6$ to $C_{30}$ aryl group, a substituted or unsubstituted $C_5$ to $C_{30}$ condensed polycyclic group, and a cyano group, with a hydrogen atom being more preferable.

$Ar^{S1}$ and $Ar^{S2}$ represent each independently a substituted or unsubstituted $C_6$ to $C_{30}$ aryl group or a substituted or unsubstituted $C_2$ to $C_{30}$ heteroaryl group. $Ar^{S1}$ and $Ar^{S2}$ are preferably a substituted or unsubstituted phenyl group.

Next, General Formula Sb-1 above will be described.

In General Formula Sb-1 above, $R^{S4}$, $R^{S5}$, $R^{S6}$, and $R^{S7}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S4}$, $R^{S5}$, $R^{S6}$, and $R^{S7}$ [groups] may bond to each other to form a saturated or unsaturated carbon ring. Examples of the saturated or unsaturated carbon ring include naphthalene, azulene, anthracene, fluorene, and phenalene. $R^{S4}$, $R^{S5}$, $R^{S6}$, and $R^{S7}$ are preferably a hydrogen atom, a substituted or unsubstituted $C_1$ to $C_{30}$ alkyl group, a substituted or unsubstituted $C_6$ to $C_{30}$ aryl group, a substituted or unsubstituted $C_5$ to $C_{30}$ condensed polycyclic group, and a cyano group, with a hydrogen atom being more preferable.

$Ar^{S3}$ represents a substituted or unsubstituted $C_6$ to $C_{30}$ aryl group or a substituted or unsubstituted $C_2$ to $C_{30}$ heteroaryl group. $Ar^{S3}$ is preferably a substituted or unsubstituted phenyl group.

Next, General Formula Sc-1 above will be described.

In General Formula Sc-1 above, $R^{S8}$ and $R^{S9}$ represent each independently a hydrogen atom, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S8}$ and $R^{S9}$ are preferably a substituted or unsubstituted $C_1$ to $C_{30}$ alkyl group and a substituted or unsubstituted $C_6$ to $C_{30}$ aryl group, with a methyl group and a phenyl group being more preferable. $R^{S10}$ represents a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S10}$ is preferably a substituted or unsubstituted $C_6$ to $C_{30}$ aryl group and more preferably a phenyl group. $R^{S11}$ and $R^{S12}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S11}$ and $R^{S12}$ [groups] may bond to each other to form a saturated or unsaturated carbon ring. Examples of the aforementioned saturated or unsaturated carbon ring include naphthalene, azulene, anthracene, fluorene, and phenalene. $R^{S11}$ and $R^{S12}$ are preferably a hydrogen atom, a substituted or unsubstituted $C_1$ to $C_{30}$ alkyl group, a substituted or unsubstituted $C_6$ to $C_{30}$ aryl group, a substituted or unsubstituted $C_5$ to $C_{30}$ condensed polycyclic group, and a cyano group, with a hydrogen atom being more preferable. $Ar^{S4}$ represents a substituted or unsubstituted $C_6$ to $C_{30}$ aryl group or a substituted or unsubstituted $C_2$ to $C_{30}$ heteroaryl group. $Y^{S1}$ and $Y^{S2}$ represent a substituted or unsubstituted $C_1$ to $C_{30}$ alkylene or a substituted or unsubstituted $C_6$ to $C_{30}$ arylene. $Y^{S1}$ and $Y^{S2}$ are preferably a substituted or unsubstituted $C_6$ to $C_{30}$ arylene, with a substituted or unsubstituted phenylene being more preferable. n is an integer from 0 to 5, preferably from 0 to 3, more preferably from 0 to 2, even more preferably 0. m is an integer from 0 to 5, preferably from 0 to 3, more preferably from 0 to 2, even more preferably 1.

General Formula Sa-1 above is preferably a compound expressed by General Formula Sa-2 below:

(In the formula, $R^{S1}$, $R^{S2}$, $R^{S3}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S1}$, $R^{S2}$, and $R^{S3}$ [groups] may bond to each other to form a saturated or unsaturated carbon ring. $Q^{Sa}$ [groups] represent each independently a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group.)

General Formula Sa-2 above will now be described. $R^{S1}$, $R^{S2}$, and $R^{S3}$ are defined the same as those in General Formula Sa-1, and the preferred ranges are also the same. $Q^{Sa}$ [groups] represent each independently a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group. $Q^{Sa}$ is preferably a hydrogen atom, a cyano group, a fluorine atom, a substituted or unsubstituted $C_1$ to $C_{30}$ alkyl group, and a substituted or unsubstituted $C_6$ to $C_{30}$ aryl group, more preferably a hydrogen atom and a substituted or unsubstituted $C_1$ to $C_{30}$ alkyl group, and even more preferably a hydrogen atom.

General Formula Sb-1 above is preferably a compound expressed by General Formula Sb-2 below:

[Forty-Fourth Chemical Formula]

General Formula Sa-2

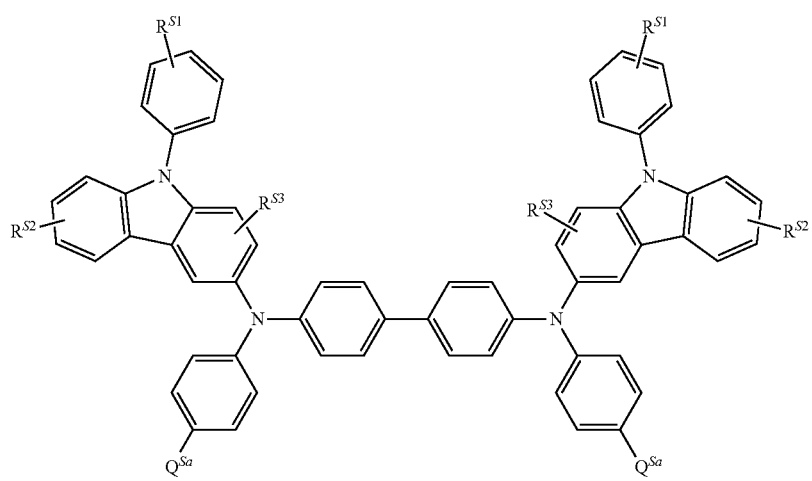

[Forty-Fifth Chemical Formula]

General Formula Sb-2

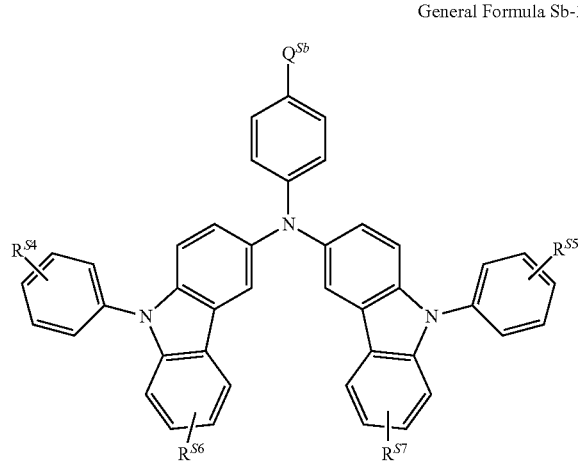

[Forty-Sixth Chemical Formula]

General Formula Sc-2

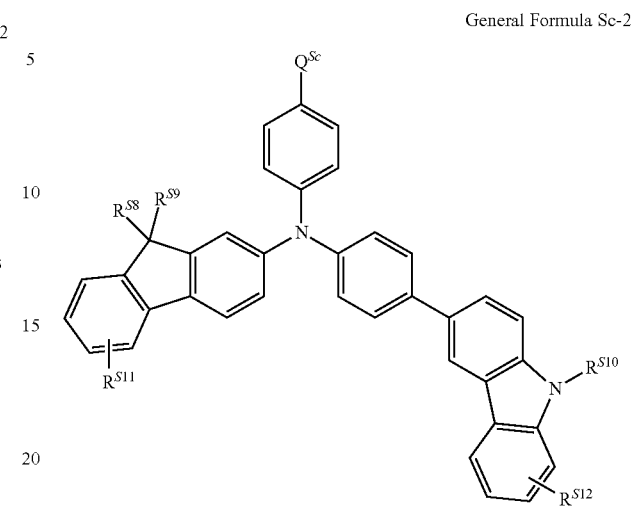

(In the formula, $R^{S4}$, $R^{S5}$, $R^{S6}$, and $R^{S7}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S4}$, $R^{S5}$, $R^{S6}$, and $R^{S7}$ [groups] may bond to each other to form a saturated or unsaturated carbon ring. $Q^{Sb}$ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group.)

General Formula Sb-2 above will now be described. $R^{S4}$, $R^{S5}$, $R^{S6}$, and $R^{S7}$ are defined the same as those in General Formula Sb-1, and the preferred ranges are also the same. $Q^{Sa}$ [sic]⁶ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group. $Q^{Sa}$ [sic] is preferably a hydrogen atom, a cyano group, a fluorine atom, a substituted or unsubstituted $C_1$ to $C_{30}$ alkyl group, and a substituted or unsubstituted $C_6$ to $C_{30}$ aryl group, more preferably a hydrogen atom and a substituted or unsubstituted $C_1$ to $C_{30}$ alkyl group, and even more preferably a hydrogen atom.

⁶Translator's note: apparent error in the original; "$Q^{Sa}$" should be "$Q^{Sb}$" (same below).

General Formula Sc-1 above is preferably a compound expressed by General Formula Sc-2 below:

(In the formula, $R^{S8}$ and $R^{S9}$ represent each independently a hydrogen atom, a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S10}$ represents a substituted or unsubstituted $C_1$ to $C_{30}$ alkyl group, a substituted or unsubstituted $C_6$ to $C_{30}$ aryl group, a substituted or unsubstituted $C_2$ to $C_{30}$ heterocyclic group, or a substituted or unsubstituted $C_5$ to $C_{30}$ condensed polycyclic group. $R^{S11}$ and $R^{S12}$ represent each independently a hydrogen atom, a substituted or unsubstituted $C_1$ to $C_{30}$ alkyl group, a substituted or unsubstituted $C_1$ to $C_{30}$ alkoxy group, a substituted or unsubstituted $C_6$ to $C_{30}$ aryl group, a substituted or unsubstituted $C_6$ to $C_{30}$ aryloxy group, a substituted or unsubstituted $C_2$ to $C_{30}$ heterocycle, a substituted or unsubstituted $C_5$ to $C_{30}$ condensed polycyclic group, a hydroxy group, a cyano group, or a substituted or unsubstituted amino group. Adjacent $R^{S11}$ and $R^{S12}$ [groups] may bond to each other to form a saturated or unsaturated carbon ring. $Q^{Sc}$ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group.)

General Formula Sc-2 above will be described. $R^{S8}$, $R^{S9}$, $R^{S10}$, $R^{S11}$, and $R^{S12}$ are defined the same as those in General Formula Sc-1, and the preferred ranges are also the same. $Q^{Sc}$ represents a hydrogen atom, a cyano group, a fluorine atom, a $C_1$ to $C_{30}$ alkoxy group, a substituted or unsubstituted $C_1$ to $C_{30}$ alkyl group, a $C_6$ to $C_{30}$ aryloxy group, a substituted or unsubstituted $C_6$ to $C_{30}$ aryl group, a substituted or unsubstituted $C_2$ to $C_{30}$ heterocycle, or a substituted or unsubstituted amino group. $Q^{Sc}$ is preferably a hydrogen atom, a cyano group, a fluorine atom, a substituted or unsubstituted $C_1$ to $C_{30}$ alkyl group, or a substituted or unsubstituted $C_6$ to $C_{30}$ aryl group, more preferably a hydrogen atom or a substituted or unsubstituted $C_6$ to $C_{30}$ aryl group, and even more preferably a phenyl group.

Concrete examples of compounds expressed by General Formulas Sa-1, Sb-1, and Sc-1 above are as follows, but the present invention is not limited to or by the following concrete examples:

[Forty-Seventh Chemical Formula]
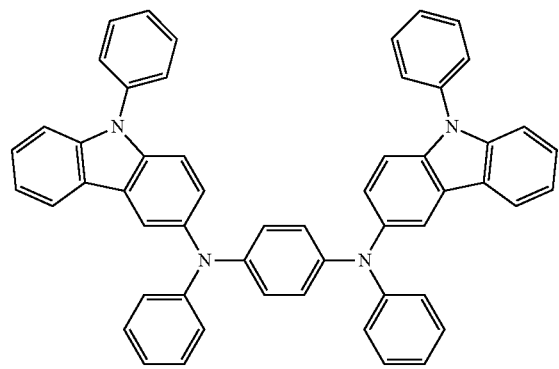
1
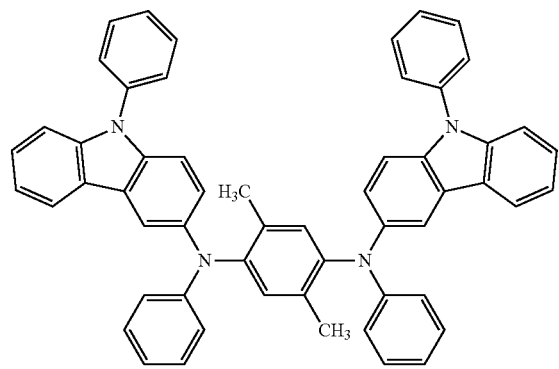
2
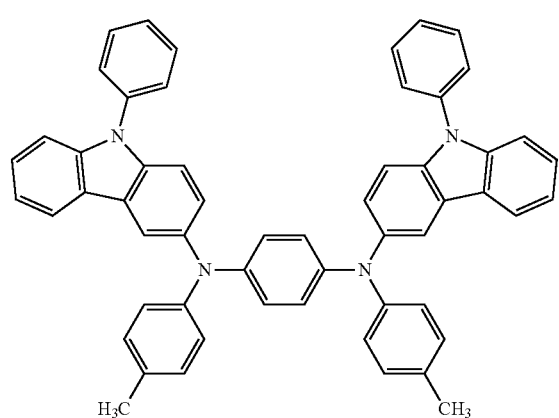
3
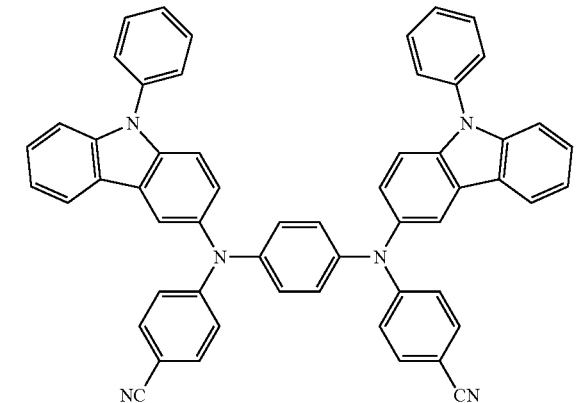
4
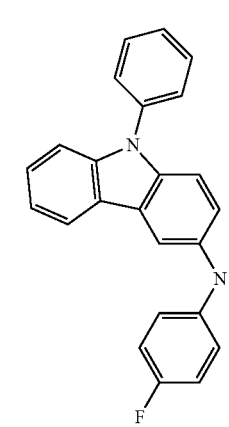
5
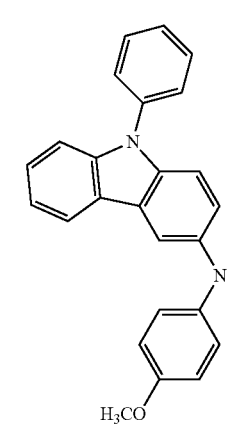 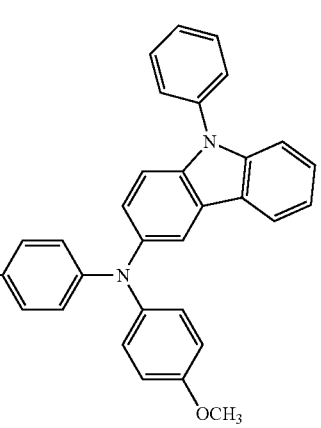
6

[Forty-Eighth Chemical Formula]

[Forty-Ninth Chemical Formula]
15
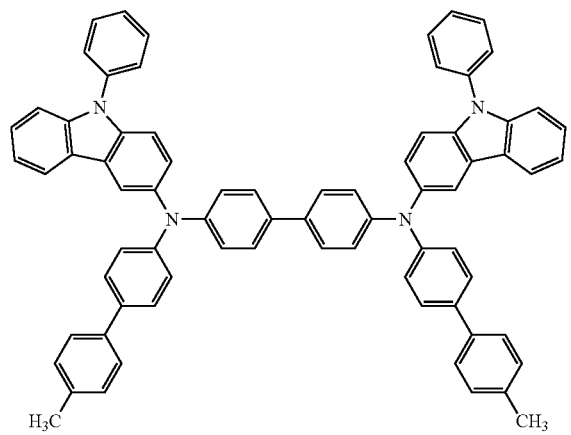
5
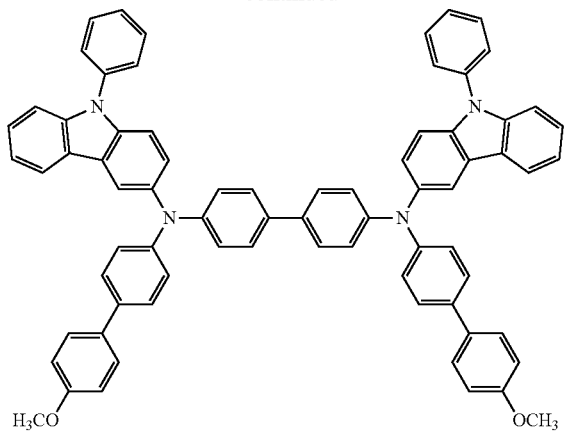
16
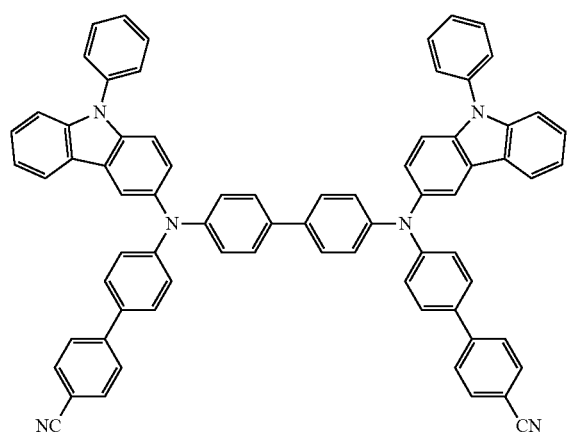
19
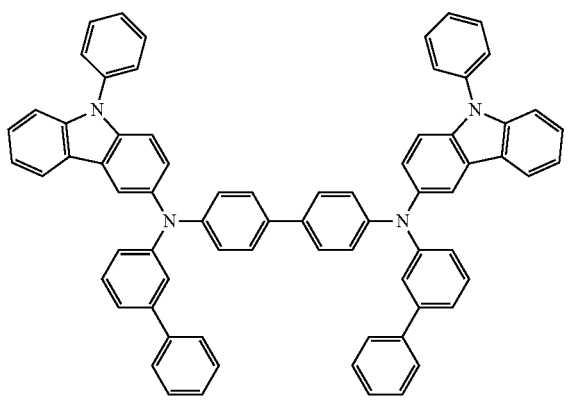
17
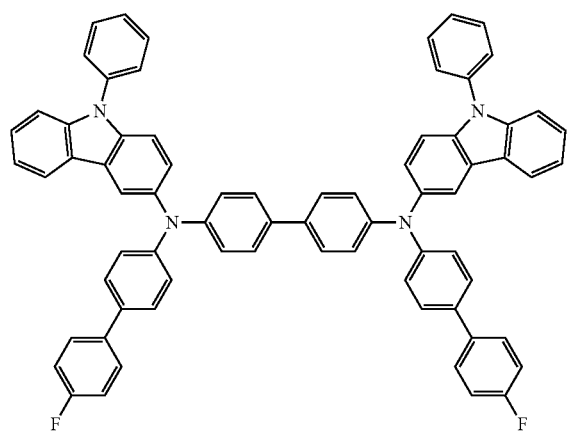
20
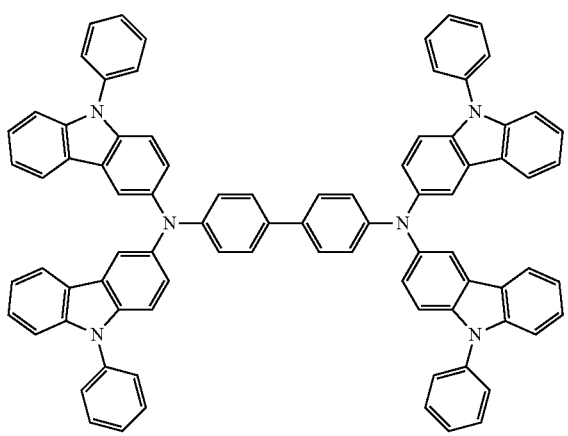

[Fiftieth Chemical Formula]
21
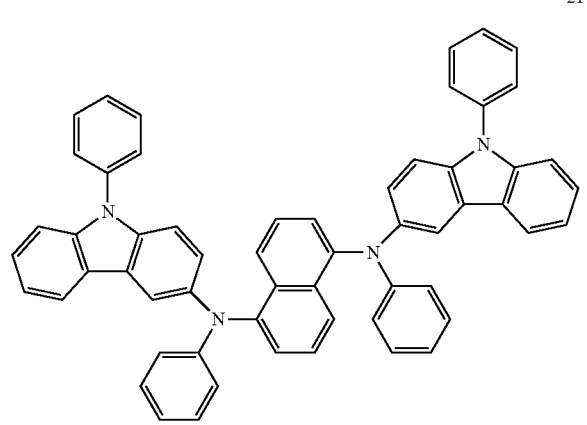
22
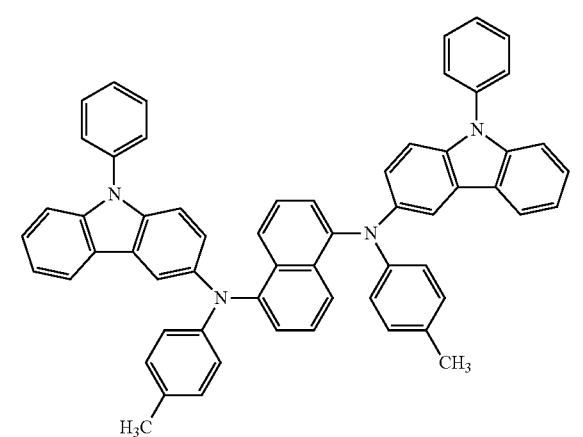
23
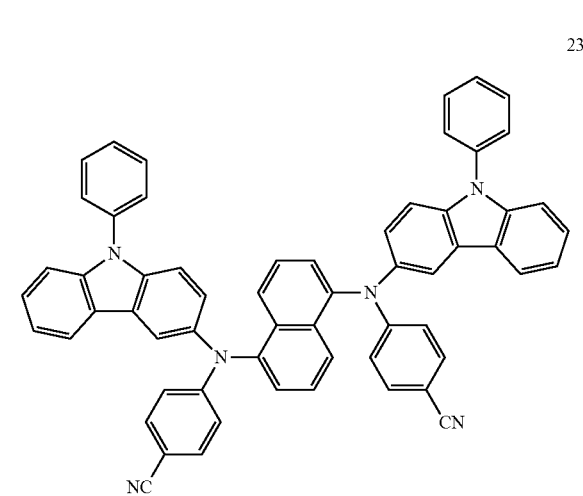
24
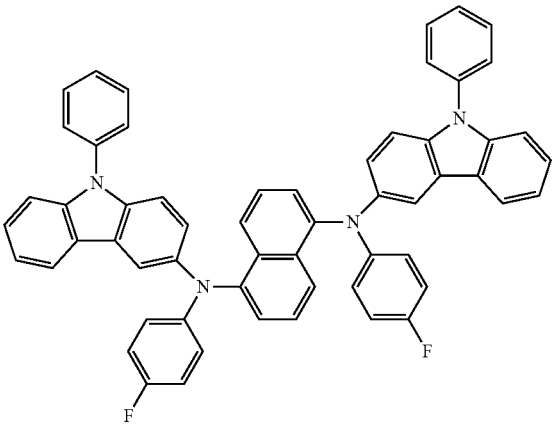
25
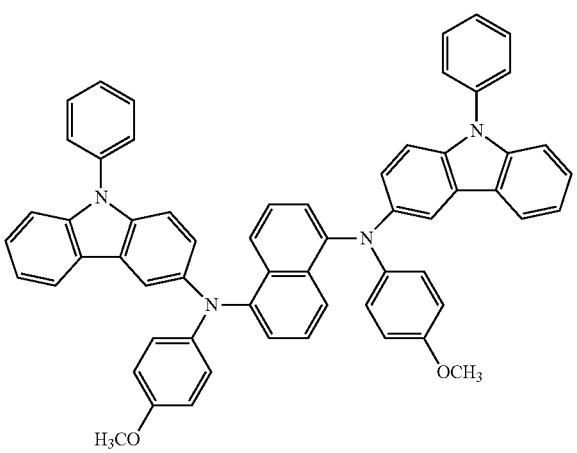
26

-continued
[Fifty-First Chemical Formula]
27
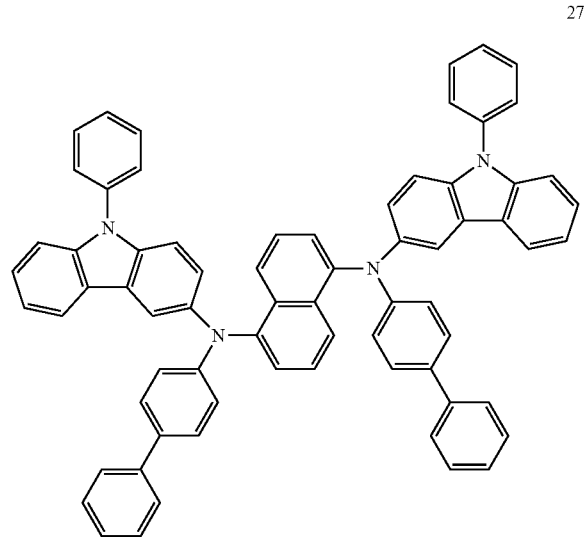
28
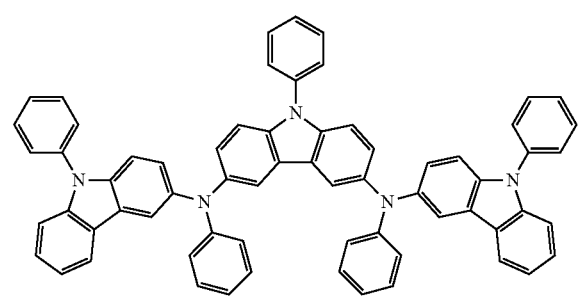
29
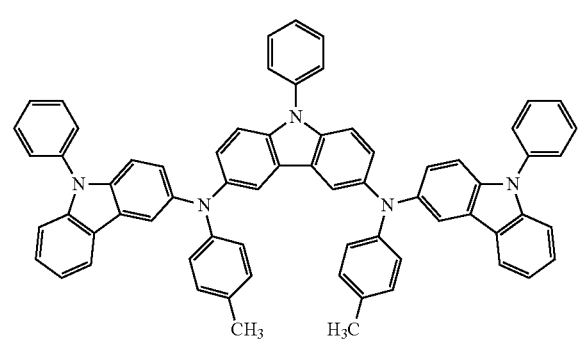
-continued
31
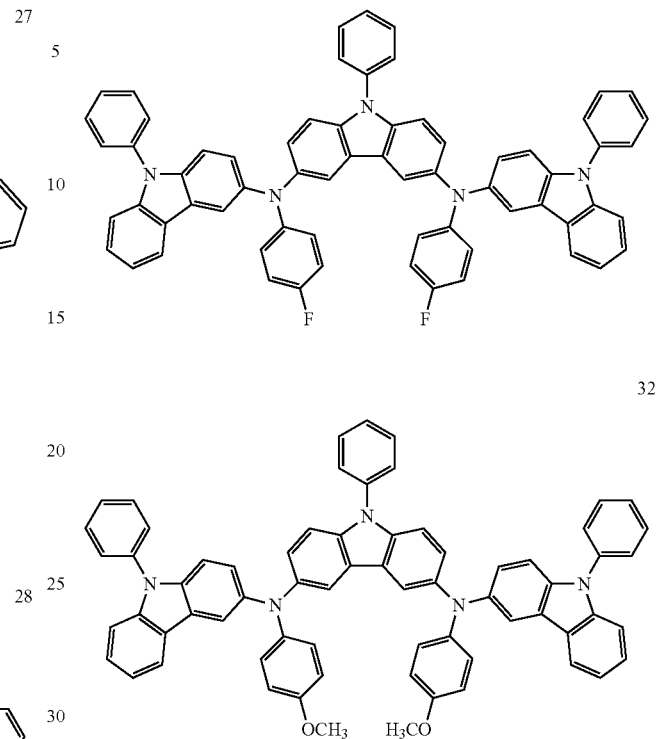
32
[Fifty-Second Chemical Formula]
33
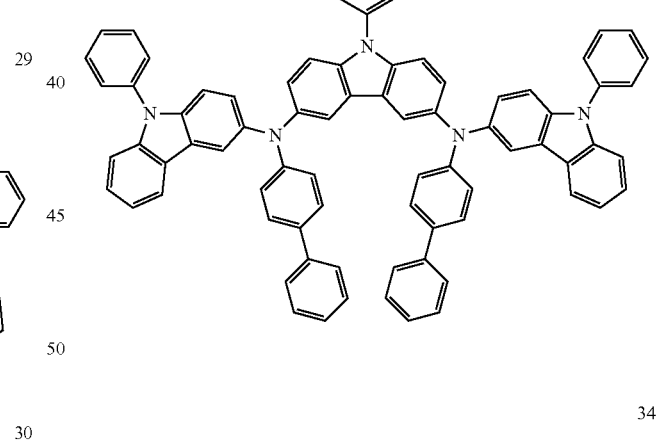
34
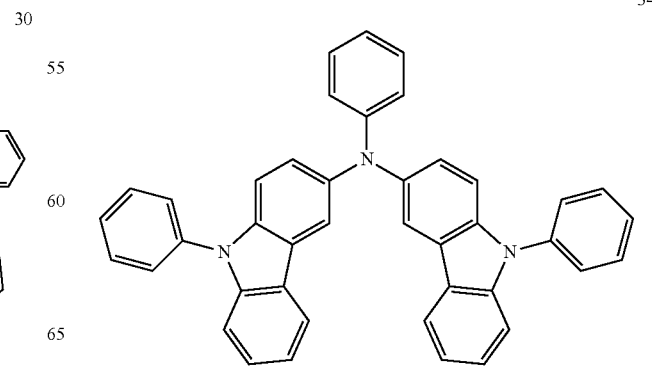

35
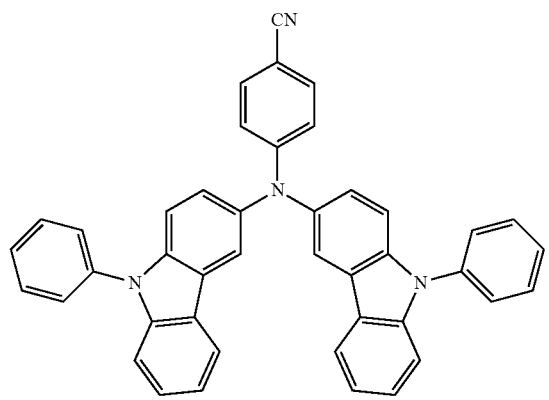
36
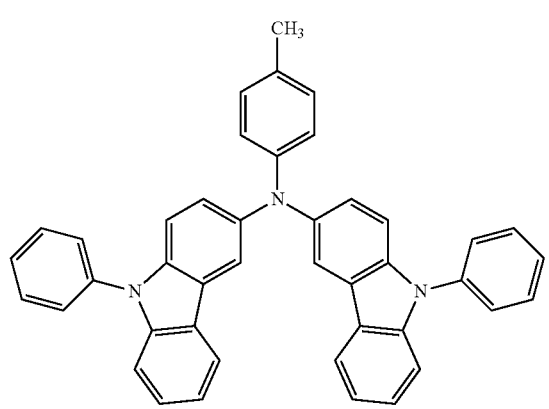
37
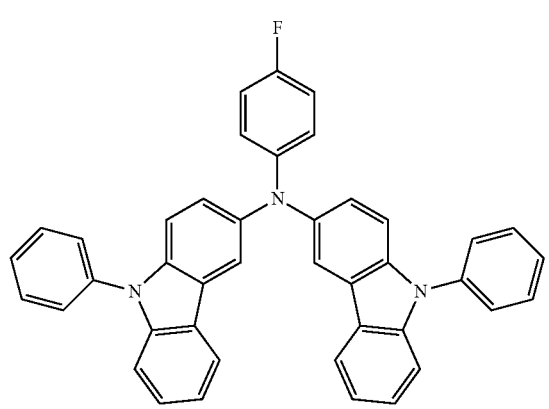
38
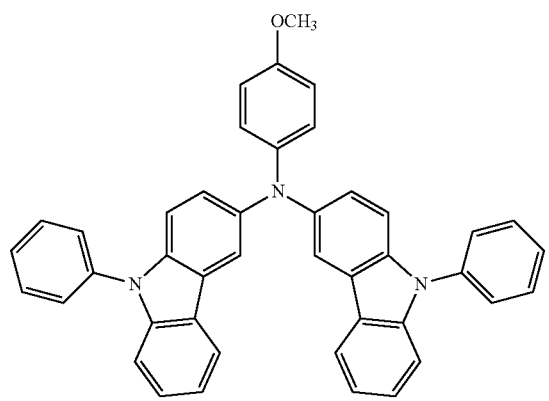
[Fifty-Third Chemical Formula]
39
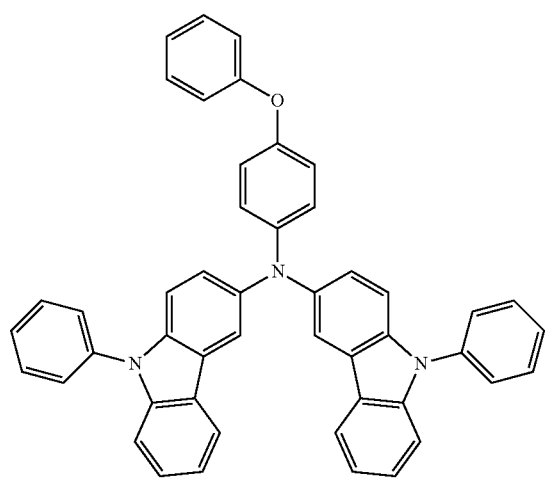
40
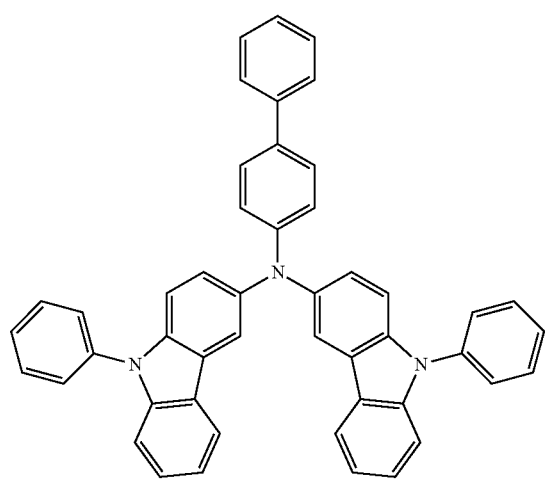

41
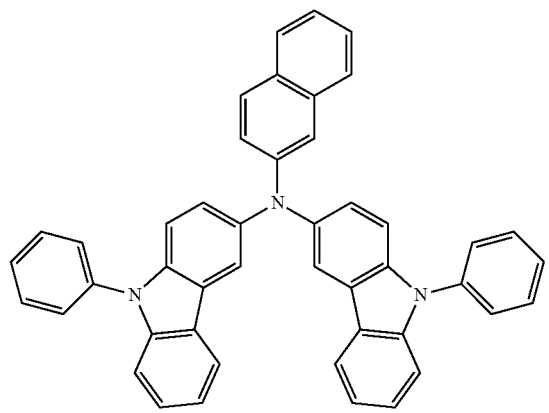
42
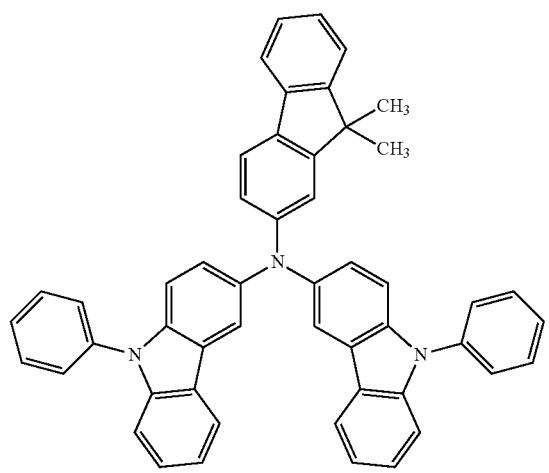
[Fifty-Fourth Chemical Formula]
43
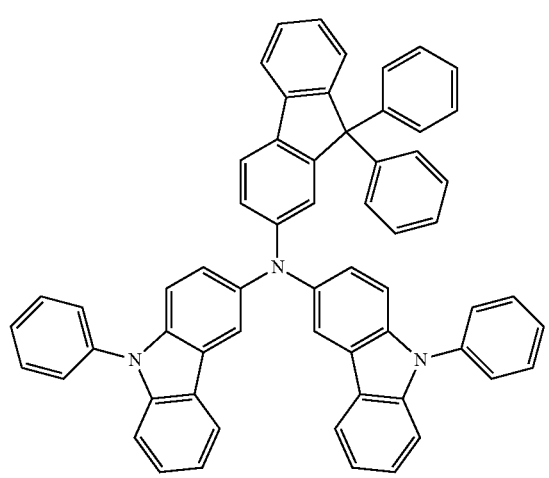
44
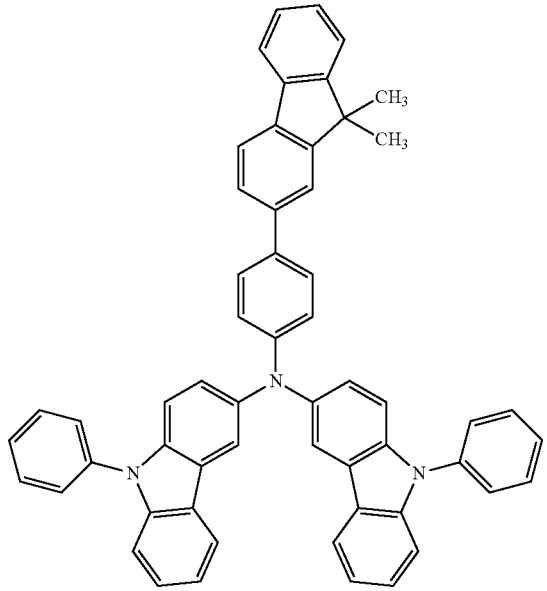
45
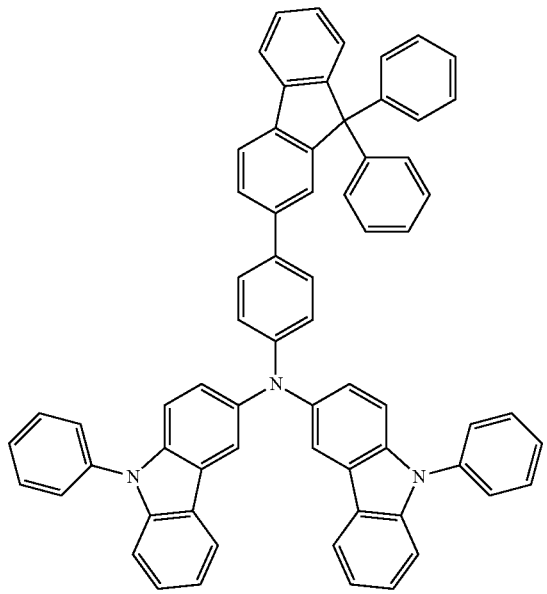
46
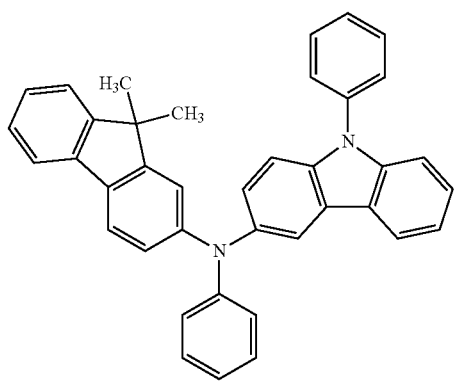

[Fifty-Fifth Chemical Formula]
47
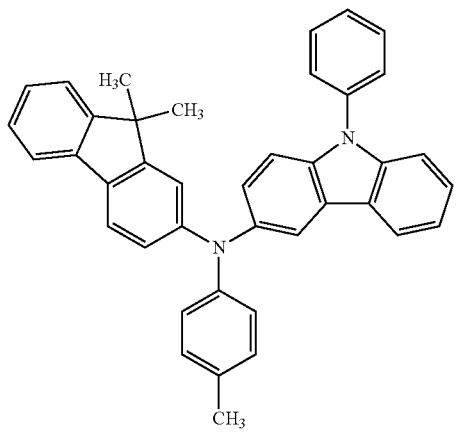
48
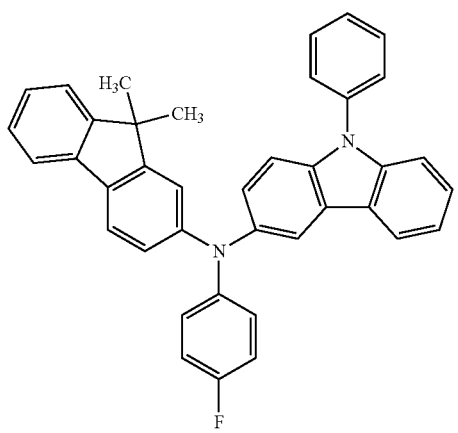
49
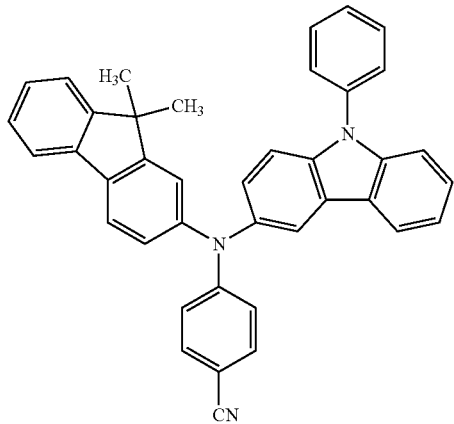
50
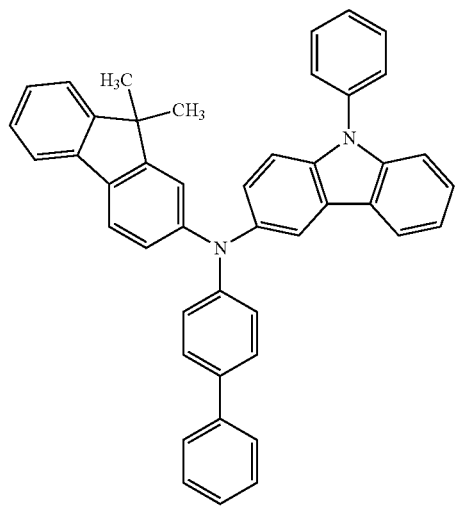
51
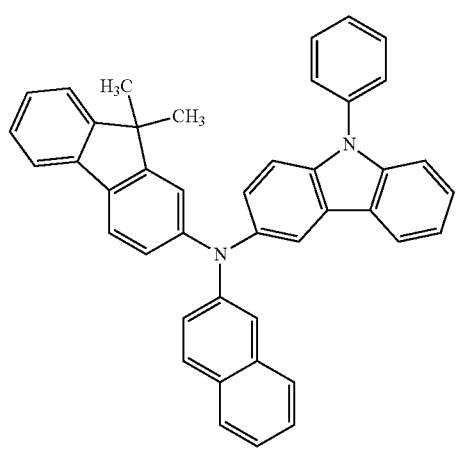
52
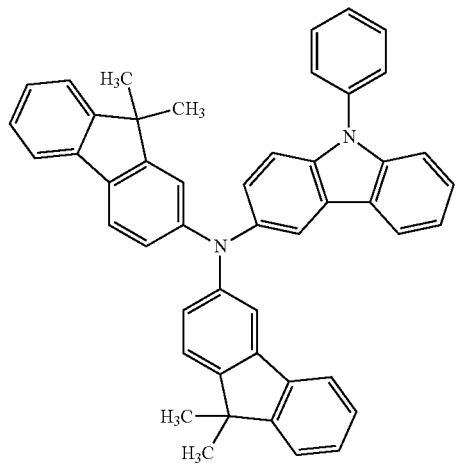

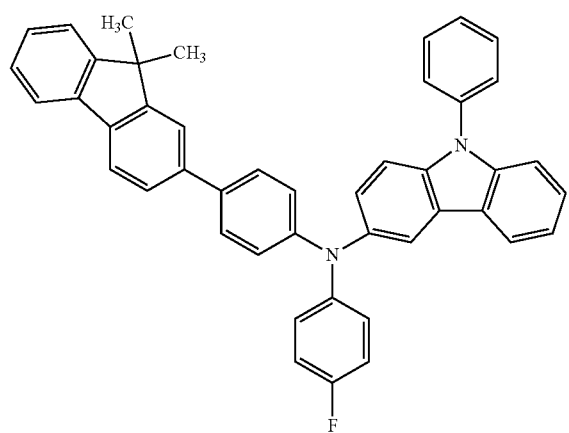
53
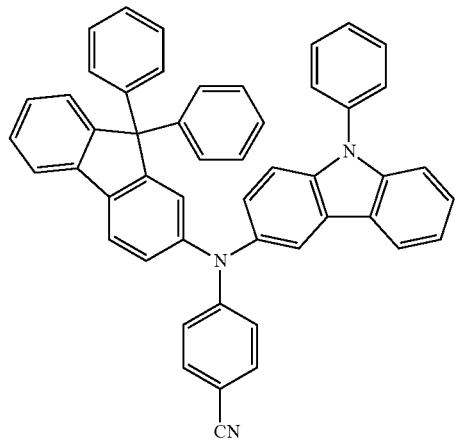
[Fifty-Sixth Chemical Formula]
56
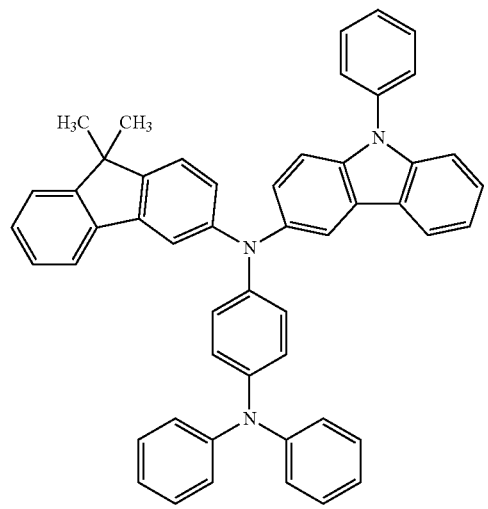
54
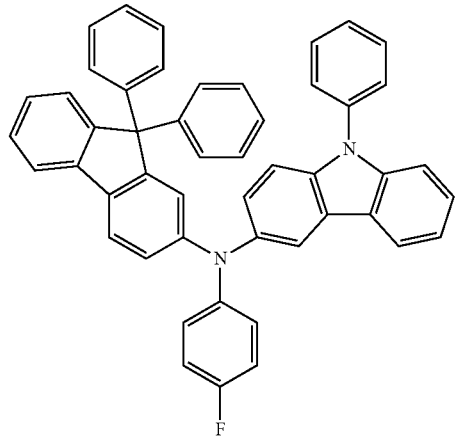
57
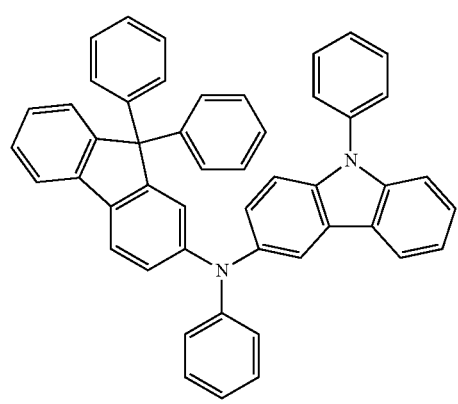
55
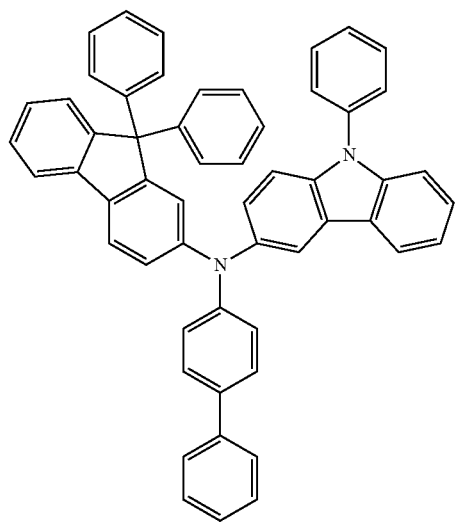
58

-continued

59
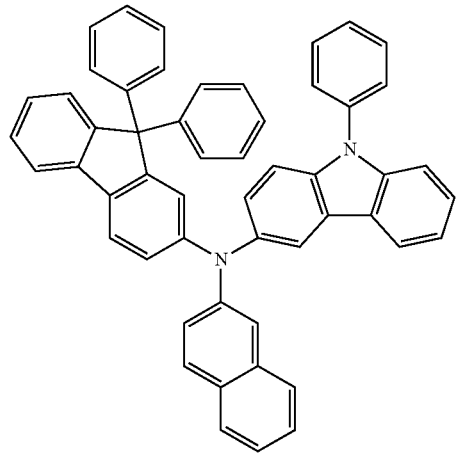

60
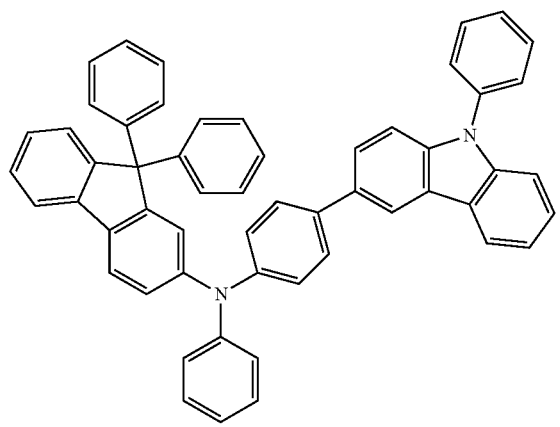

61
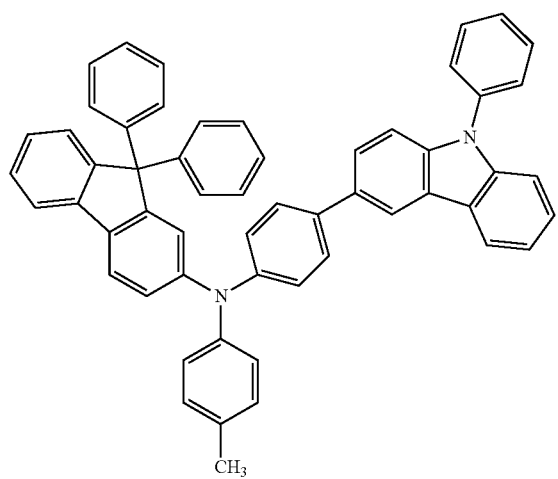

-continued

62
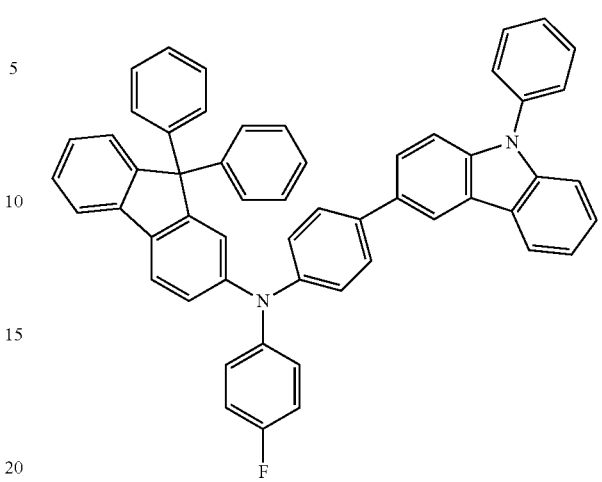

63
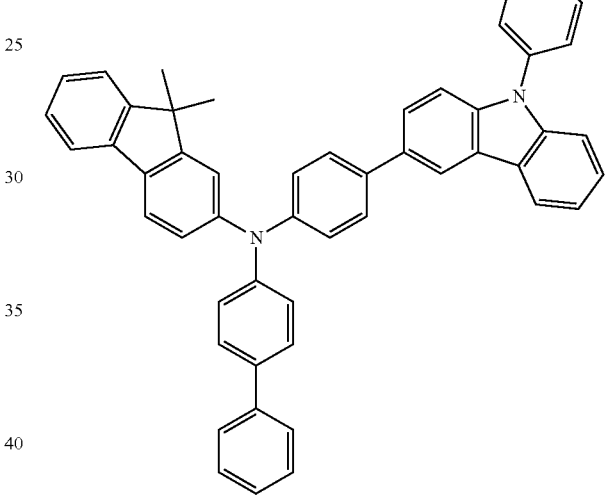

The compounds expressed by General Formula Sa-1, Sb-1, or Sc-1 above can be synthesized by the methods described in Japanese Laid-Open Patent Application 2007-318101. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the light-emitting element of the present invention, the compound expressed by General Formula Sa-1, Sb-1, or Sc-1 above is preferably contained in an organic layer between the aforementioned light-emitting layer and the aforementioned anode, and is more preferably contained in the layer adjacent to the light-emitting layer on the anode side among the [organic layers]. It is especially preferable if it is the hole transport material contained in the hole transport layer.

The compound expressed by General Formula Sa-1, Sb-1, or Sc-1 above is preferably contained in an amount of 70 to 100 wt % and more preferably 85 to 100 wt % with respect to the total weight of the organic layer to which [this compound is] added.

[Compound Expressed by General Formula M-3]

With the organic electroluminescence element of the present invention, at least one type of compound expressed by General Formula M-3 below can be cited as the material especially preferably used for the organic layers preferably disposed between the anode and the aforementioned light-emitting layer of (A) above.

The compound expressed by the aforementioned General Formula M-3 is more preferably contained in the organic layer adjacent to the light-emitting layer between the light-emitting layer and the anode, but there are no restrictions on its application, and it may additionally be contained in any of the [other] organic layers. The layer for introducing the compound expressed by the aforementioned General Formula M-3 can be one of the light-emitting layer, hole injection layer, hole transport layer, electron transport layer, electron injection layer, and charge blocking layer, or a plurality of [these layers].

The organic layer which is adjacent to the light-emitting layer between the light-emitting layer and the anode and which contains the compound expressed by the aforementioned General Formula M-3 is more preferably the electron blocking layer or hole transport layer.

[Fifty-Seventh Chemical Formula]

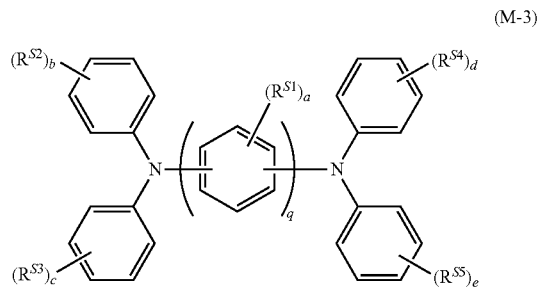

(M-3)

In General Formula M-3 above, $R^{S1}$ to $R^{S5}$ represent each independently an alkyl group, a cycloalkyl group, an alkenyl group, an alkynyl group, —CN, a perfluoroalkyl group, a trifluorovinyl group, —$CO_2R$, —C(O)R, —$NR_2$, —$NO_2$, —OR, a halogen atom, an aryl group, or a heteroaryl group, and may further have a substituent Z. The R [groups] represent each independently a hydrogen atom, an alkyl group, a perhaloalkyl group, an alkenyl group, an alkynyl group, a heteroalkyl group, an aryl group, or a heteroaryl group. When there are a plurality of $R^{S1}$ to $R^{S5}$ [groups], these may bond to each other to form a ring and may further have a substituent Z.

a represents an integer from 0 to 4, and when there are a plurality of $R^{S1}$ [groups], these may be the same or different and may also bond to each other to form a ring. b to e represent each independently an integer from 0 to 5. When there are a plurality of each of the $R^{S2}$ to $R^{S5}$ [groups], these may be the same or different, and any two may also bond together to form a ring.

q represents an integer from 1 to 5, and when q is 2 or more, the plurality of $R^{S1}$ [groups] may be the same or different and may also bond to each other to form a ring.

The alkyl group may have a substituent and may be either saturated or unsaturated, and examples of groups that may be substituted include the aforementioned substituents Z. The alkyl groups expressed by $R^{S1}$ to $R^{S5}$ are preferably alkyl groups with a total number of carbon atoms of 1 to 8 and more preferably alkyl groups with a total number of carbon atoms of 1 to 6, examples of which include a methyl group, ethyl group, i-propyl group, cyclohexyl group, and tert-butyl group.

The cycloalkyl group may have a substituent and may be either saturated or unsaturated, and examples of groups that may be substituted include the aforementioned substituents Z. The cycloalkyl groups represented by $R^{S1}$ to $R^{S5}$ are preferably cycloalkyl groups with 4 to 7 ring members and more preferably cycloalkyl groups with a total number of carbon atoms[7] of 5 or 6, examples of which include a cyclopentyl group and a cyclohexyl group.

[7]Translator's note: In the Japanese original document, the term for "ring members" and the term for "total number of carbon atoms" are used in the same phrase to specify the conditions being preferred, where only one or the other would be expected. Our translation faithfully reflects the Japanese source text.

The alkenyl group represented by $R^{S1}$ to $R^{S5}$ preferably has a carbon number of 2 to 30, more preferably a carbon number of 2 to 20, and especially preferably a carbon number of 2 to 10, examples including a vinyl, aryl, 1-propenyl, 1-isopropenyl, 1-butenyl, 2-butenyl, and 3-pentenyl.

The alkynyl group represented by $R^{S1}$ to $R^{S5}$ preferably has a carbon number of 2 to 30, more preferably a carbon number of 2 to 20, and especially preferably a carbon number of 2 to 10, examples including an ethynyl, propargyl, 1-propynyl, and 3-pentynyl.

Examples of the perfluoroalkyl group represented by $R^{S1}$ to $R^{S5}$ include the aforementioned alkyl groups in which all of the hydrogen atoms are substituted with fluorine atoms.

The aryl group represented by $R^{S1}$ to $R^{S5}$ is preferably a $C_6$ to $C_{30}$ substituted or unsubstituted aryl group, examples including a phenyl group, a tolyl group, a biphenyl group, and a terphenyl group.

The heteroaryl group represented by $R^{S1}$ to $R^{S5}$ is preferably a $C_5$ to $C_8$ heteroaryl group and more preferably a substituted or unsubstituted heteroaryl group with 5 or 6 members, examples including a pyridyl group, a pyrazinyl group, a pyridazinyl group, a pyrimidinyl group, a triazinyl group, a quinolinyl group, an isoquinolinyl group, a quinazolinyl group, a cinnolinyl group, a phthalazinyl group, a quinoxalinyl group, a pyrrolyl group, an indolyl group, a furyl group, a benzofuryl group, a thienyl group, a benzothienyl group, a pyrazolyl group, an imidazolyl group, a benzimidazolyl group, a triazolyl group, an oxazolyl group, a benzoxazolyl group, a thiazolyl group, a benzothiazolyl group, an isothiazolyl group, a benzisothiazolyl group, a thiadiazolyl group, an isoxazolyl group, a benzisoxazolyl group, a pyrrolidinyl group, a piperidinyl group, a piperazinyl group, an imidazolidinyl group, a thiazolinyl group, a sulfolanyl group, a carbazolyl group, a dibenzofuryl group, a dibenzothienyl group, and a pyridoindolyl group. Preferable examples are a pyridyl group, a pyrimidinyl group, an imidazolyl group, and a thienyl group, and more preferable are a pyridyl group and a pyrimidinyl group.

$R^{S1}$ to $R^{S5}$ are preferably a hydrogen atom, an alkyl group, a cyano group, a trifluoromethyl group, a perfluoroalkyl group, a dialkylamino group, a fluoro group, an aryl group, or a heteroaryl group, more preferably a hydrogen atom, an alkyl group, a cyano group, a trifluoromethyl group, a fluoro group, or an aryl group, and even more preferably a hydrogen atom, an alkyl group, or an aryl group. The substituents Z are preferably an alkyl group, an alkoxy group, a fluoro group, a cyano group, or a dialkylamino group, with a halogen atom or an alkyl group being more favorable.

Any two of $R^{S1}$ to $R^{S5}$ may bond to each other to form a condensed four- to seven-membered ring, this condensed four- to seven-membered ring is a cycloalkyl, aryl, or heteroaryl, and this condensed four- to seven-membered ring may further have a substituent Z. The definitions and preferred ranges for the cycloalkyl, aryl, or heteroaryl thus formed are the same as for the cycloalkyl group, aryl group, and heteroaryl group defined by $R^{S1}$ to $R^{S5}$.

When the compound expressed by General Formula M-3 above is used in the hole transport layer, the compound expressed by General Formula M-3 above is preferably contained in an amount of 50 to 100 wt %, [more] preferably 80 to 100 wt %, and especially preferably 95 to 100 wt %.

Furthermore, when the compound expressed by General Formula M-3 above is used in a plurality of organic layers, it is preferably contained in each of these layers in an amount within the aforementioned range.

The thickness of the hole transport layer that contains the compound expressed by General Formula M-3 above is preferably 1 to 500 nm, more preferably 3 to 200 nm, and even more preferably 5 to 100 nm. Moreover, this hole transport layer is preferably provided so as to be in contact with the light-emitting layer.

Concrete examples of the compound expressed by General Formula M-3 above are shown below, but the present invention is not limited to or by these:

[Fifty-Eighth Chemical Formula]

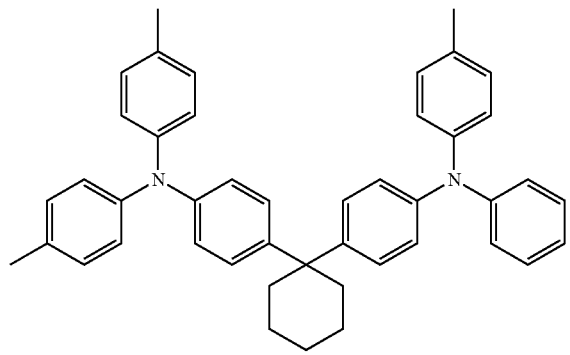
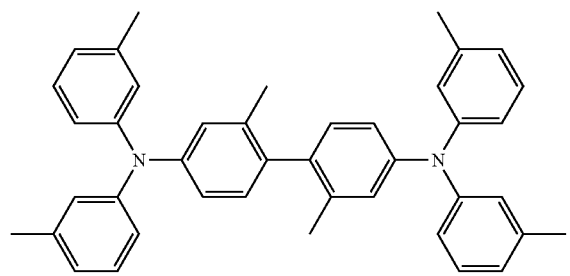
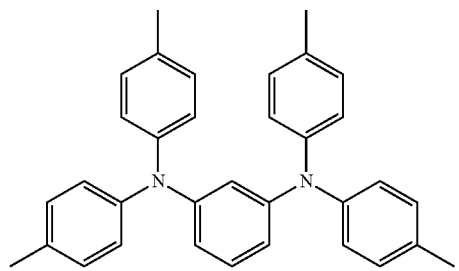
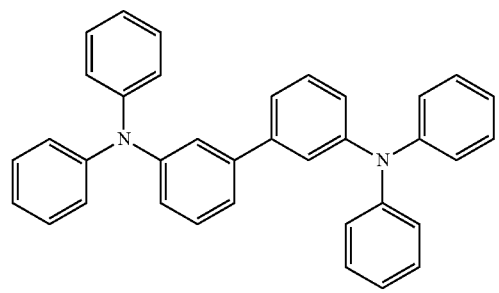
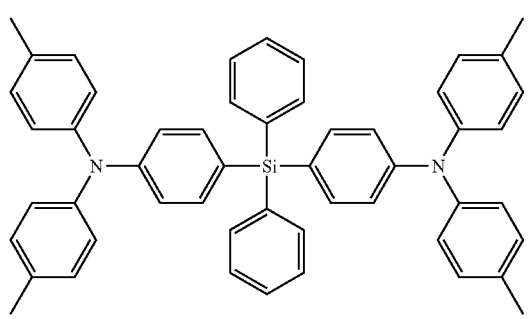
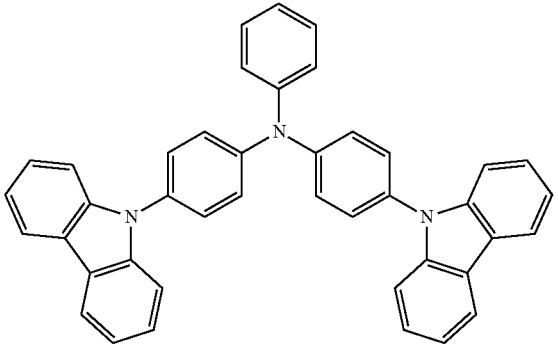

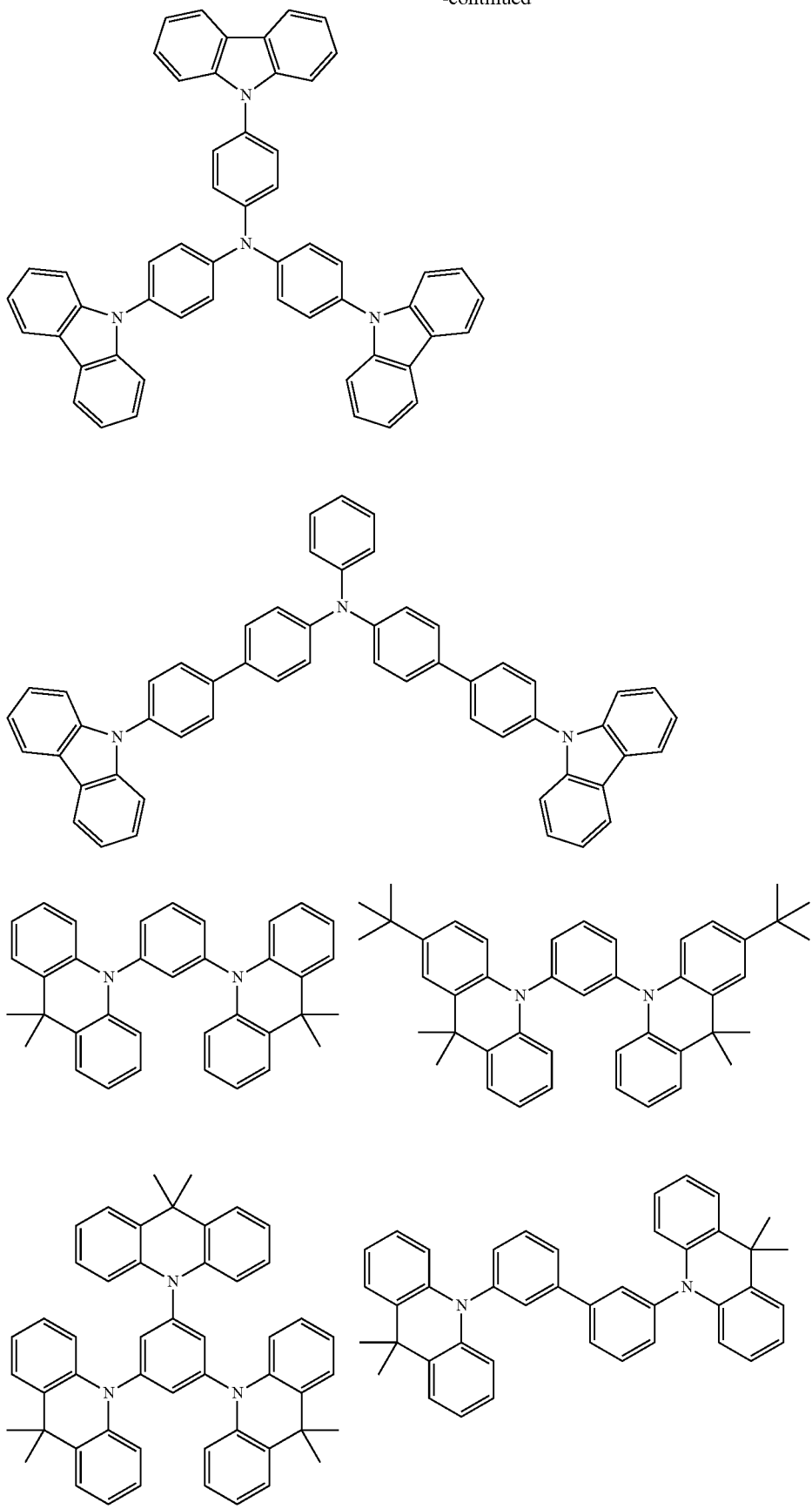

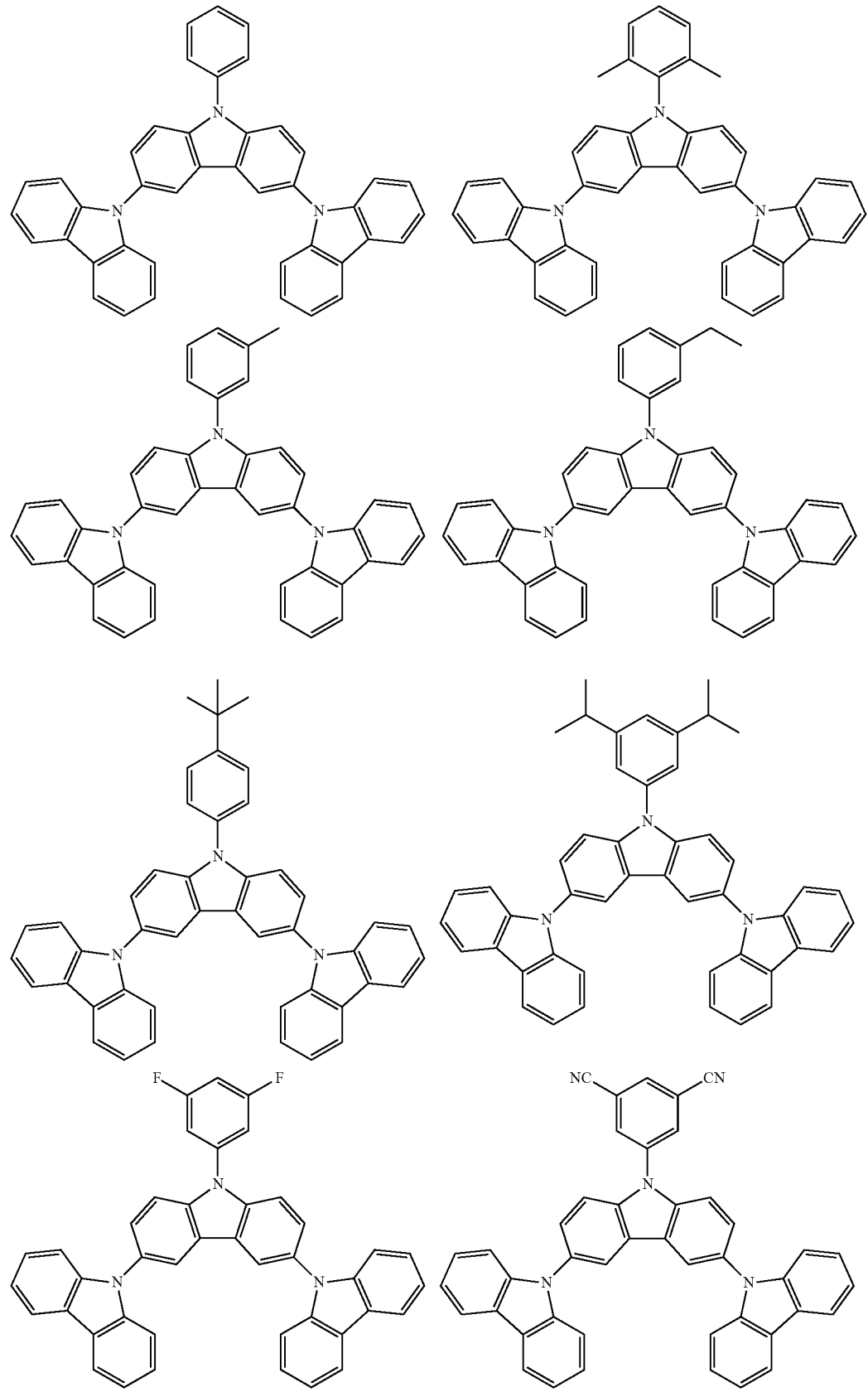
[Fifty-Ninth Chemical Formula]

127
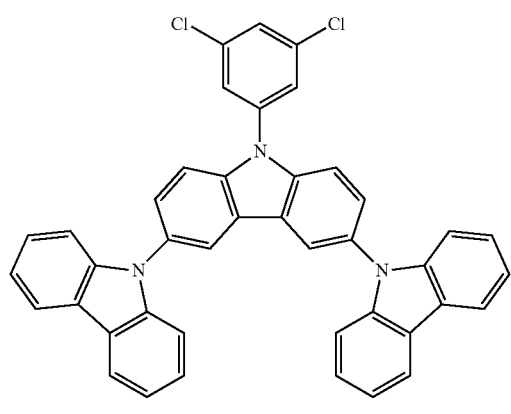
128
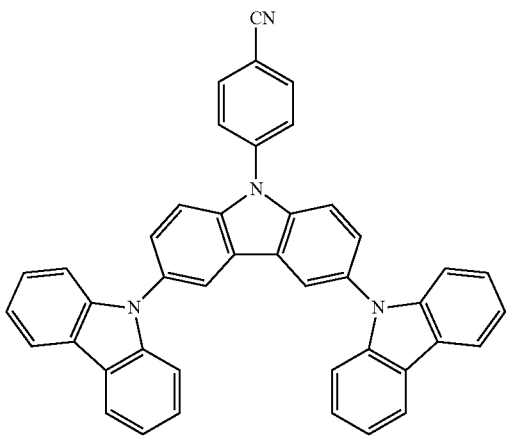
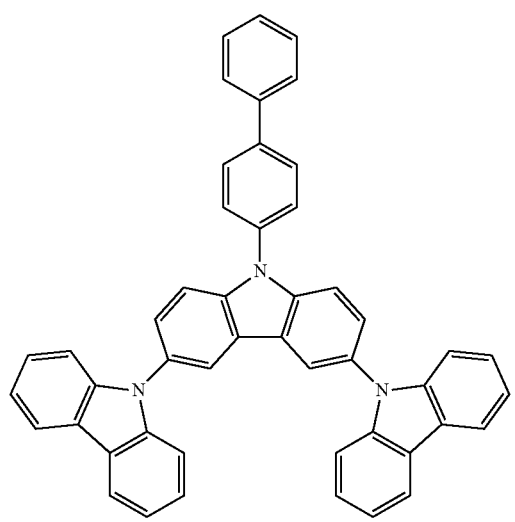
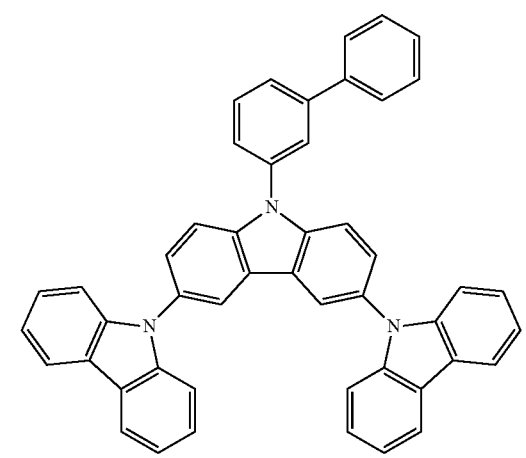
[Sixtieth Chemical Formula]
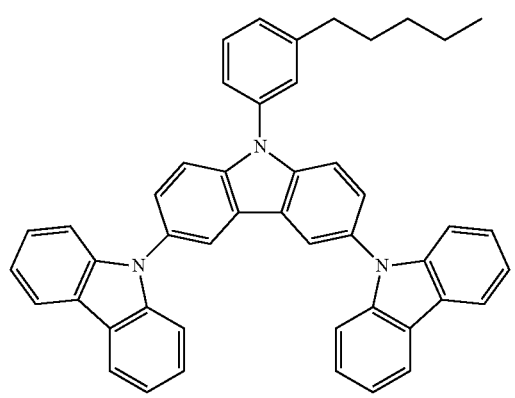
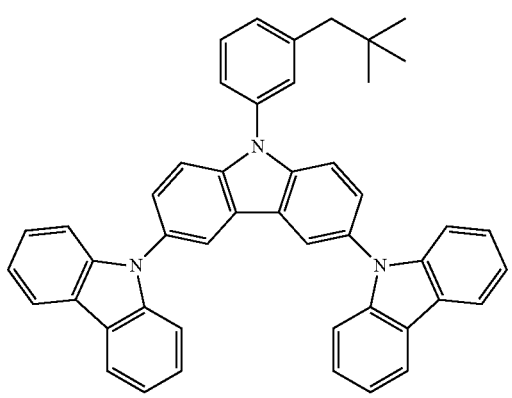

129 130
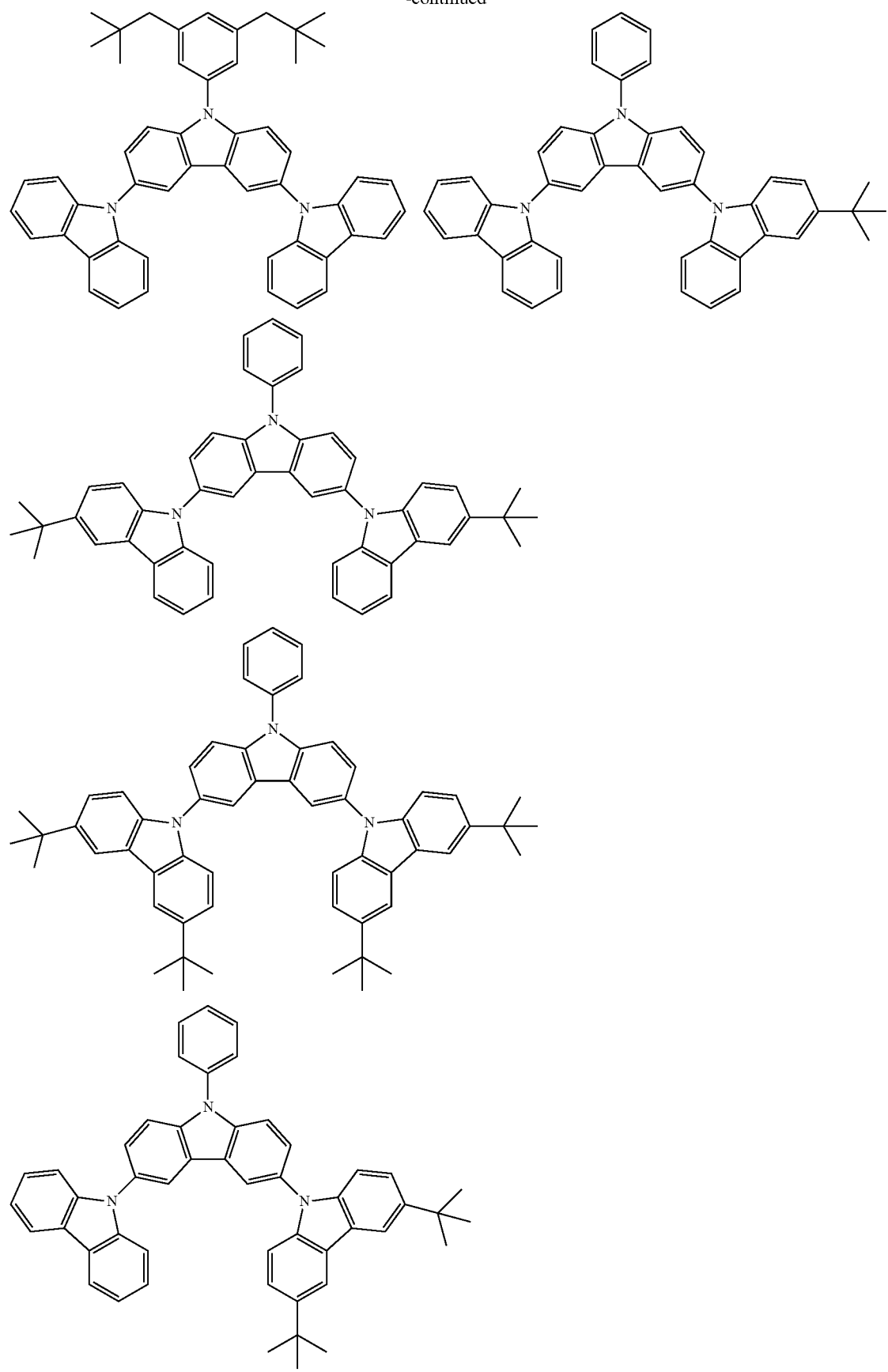
-continued

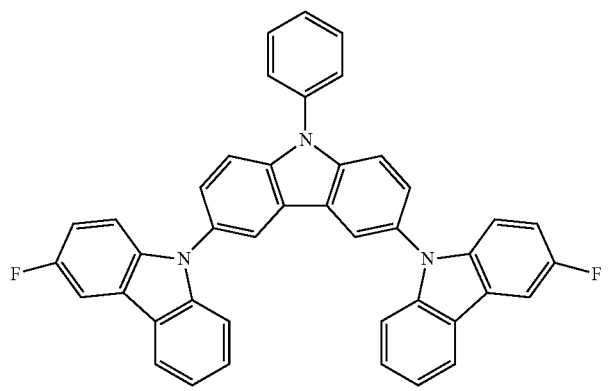
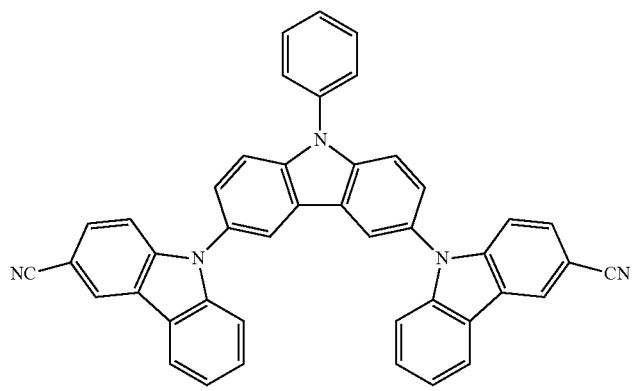
[Sixty-First Chemical Formula]
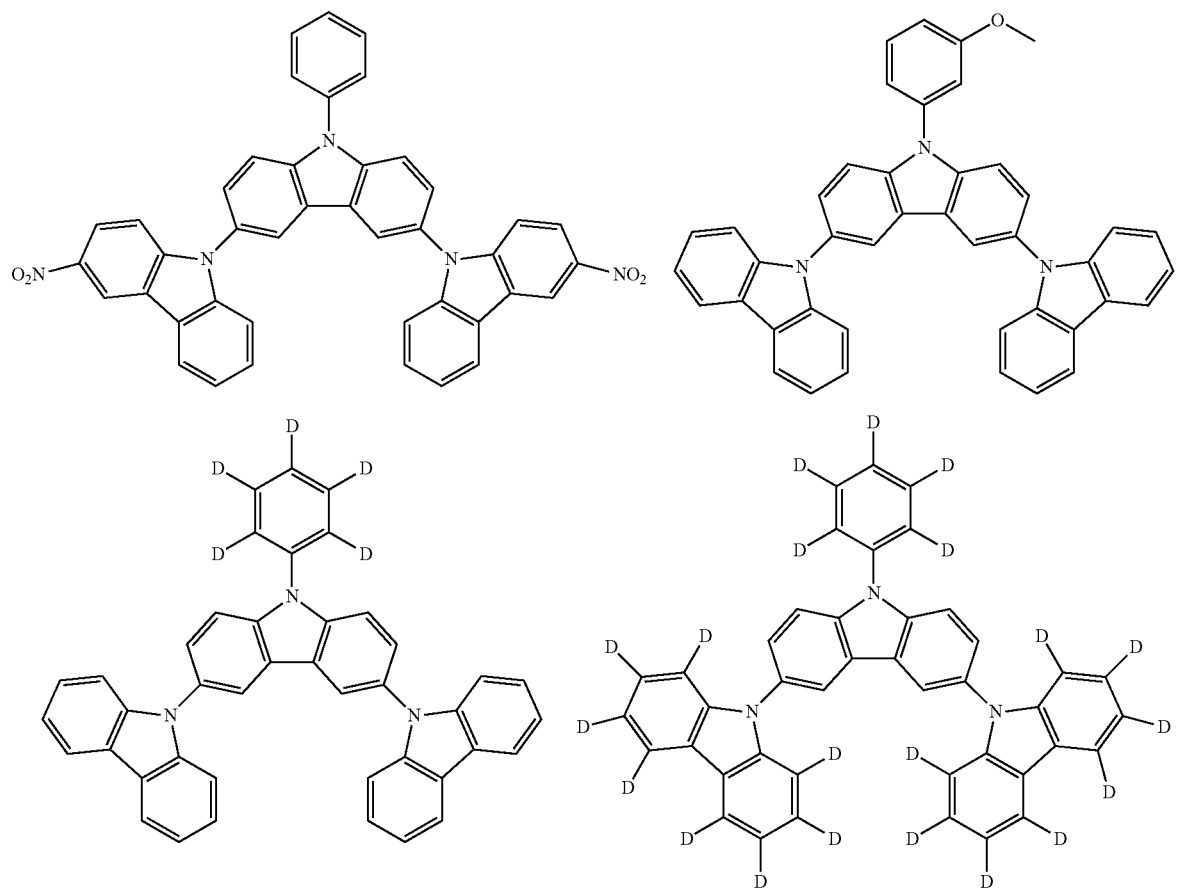

-continued
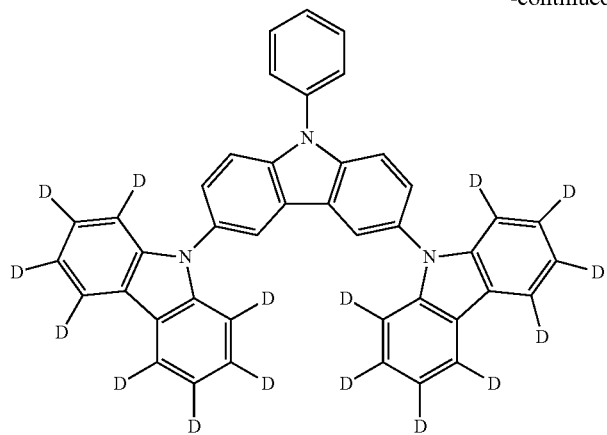
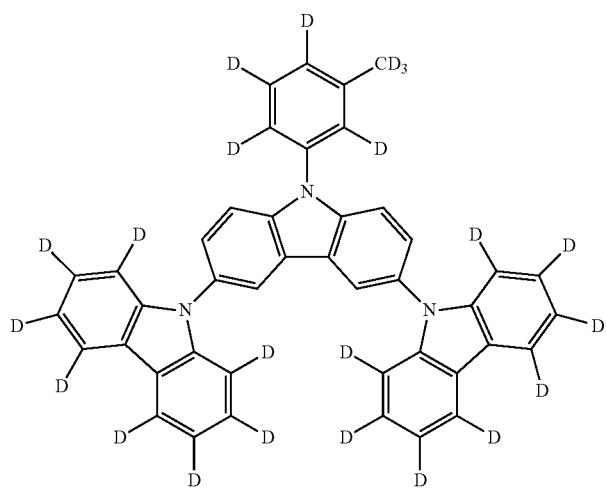
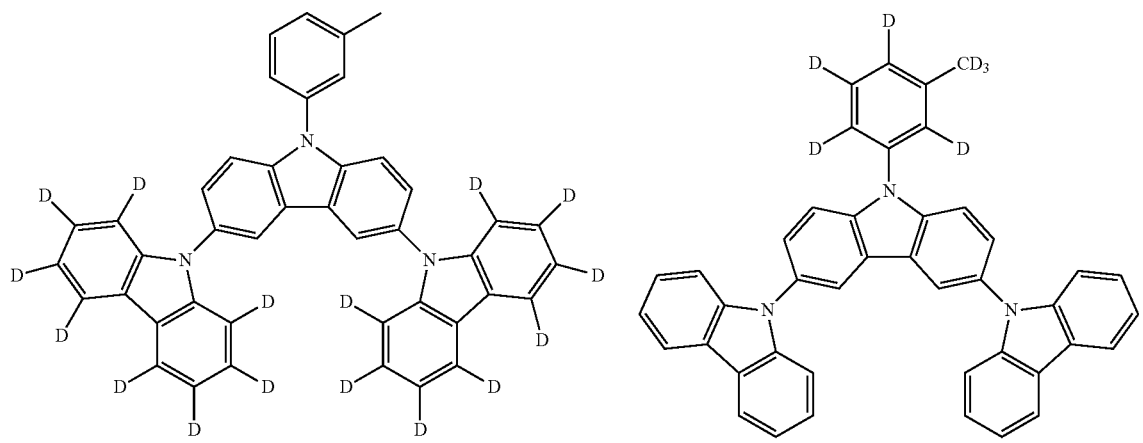

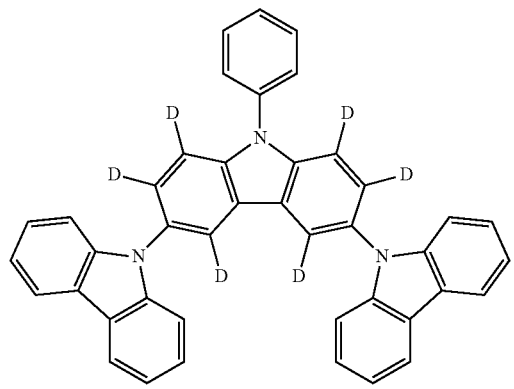
[Sixty-Second Chemical Formula]
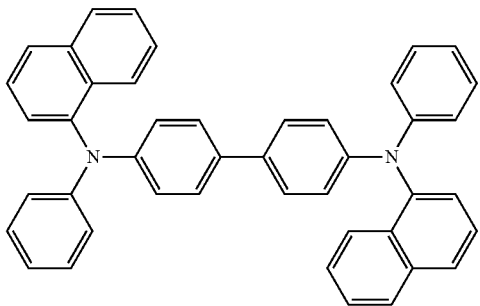
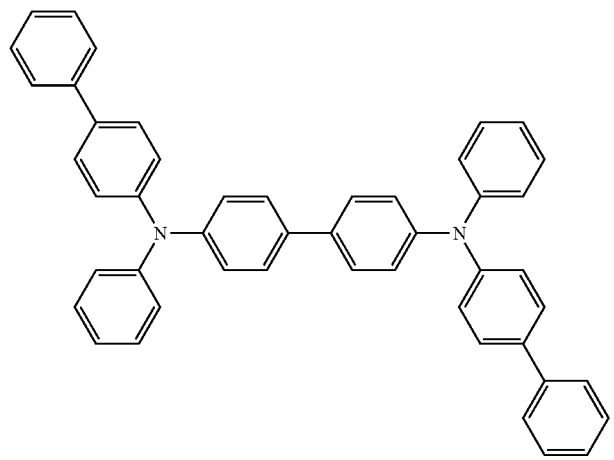
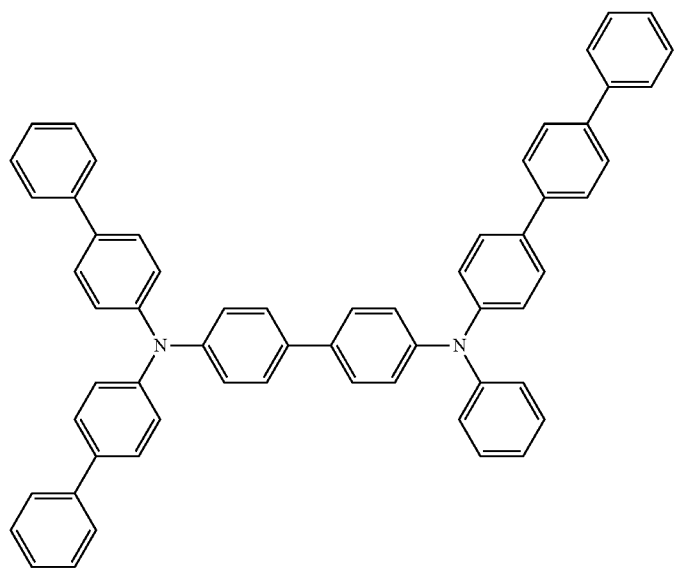

-continued

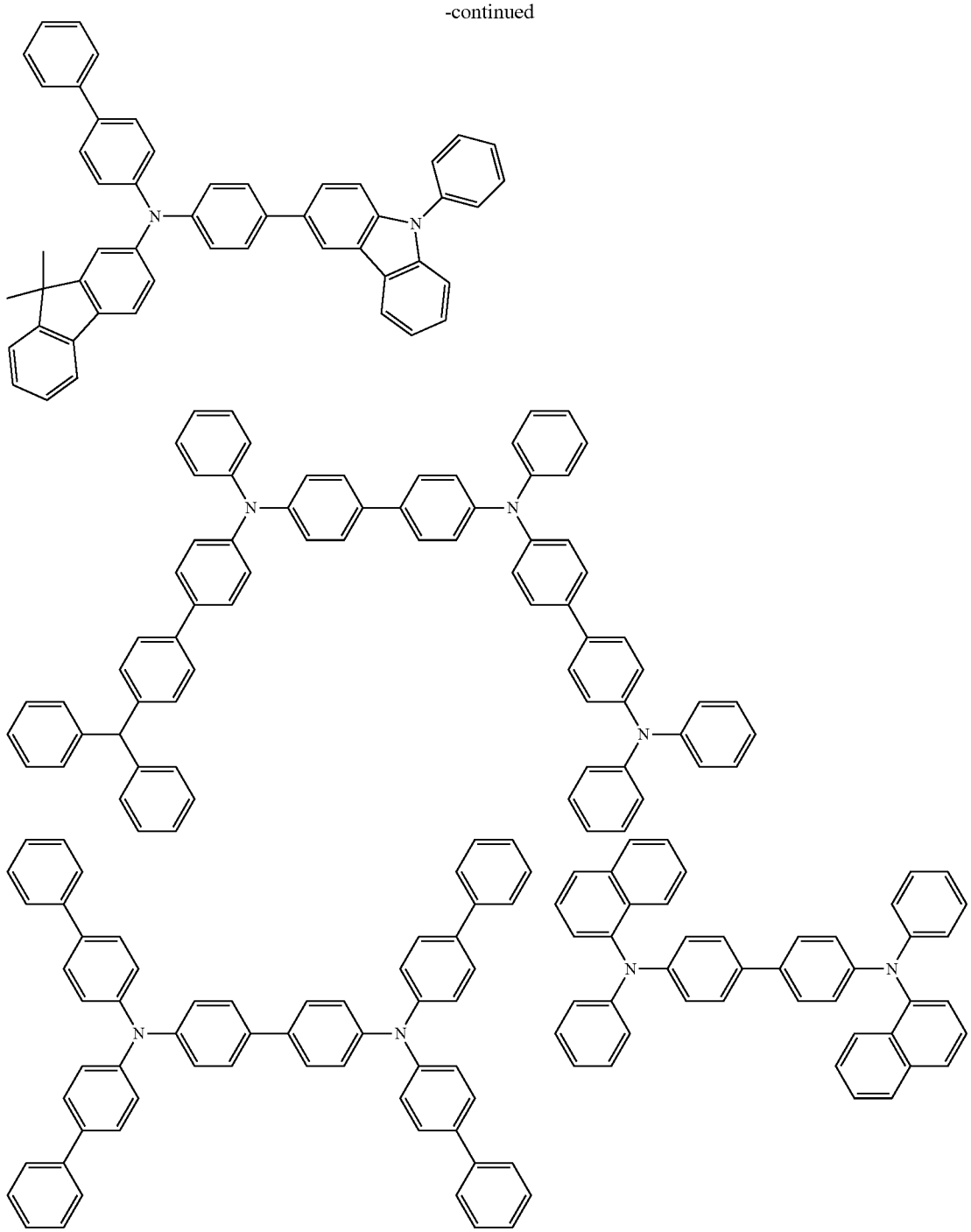

Besides these, regarding the hole injection layer and hole transport layer, what is stated in paragraph numbers [0165] to [0167] of Japanese Laid-Open Patent Application 2008-270736 can be applied to the present invention. In addition, what is stated in [0250] to [0339] of Japanese Laid-Open Patent Application 2011-71452 can also be applied to the hole injection layer and hole transport layer of the present invention. It is also preferable for the compound expressed by General Formula 1 above to be applied to the hole injection layer and hole transport layer.

The hole injection layer preferably contains an electron-accepting dopant. The effects of having the hole injection layer contain an electron-accepting dopant are that hole injection is enhanced, drive voltage decreases, efficiency is higher, and so forth. The electron-accepting dopant may be either an organic material or inorganic material as long as it is a material capable of pulling electrons from the doped material and generating radical cations, but examples include tetracyanoquinodimethane (TCNQ), tetrafluorotetracyanoquinodimethane ($F_4$-TCNQ), and molybdenum oxide.

The electron-accepting dopant in the hole injection layer is preferably contained in an amount of 0.01 to 50 wt %, more preferably 0.1 to 40 wt %, and even more preferably 0.2 to 30 wt %, with respect to the weight of all the compounds forming the hole injection layer.

(A-2) Electron Blocking Layer

The electron blocking layer is a layer having the function of preventing the electrons transported from the cathode side to the light-emitting layer from escaping to the anode side. In the present invention, an electron blocking layer can be provided as an organic layer that is adjacent to the light-emitting layer on the anode side.

As examples of organic compounds that constitute an electron blocking layer, those listed above as examples of hole transport materials can be used.

The thickness of the electron blocking layer is preferably 1 to 500 nm, more preferably 3 to 100 nm, and even more preferably 5 to 50 nm.

The electron blocking layer may have a single-layer structure composed of one or more types of the aforementioned materials, or may have a multilayer structure composed of a plurality of layers of the same composition or different compositions.

From the standpoints of color purity, luminous efficiency, and drive durability, the material used in the electron blocking layer preferably has [a $S_1$ energy] higher than the $S_1$ energy of the aforementioned light-emitting material. The $S_1$ in a film state of the material used in the electron blocking layer is preferably at least 0.1 eV higher than the $S_1$ of the light-emitting material, more preferably at least 0.2 eV higher, and even more preferably at least 0.3 eV higher.

(B) Organic Layers Preferably Disposed Between the Cathode and the Aforementioned Light-Emitting Layer Next, (B) organic layers preferably disposed between the aforementioned cathode and the aforementioned light-emitting layer will be described.

(B-1) Electron Injection Layer and Electron Transport Layer

The electron injection layer and the electron transport layer are layers having the function of accepting electrons from the cathode or the cathode side and transporting them to the anode side. The electron injection material and electron transport material used for these layers may be compounds with either a low or a high molecular weight.

The compounds expressed by General Formula 1 above, for example, can be used as electron transport materials. Other electron transport materials are preferably selected from among a pyridine derivative, a quinoline derivative, a pyrimidine derivative, a pyrazine derivative, a phthalazine derivative, a phenanthroline derivative, a triazine derivative, a triazole derivative, an oxazole derivative, an oxadiazole derivative, an imidazole derivative, a benzimidazole derivative, an imidazopyridine derivative, a fluorenone derivative, an anthraquinodimethane derivative, an anthrone derivative, a diphenylquinone derivative, a thiopyran dioxide derivative, a carbodiimide derivative, a fluorenylidenemethane derivative, a distyrylpyrazine derivative, an aromatic tetracarboxylic acid anhydride such as naphthalene and perylene, a phthalocyanine derivative, various metal complexes typified by metal complexes of an 8-quinolinol derivative, metal phthalocyanine, and metal complexes having benzoxazole or benzothiazole as a ligand, an organic silane derivative typified by silole, and condensed ring hydrocarbon compounds (such as naphthalene, anthracene, phenanthrene, triphenylene, and pyrene), and the like, with a pyridine derivative, a benzimidazole derivative, an imidazopyridine derivative, a metal complex, or a condensed ring hydrocarbon compound being more preferable.

From the standpoint of lowering the drive voltage, the thickness of the electron injection layer and electron transport layer is preferably no more than 500 nm for each.

The thickness of the electron transport layer is preferably 1 to 500 nm, more preferably 5 to 200 nm, and even more preferably 10 to 100 nm. In addition, the thickness of the electron injection layer is preferably 0.1 to 200 nm, more preferably 0.2 to 100 nm, and even more preferably 0.5 to 50 nm.

The electron injection layer and the electron transport layer may have a single-layer structure composed of one or more types of the aforementioned materials, or a multilayer structure composed of a plurality of layers of the same composition or different compositions.

The electron injection layer preferably contains an electron-donating dopant. The effects of having the electron injection layer contain an electron-donating dopant are that electron injection is enhanced, drive voltage decreases, efficiency is higher, and so forth. The electron-donating dopant may be either an organic material or inorganic material as long as it is a material capable of giving electrons to the doped material and generating radical anions, but examples include tetrathiafulvalene (TTF), tetrathianaphthacene (TTT)[sic][8], bis-[1,3-diethyl-2-methyl-1,2-dihydrobenzimidazolyl] and other such dihydroimidazole compounds, lithium, and cesium.

[8]Translator's note: The abbreviation of "tetrathianaphthacene" should be "TTN," and "TTT" is "tetrathiatetracene," so this abbreviation "TTT" here seems to be an error in the original for "TTN."

The electron-donating dopant in the electron injection layer is preferably contained in an amount of 0.01 to 50 wt %, more preferably 0.1 to 40 wt %, and even more preferably 0.5 to 30 wt %, with respect to the weight of all the compounds forming the electron injection layer.

(B-2) Hole Blocking Layer

The hole blocking layer is a layer having the function of preventing the holes transported from the anode side to the light-emitting layer from escaping to the cathode side. In the present invention, a hole blocking layer can be provided as an organic layer that is adjacent to the light-emitting layer on the cathode side.

The $S_1$ energy in a film state of the organic compound constituting the hole blocking layer is preferably higher than the $S_1$ energy of the light-emitting material for the purpose of preventing energy movement of excitons generated in the light-emitting layer, thus preventing a decrease in luminous efficiency.

The compounds expressed by General Formula 1 above can be used as examples of organic compounds that constitute a hole blocking layer.

Examples of other organic compounds that constitute a hole blocking layer other than the compounds expressed by General Formula 1 above include aluminum(III) bis(2-methyl-8-quinolinato) 4-phenylphenolate (abbreviated as BAlq) and other such aluminum complexes, triazole derivatives, and phenanthroline derivatives such as 2,9-dimethyl-4,7-diphenyl-1,10-phenanthroline (abbreviated as BCP).

The thickness of the hole blocking layer is preferably 1 to 500 nm, more preferably 3 to 100 nm, and even more preferably 5 to 50 nm.

The hole blocking layer may have a single-layer structure composed of one or more types of the aforementioned materials, or may have a multilayer structure composed of a plurality of layers of the same composition or different compositions.

From the standpoints of color purity, luminous efficiency, and drive durability, the material used in the hole blocking layer preferably has [a $S_1$ energy] higher than the $S_1$ energy of the aforementioned light-emitting material. The $S_1$ in a film state of the material used in the hole blocking layer is preferably at least 0.1 eV higher than the $S_1$ of the light-emitting material, more preferably at least 0.2 eV higher, and even more preferably at least 0.3 eV higher.

(B-3) Materials Especially Preferably Used in the Organic Layers Preferably Disposed Between the Cathode and the Aforementioned Light-Emitting Layer In the organic electroluminescence element of the present invention, examples of materials especially preferably used as the materials of (B) the organic layers preferably disposed between the cathode and the aforementioned light-emitting layer include a compound expressed by General Formula 1 above, a compound expressed by General Formula P-1 below, and a compound expressed by General Formula O-1 below.

Compounds expressed by the aforementioned General Formula O-1 and compounds expressed by the aforementioned General Formula P-1 will be described below.

The organic electroluminescence element of the present invention preferably includes at least one organic layer between the light-emitting layer and the cathode, and from the standpoints of the drive voltage and efficiency of the element, this organic layer preferably contains at least one type of compound expressed by General Formula O-1 below. General Formula O-1 will be described below:

[Sixty-Third Chemical Formula]

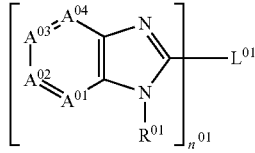

General Formula O-1

(In General Formula O-1, $R^{O1}$ represents an alkyl group, an aryl group, or a heteroaryl group. $A^{O1}$ to $A^{O4}$ represent each independently C—$R^A$ or a nitrogen atom. $R^A$ represents a hydrogen atom, an alkyl group, an aryl group, or a heteroaryl group, and the plurality of $R^A$ [groups] may be the same or different. $L^{O1}$ represents a divalent to hexavalent linking group composed of an aryl ring or a heteroaryl ring. $n^{O1}$ represents an integer from 2 to 6.)

$R^{O1}$ represents an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. $R^{O1}$ is preferably an aryl group or a heteroaryl group and more preferably an aryl group. Substituents that are preferable when the aryl group of $R^{O1}$ has a substituent include an alkyl group, an aryl group, and a cyano group, with an alkyl group or aryl group being more preferable, and an aryl group being even more preferable. If the aryl group of $R^{O1}$ has a plurality of substituents, the plurality of substituents may bond to each other to form a five- or six-membered ring. The aryl group of $R^{O1}$ is preferably a phenyl group that may have a substituent selected from Substituent Group A, more preferably a phenyl group that may be substituted with an alkyl group or an aryl group, and even more preferably an unsubstituted phenyl group or a 2-phenylphenyl group.

$A^{O1}$ to $A^{O4}$ represent each independently C—$R^A$ or a nitrogen atom. It is preferable for zero to two of $A^{O1}$ to $A^{O4}$ to be a nitrogen atom, and it is more preferable for zero or one to be a nitrogen atom. Preferably all of $A^{O1}$ to $A^{O4}$ are C—$R^A$, or $A^{O1}$ is a nitrogen atom and $A^{O2}$ to $A^{O4}$ are C—$R^A$, more preferably $A^{O1}$ is a nitrogen atom and $A^{O2}$ to $A^{O4}$ are C—$R^A$, and even more preferably $A^{O1}$ is a nitrogen atom, $A^{O2}$ to $A^{O4}$ are C—$R^A$, and all of the $R^A$ [groups] are hydrogen atoms.

$R^A$ represents a hydrogen atom, an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. Furthermore, the plurality of $R^A$ [groups] may be the same or different. $R^A$ is preferably a hydrogen atom or an alkyl group and more preferably a hydrogen atom.

$L^{O1}$ represents a divalent to hexavalent linking group composed of an aryl ring (preferably $C_6$ to $C_M$) or a heteroaryl ring (preferably $C_4$ to $C_{12}$). $L^{O1}$ is preferably an arylene group, a heteroarylene group, an aryltolyl group, or a heteroaryltolyl group, more preferably a phenylene group, a biphenylene group, or a benzenetriyl group, and even more preferably a biphenylene group or a benzenetriyl group. $L^{O1}$ may have a substituent selected from the aforementioned Substituent Group A, and if there is a substituent, the substituent is preferably an alkyl group, an aryl group, or a cyano group. Concrete examples of $L^{O1}$ are listed below:

[Sixty-Fourth Chemical Formula]

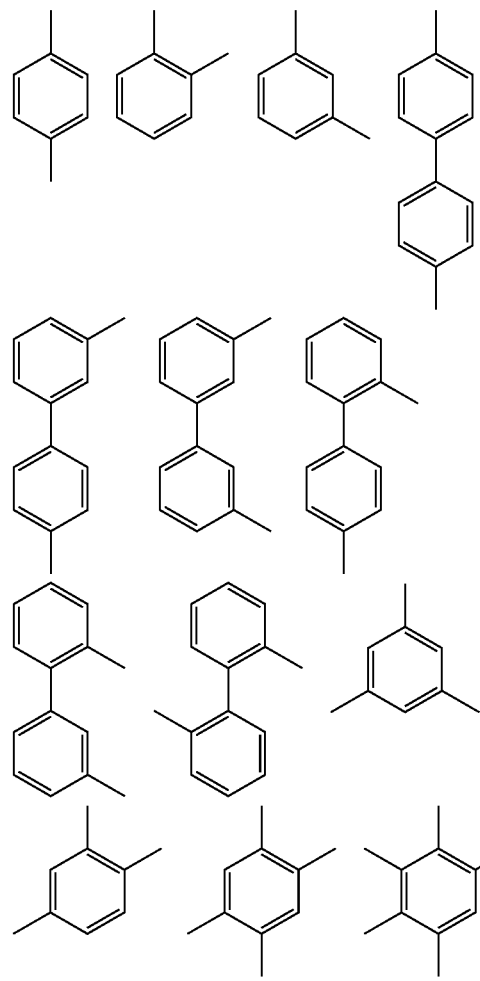

-continued

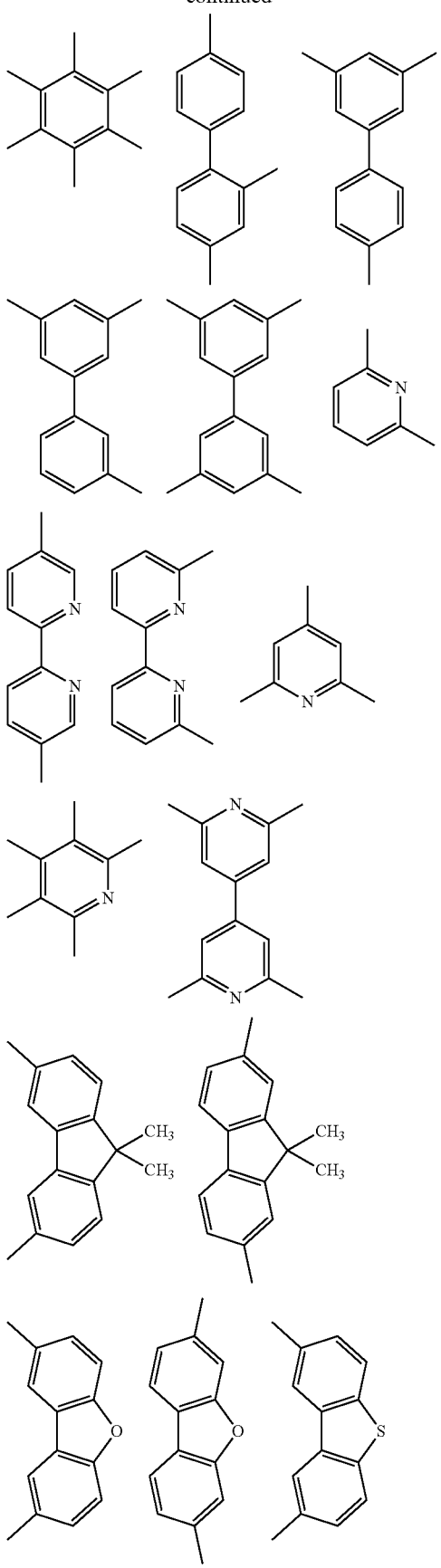

-continued

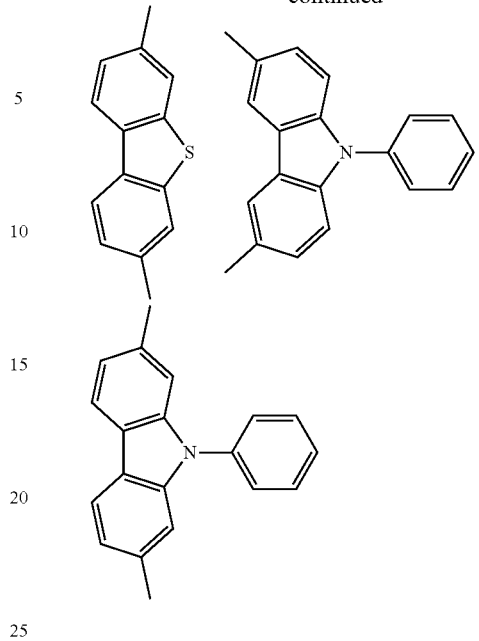

$n^{O1}$ represents an integer from 2 to 6, preferably an integer from 2 to 4, and more preferably 2 or 3. From the standpoint of efficiency of the element, $n^{O1}$ is most preferably 3, and from the standpoint of durability of the element, 2 is most preferable.

From the standpoints of stability during high-temperature storage and stable operation with respect to heat emission during high-temperature drive and during drive [sic], the glass transition temperature (Tg) of the compound expressed by General Formula O-1 above is preferably from 100° C. to 300° C., more preferably from 120° C. to 300° C., even more preferably from 120° C. to 300° C. [sic][9], and even still more preferably from 140° C. to 300° C.

[9]Translator's note: The phrase "from 120° C. to 300° C." is erroneously repeated in the original to describe even more preferable conditions.

Concrete examples of the compound expressed by General Formula O-1 will be given below, but it should not be construed that the compounds expressed by General Formula O-1 that can be used in the present invention are limited to or by these concrete examples:

[Sixty-Fifth Chemical Formula]

OM-1

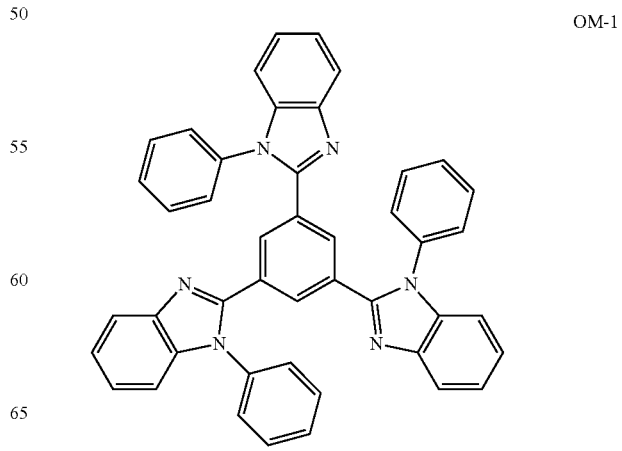

OM-2
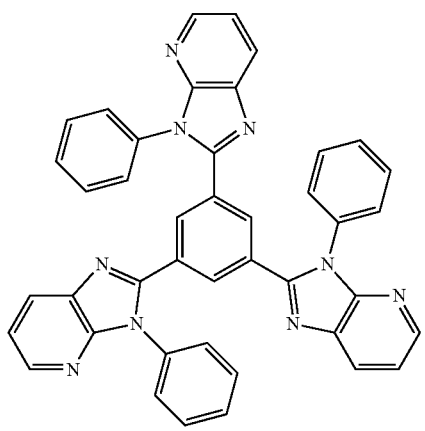
OM-3
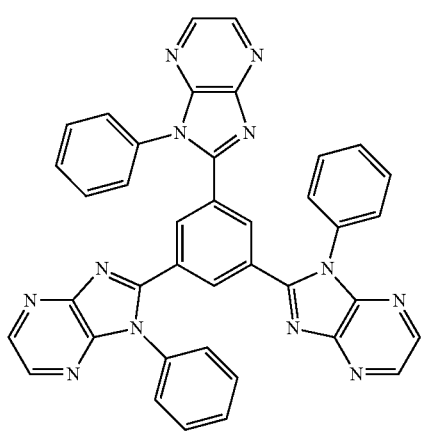
OM-4
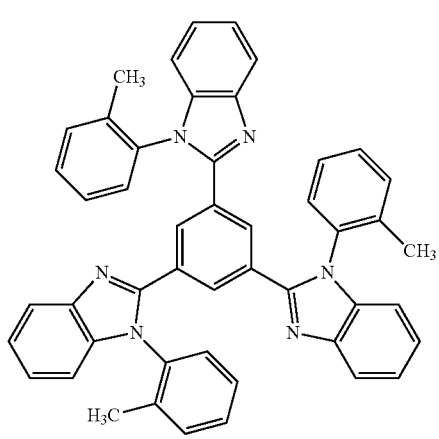
OM-5
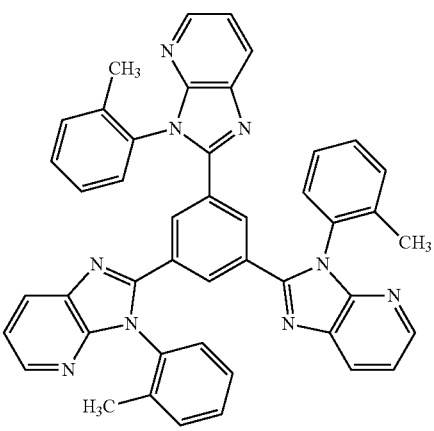
OM-6
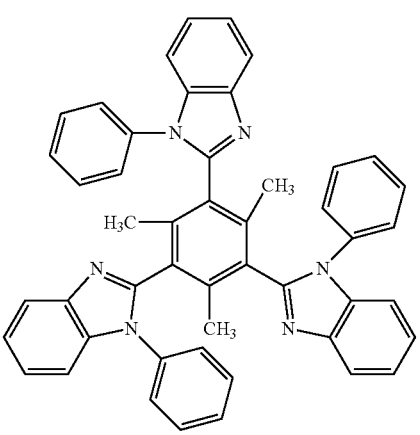
OM-7
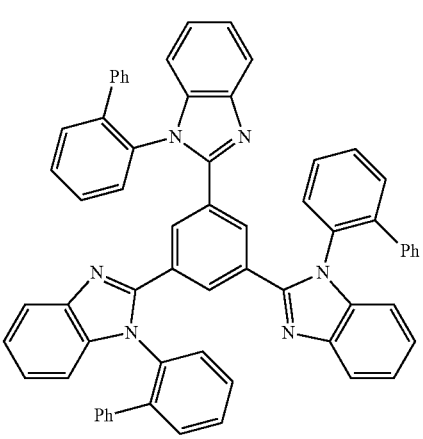

OM-8
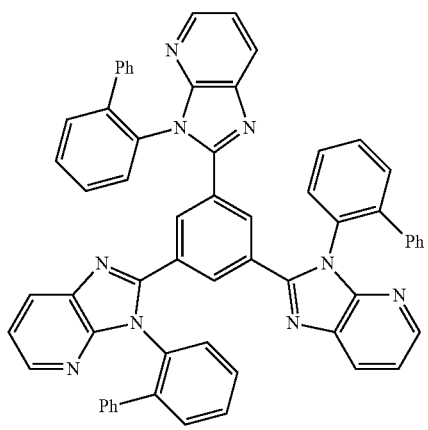
OM-9
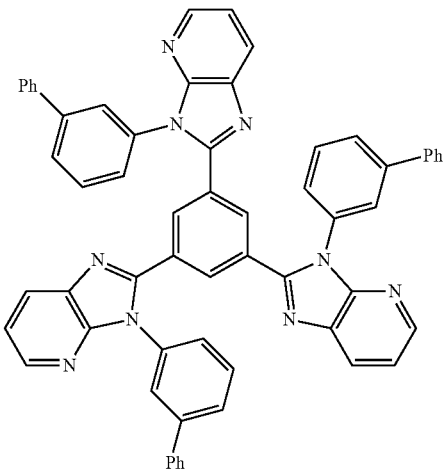
[Sixty-Sixth Chemical Formula]
OM-10
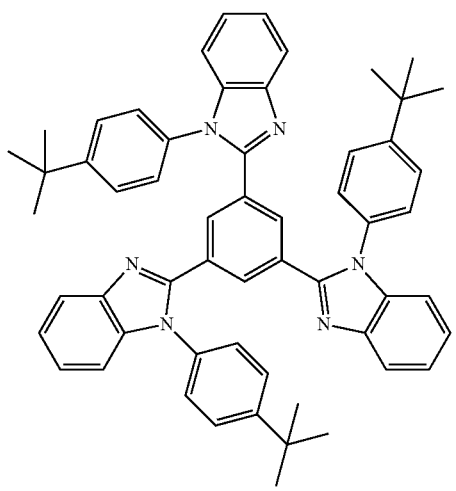
OM-11
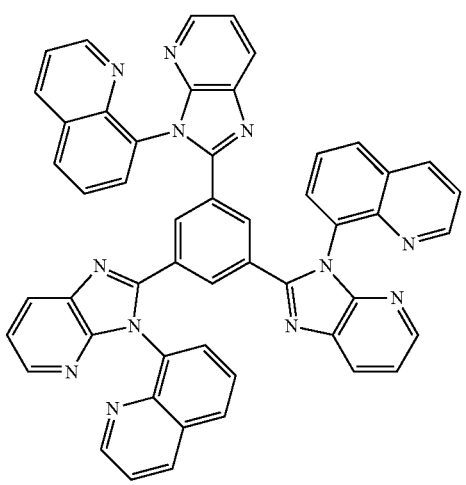
OM-12
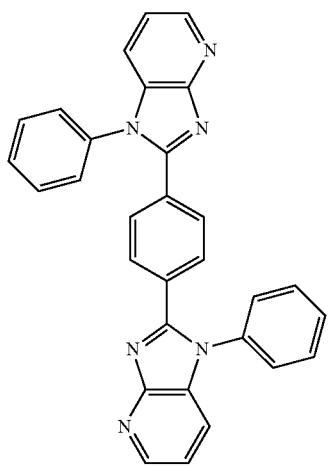
OM-13
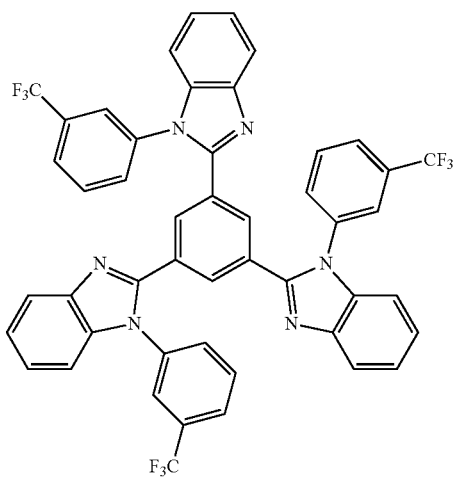

OM-14
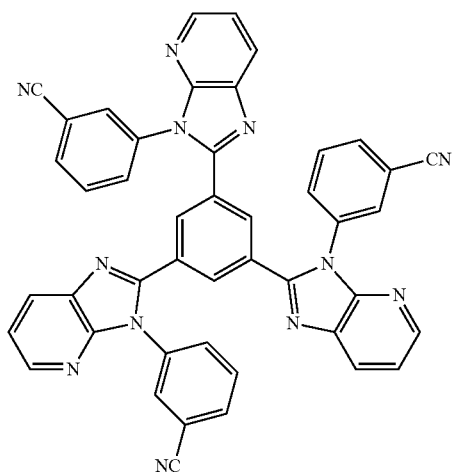
OM-15
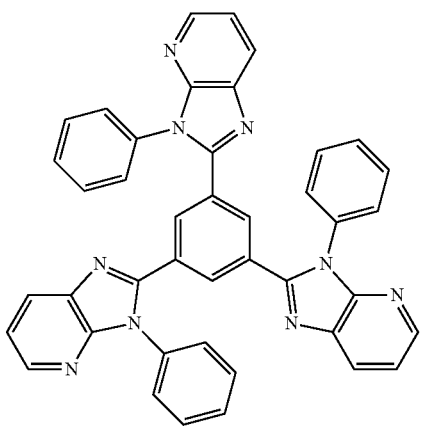
OM-16
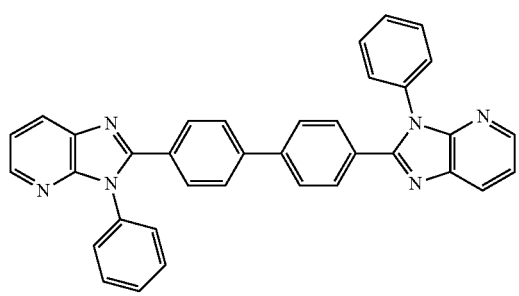
OM-17
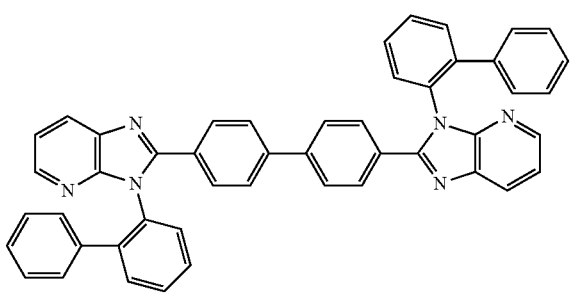
OM-18
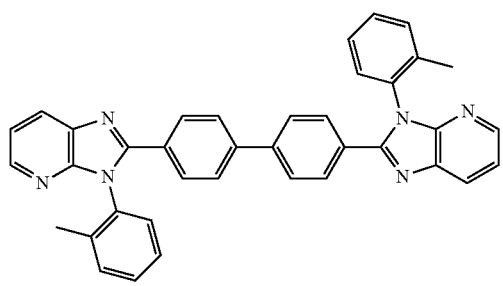
OM-19
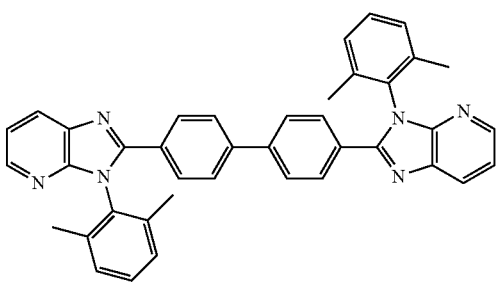
OM-20
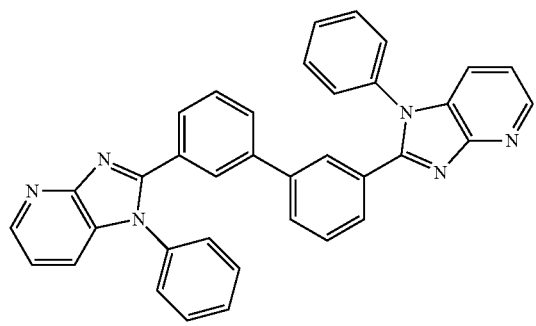

-continued

OM-21

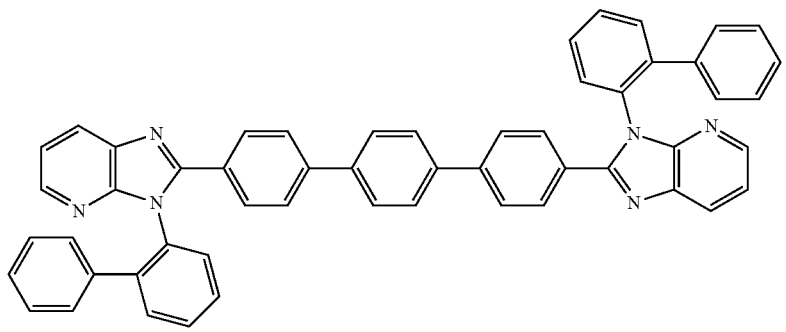

OM-22

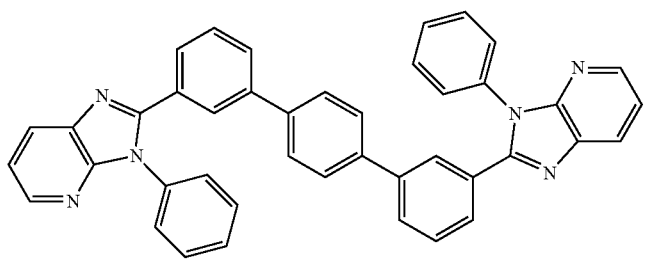

OM-23

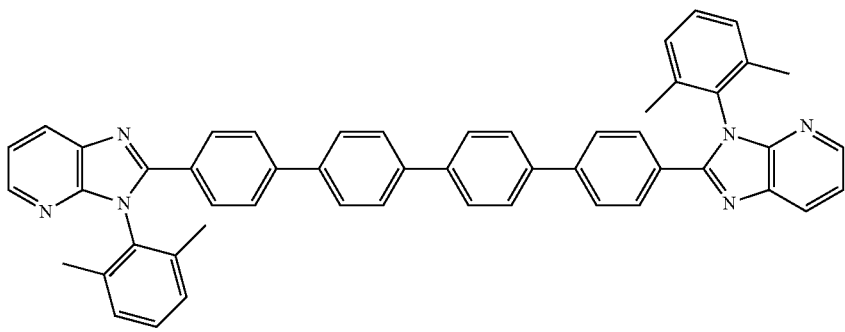

OM-24

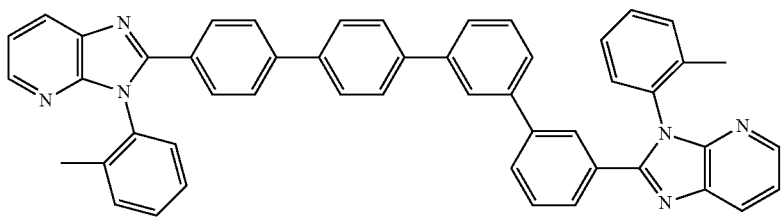

The compounds expressed by General Formula O-1 above can be synthesized by the method described in Japanese Laid-Open Patent Application 2001-335776. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the organic electroluminescence element of the present invention, a compound expressed by General Formula O-1 is preferably contained in an organic layer between the light-emitting layer and the cathode, but it is more preferably contained in the layer adjacent to the light-emitting layer on the cathode side.

The compound expressed by General Formula O-1 is preferably contained in an amount of 70 to 100 wt % and more preferably 85 to 100 wt % with respect to the total weight of the organic layer to which [this compound is] added.

The organic electroluminescence element of the present invention preferably includes at least one organic layer between the light-emitting layer and the cathode, and from the standpoints of the drive voltage and efficiency of the element, this organic layer preferably contains at least one type of compound expressed by General Formula P below. General Formula P will be described below:

[Sixty-Seventh Chemical Formula]

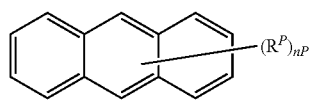

General Formula P

In General Formula P, $R^P$ represents an alkyl group (preferably $C_1$ to $C_8$), an aryl group (preferably $C_6$ to $C_{30}$), or a heteroaryl group (preferably $C_4$ to $C_{12}$), and these may have substituents selected from the aforementioned Substituent Group A. nP represents an integer from 1 to 10, and if there are a plurality of $R^P$ [groups], these may be the same or different. At least one $R^P$ is a substituent expressed by General Formulas P-1 to P-5 below:

[Sixty-Eighth Chemical Formula]

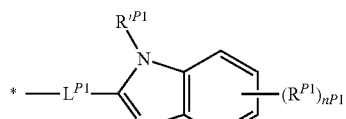

General Formula P-1

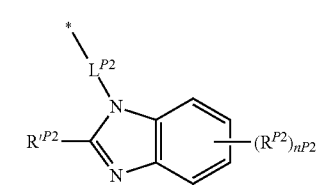

General Formula P-2

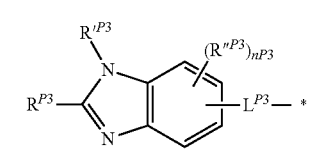

General Formula P-3

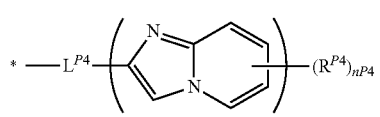

General Formula P-4

-continued

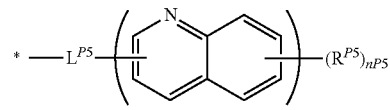

General Formula P-5

General Formula P-4 is more preferably General Formula P-4' below:

[Sixty-Ninth Chemical Formula]

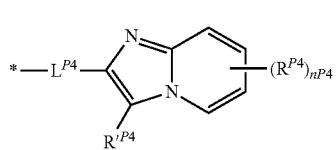

General Formula P-4'

General Formula P-5 is more preferably General Formula P-5' below:

[Seventieth Chemical Formula]

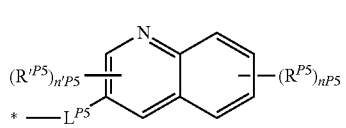

General Formula P-5'

(In General Formulas P-1 to P-5, $R^{P1}$ to $R^{P5}$, $R'^{P1}$ to $R'^{P3}$, $R'^{P5}$, and $R''^{P3}$ represent each [independently] an alkyl group (preferably $C_1$ to $C_8$), an aryl group (preferably $C_6$ to $C_{30}$), or a heteroaryl group (preferably $C_4$ to $C_{12}$), and these may have a substituent selected from the aforementioned Substituent Group A. $n^{P1}$, $n^{P2}$, $n^{P4}$, and $n^{P5}$ represent an integer from 0 to 4, $n^{P3}$ and $n^{P5}$ [sic] represent an integer from 0 to 2, and if there are a plurality of $R^{P1}$ to $R^{P5}$, $R'^{P1}$ to $R'^{P3}$, $R'^{P5}$, and $R''^{P3}$ [groups], these may be the same or different. $L^{P1}$ to $L^{P5}$ represent either a single bond or a divalent linking group composed of an aryl ring or a heteroaryl ring. The asterisk indicates the bonding position with an anthracene ring in General Formula P.)

A substituent favorable as $R^P$ other than the substituents expressed by P-1 to P-5 is an aryl group, and more preferably a phenyl group, a biphenyl group, a terphenyl group, or a naphthyl group, with a naphthyl group being even more preferable.

$R^{P1}$ to $R^{P5}$, $R'^{P1}$ to $R'^{P3}$, $R'^{P5}$, and $R''^{P3}$ are preferably either an aryl group or a heteroaryl group, more preferably an aryl group, and even more preferably a phenyl group, a biphenyl group, a terphenyl group, or a naphthyl group, with a phenyl group being most preferable.

$L^{P1}$ to $L^{P5}$ are preferably either a single bond or a divalent linking group composed of an aryl ring, more preferably a single bond, phenylene, biphenylene, terphenylene, or naphthylene, and even more preferably a single bond, phenylene, or naphthylene.

Concrete examples of the compounds expressed by General Formula P are given below, but it should not be construed that the compounds expressed by General Formula P that can be used in the present invention are limited to or by these concrete examples:

[Seventy-First Chemical Formula]
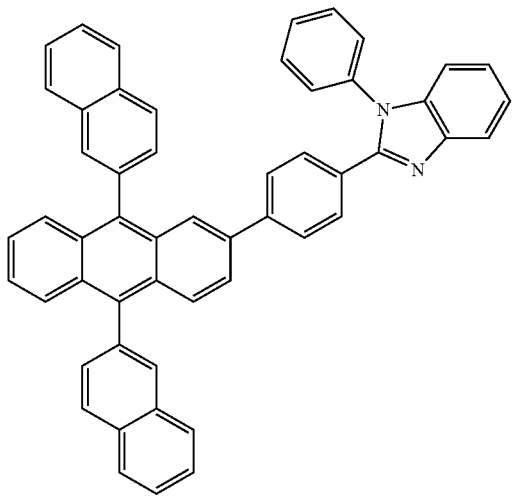
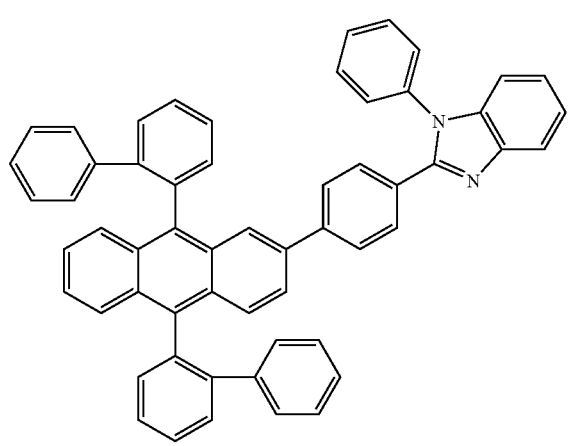
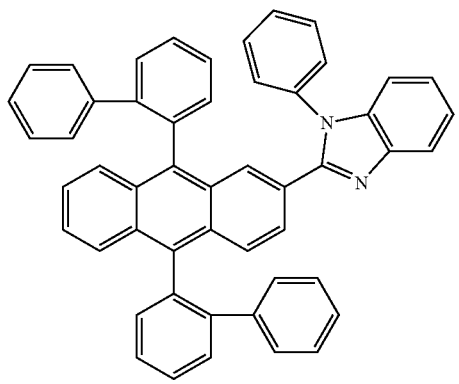
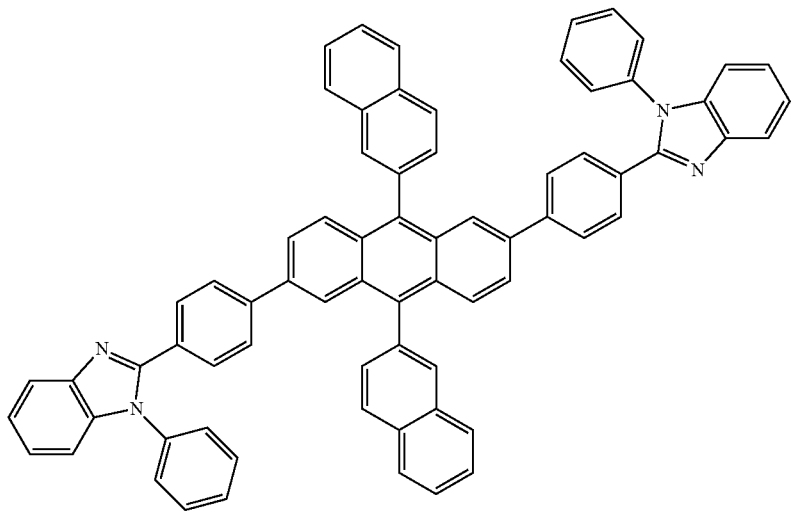

-continued
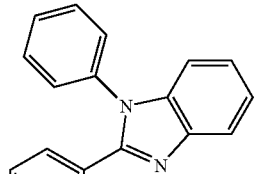
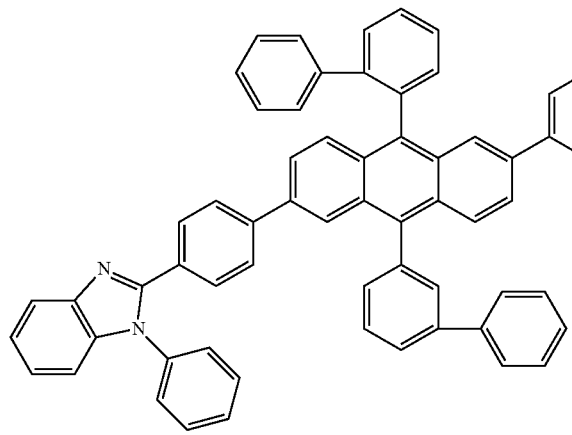
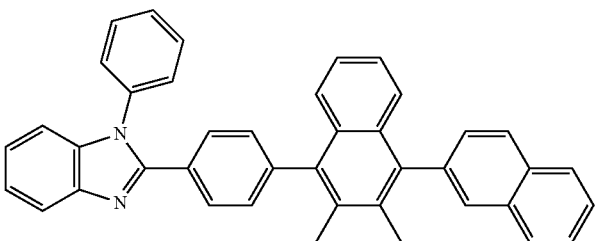
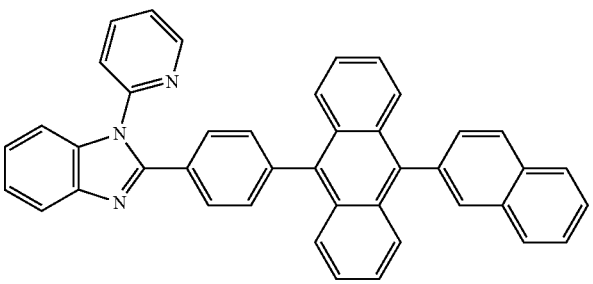
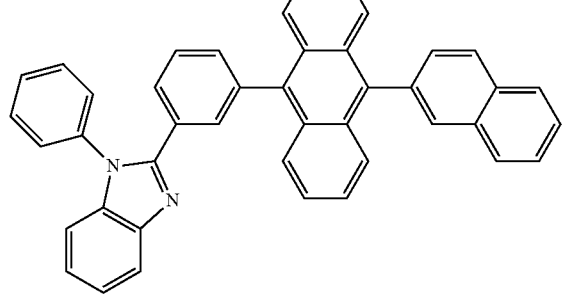
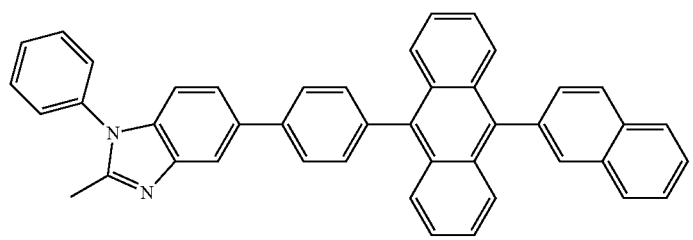
[Seventy-Second Chemical Formula]
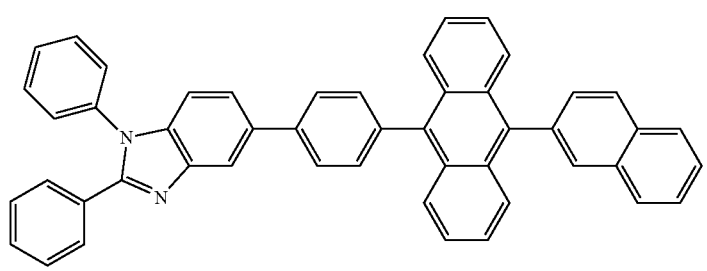

159 160
-continued
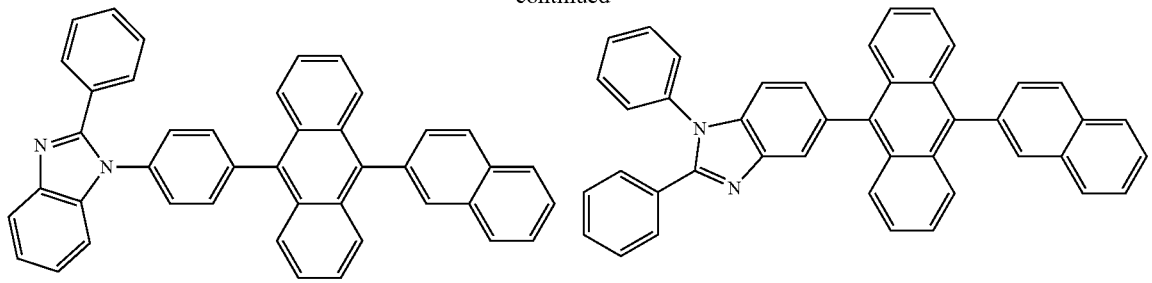
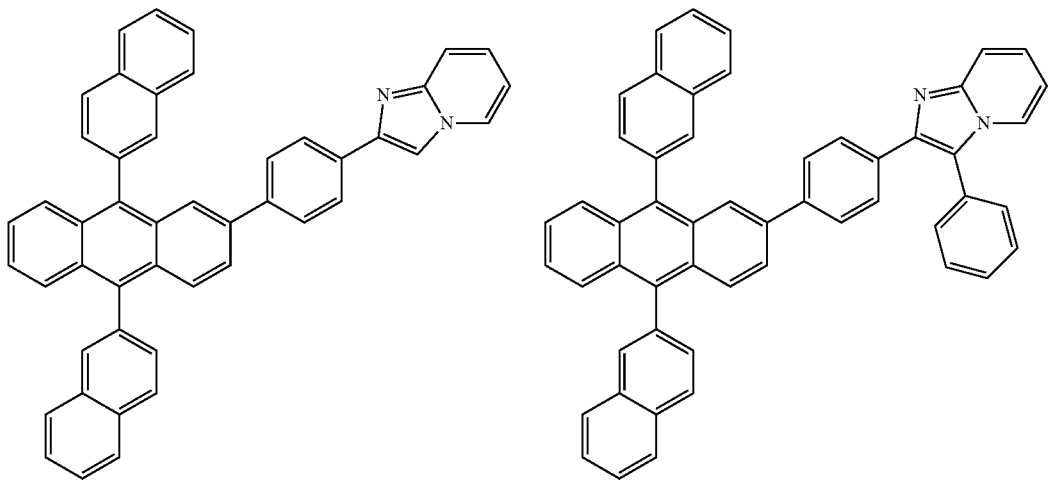
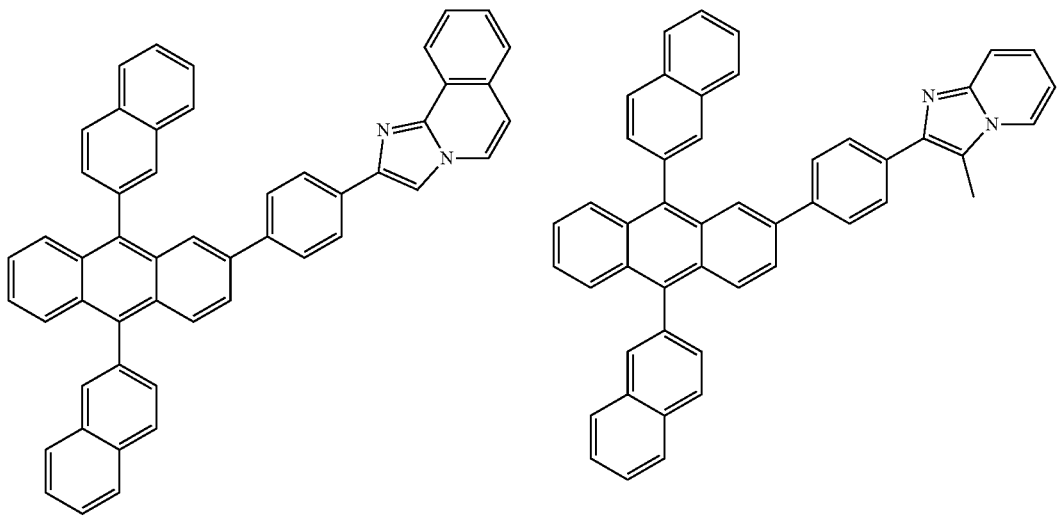
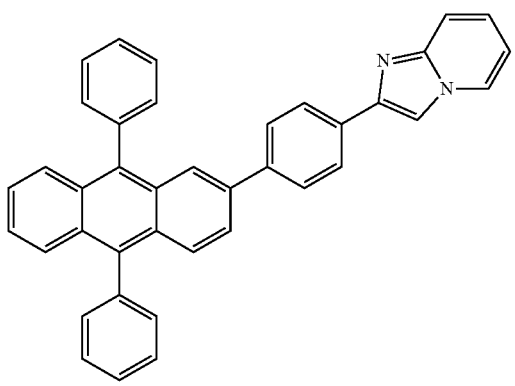

-continued
[Seventy-Third Chemical Formula]
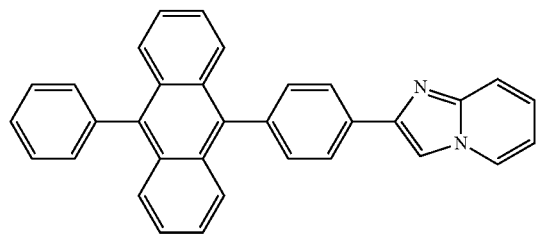
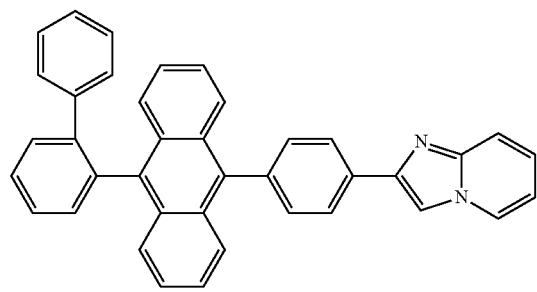
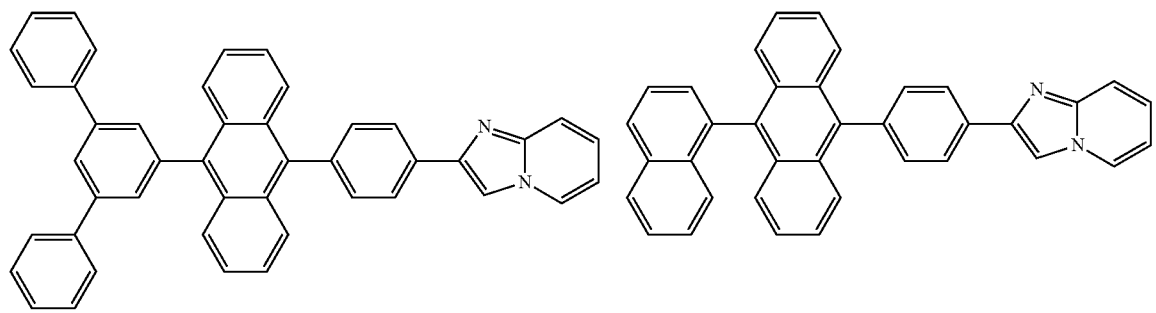
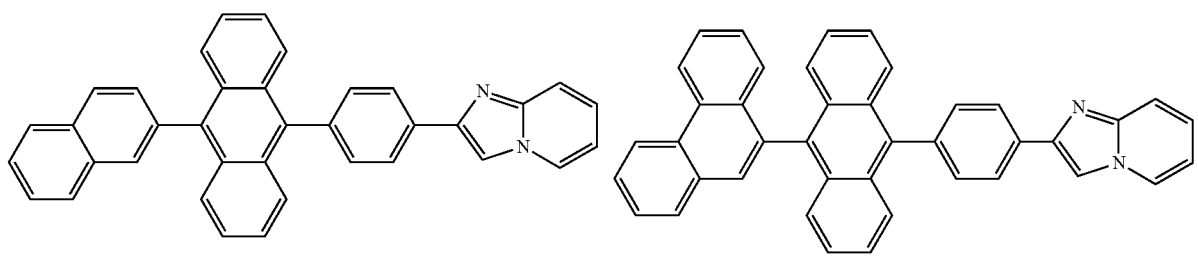
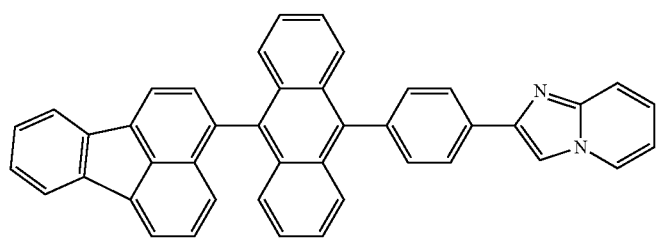
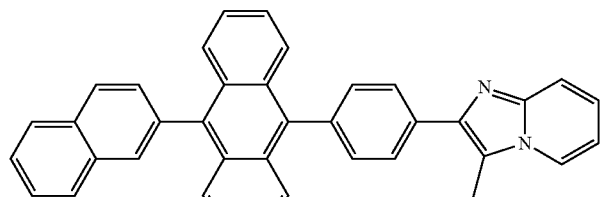
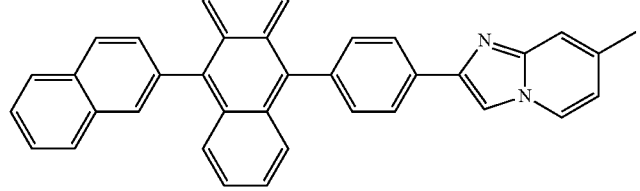

-continued
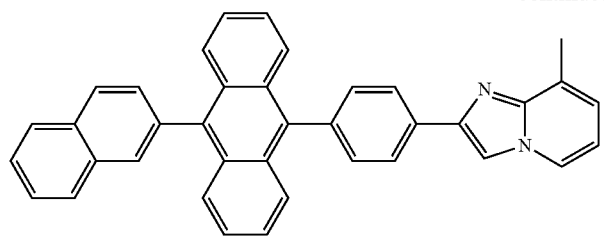
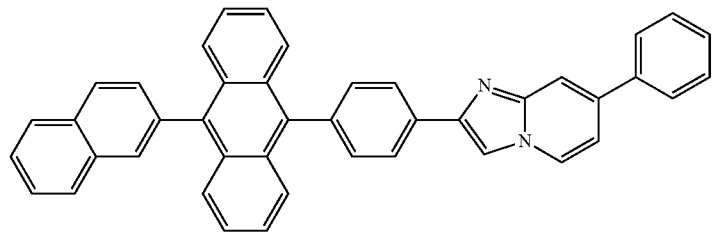
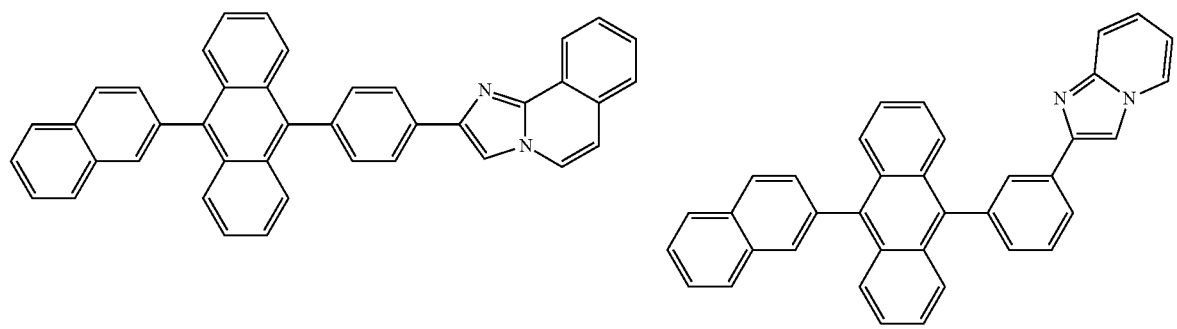
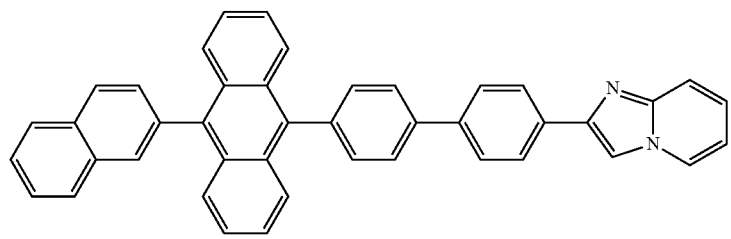
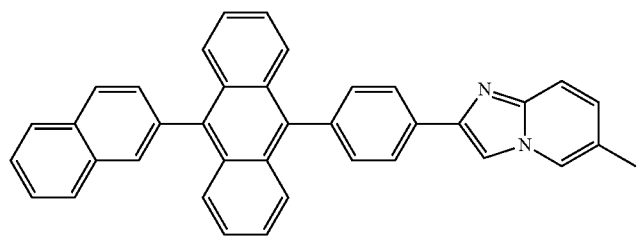
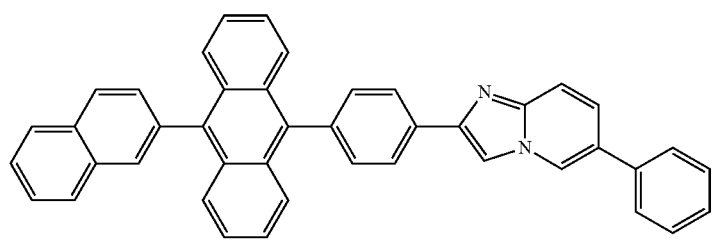

-continued

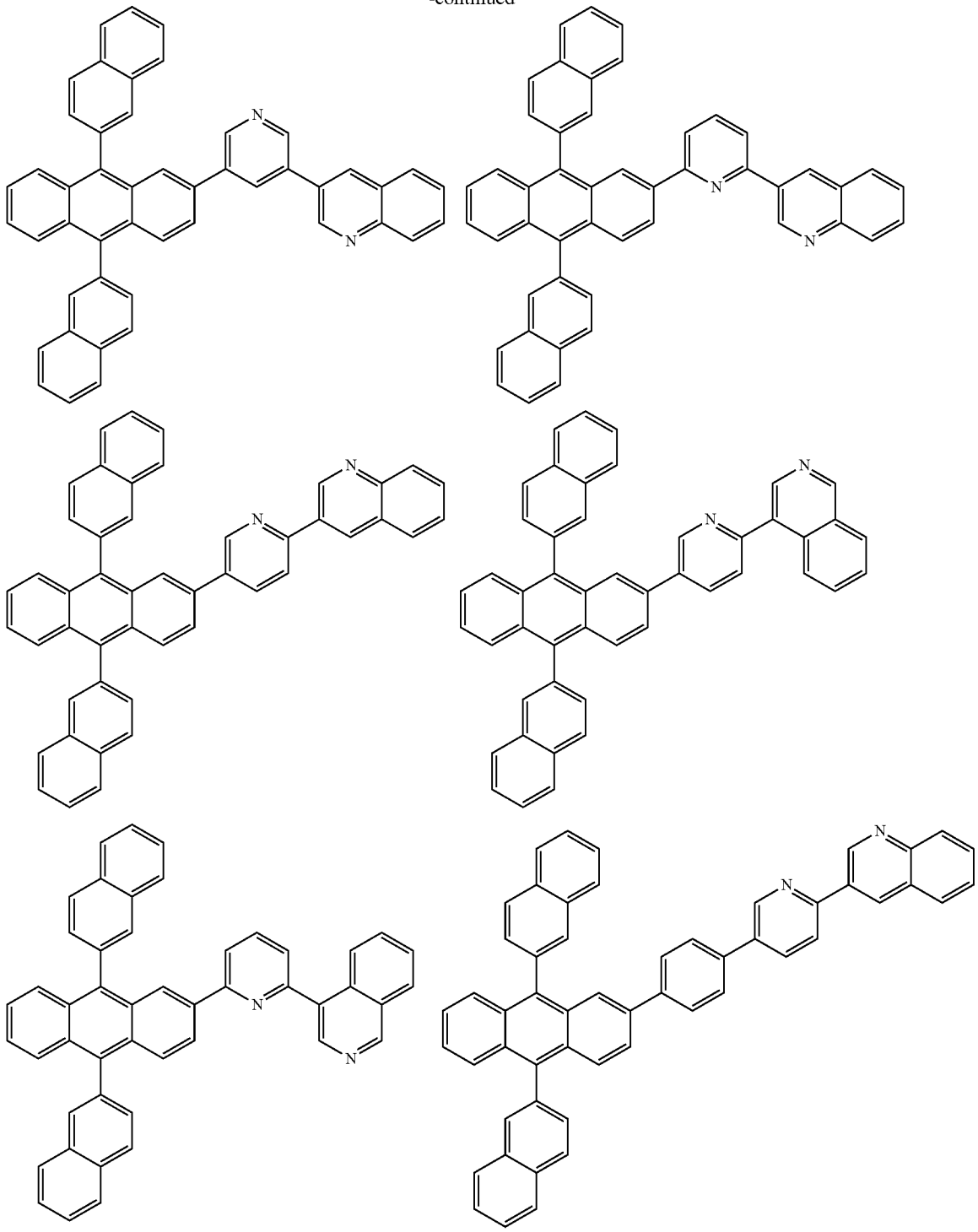

The compounds expressed by General Formula P above can be synthesized by the methods described in WO 2003/060956, WO 2004/080975, and the like. After synthesis, it is preferable for purification by column chromatography, recrystallization, reprecipitation, or the like to be performed, followed by sublimation purification. Sublimation purification not only allows organic impurities to be separated, but also allows inorganic salts, residual solvents, moisture, and the like to be effectively removed.

In the organic electroluminescence element of the present invention, the compound expressed by General Formula P is preferably contained in an organic layer between the light-emitting layer and the cathode, but it is more preferably contained in the layer adjacent to the cathode.

The compound expressed by General Formula P is preferably contained in an amount of 70 to 100 wt % and more preferably 85 to 100 wt % with respect to the total weight of the organic layer to which [this compound is] added.

Examples of other favorable materials that can be used in the electron injection layer and electron transport layer in the organic electroluminescence element of the present invention include the silole compounds described in Japanese Laid-Open Patent Application H9-194487 and the like, the phosphine oxide compounds described in Japanese Laid-Open Patent Application 2006-73581 and the like, the nitrogen-containing aromatic hetero six-membered ring compounds described in Japanese Laid-Open Patent Application 2005-276801, Japanese Laid-Open Patent Application 2006-225320, WO 2005/085387, and the like, those having a carbazole structure and a nitrogen-containing aromatic hetero six-membered structure described in WO 2003/080760, WO 2005/085387, and the like, the aromatic hydrocarbon compounds (such as naphthalene compounds, anthracene compounds, triphenylene compounds, phenanthrene compounds, pyrene compounds, and fluoranthene compounds) described in US 2009/0009065, WO 2010/134350, Japanese Translation of PCT International Application 2010-535806, and the like.

<Protective Layer>

In the present invention, the entire organic electroluminescence element may be protected by a protective layer.

Regarding the protective layer, what is stated in paragraph numbers [0169] and [0170] in Japanese Laid-Open Patent Application 2008-270736 can be applied to the present invention. Note that the material of the protective layer may be either an inorganic material or organic material.

<Sealing Container>

The organic electroluminescence element of the present invention may be entirely sealed by using a sealing container.

Regarding the sealing container, what is stated in paragraph number [0171] in Japanese Laid-Open Patent Application 2008-270736 can be applied to the present invention.

<Drive Method>

The organic electroluminescence element of the present invention can emit light by applying direct current (may include an alternating current component as needed) voltage (usually 2 to 15 volts) or DC current between the anode and the cathode.

For the method for driving the organic electroluminescence element of the present invention, it is possible to apply the drive methods described in the respective Specifications or the like of Japanese Laid-Open Patent Applications H2-148687, H6-301355, H5-29080, H7-134558, H8-234685, and H8-241047, Japanese Patent 2,784,615, and U.S. Pat. Nos. 5,828,429 and 6,023,308.

The external quantum efficiency of the organic electroluminescence element of the present invention is preferably at least 5%, more preferably at least 7%, and even more preferably at least 10%. The numerical value of the external quantum efficiency that can be used is the maximum value for external quantum efficiency when the element is driven at 20° C., or the value for external quantum efficiency near 300 to 400 cd/m$^2$ when the element is driven at 20° C.

The internal quantum efficiency of the organic electroluminescence element of the present invention is preferably at least 10%, more preferably at least 15%, and even more preferably at least 20%. The internal quantum efficiency of the element is calculated by dividing the external quantum efficiency by the light extraction efficiency. The light extraction efficiency is approximately 20% with an ordinary organic EL element, but the light extraction efficiency can be raised to over 20% by modifying the shape of the substrate, the shape of the electrodes, the thickness of the organic layers, the orientation of the light-emitting material, the thickness of the inorganic layers, the refractive index of the organic layers, the refractive index of the inorganic layers, and so forth.

<Emission Wavelength>

There are no particular restrictions on the emission wavelength of the organic electroluminescence element of the present invention. For example, of the three primary colors of light, it may be used for emission of red light, for emission of green light, or for emission of blue light. Of these, with the organic electroluminescence element of the present invention, it is preferable to use a compound expressed by General Formula 1 above as the light-emitting material to cause emission of light, and it is especially preferable to cause emission of blue light.

<Applications of the Organic Electroluminescence Element of the Present Invention>

The organic electroluminescence element of the present invention can be utilized favorably in display elements, displays, backlights, electronic photography, illumination light sources, recording light sources, exposure light sources, reading light sources, road signs, trade signs, interior decorating, optical communications, and so forth. [This element] can be especially favorably used in devices that are driven in areas of high light emission brightness, such as in light-emitting devices, illumination devices, and display devices.

Light-Emitting Device

The light-emitting device of the present invention is characterized by including the organic electroluminescence element of the present invention.

Next, the light-emitting device of the present invention will be described with reference to FIG. 2.

The light-emitting device of the present invention makes use of the aforementioned organic electroluminescence element.

Figure 2:
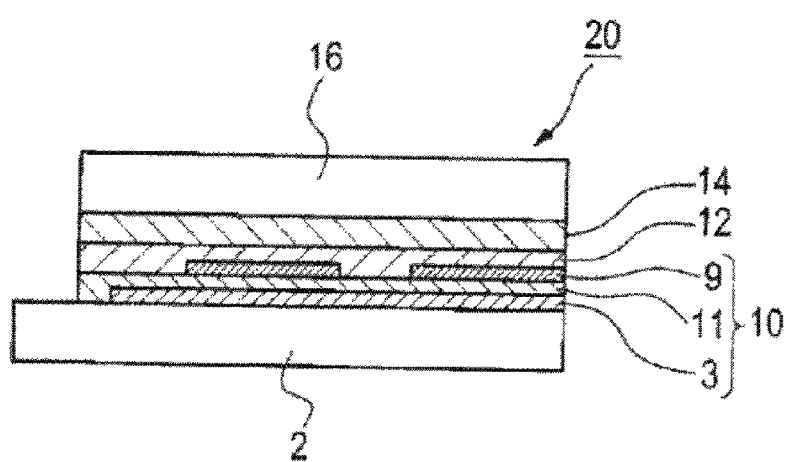
FIG. 2 is a schematic diagram illustrating one example of the light-emitting device according to the present invention.

FIG. 2 is a sectional view schematically showing one example of the light-emitting device of the present invention. The light-emitting device 20 in FIG. 2 is made up of a transparent substrate (support substrate) 2, an organic electroluminescence element 10, a sealing container 16, and the like.

The organic electroluminescence element 10 is configured such that an anode (first electrode) 3, an organic layer 11, and a cathode (second electrode) 9 are sequentially laminated over the substrate 2. Furthermore, a protective layer 12 is laminated over the cathode 9, and in addition, the sealing container 16 is provided on the protective layer 12 via an adhesive layer 14. Note that parts of the electrodes 3 and 9, partitions, insulating layers, and so forth are not depicted.

Here, an epoxy resin or other such photosetting adhesive or thermosetting adhesive can be used as the adhesive layer 14. For example, a thermosetting adhesive sheet can also be used.

There are no particular restrictions on the applications of the light-emitting device of the present invention, but examples other than illumination devices include television sets, personal computers, portable telephones, electronic paper, and other such display devices.

Illumination Device

The illumination device of the present invention is characterized by including the organic electroluminescence element of the present invention.

Next, the illumination device of the present invention will be described with reference to FIG. 3.

Figure 3:
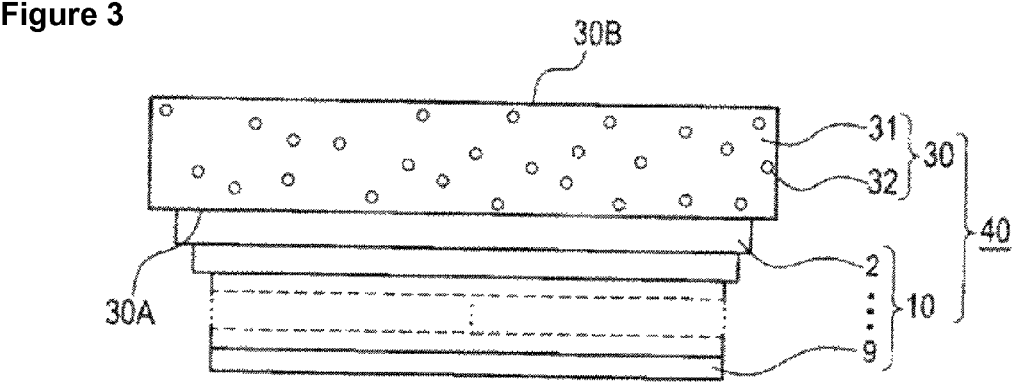
FIG. 3 is a schematic diagram illustrating one example of the illumination device according to the present invention.

FIG. 3 is a sectional view schematically showing one example of the illumination device of the present invention. As is shown in FIG. 3, the illumination device 40 of the present invention comprises the aforementioned organic EL element 10 and a light-scattering member 30. More concretely, the illumination device 40 is configured such that the substrate 2 of the organic EL element 10 is in contact with the light-scattering member 30.

There are no particular restrictions on the light-scattering member 30 as long as it is capable of scattering light, but in FIG. 3, it is a member in which microparticles 32 are dispersed in a transparent substrate 31. A glass substrate, for example, can be used favorably as the transparent substrate 31. Transparent resin microparticles can be used favorably as the microparticles 32. The glass substrate and the transparent resin microparticles can both be from prior art. This type of illumination device 40 is devised such that when light emitted from the organic electroluminescence element 10 is incident on a light incidence face 30A of the light-scattering member 30, the incident light is scattered by the light-scattering member 30, and the scattered light exits a light emission face 30B as illuminating light.

Display Device

The display device of the present invention is characterized by including the organic electroluminescence element of the present invention.

Examples of the display device of the present invention include television sets, personal computers, portable telephones, electronic paper, and other such display devices.

WORKING EXAMPLES

The characteristic features of the present invention will be described below in more concrete terms by giving working examples and comparative examples. The materials, usage amounts, proportions, processing details, processing procedures, and so forth mentioned in the following working examples can be suitably modified as long as it does not depart from the gist of the present invention. Therefore, it should not be construed that the scope of the present invention is limited to or by the concrete examples given below.

The structural formulas of the compounds used in the working examples and comparative examples are shown altogether below:

[Seventy-Fourth Chemical Formula]

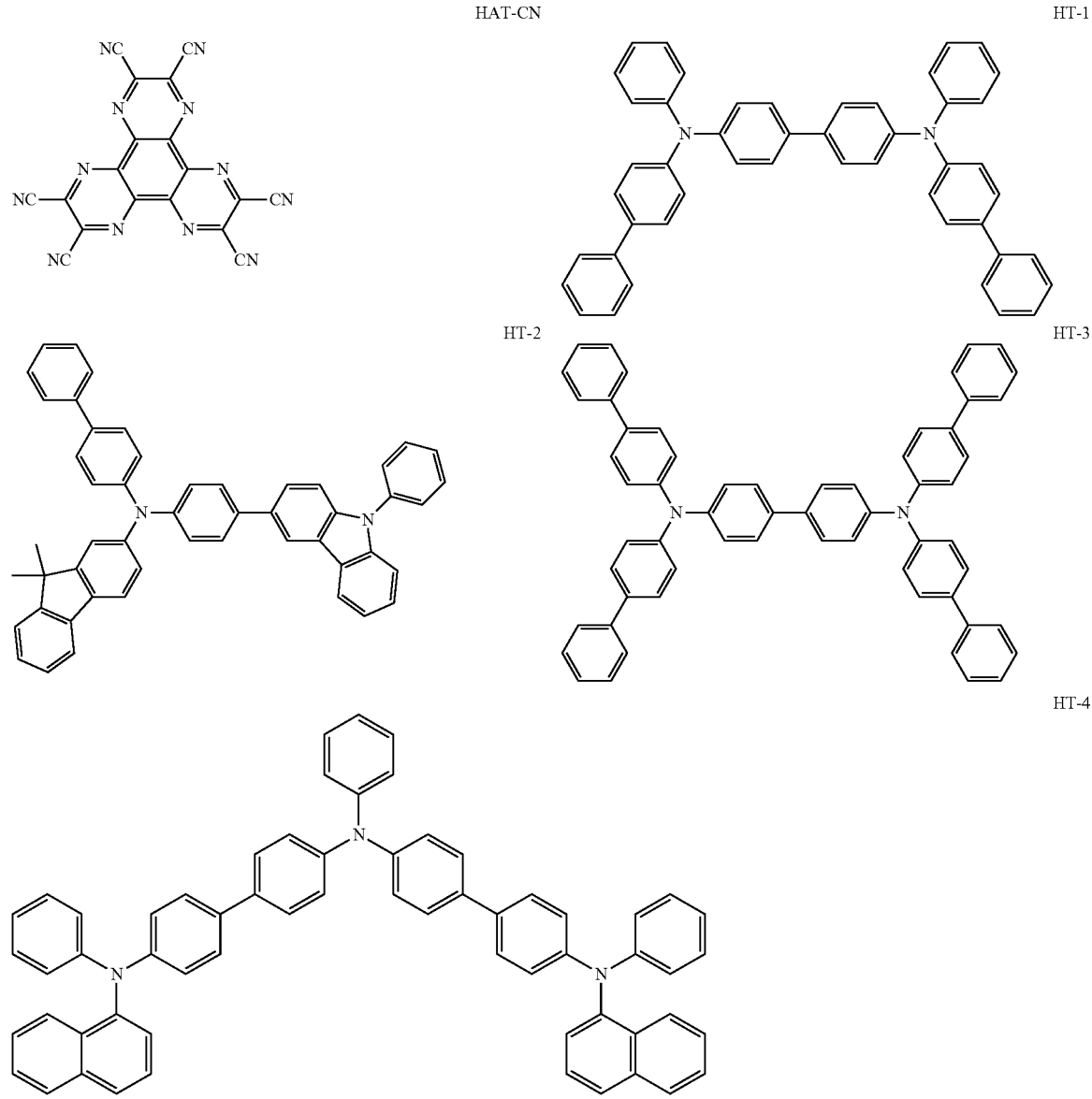

-continued
HT-5
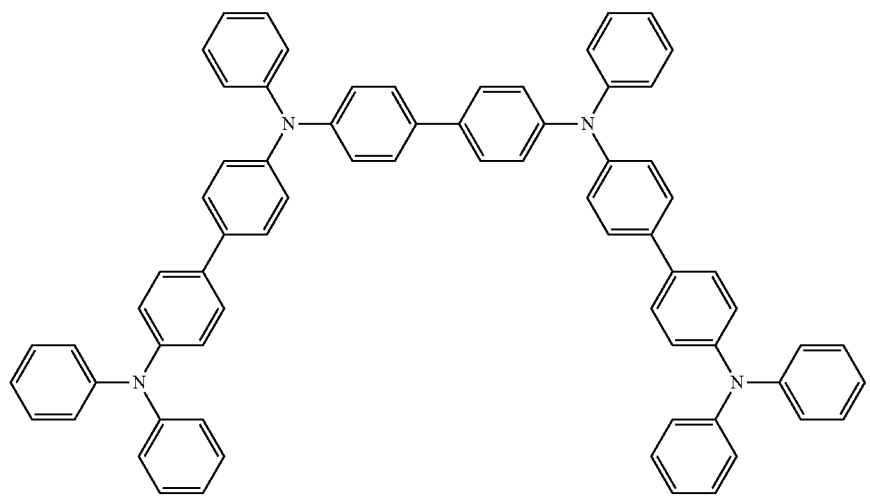
H-1
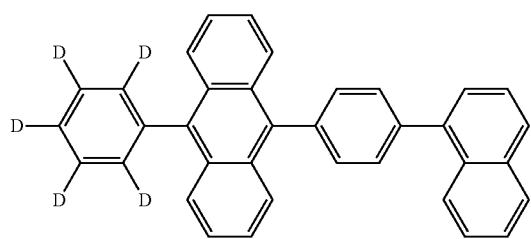
H-2
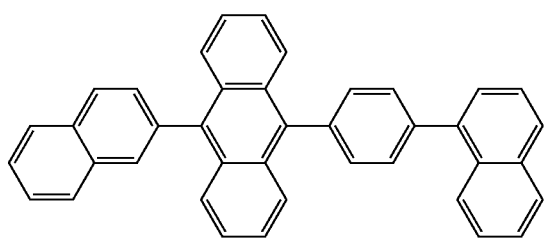
H-3
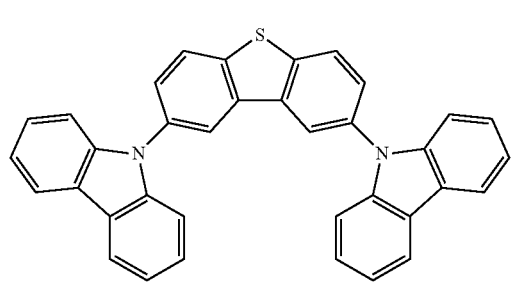
H-4
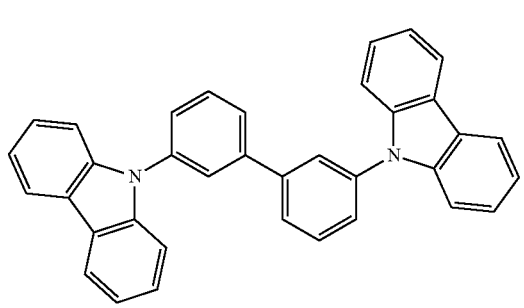
ET-1
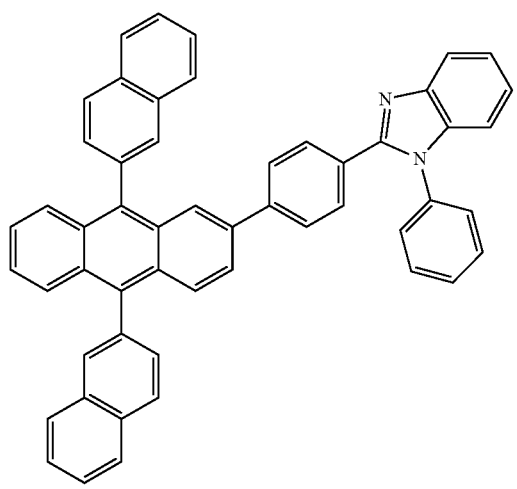
ET-2
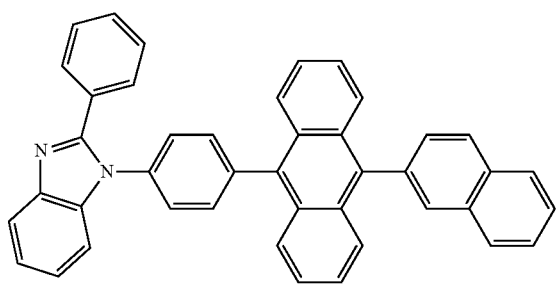

-continued
ET-3
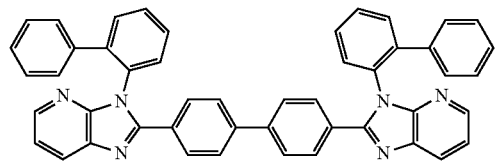
ET-4
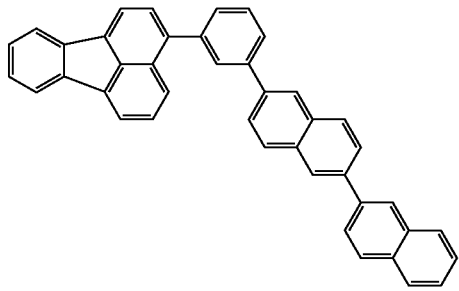
ET-3
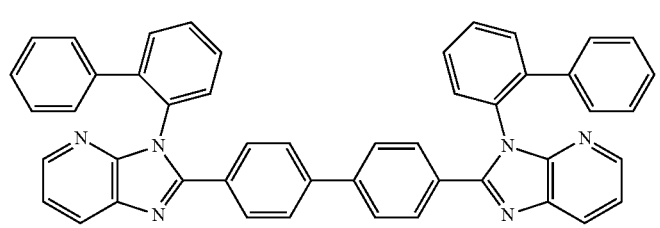
[Seventy-Fifth Chemical Formula]
comparitive compound 1
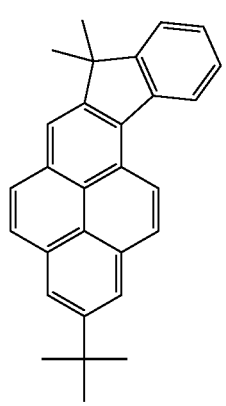
comparitive compound 2
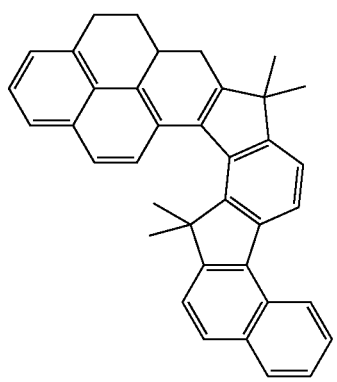
comparative compound 3
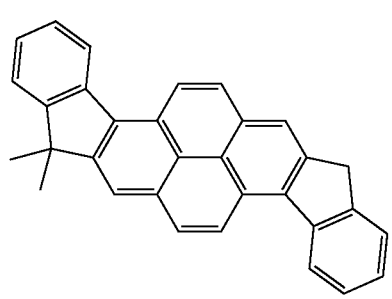

1. Synthesis Example

The compounds expressed by General Formula 1 can be synthesized by the methods described in Japanese Laid-Open Patent Applications 2010-111620 and 2008-127291, or by a combination of other publicly known reactions. Typical examples of concrete procedures for synthesizing the compounds expressed by General Formula 1 will be described below:

Synthesis Example 1

Synthesis of Compound 1

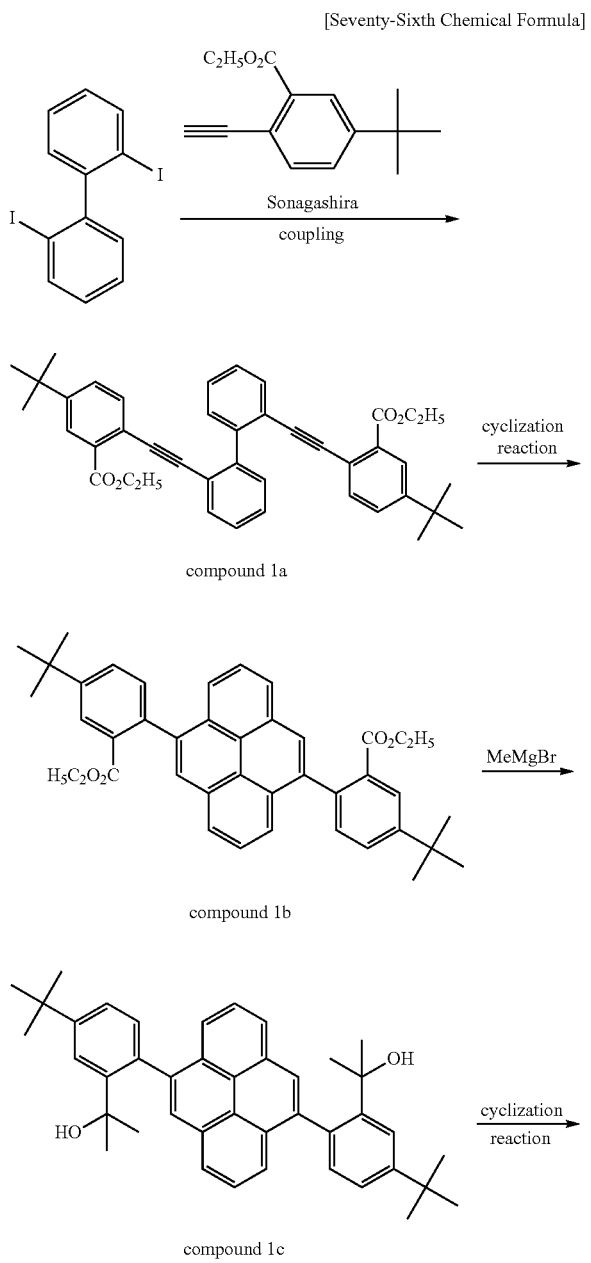

[Seventy-Sixth Chemical Formula]

compound 1a compound 1b compound 1c

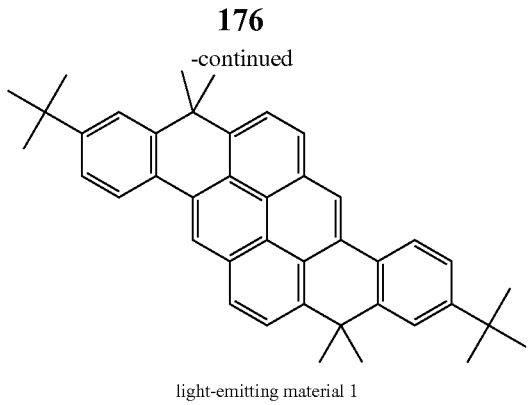

light-emitting material 1

Synthesis of Compound 1a 5 mol % Pd(PPh$_3$)$_4$ was added to a toluene/piperidine solution (100 mL) of 2,2'-diiodobiphenyl (10 g), ethyl 5-t-butyl-2-ethynylbenzoate (15.9 g), and copper iodide (0.47 g), and a Sonogashira coupling reaction was conducted. The reaction solution was poured into ethyl acetate/dilute hydrochloric acid (mix ratio of ethyl acetate/dilute hydrochloric acid=1/1), and the organic layer was washed with brine and dried with magnesium sulfate, upon which [this product] was concentrated under reduced pressure. The concentrated residue was purified by silica gel column chromatography, which gave 11.4 g of compound 1a.

Synthesis of Compound 1b

A 10 mol % PtCl$_2$ benzonitrile complex was added under a nitrogen atmosphere to a dichloroethane solution (100 mL) of compound 1a (10 g), and this was reacted under heating to reflux. The reaction solution was poured into ethyl acetate/dilute hydrochloric acid (mix ratio of ethyl acetate/dilute hydrochloric acid=1/1), and the organic layer was washed with brine and dried with magnesium sulfate, upon which [this product] was concentrated under reduced pressure. The concentrated residue was purified by silica gel column chromatography, which gave 3.7 g of compound 1b.

Synthesis of Compound 1c 5 equivalents of a methyl Grignard reagent were allowed to act on compound 1b (3.5 g), which gave 2.7 g of compound 1c.

(Synthesis of Light-Emitting Material 1)

0.2 equivalent of methanesulfonic acid was added to a dichloromethane solution (10 mL) of compound 1c (2.5 g), and a reaction was conducted. The reaction solution was poured into ethyl acetate/dilute hydrochloric acid (mix ratio of ethyl acetate/dilute hydrochloric acid=1/1), and the organic layer was washed with brine and dried with magnesium sulfate, upon which [this product] was concentrated under reduced pressure. The concentrated residue was purified by silica gel column chromatography, which gave 1.6 g of light-emitting material 1. Note that the obtained compound was identified by elemental analysis, NMR, and mass spectrometry.

Synthesis Example 2
Synthesis of Compound 14
[Seventy-Seventh Chemical Formula]
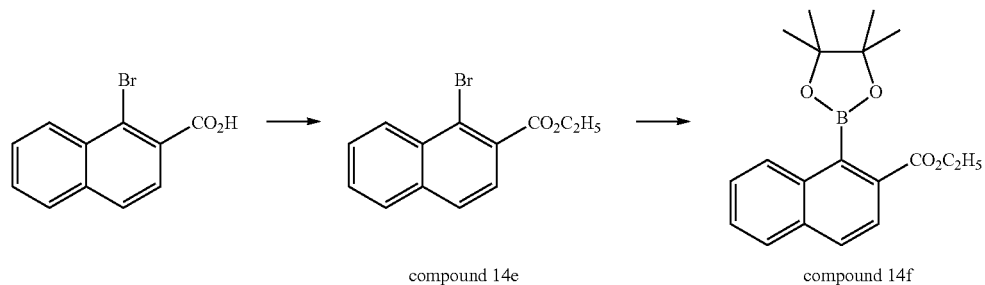
compound 14e            compound 14f
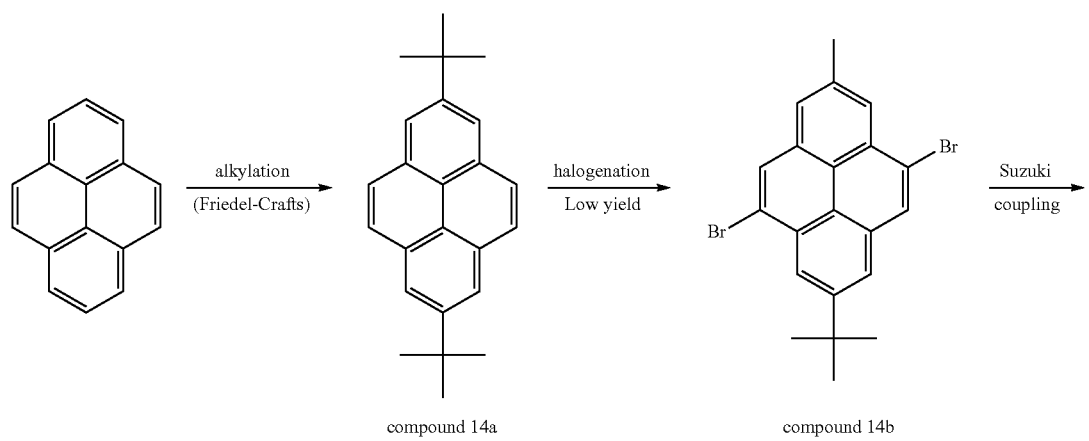
compound 14a            compound 14b
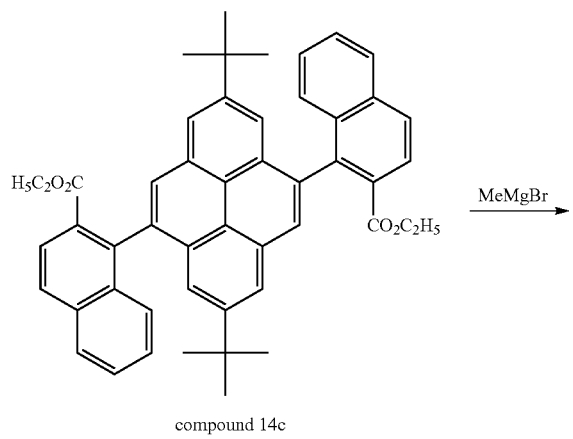
compound 14c

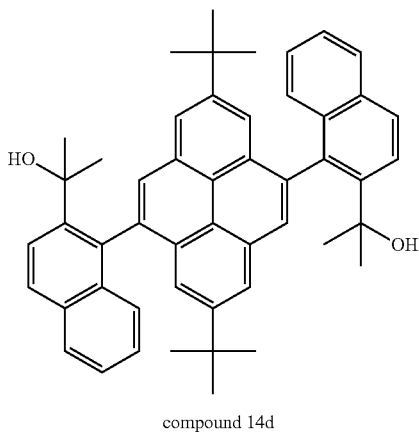

compound 14d cyclization reaction

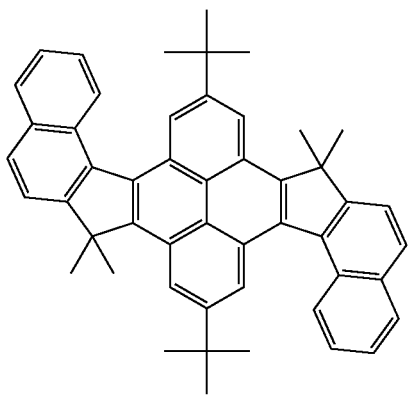

light-emitting compound 14

Synthesis of Compound 14a 57 g [of this compound] was synthesized according to the method described in Japanese Laid-Open Patent Application 2008-127291.

Synthesis of Compound 14b

Bromine (2 equivalents) was added dropwise at room temperature to a dichloromethane solution (500 mL) of compound 14a (50 g) and stirred for 2 hours. The reaction solution was poured into ethyl acetate+n-hexane/dilute hydrochloric acid (mix ratio of ethyl acetate/dilute hydrochloric acid=1/1), and the organic layer was washed with brine and dried with magnesium sulfate, upon which [this product] was concentrated under reduced pressure. The concentrated residue was purified by silica gel column chromatography, and then separated by GPC, which gave 2.3 g of compound 14b.

Synthesis of Compound 14e

1-Bromonaphthalene-2-carboxylic acid was esterified with a catalytic amount of sulfuric acid+ethanol solvent, the reaction solution was concentrated under reduced pressure, and the concentrated residue was purified by silica gel column chromatography, which gave 12.1 g of compound 14e.

Synthesis of Compound 14f

Compound 14e (10 g) and bis(pinacolato)diboron (11.8 g) were coupled with a $PdCl_2$ (dppf) catalyst, which gave 11.2 g of compound 14f.

Synthesis of Compound 14c

Compound 14b (0.7 g) and compound 14f (1.26 g) were subjected to a coupling reaction with a palladium catalyst in a toluene/aqueous solvent. The reaction solution was poured into ethyl acetate/dilute hydrochloric acid (mix ratio of ethyl acetate/dilute hydrochloric acid=1/1), and the organic layer was washed with brine and dried with magnesium sulfate, upon which [this product] was concentrated under reduced pressure. The concentrated residue was purified by silica gel column chromatography, which gave 0.74 g of compound 14c.

Synthesis of Compound 14d 5 equivalents of a methyl Grignard reagent were allowed to act on compound 14c (0.7 g), and a reaction was conducted. The reaction solution was poured into ethyl acetate/dilute hydrochloric acid (mix ratio of ethyl acetate/dilute hydrochloric acid=1/1), and the organic layer was washed with brine and dried with magnesium sulfate, upon which [this product] was concentrated under reduced pressure. The concentrated residue was purified by silica gel column chromatography, which gave 0.63 g of compound 14d.

(Synthesis of Light-Emitting Material 14)

0.2 equivalent of methanesulfonic acid was added to a dichloromethane solution (10 mL) of compound 14d (0.6 g), and a reaction was conducted. The reaction solution was poured into ethyl acetate/dilute hydrochloric acid (mix ratio of ethyl acetate/dilute hydrochloric acid=1/1), and the organic layer was washed with brine and dried with magnesium sulfate, upon which [this product] was concentrated under reduced pressure. The concentrated residue was purified by silica gel column chromatography, which gave 0.47 g of light-emitting material 14. Note that the obtained compound was identified by elemental analysis, NMR, and mass spectrometry.

Synthesis Example 3

Synthesis of Compound 20

[Seventy-Eighth Chemical Formula]

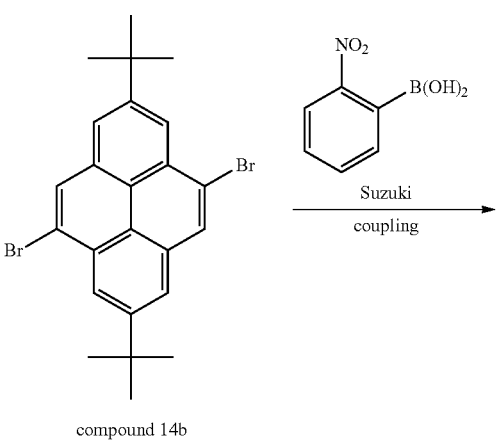

compound 14b

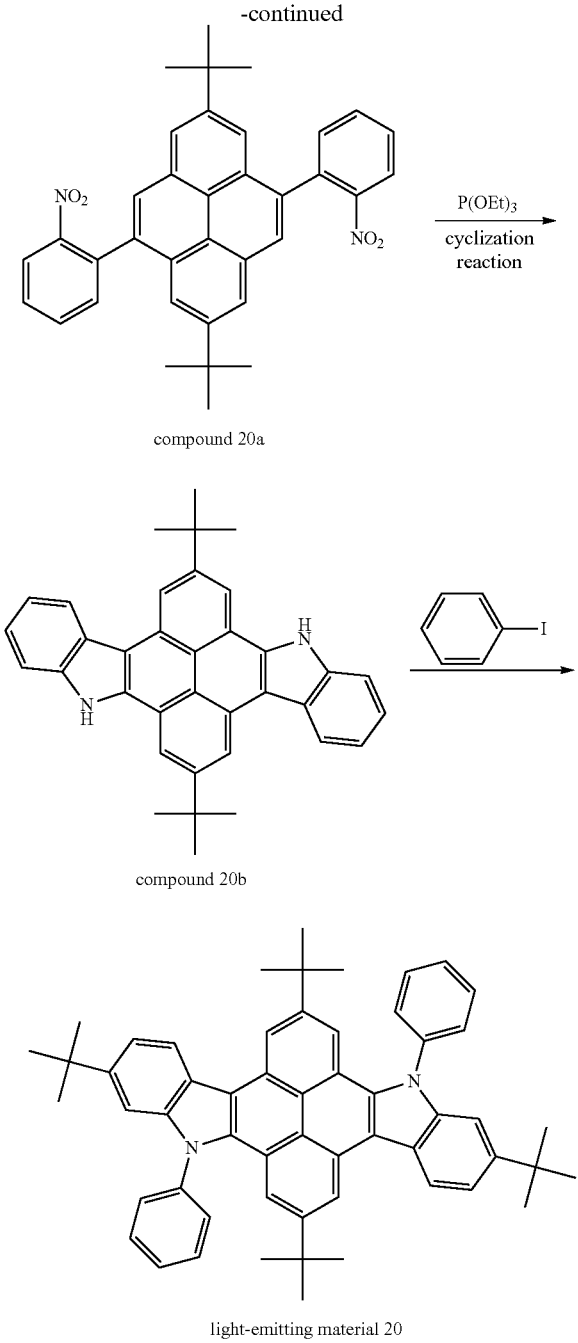

Synthesis of Compound 20a 5 mol % Pd(PPh$_3$)$_4$ was added to a DMF solution (10 mL) of compound 14b (1.5 g), 2-nitrophenylboric acid (3.0 g), and potassium carbonate (2.6 g), and a Suzuki coupling reaction was conducted. The reaction solution was poured into ethyl acetate/dilute hydrochloric acid (mix ratio of ethyl acetate/dilute hydrochloric acid=1/1), and the organic layer was washed with brine and dried with magnesium sulfate, upon which [this product] was concentrated under reduced pressure. The concentrated residue was purified by silica gel column chromatography, which gave 1.2 g of compound 20a.

Synthesis of Compound 20b

Compound 20b was synthesized by allowing triethyl phosphite to act on compound 20a according to the method described in German Laid-Open Patent Application 2009031021.

(Synthesis of Light-Emitting Material 20)

Pd(dba)$_2$ (0.03 g) was added under a nitrogen atmosphere to a toluene solution (10 mL) of compound 20b (0.7 g), iodobenzene (0.7 g), tBuONa (0.82 g), and 2-dichlorohexylphosphino-2',4',6'-triisopropylbiphenyl (0.04 g; made by Aldrich), and [the system] was stirred for 18 hours under heating to reflux. The reaction solution was poured into ethyl acetate/dilute hydrochloric acid (mix ratio of ethyl acetate/dilute hydrochloric acid=1/1), and the organic layer was washed with brine and dried with magnesium sulfate, upon which [this product] was concentrated under reduced pressure. The concentrated residue was purified by silica gel column chromatography, which gave 0.81 g of light-emitting material 20. Note that the obtained compound was identified by elemental analysis, NMR, and mass spectrometry.

2. Material Properties Evaluation

Test Example 1

Evaluation of Inter-Molecular Interaction

For the various compounds listed in Table 1, the temperature at which the weight decreased by 10% (as measured by vacuum TG-DTA) was termed the sublimation temperature, and this was used to find inter-molecular interaction P=sublimation temperature (units: ° C.)/molecular weight× 0.5). The smaller is this value, the lower is the inter-molecular interaction, and the better is the sublimation. Inter-molecular interaction was evaluated on the following three levels:

○: P≤0.8
Δ: 0.8<P≤0.95
x: 0.95<P

TABLE 1

| Compound | Inter-molecular interaction | Remarks |
|---|---|---|
| compound 1 | Δ | present invention |
| compound 4 | ○ | present invention |
| compound 6 | ○ | present invention |
| compound 8 | Δ | present invention |
| compound 10 | Δ | present invention |
| compound 11 | Δ | present invention |
| compound 12 | Δ | present invention |
| compound 13 | ○ | present invention |
| compound 14 | ○ | present invention |
| compound 15 | ○ | present invention |
| compound 20 | ○ | present invention |
| compound 21 | Δ | present invention |
| compound 23 | Δ | present invention |
| compound 27 | Δ | present invention |
| compound 28 | ○ | present invention |
| compound 33 | ○ | present invention |
| compound 34 | ○ | present invention |
| compound 35 | ○ | present invention |
| compound 38 | ○ | present invention |
| compound 40 | Δ | present invention |
| compound 41 | ○ | present invention |
| compound 42 | Δ | present invention |
| compound 44 | ○ | present invention |
| compound 45 | ○ | present invention |
| compound 46 | ○ | present invention |

TABLE 1-continued

| Compound | Inter-molecular interaction | Remarks |
|---|---|---|
| compound 47 | ○ | present invention |
| compound 48 | Δ | present invention |
| compound 49 | ○ | present invention |
| compound 52 | Δ | present invention |
| compound 53 | ○ | present invention |
| compound 62 | Δ | present invention |
| compound 63 | Δ | present invention |
| compound 67 | ○ | present invention |
| compound 68 | Δ | present invention |
| compound 69 | Δ | present invention |
| compound 70 | Δ | present invention |
| compound 76 | Δ | present invention |
| compound 81 | ○ | present invention |
| compound 83 | ○ | present invention |
| compound 88 | Δ | present invention |
| compound 92 | Δ | present invention |
| compound 93 | Δ | present invention |
| compound 104 | ○ | present invention |
| compound 105 | Δ | present invention |
| compound 106 | Δ | present invention |
| compound 108 | ○ | present invention |
| compound 109 | Δ | present invention |
| compound 110 | ○ | present invention |
| compound 111 | Δ | present invention |
| compound 112 | Δ | present invention |
| compound 113 | Δ | present invention |
| compound 116 | ○ | present invention |
| compound 117 | Δ | present invention |
| compound 118 | Δ | present invention |
| compound 122 | ○ | present invention |
| comparative compound 1 | x | comparative example |
| comparative compound 2 | x | comparative example |
| comparative compound 3 | x | comparative example |

Test Example 2

Evaluation of Orientation

A film was formed by depositing the host material and light-emitting material listed in Table 2 in a weight ratio of 90:10 by vacuum vapor deposition over a quartz glass substrate measuring 25×25×0.7 mm. The orientation of the light-emitting material was calculated by polarized ATR-IR analysis, as the horizontal orientation degree of order S.

TABLE 2

| | Orientation S | | |
|---|---|---|---|
| Light-emitting material | When host material H-1 was used | When host material H-2 was used | Remarks |
| compound 1 | 0.58 | 0.61 | present invention |
| compound 4 | 0.54 | 0.55 | present invention |
| compound 6 | 0.61 | 0.63 | present invention |
| compound 8 | 0.59 | 0.60 | present invention |
| compound 10 | 0.60 | 0.60 | present invention |
| compound 11 | 0.60 | 0.61 | present invention |
| compound 12 | 0.59 | 0.58 | present invention |
| compound 13 | 0.67 | 0.67 | present invention |
| compound 14 | 0.53 | 0.55 | present invention |
| compound 15 | 0.61 | 0.64 | present invention |
| compound 20 | 0.51 | 0.52 | present invention |
| compound 21 | 0.58 | 0.60 | present invention |
| compound 23 | 0.59 | 0.59 | present invention |
| compound 27 | 0.64 | 0.63 | present invention |
| compound 28 | 0.62 | 0.63 | present invention |
| compound 33 | 0.57 | 0.56 | present invention |
| compound 34 | 0.72 | 0.74 | present invention |
| compound 35 | 0.68 | 0.67 | present invention |
| compound 38 | 0.71 | 0.70 | present invention |
| compound 40 | 0.69 | 0.68 | present invention |
| compound 41 | 0.67 | 0.67 | present invention |
| compound 42 | 0.68 | 0.66 | present invention |
| compound 44 | 0.73 | 0.72 | present invention |
| compound 45 | 0.68 | 0.69 | present invention |
| compound 46 | 0.75 | 0.76 | present invention |
| compound 47 | 0.74 | 0.72 | present invention |
| compound 48 | 0.70 | 0.69 | present invention |
| compound 49 | 0.68 | 0.67 | present invention |
| compound 52 | 0.71 | 0.72 | present invention |
| compound 53 | 0.70 | 0.69 | present invention |
| compound 62 | 0.70 | 0.70 | present invention |
| compound 63 | 0.71 | 0.72 | present invention |
| compound 67 | 0.68 | 0.66 | present invention |
| compound 68 | 0.78 | 0.76 | present invention |
| compound 69 | 0.77 | 0.78 | present invention |
| compound 70 | 0.77 | 0.77 | present invention |
| compound 76 | 0.64 | 0.62 | present invention |
| compound 81 | 0.62 | 0.61 | present invention |
| compound 83 | 0.67 | 0.67 | present invention |
| compound 88 | 0.66 | 0.65 | present invention |
| compound 92 | 0.68 | 0.69 | present invention |
| compound 93 | 0.67 | 0.68 | present invention |
| compound 104 | 0.56 | 0.54 | present invention |
| compound 105 | 0.57 | 0.55 | present invention |
| compound 106 | 0.57 | 0.56 | present invention |

TABLE 2-continued

| | Orientation S | | |
|---|---|---|---|
| Light-emitting material | When host material H-1 was used | When host material H-2 was used | Remarks |
| compound 108 | 0.64 | 0.66 | present invention |
| compound 109 | 0.71 | 0.69 | present invention |
| compound 110 | 0.69 | 0.67 | present invention |
| compound 111 | 0.73 | 0.71 | present invention |
| compound 112 | 0.75 | 0.75 | present invention |
| compound 113 | 0.74 | 0.73 | present invention |
| compound 116 | 0.53 | 0.54 | present invention |
| compound 117 | 0.54 | 0.52 | present invention |
| compound 118 | 0.54 | 0.53 | present invention |
| compound 122 | 0.53 | 0.54 | present invention |
| comparative compound 1 | 0.28 | 0.32 | comparative example |
| comparative compound 2 | 0.34 | 0.38 | comparative example |
| comparative compound 3 | 0.42 | 0.44 | comparative example |

Test Example 3

Evaluation of Half-Value Width of Emission Spectrum 1 mg of each of the compounds listed in Table 3 was dissolved in 10 mL of commercial grade (electronics) xylene, and the emission spectrum was measured with a spectrofluorometer (FP-6300 made by JASCO). The evaluation was made in the following four levels on the basis of the half-value width of emission spectrum β (the energy differential between short and long wavelengths of 0.5, when 1 is the maximum emission value) at this point:

⊚ : β<0.25 eV
○: 0.25 eV≤β<0.30 eV
Δ: 0.30 eV≤β<0.35 eV
x: 0.35 eV≤β

Test Example 4

Evaluation of Chromaticity

A thin film was formed in a thickness of 50 nm by depositing the following host material H-4 and the various light-emitting materials listed in Table 3 in a weight ratio of 95:5 by vacuum vapor deposition over a quartz glass substrate measuring 25×25×0.7 mm. The film thus obtained was irradiated with UV light of 350 nm, the emission spectrum at the time of light emission was measured using a spectrofluorometer (FP-6300 made by JASCO), and the chromaticity (x, y) was found. The chromaticity was evaluated in the following four levels on the basis of the y value at this point:

⊚ : 0.03≤y≤0.08
○: 0.25≤y<0.03, 0.08<y≤0.12
Δ: 0.02≤y<0.25, 0.12<y≤0.15
x: y<0.02, 0.15<y

[Seventy-Ninth Chemical Formula]

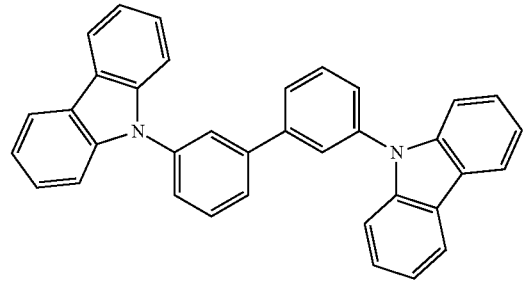

H-4

Test Example 5

Evaluation of Aggregate Formation

For the various compounds listed in Table 3, the half-value widths of the emission spectrum in the solution spectrum in Test Example 2 and in the film spectrum in Test Example 3 were calculated, and the relative ratio γ of the film with respect to the solution (film spectrum half-value width/solution spectrum half-value width) was calculated. It is believed that the closer this value is to 1.0, the less the aggregation effect will be, and the lower the likelihood of aggregate formation, which is preferable. The aggregate formation was evaluated in the following three levels on the basis of the γ value at this point:

○: γ≤1.1
Δ: 1.1<γ≤1.2
x: 1.2<γ

TABLE 3

| | Evaluation and measurement results | | | |
|---|---|---|---|---|
| Compound | Chromaticity | Half-value width of emission spectrum | Aggregate formation | Remarks |
| compound 1 | ⊚ | ○ | Δ | present invention |
| compound 4 | ○ | ○ | ○ | present invention |
| compound 6 | ⊚ | ○ | ○ | present invention |
| compound 8 | Δ | ○ | Δ | present invention |

TABLE 3-continued

Evaluation and measurement results

| Compound | Chromaticity | Half-value width of emission spectrum | Aggregate formation | Remarks |
|---|---|---|---|---|
| compound 12 | ○ | ○ | △ | present invention |
| compound 13 | ◎ | ○ | ○ | present invention |
| compound 14 | ○ | ○ | ○ | present invention |
| compound 15 | ◎ | ○ | ○ | present invention |
| compound 20 | △ | ◎ | ○ | present invention |
| compound 21 | △ | ○ | △ | present invention |
| compound 23 | △ | ○ | △ | present invention |
| compound 27 | ◎ | ○ | △ | present invention |
| compound 28 | ◎ | ○ | ○ | present invention |
| compound 33 | ◎ | ○ | ○ | present invention |
| compound 34 | ○ | ○ | ○ | present invention |
| compound 35 | ◎ | ○ | ○ | present invention |
| compound 38 | ◎ | ○ | ○ | present invention |
| compound 40 | ○ | ◎ | △ | present invention |
| compound 41 | ◎ | ○ | ○ | present invention |
| compound 42 | ○ | △ | △ | present invention |
| compound 44 | ◎ | ○ | ○ | present invention |
| compound 45 | ◎ | ○ | ○ | present invention |
| compound 46 | ◎ | ○ | ○ | present invention |
| compound 47 | ○ | ○ | ○ | present invention |
| compound 48 | ○ | ○ | △ | present invention |
| compound 49 | ○ | ○ | ○ | present invention |
| compound 52 | ○ | ○ | △ | present invention |
| compound 53 | ○ | ○ | ○ | present invention |
| compound 62 | ○ | ○ | △ | present invention |
| compound 63 | ○ | ○ | △ | present invention |
| compound 67 | ○ | ○ | ○ | present invention |
| compound 68 | ○ | ○ | △ | present invention |
| compound 69 | ◎ | ○ | △ | present invention |
| compound 70 | ○ | ○ | △ | present invention |
| compound 76 | ○ | ◎ | △ | present invention |
| compound 81 | ○ | ◎ | ○ | present invention |
| compound 83 | ○ | ◎ | ○ | present invention |
| compound 88 | △ | ○ | △ | present invention |
| compound 92 | ○ | ○ | △ | present invention |
| compound 93 | ○ | ○ | △ | present invention |
| compound 104 | △ | ○ | ○ | present invention |
| compound 105 | ○ | ○ | △ | present invention |
| compound 106 | ○ | ○ | △ | present invention |
| compound 108 | △ | △ | ○ | present invention |
| compound 109 | △ | △ | △ | present invention |
| compound 110 | ○ | ◎ | ○ | present invention |
| compound 111 | ○ | ○ | △ | present invention |
| compound 112 | △ | ○ | △ | present invention |
| compound 113 | △ | ○ | △ | present invention |
| compound 116 | ○ | ○ | ○ | present invention |
| compound 117 | ○ | ○ | △ | present invention |
| compound 118 | ○ | ○ | △ | present invention |
| compound 122 | ○ | △ | ○ | present invention |
| comparative compound 1 | X | △ | X | comparative example |
| comparative compound 2 | △ | △ | X | comparative example |
| comparative compound 3 | △ | △ | X | comparative example |

3. Production and Evaluation of Organic Electroluminescence Elements

All the materials used in the production of the organic electroluminescence elements were subjected to sublimation purification, and it was confirmed by high-performance liquid chromatography (Tosoh TSK gel ODS-100Z) that the purity (absorption intensity surface area ratio at 254 nm) was 99.9% or higher.

Working Example 1

A glass substrate (made by Geomatec Co., surface resistance of 10 ohms/square) having an ITO film measuring 2.5 cm² and 0.5 mm thick was put into a washing vessel and ultrasonically washed in 2-propanol, upon which it was subjected to treatment with UV-ozone for 30 minutes. The following organic compound layers were sequentially deposited onto this transparent anode (ITO film) by a vacuum vapor deposition method.

Note that the vapor deposition rate described below is 0.1 nm/second unless otherwise specified. The vapor deposition rate was measured using a crystal oscillator. The thickness of each of the following layers was also measured using a crystal oscillator:

First layer: HAT-CN; film thickness of 10 nm
Second layer: HT-1; film thickness of 30 nm
Third layer: H-1 and the light-emitting material listed in Table 4 (weight ratio of 93:7); film thickness of 30 nm
Fourth layer: ET-3; film thickness of 30 nm Over this, lithium fluoride (1 nm) and metallic aluminum (100 nm) were vapor-deposited in this order to form a cathode. A patterned mask (a mask in which the emission region measured 2×2 mm) was installed over the lithium fluoride layer here, and metallic aluminum was vapor-deposited.

Without being allowed to come into contact with the air, the laminate thus obtained was placed in a glove box that had been replaced with nitrogen gas, and was sealed using a glass sealing jar and a UV-setting adhesive (XNR5516HV, made by Nagase Chiba[10]), which gave organic electroluminescence elements 1-1 to 1-53 and comparative organic electroluminescence elements 1-1 to 1-3, in which the emission portion measured 2 mm square. Emission originating in the light-emitting material was observed for each of the elements. The various organic electroluminescence elements thus obtained were tested as follows:

[10]Translator's note: "Nagase Chiba" is now called "Nagase ChemteX."

(a) External Quantum Efficiency

Using a source measurement unit 2400 made by Keithley, DC voltage was applied to each element to make it emit light, and the brightness thereof was measured using a BM-8 brightness meter made by Topcon. The emission spectrum and the emission wavelength were measured using a PMA-11 spectral analyzer made by Hamamatsu Photonics. Based on these results, the external quantum efficiency (η) when the brightness was close to 1000 cd/m² was calculated by brightness conversion method, and this was expressed as a relative value versus 1.0, which was the value for the organic electroluminescence element in which comparative compound 1 was used. Larger numbers indicate higher efficiency and are therefore preferable.

(b) Chromaticity

The chromaticity (x, y) was found from the emission spectrum when DC voltage was applied to make each organic electroluminescence element emit light so as to obtain a brightness of 1000 cd/m². The chromaticity was evaluated in the following four levels from the y value at this point:

◉: $0.03 \leq y \leq 0.08$
○: $0.25 \leq y < 0.03$, $0.08 < y \leq 0.12$
Δ: $0.02 \leq y < 0.25$, $0.12 < y \leq 0.15$
×: $y < 0.02$, $0.15 < y$ (c) Change in Chromaticity after Drive Deterioration DC voltage was applied to make each organic electroluminescence element emit light continuously such that the brightness would be 1000 cd/m², and the chromaticity (x', y') at the point when the brightness decreased to 500 cd/m² was found from the emission spectrum. The change in chromaticity after drive deterioration was evaluated in the following three levels from the change Δy in the y value before and after drive deterioration (=|y'−Δy|):

○: $\Delta y \leq 0.01$
Δ: $0.01 < \Delta y \leq 0.02$
×: $0.02 < \Delta y$

TABLE 4

| Element number | Light-emitting material | Relative external quantum efficiency | Chromaticity | Change in chromaticity after drive deterioration | Remarks |
| --- | --- | --- | --- | --- | --- |
| element 1-1 | compound 1 | 1.2 | ◉ | Δ | present invention |
| element 1-2 | compound 4 | 1.2 | ○ | ○ | present invention |
| element 1-3 | compound 6 | 1.3 | ◉ | ○ | present invention |
| element 1-4 | compound 8 | 1.4 | Δ | Δ | present invention |
| element 1-5 | compound 12 | 1.2 | ○ | Δ | present invention |
| element 1-6 | compound 13 | 1.3 | ◉ | ○ | present invention |
| element 1-7 | compound 14 | 1.2 | ○ | ○ | present invention |
| element 1-8 | compound 15 | 1.3 | ◉ | ○ | present invention |
| element 1-9 | compound 20 | 1.2 | Δ | ○ | present invention |
| element 1-10 | compound 21 | 1.2 | Δ | Δ | present invention |
| element 1-11 | compound 23 | 1.2 | Δ | Δ | present invention |
| element 1-12 | compound 27 | 1.2 | ◉ | Δ | present invention |
| element 1-13 | compound 28 | 1.2 | ◉ | ○ | present invention |
| element 1-14 | compound 33 | 1.2 | ◉ | ○ | present invention |
| element 1-15 | compound 34 | 1.4 | ○ | ○ | present invention |
| element 1-16 | compound 35 | 1.3 | ◉ | ○ | present invention |
| element 1-17 | compound 38 | 1.3 | ◉ | ○ | present invention |
| element 1-18 | compound 40 | 1.5 | ○ | Δ | present invention |
| element 1-19 | compound 41 | 1.3 | ◉ | ○ | present invention |
| element 1-20 | compound 42 | 1.3 | ○ | Δ | present invention |
| element 1-21 | compound 44 | 1.5 | ◉ | ○ | present invention |
| element 1-22 | compound 45 | 1.4 | ◉ | ○ | present invention |
| element 1-23 | compound 46 | 1.4 | ◉ | ○ | present invention |
| element 1-24 | compound 47 | 1.3 | ○ | ○ | present invention |
| element 1-25 | compound 48 | 1.5 | ○ | Δ | present invention |
| element 1-26 | compound 49 | 1.5 | ○ | ○ | present invention |
| element 1-27 | compound 52 | 1.3 | ○ | Δ | present invention |
| element 1-28 | compound 53 | 1.3 | ○ | ○ | present invention |
| element 1-29 | compound 62 | 1.3 | ○ | Δ | present invention |
| element 1-30 | compound 63 | 1.4 | ○ | Δ | present invention |
| element 1-31 | compound 67 | 1.4 | ○ | ○ | present invention |
| element 1-32 | compound 68 | 1.5 | ○ | Δ | present invention |
| element 1-33 | compound 69 | 1.5 | ◉ | Δ | present invention |
| element 1-34 | compound 70 | 1.5 | ○ | Δ | present invention |
| element 1-35 | compound 76 | 1.4 | ○ | Δ | present invention |
| element 1-36 | compound 81 | 1.4 | ○ | ○ | present invention |
| element 1-37 | compound 83 | 1.5 | ○ | ○ | present invention |
| element 1-38 | compound 88 | 1.4 | Δ | Δ | present invention |

TABLE 4-continued

| Element number | Light-emitting material | Relative external quantum efficiency | Chromaticity | Change in chromaticity after drive deterioration | Remarks |
|---|---|---|---|---|---|
| element 1-39 | compound 92 | 1.4 | ○ | Δ | present invention |
| element 1-40 | compound 93 | 1.4 | ○ | Δ | present invention |
| element 1-41 | compound 104 | 1.3 | Δ | ○ | present invention |
| element 1-42 | compound 105 | 1.3 | ○ | Δ | present invention |
| element 1-43 | compound 106 | 1.3 | ○ | Δ | present invention |
| element 1-44 | compound 108 | 1.3 | Δ | ○ | present invention |
| element 1-45 | compound 109 | 1.4 | Δ | Δ | present invention |
| element 1-46 | compound 110 | 1.4 | ○ | ○ | present invention |
| element 1-47 | compound 111 | 1.5 | ○ | Δ | present invention |
| element 1-48 | compound 112 | 1.3 | Δ | Δ | present invention |
| element 1-49 | compound 113 | 1.4 | Δ | Δ | present invention |
| element 1-50 | compound 116 | 1.3 | ○ | ○ | present invention |
| element 1-51 | compound 117 | 1.3 | ○ | Δ | present invention |
| element 1-52 | compound 118 | 1.3 | ○ | Δ | present invention |
| element 1-53 | compound 122 | 1.2 | ○ | ○ | present invention |
| comparative element 1-1 | comparative compound 1 | 1.0 | X | X | comparative example |
| comparative element 1-2 | comparative compound 2 | 0.9 | Δ | X | comparative example |
| comparative element 1-3 | comparative compound 3 | 1.1 | Δ | X | comparative example |

Working Example 2

Other than changing the layer configuration as shown below, organic electroluminescence elements were produced in the same manner as in Working Example 1, and the same evaluations as in Working Example 1 were made. The results are shown in Table 5. Note that the external quantum efficiency in Table 5 is a relative value versus 1.0, which is the external quantum efficiency of an organic electroluminescence element in which comparative compound 1 was used.

First layer: HT-5; film thickness of 10 nm
Second layer: HT-3; film thickness of 20 nm
Third layer: H-2 and the light-emitting material listed in Table 5 (weight ratio of 90:10); film thickness of 30 nm
Fourth layer: ET-2; film thickness of 30 nm

TABLE 5

| Element number | Light-emitting material | Relative external quantum efficiency | Chromaticity | Change in chromaticity after drive deterioration | Remarks |
|---|---|---|---|---|---|
| element 2-1 | compound 1 | 1.3 | ○ | Δ | present invention |
| element 2-2 | compound 4 | 1.3 | Δ | ○ | present invention |
| element 2-3 | compound 6 | 1.5 | ○ | ○ | present invention |
| element 2-4 | compound 8 | 1.3 | Δ | Δ | present invention |
| element 2-5 | compound 12 | 1.3 | Δ | ○ | present invention |
| element 2-6 | compound 13 | 1.5 | ○ | ○ | present invention |
| element 2-7 | compound 14 | 1.3 | ○ | ○ | present invention |
| element 2-8 | compound 15 | 1.3 | ○ | ○ | present invention |
| element 2-9 | compound 20 | 1.3 | Δ | ○ | present invention |
| element 2-10 | compound 21 | 1.3 | Δ | Δ | present invention |
| element 2-11 | compound 23 | 1.3 | Δ | Δ | present invention |
| element 2-12 | compound 27 | 1.3 | ○ | Δ | present invention |
| element 2-13 | compound 28 | 1.5 | ○ | ○ | present invention |
| element 2-14 | compound 33 | 1.3 | ○ | ○ | present invention |
| element 2-15 | compound 34 | 2.1 | ○ | ○ | present invention |
| element 2-16 | compound 35 | 1.6 | ○ | ○ | present invention |
| element 2-17 | compound 38 | 1.4 | ◎ | ○ | present invention |
| element 2-18 | compound 40 | 1.9 | ○ | Δ | present invention |
| element 2-19 | compound 41 | 2.0 | ◎ | ○ | present invention |
| element 2-20 | compound 42 | 1.4 | ○ | Δ | present invention |
| element 2-21 | compound 44 | 2.0 | ◎ | ○ | present invention |
| element 2-22 | compound 45 | 1.9 | ◎ | ○ | present invention |
| element 2-23 | compound 46 | 1.9 | ◎ | ○ | present invention |
| element 2-24 | compound 47 | 2.0 | ○ | ○ | present invention |
| element 2-25 | compound 48 | 2.2 | ○ | Δ | present invention |
| element 2-26 | compound 49 | 2.3 | ○ | ○ | present invention |
| element 2-27 | compound 52 | 1.9 | ○ | Δ | present invention |
| element 2-28 | compound 53 | 1.8 | ○ | ○ | present invention |
| element 2-29 | compound 62 | 1.8 | ○ | Δ | present invention |
| element 2-30 | compound 63 | 1.9 | ○ | Δ | present invention |
| element 2-31 | compound 67 | 2.0 | ○ | ○ | present invention |
| element 2-32 | compound 68 | 2.3 | ○ | Δ | present invention |

TABLE 5-continued

| Element number | Light-emitting material | Relative external quantum efficiency | Chromaticity | Change in chromaticity after drive deterioration | Remarks |
|---|---|---|---|---|---|
| element 2-33 | compound 69 | 2.2 | ◎ | Δ | present invention |
| element 2-34 | compound 70 | 2.2 | ○ | Δ | present invention |
| element 2-35 | compound 76 | 1.9 | ○ | Δ | present invention |
| element 2-36 | compound 81 | 1.8 | ○ | ○ | present invention |
| element 2-37 | compound 83 | 1.8 | ○ | ○ | present invention |
| element 2-38 | compound 88 | 2.0 | Δ | ○ | present invention |
| element 2-39 | compound 92 | 2.1 | ○ | Δ | present invention |
| element 2-40 | compound 93 | 2.0 | ○ | Δ | present invention |
| element 2-41 | compound 104 | 2.0 | Δ | ○ | present invention |
| element 2-42 | compound 105 | 2.1 | ○ | Δ | present invention |
| element 2-43 | compound 106 | 1.9 | ○ | Δ | present invention |
| element 2-44 | compound 108 | 1.7 | Δ | ○ | present invention |
| element 2-45 | compound 109 | 1.9 | Δ | Δ | present invention |
| element 2-46 | compound 110 | 2.0 | ○ | ○ | present invention |
| element 2-47 | compound 111 | 1.5 | ○ | Δ | present invention |
| element 2-48 | compound 112 | 1.4 | Δ | Δ | present invention |
| element 2-49 | compound 113 | 1.6 | Δ | Δ | present invention |
| element 2-50 | compound 116 | 1.9 | ○ | ○ | present invention |
| element 2-51 | compound 117 | 1.8 | ○ | Δ | present invention |
| element 2-52 | compound 118 | 1.8 | ○ | Δ | present invention |
| element 2-53 | compound 122 | 1.3 | ○ | ○ | present invention |
| comparative element 2-1 | comparative compound 1 | 1.0 | X | X | comparative example |
| comparative element 2-2 | comparative compound 2 | 1.2 | X | X | comparative example |
| comparative element 2-3 | comparative compound 3 | 1.4 | Δ | X | comparative example |

Working Example 3

Other than changing the layer configuration as shown below, organic electroluminescence elements were produced in the same manner as in Working Example 1, and the same evaluations as in Working Example 1 were made. The results are shown in Table 6. Note that the external quantum efficiency in Table 6 is a relative value versus 1.0, which is the external quantum efficiency of an organic electroluminescence element in which comparative compound 1 was used.

First layer: HAT-CN; film thickness of 10 nm

Second layer: HT-2; film thickness of 60 nm

Third layer: H-1 and the light-emitting material listed in Table 6 (weight ratio of 97:3); film thickness of 30 nm Fourth layer: ET-1: Liq (mono(8-quinolinolato) lithium complex)=1:1; film thickness of 20 nm

TABLE 6

| Element number | Light-emitting material | Relative external quantum efficiency | Chromaticity | Change in chromaticity after drive deterioration | Remarks |
|---|---|---|---|---|---|
| element 3-1 | compound 1 | 1.3 | ◎ | Δ | present invention |
| element 3-2 | compound 4 | 1.2 | ○ | ○ | present invention |
| element 3-3 | compound 6 | 1.3 | ◎ | ○ | present invention |
| element 3-4 | compound 8 | 1.4 | Δ | Δ | present invention |
| element 3-5 | compound 12 | 1.3 | ○ | Δ | present invention |
| element 3-6 | compound 13 | 1.3 | ◎ | ○ | present invention |
| element 3-7 | compound 14 | 1.3 | ○ | ○ | present invention |
| element 3-8 | compound 15 | 1.4 | ◎ | ○ | present invention |
| element 3-9 | compound 20 | 1.2 | Δ | ○ | present invention |
| element 3-10 | compound 21 | 1.2 | Δ | ○ | present invention |
| element 3-11 | compound 23 | 1.3 | Δ | Δ | present invention |
| element 3-12 | compound 27 | 1.2 | ◎ | Δ | present invention |
| element 3-13 | compound 28 | 1.2 | ◎ | ○ | present invention |
| element 3-14 | compound 33 | 1.3 | ◎ | ○ | present invention |
| element 3-15 | compound 34 | 1.4 | ○ | ○ | present invention |
| element 3-16 | compound 35 | 1.3 | ◎ | ○ | present invention |
| element 3-17 | compound 38 | 1.3 | ◎ | ○ | present invention |
| element 3-18 | compound 40 | 1.5 | ○ | Δ | present invention |
| element 3-19 | compound 41 | 1.4 | ◎ | 0 | present invention |
| element 3-20 | compound 42 | 1.3 | ○ | Δ | present invention |
| element 3-21 | compound 44 | 1.5 | ○ | ○ | present invention |
| element 3-22 | compound 45 | 1.4 | ◎ | ○ | present invention |
| element 3-23 | compound 46 | 1.4 | ○ | ○ | present invention |
| element 3-24 | compound 47 | 1.3 | ○ | ○ | present invention |

TABLE 6-continued

| Element number | Light-emitting material | Relative external quantum efficiency | Chromaticity | Change in chromaticity after drive deterioration | Remarks |
|---|---|---|---|---|---|
| element 3-25 | compound 48 | 1.4 | ○ | Δ | present invention |
| element 3-26 | compound 49 | 1.4 | ○ | ○ | present invention |
| element 3-27 | compound 52 | 1.3 | ○ | Δ | present invention |
| element 3-28 | compound 53 | 1.3 | ○ | ○ | present invention |
| element 3-29 | compound 62 | 1.3 | ○ | Δ | present invention |
| element 3-30 | compound 63 | 1.4 | ○ | Δ | present invention |
| element 3-31 | compound 67 | 1.4 | ○ | ○ | present invention |
| element 3-32 | compound 68 | 1.5 | ○ | Δ | present invention |
| element 3-33 | compound 69 | 1.4 | ○ | Δ | present invention |
| element 3-34 | compound 70 | 1.5 | ○ | Δ | present invention |
| element 3-35 | compound 76 | 1.4 | ○ | Δ | present invention |
| element 3-36 | compound 81 | 1.4 | ○ | ○ | present invention |
| element 3-37 | compound 83 | 1.4 | ○ | ○ | present invention |
| element 3-38 | compound 88 | 1.4 | Δ | ○ | present invention |
| element 3-39 | compound 92 | 1.4 | ○ | Δ | present invention |
| element 3-40 | compound 93 | 1.4 | ○ | Δ | present invention |
| element 3-41 | compound 104 | 1.3 | Δ | ○ | present invention |
| element 3-42 | compound 105 | 1.3 | ○ | Δ | present invention |
| element 3-43 | compound 106 | 1.2 | ○ | Δ | present invention |
| element 3-44 | compound 108 | 1.3 | Δ | ○ | present invention |
| element 3-45 | compound 109 | 1.4 | Δ | Δ | present invention |
| element 3-46 | compound 110 | 1.4 | ○ | ○ | present invention |
| element 3-47 | compound 111 | 1.4 | ○ | Δ | present invention |
| element 3-48 | compound 112 | 1.3 | Δ | ○ | present invention |
| element 3-49 | compound 113 | 1.4 | Δ | Δ | present invention |
| element 3-50 | compound 116 | 1.3 | ○ | ○ | present invention |
| element 3-51 | compound 117 | 1.3 | ○ | Δ | present invention |
| element 3-52 | compound 118 | 1.3 | ○ | Δ | present invention |
| element 3-53 | compound 122 | 1.2 | ○ | ○ | present invention |
| comparative element 3-1 | comparative compound 1 | 1.0 | X | X | comparative example |
| comparative element 3-2 | comparative compound 2 | 1.0 | Δ | X | comparative example |
| comparative element 3-3 | comparative compound 3 | 1.1 | Δ | X | comparative example |

Working Example 4

Other than changing the layer configuration as shown below, organic electroluminescence elements were produced in the same manner as in Working Example 1, and the same evaluations as in Working Example 1 were made. The results are shown in Table 7. Note that the external quantum efficiency in Table 7 is a relative value versus 1.0, which is the external quantum efficiency of an organic electroluminescence element in which comparative compound 1 was used.

First layer: HAT-CN; film thickness of 10 nm
Second layer: HT-2; film thickness of 30 nm
Third layer: H-1 and the light-emitting material listed in Table 7 (weight ratio of 97:3); film thickness of 30 nm
Fourth layer: ET-3; film thickness of 30 nm

TABLE 7

| Element number | Light-emitting material | Relative external [quantum efficiency] | Chromaticity | Change in chromaticity after drive deterioration | Remarks |
|---|---|---|---|---|---|
| element 4-1 | compound 1 | 1.2 | ◎ | Δ | present invention |
| element 4-2 | compound 4 | 1.2 | ◎ | ○ | present invention |
| element 4-3 | compound 6 | 1.3 | ◎ | ○ | present invention |
| element 4-4 | compound 8 | 1.3 | ○ | Δ | present invention |
| element 4-5 | compound 12 | 1.2 | ◎ | ○ | present invention |
| element 4-6 | compound 13 | 1.3 | ◎ | ○ | present invention |
| element 4-7 | compound 14 | 1.3 | ○ | ○ | present invention |
| element 4-8 | compound 15 | 1.3 | ◎ | ○ | present invention |
| element 4-9 | compound 20 | 1.2 | Δ | ○ | present invention |
| element 4-10 | compound 21 | 1.3 | Δ | ○ | present invention |
| element 4-11 | compound 23 | 1.3 | Δ | ○ | present invention |
| element 4-12 | compound 27 | 1.3 | ◎ | Δ | present invention |
| element 4-13 | compound 28 | 1.3 | ◎ | ○ | present invention |
| element 4-14 | compound 33 | 1.3 | ◎ | ○ | present invention |
| element 4-15 | compound 34 | 1.4 | ○ | ○ | present invention |
| element 4-16 | compound 35 | 1.3 | ◎ | ○ | present invention |
| element 4-17 | compound 38 | 1.3 | ◎ | Δ | present invention |

TABLE 7-continued

| Element number | Light-emitting material | Relative external [quantum efficiency] | Chromaticity | Change in chromaticity after drive deterioration | Remarks |
|---|---|---|---|---|---|
| element 4-18 | compound 40 | 1.4 | ○ | Δ | present invention |
| element 4-19 | compound 41 | 1.3 | ◎ | ○ | present invention |
| element 4-20 | compound 42 | 1.3 | ○ | ○ | present invention |
| element 4-21 | compound 44 | 1.4 | ○ | ○ | present invention |
| element 4-22 | compound 45 | 1.4 | ◎ | ○ | present invention |
| element 4-23 | compound 46 | 1.4 | ◎ | ○ | present invention |
| element 4-24 | compound 47 | 1.4 | ○ | ○ | present invention |
| element 4-25 | compound 48 | 1.5 | ○ | Δ | present invention |
| element 4-26 | compound 49 | 1.4 | ○ | ○ | present invention |
| element 4-27 | compound 52 | 1.3 | ○ | ○ | present invention |
| element 4-28 | compound 53 | 1.3 | ○ | ○ | present invention |
| element 4-29 | compound 62 | 1.3 | ○ | ○ | present invention |
| element 4-30 | compound 63 | 1.4 | ○ | ○ | present invention |
| element 4-31 | compound 67 | 1.3 | ○ | ○ | present invention |
| element 4-32 | compound 68 | 1.4 | ○ | ○ | present invention |
| element 4-33 | compound 69 | 1.4 | ○ | ○ | present invention |
| element 4-34 | compound 70 | 1.4 | ○ | Δ | present invention |
| element 4-35 | compound 76 | 1.3 | ○ | Δ | present invention |
| element 4-36 | compound 81 | 1.3 | ○ | ○ | present invention |
| element 4-37 | compound 83 | 1.4 | ○ | ○ | present invention |
| element 4-38 | compound 88 | 1.3 | Δ | ○ | present invention |
| element 4-39 | compound 92 | 1.3 | ○ | Δ | present invention |
| element 4-40 | compound 93 | 1.4 | ○ | Δ | present invention |
| element 4-41 | compound 104 | 1.3 | Δ | ○ | present invention |
| element 4-42 | compound 105 | 1.2 | ○ | Δ | present invention |
| element 4-43 | compound 106 | 1.2 | Δ | ○ | present invention |
| element 4-44 | compound 108 | 1.3 | Δ | ○ | present invention |
| element 4-45 | compound 109 | 1.3 | Δ | Δ | present invention |
| element 4-46 | compound 110 | 1.3 | Δ | ○ | present invention |
| element 4-47 | compound 111 | 1.3 | ○ | Δ | present invention |
| element 4-48 | compound 112 | 1.3 | Δ | ○ | present invention |
| element 4-49 | compound 113 | 1.3 | Δ | Δ | present invention |
| element 4-50 | compound 116 | 1.3 | ○ | ○ | present invention |
| element 4-51 | compound 117 | 1.3 | ○ | Δ | present invention |
| element 4-52 | compound 118 | 1.2 | ○ | Δ | present invention |
| element 4-53 | compound 122 | 1.2 | ○ | ○ | present invention |
| comparative element 4-1 | comparative compound 1 | 1.0 | X | Δ | comparative example |
| comparative element 4-2 | comparative compound 2 | 1.2 | Δ | X | comparative example |
| comparative element 4-3 | comparative compound 3 | 1.1 | Δ | X | comparative example |

Working Example 5

Other than changing the layer configuration as shown below, organic electroluminescence elements were produced in the same manner as in Working Example 1, and the same evaluations as in Working Example 1 were made. The results are shown in Table 8. Note that the external quantum efficiency in Table 8 is a relative value versus 1.0, which is the external quantum efficiency of an organic electroluminescence element in which comparative compound 1 was used.

First layer: HT-4; film thickness of 50 nm
Second layer: HT-3; film thickness of 45 nm
Third layer: H-2 and the light-emitting material listed in Table 8 (weight ratio of 95:5); film thickness of 25 nm
Fourth layer: ET-4; film thickness of 5 nm
Fifth layer: ET-2; film thickness of 20 nm

TABLE 8

| Element number | Light-emitting material | Relative external quantum efficiency | Chromaticity | Change in chromaticity after drive deterioration | Remarks |
|---|---|---|---|---|---|
| element 5-1 | compound 1 | 1.3 | ◎ | Δ | present invention |
| element 5-2 | compound 4 | 1.3 | ○ | ○ | present invention |
| element 5-3 | compound 6 | 1.4 | ◎ | ○ | present invention |
| element 5-4 | compound 8 | 1.3 | Δ | Δ | present invention |
| element 5-5 | compound 12 | 1.3 | ○ | Δ | present invention |
| element 5-6 | compound 13 | 1.4 | ◎ | ○ | present invention |
| element 5-7 | compound 14 | 1.4 | ○ | ○ | present invention |
| element 5-8 | compound 15 | 1.4 | ◎ | ○ | present invention |
| element 5-9 | compound 20 | 1.2 | Δ | ○ | present invention |
| element 5-10 | compound 21 | 1.3 | Δ | ○ | present invention |

TABLE 8-continued

| Element number | Light-emitting material | Relative external quantum efficiency | Chromaticity | Change in chromaticity after drive deterioration | Remarks |
|---|---|---|---|---|---|
| element 5-11 | compound 23 | 1.3 | Δ | ○ | present invention |
| element 5-12 | compound 27 | 1.3 | ◉ | ○ | present invention |
| element 5-13 | compound 28 | 1.4 | ◉ | ○ | present invention |
| element 5-14 | compound 33 | 1.2 | ◉ | ○ | present invention |
| element 5-15 | compound 34 | 1.6 | ○ | ○ | present invention |
| element 5-16 | compound 35 | 1.4 | ◉ | ○ | present invention |
| element 5-17 | compound 38 | 1.3 | ◉ | ○ | present invention |
| element 5-18 | compound 40 | 1.5 | ○ | Δ | present invention |
| element 5-19 | compound 41 | 1.4 | ◉ | ○ | present invention |
| element 5-20 | compound 42 | 1.3 | ○ | Δ | present invention |
| element 5-21 | compound 44 | 1.5 | ◉ | ○ | present invention |
| element 5-22 | compound 45 | 1.5 | ◉ | ○ | present invention |
| element 5-23 | compound 46 | 1.6 | ◉ | ○ | present invention |
| element 5-24 | compound 47 | 1.4 | ○ | ○ | present invention |
| element 5-25 | compound 48 | 1.6 | ○ | Δ | present invention |
| element 5-26 | compound 49 | 1.6 | ○ | ○ | present invention |
| element 5-27 | compound 52 | 1.4 | ○ | Δ | present invention |
| element 5-28 | compound 53 | 1.4 | ○ | ○ | present invention |
| element 5-29 | compound 62 | 1.4 | ○ | Δ | present invention |
| element 5-30 | compound 63 | 1.5 | ○ | Δ | present invention |
| element 5-31 | compound 67 | 1.5 | ○ | ○ | present invention |
| element 5-32 | compound 68 | 1.5 | ○ | Δ | present invention |
| element 5-33 | compound 69 | 1.5 | ◉ | Δ | present invention |
| element 5-34 | compound 70 | 1.5 | ○ | Δ | present invention |
| element 5-35 | compound 76 | 1.5 | ○ | Δ | present invention |
| element 5-36 | compound 81 | 1.5 | ○ | ○ | present invention |
| element 5-37 | compound 83 | 1.5 | ○ | ○ | present invention |
| element 5-38 | compound 88 | 1.4 | Δ | Δ | present invention |
| element 5-39 | compound 92 | 1.4 | ○ | Δ | present invention |
| element 5-40 | compound 93 | 1.4 | ○ | Δ | present invention |
| element 5-41 | compound 104 | 1.5 | Δ | ○ | present invention |
| element 5-42 | compound 105 | 1.5 | ○ | Δ | present invention |
| element 5-43 | compound 106 | 1.5 | ○ | ○ | present invention |
| element 5-44 | compound 108 | 1.3 | Δ | ○ | present invention |
| element 5-45 | compound 109 | 1.3 | Δ | Δ | present invention |
| element 5-46 | compound 110 | 1.4 | ○ | ○ | present invention |
| element 5-47 | compound 111 | 1.3 | ○ | Δ | present invention |
| element 5-48 | compound 112 | 1.3 | Δ | Δ | present invention |
| element 5-49 | compound 113 | 1.3 | Δ | Δ | present invention |
| element 5-50 | compound 116 | 1.4 | ○ | ○ | present invention |
| element 5-51 | compound 117 | 1.4 | ○ | Δ | present invention |
| element 5-52 | compound 118 | 1.4 | ○ | Δ | present invention |
| element 5-53 | compound 122 | 1.2 | ○ | ○ | present invention |
| comparative element 5-1 | comparative compound 1 | 1.0 | X | X | comparative example |
| comparative element 5-2 | comparative compound 2 | 1.2 | Δ | X | comparative example |
| comparative element 5-3 | comparative compound 3 | 1.3 | Δ | X | comparative example |

Working Example 6

Other than changing the layer configuration as shown below, organic electroluminescence elements were produced in the same manner as in Working Example 1, and the same evaluations as in Working Example 1 were made. The results are shown in Table 9. Note that the external quantum efficiency in Table 9 is a relative value versus 1.0, which is the external quantum efficiency of an organic electroluminescence element in which comparative compound 1 was used.

First layer: HAT-CN; film thickness of 10 nm
Second layer: HT-1; film thickness of 30 nm
Third layer: H-3 and the light-emitting material listed in Table 9 (weight ratio of 93:7); film thickness of 30 nm
Fourth layer: ET-3; film thickness of 30 nm

TABLE 9

| Element number | Light-emitting material | Relative external quantum efficiency | Chromaticity | Change in chromaticity after drive deterioration | Remarks |
|---|---|---|---|---|---|
| element 6-1 | compound 1 | 1.1 | ◉ | ○ | present invention |
| element 6-2 | compound 4 | 1.1 | ○ | ○ | present invention |
| element 6-3 | compound 6 | 1.2 | ◉ | ○ | present invention |

TABLE 9-continued

| Element number | Light-emitting material | Relative external quantum efficiency | Chromaticity | Change in chromaticity after drive deterioration | Remarks |
|---|---|---|---|---|---|
| element 6-4 | compound 8 | 1.2 | Δ | ○ | present invention |
| element 6-5 | compound 12 | 1.1 | ○ | ○ | present invention |
| element 6-6 | compound 13 | 1.2 | ◎ | ○ | present invention |
| element 6-7 | compound 14 | 1.2 | ○ | ○ | present invention |
| element 6-8 | compound 15 | 1.2 | ◎ | ○ | present invention |
| element 6-9 | compound 20 | 1.1 | Δ | ○ | present invention |
| element 6-10 | compound 21 | 1.2 | Δ | ○ | present invention |
| element 6-11 | compound 23 | 1.2 | Δ | ○ | present invention |
| element 6-12 | compound 27 | 1.1 | ◎ | Δ | present invention |
| element 6-13 | compound 28 | 1.2 | ◎ | ○ | present invention |
| element 6-14 | compound 33 | 1.1 | ◎ | ○ | present invention |
| element 6-15 | compound 34 | 1.3 | ○ | ○ | present invention |
| element 6-16 | compound 35 | 1.2 | ◎ | ○ | present invention |
| element 6-17 | compound 38 | 1.2 | ◎ | ○ | present invention |
| element 6-18 | compound 40 | 1.3 | ○ | ○ | present invention |
| element 6-19 | compound 41 | 1.2 | ◎ | ○ | present invention |
| element 6-20 | compound 42 | 1.2 | ○ | Δ | present invention |
| element 6-21 | compound 44 | 1.3 | ◎ | ○ | present invention |
| element 6-22 | compound 45 | 1.3 | ◎ | ○ | present invention |
| element 6-23 | compound 46 | 1.3 | ◎ | ○ | present invention |
| element 6-24 | compound 47 | 1.2 | ○ | ○ | present invention |
| element 6-25 | compound 48 | 1.3 | ○ | ○ | present invention |
| element 6-26 | compound 49 | 1.3 | ○ | ○ | present invention |
| element 6-27 | compound 52 | 1.3 | ○ | ○ | present invention |
| element 6-28 | compound 53 | 1.3 | ○ | ○ | present invention |
| element 6-29 | compound 62 | 1.3 | ○ | ○ | present invention |
| element 6-30 | compound 63 | 1.3 | ○ | ○ | present invention |
| element 6-31 | compound 67 | 1.3 | ○ | ○ | present invention |
| element 6-32 | compound 68 | 1.3 | ○ | ○ | present invention |
| element 6-33 | compound 69 | 1.3 | ◎ | ○ | present invention |
| element 6-34 | compound 70 | 1.2 | ○ | ○ | present invention |
| element 6-35 | compound 76 | 1.3 | ○ | Δ | present invention |
| element 6-36 | compound 81 | 1.3 | ○ | ○ | present invention |
| element 6-37 | compound 83 | 1.3 | ○ | ○ | present invention |
| element 6-38 | compound 88 | 1.3 | Δ | ○ | present invention |
| element 6-39 | compound 92 | 1.3 | ○ | ○ | present invention |
| element 6-40 | compound 93 | 1.2 | ○ | ○ | present invention |
| element 6-41 | compound 104 | 1.2 | Δ | ○ | present invention |
| element 6-42 | compound 105 | 1.2 | ○ | ○ | present invention |
| element 6-43 | compound 106 | 1.2 | ○ | ○ | present invention |
| element 6-44 | compound 108 | 1.1 | Δ | ○ | present invention |
| element 6-45 | compound 109 | 1.2 | Δ | ○ | present invention |
| element 6-46 | compound 110 | 1.1 | ○ | ○ | present invention |
| element 6-47 | compound 111 | 1.1 | ○ | ○ | present invention |
| element 6-48 | compound 112 | 1.1 | Δ | ○ | present invention |
| element 6-49 | compound 113 | 1.1 | Δ | ○ | present invention |
| element 6-50 | compound 116 | 1.2 | ○ | ○ | present invention |
| element 6-51 | compound 117 | 1.2 | ○ | ○ | present invention |
| element 6-52 | compound 118 | 1.2 | ○ | ○ | present invention |
| element 6-53 | compound 122 | 1.1 | ○ | ○ | present invention |
| comparative element 6-1 | comparative compound 1 | 1.0 | X | X | comparative example |
| comparative element 6-2 | comparative compound 2 | 1.1 | Δ | X | comparative example |
| comparative element 6-3 | comparative compound 3 | 1.1 | Δ | X | comparative example |

Working Example 5 [sic][11]

[11]Translator's note: apparent error in the original; "Working Example 5" should be "Working Example 7."

Preparation of Coating Solution for Forming Light-Emitting Layer

Methyl ethyl ketone (98.99 wt %) was mixed with the light-emitting material 20 (0.1 wt %) and the following host material PH-1 (0.9 wt %), which gave a light-emitting layer formation coating solution 1:

Other than changing the light-emitting material 20 in the light-emitting layer formation coating solution 1 to the light-emitting materials 28, 34, 35, and 53, light-emitting layer formation coating solutions 2 to 5 were prepared in the same manner as the light-emitting layer formation coating solution 1.

Furthermore, other than changing the host material PH-1 to the host material H-2 in the light-emitting layer formation coating solutions 1 to 5, light-emitting layer formation coating solutions 6 to 10 were prepared in the same manner as in the light-emitting layer formation coating solutions 1 to 5, respectively.

[Eightieth Chemical Formula]

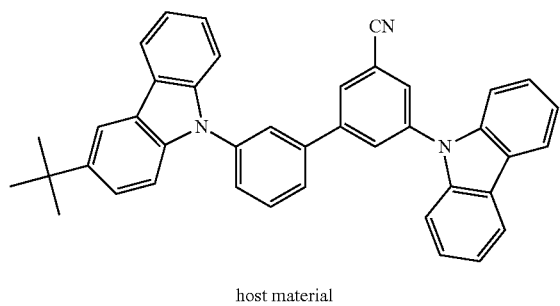

host material

Moreover, for comparison, other than changing the light-emitting material 20 in the light-emitting layer formation coating solution 1 to a comparative compound 1, a comparative light-emitting layer formation coating solution 1 was prepared in the same manner as the light-emitting layer formation coating solution 1, and other than changing the light-emitting material 20 in the light-emitting layer formation coating solution 6 to the comparative compound 1, a comparative light-emitting layer formation coating solution 2 was prepared in the same manner as the light-emitting layer formation coating solution 6.

—Production of Organic Electroluminescence Element P1—

A transparent support substrate was produced by forming a film of ITO in a thickness of 150 nm by vapor deposition over a glass substrate measuring 25×25×0.7 mm. This transparent support substrate was etched and washed.

2 weight parts of PTPDES-2 (made by Chemipro Kasei; Tg=205° C.) expressed by the following structural formula was dissolved in 98 weight parts of commercial grade (electronics) cyclohexanone (made by Kanto Chemical), and [this product] was applied over the ITO glass substrate by spin coating (2000 rpm for 20 seconds) such that the thickness would be approximately 40 nm, upon which [the coating] was dried for 30 minutes at 120° C. and annealed for 10 minutes at 160° C., thereby forming a hole injection layer.

[Eighty-first Chemical Formula]

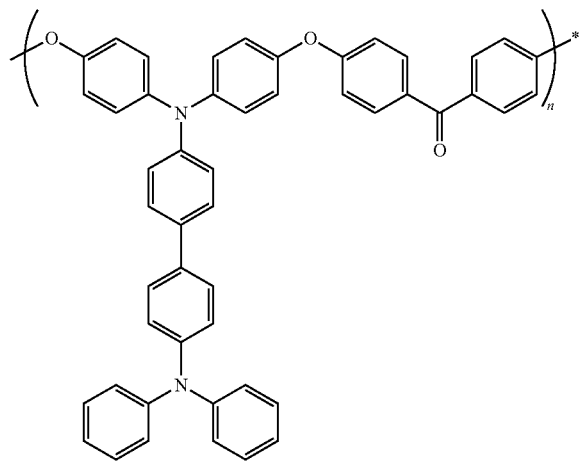

PTPDES-2

The aforementioned light-emitting layer formation coating solution 1 was applied over this hole injection layer by spin coating (1300 rpm for 30 seconds) such that the thickness would be approximately 40 nm, thereby forming a light-emitting layer.

Then, over this light-emitting layer, BAlq (bis-(2-methyl-8-quinolinolato)-4-(phenylphenolato)-aluminum(III)) expressed by the following structural formula was formed as an electron transport layer by vacuum vapor deposition such that the thickness would be 40 nm:

[Eighty-Second Chemical Formula]

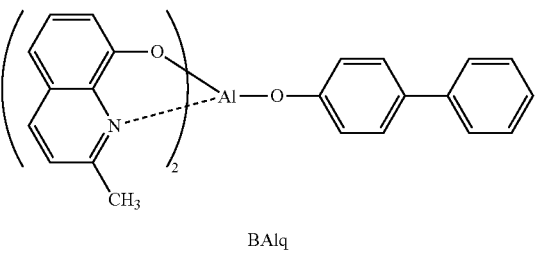

BAlq

Lithium fluoride (LiF) was formed over the electron transport layer as an electron injection layer by vacuum vapor deposition such that the thickness would be 1 nm, and metallic aluminum (70 nm) was additionally vapor-deposited, which gave a cathode.

The laminate thus produced was placed in a glove box that had been replaced with argon gas, and was sealed using a stainless steel sealing jar and a UV-setting adhesive (XNR5516HV, made by Nagase Chiba), thereby producing the organic electroluminescence element P1.

In the organic electroluminescence element P1, other than changing the light-emitting layer formation coating solution 1 to [solutions] 2 to 10, organic electroluminescence elements P2 to P10 were produced in the same manner as the organic electroluminescence element P1.

In addition, for comparison, in the organic electroluminescence element P1, other than changing the light-emitting layer formation coating solution 1 to the comparative light-emitting layer formation coating solutions 1 and 2, organic electroluminescence elements P11 and P12 were produced in the same manner as the organic electroluminescence element P1.

The same evaluations as in Working Example 1 were made. The results are shown in Table 10. Note that the external quantum efficiency in Table 10 is a relative value versus 1.0, which is the external quantum efficiency of an organic electroluminescence element in which comparative compound 1 was used.

TABLE 10

| Organic electroluminescence element | Light-emitting material | Host material | External quantum efficiency | Chromaticity | Change in chromaticity after drive deterioration | Remarks |
|---|---|---|---|---|---|---|
| P1 | compound 20 | PH-1 | 1.1 | Δ | ○ | present invention |
| P2 | compound 28 | PH-1 | 1.2 | ◉ | ○ | present invention |
| P3 | compound 34 | PH-1 | 1.3 | ○ | ○ | present invention |
| P4 | compound 35 | PH-1 | 1.2 | ◉ | ○ | present invention |
| P5 | compound 53 | PH-1 | 1.3 | ○ | ○ | present invention |
| P11 | comparative compound 1 | PH-1 | 1.0 | Δ | X | comparative example |
| P6 | compound 20 | H-2 | 1.4 | ○ | Δ | present invention |
| P7 | compound 28 | H-2 | 1.5 | ○ | ○ | present invention |
| P8 | compound 34 | H-2 | 1.8 | ○ | ○ | present invention |
| P9 | compound 35 | H-2 | 1.5 | ○ | ○ | present invention |
| P10 | compound 53 | H-2 | 1.6 | ○ | ○ | present invention |
| P12 | comparative compound 1 | H-2 | 1.0 | X | X | comparative example |

DESCRIPTION OF SYMBOLS 2 substrate
3 anode
4 hole injection layer
5 hole transport layer
6 light-emitting layer
7 hole blocking layer
8 electron transport layer
9 cathode
10 organic electroluminescence element
11 organic layer
12 protective layer
14 adhesive layer
16 sealing container
20 light-emitting device
30 light-scattering member
31 transparent substrate
30A light incidence face
30B light emission face
32 microparticles
40 illumination device

The invention claimed is:

1. An organic electroluminescence element having
a substrate,
a pair of electrodes that is disposed on this substrate and that includes an anode and a cathode, and
an organic layer disposed between these electrodes, wherein
said organic layer contains a compound expressed by General Formula 1 below:

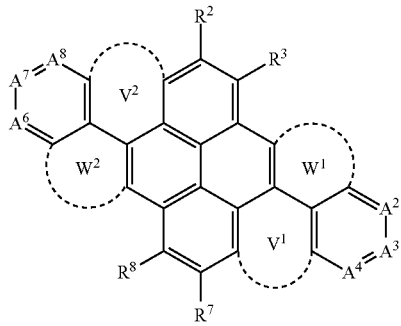

General Formula 1 either $V^1$ or $W^1$ forms a ring, either $V^2$ or $W^2$ also forms a ring, the ring formed by $V^1$ and $V^2$ is a six-membered ring, and the ring formed by $W^1$ and $W^2$ is a five-membered ring,
wherein when both $V^1$ and $V^2$ form a six-membered ring, at least one of $V^1$ and $V^2$ has a linking group E that links the portion represented by a dotted line in General Formula 1, wherein E is $CR^xR^y$, $SiR^aR^b$, or O;
each of $R^x$ and $R^y$ independently represents an alkyl group, an aryl group, or a silyl group;
each of $R^a$ and $R^b$ independently represents an alkyl group or an aryl group;
each of $A^2$ to $A^4$ and $A^6$ to $A^8$ independently represents $CR^z$ or N, wherein two adjacent $CR^z$ groups may together form a five- or six-membered ring, and
$R^z$ represents a hydrogen atom or a substituent; and
each of $R^2$, $R^3$, $R^7$, and $R^8$ independently represents an alkyl group, an aryl group, a heteroaryl group, a fluorine atom, a hydrogen atom, or a deuterium atom.

2. The organic electroluminescence element according to claim 1, wherein the compound expressed by General Formula 1 above is expressed by General Formula 2 below:

General Formula 2

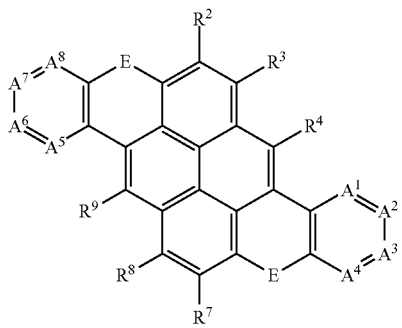

wherein $A^1$ to $A^8$ represent $CR^Z$ or N, and $R^Z$ represents a hydrogen atom or a substituent; E represents $CR^xR^y$, $SiR^aR^b$, or O; each of $R^x$ and $R^y$ independently represents an alkyl group, an aryl group, or a silyl group; each of $R^a$ and $R^b$ independently represents an alkyl group or an aryl group; and each of $R^2$ to $R^4$ and $R^7$ to $R^9$ independently represents an alkyl group, an aryl group, a heteroaryl group, a fluorine atom, a hydrogen atom, or a deuterium atom.

3. The organic electroluminescence element according to claim 1, wherein the compound expressed by General Formula 1 above is expressed by General Formula 3 below:

General Formula 3

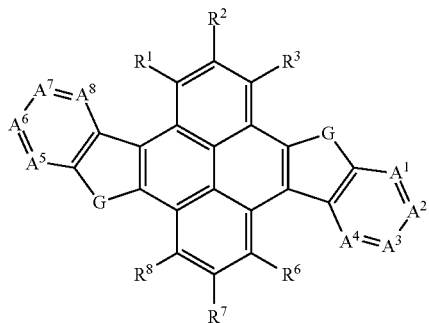

wherein $A^1$ to $A^8$ represent $CR^Z$ or N, and $R^Z$ represents a hydrogen atom or a substituent; G represents $CR^xR^y$, $SiR^aR^b$, $NR^c$, S, or O; each of $R^x$ and $R^y$ independently represents an alkyl group, an aryl group, or a silyl group; $R^a$, $R^b$, and $R^c$ represent each independently an alkyl group or an aryl group; and each of $R^1$ to $R^3$ and $R^6$ to $R^8$ independently represents an alkyl group, an aryl group, a heteroaryl group, a fluorine atom, a hydrogen atom, or a deuterium atom.

4. The organic electroluminescence element according to claim 2, wherein the compound expressed by General Formula 2 above is expressed by General Formula 4 below:

General Formula 4

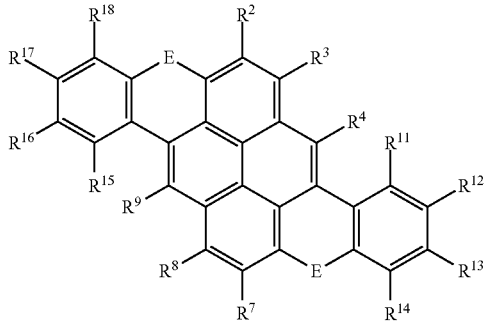

wherein E represents $CR^xR^y$, $SiR^aR^b$, or O; each of $R^x$ and $R^y$ independently represents an alkyl group, an aryl group, or a silyl group; $R^a$ and $R^b$ represent each independently represents an alkyl group or an aryl group; each of $R^2$ to $R^4$ and $R^7$ to $R^9$ independently an alkyl group, an aryl group, a heteroaryl group, a fluorine atom, a hydrogen atom, or a deuterium atom; each of $R^{11}$ to $R^{18}$ independently represents an alkyl group, an alkoxy group, an alkylthio group, an aryl group, a heteroaryl group, an arylthio group, a fluorine atom, a hydrogen atom, a deuterium atom, a cyano group, or an amino group; and each pair of $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.

5. The organic electroluminescence element according to claim 4, wherein in General Formula 4 above, one of $R^{12}$ to $R^{14}$ and $R^{16}$ to $R^{18}$ is $NR^{19}R^{20}$, wherein each of $R^{19}$ and $R^{20}$ independently represents an alkyl group or an aryl group, and these may bond to each other to form a ring.

6. The organic electroluminescence element according to claim 3, wherein the compound expressed by General Formula 3 above is expressed by General Formula 5 below:

General Formula 5

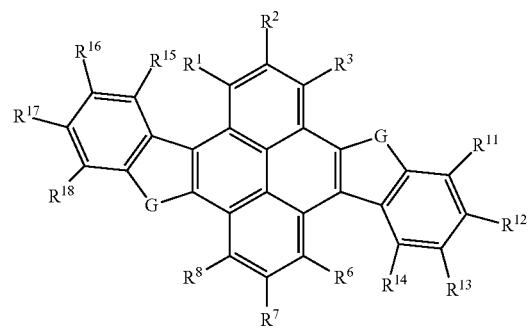

wherein G represents $CR^xR^y$, $SiR^aR^b$, $NR^c$, S, or O; each of $R^x$ and $R^y$ independently represents an alkyl group, an aryl group, or a silyl group; each of $R^a$, $R^b$, and $R^c$ represent each independently represents an alkyl group or an aryl group; each of $R^1$ to $R^3$ and $R^6$ to $R^8$ independently represents an alkyl group, an aryl group, a heteroaryl group, a fluorine atom, a hydrogen atom, or a deuterium atom; each of $R^{11}$ to $R^{18}$ independently represents an alkyl group, an alkoxy group, an alkylthio group, an aryl group, a heteroaryl group, an arylthio group, a fluorine atom, a hydrogen atom, a deuterium atom, a cyano group, or an amino group; and each pair of $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.

7. The organic electroluminescence element according to claim 6, wherein in General Formula 5 above, one of $R^{11}$ to $R^{13}$ and $R^{16}$ to $R^{18}$ is $NR^{19}R^{20}$, wherein each of $R^{19}$ and $R^{20}$ independently represents an alkyl group or an aryl group, and these may bond to each other to form a ring.

8. The organic electroluminescence element according to claim 6, wherein in General Formula 5 above, G is $CR^xR^y$, S, or O, wherein each of $R^x$ and $R^y$ independently represents an alkyl group, an aryl group, or a silyl group.

9. The organic electroluminescence element according to claim 4, wherein the compound expressed by General Formula 4 above is expressed by General Formula 6 below:

General Formula 6

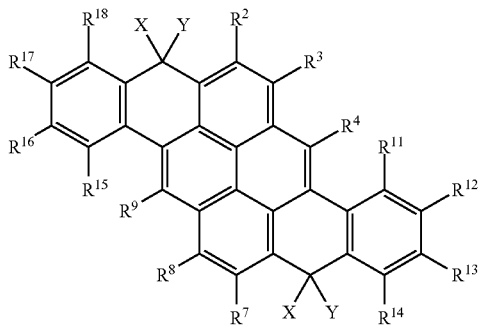

wherein X and Y represent each independently an alkyl group, an aryl group, or a silyl group; each of $R^2$ to $R^4$ and $R^7$ to $R^9$ independently represents an alkyl group, an aryl group, a heteroaryl group, a fluorine atom, a hydrogen atom, or a deuterium atom; each of $R^{11}$ to $R^{18}$ independently represents an alkyl group, an alkoxy group, an alkylthio group, an aryl group, a heteroaryl group, an arylthio group, a fluorine atom, a hydrogen atom, a deuterium atom, a cyano group, or an amino group; and each pair of $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.

10. The organic electroluminescence element according to claim 9, wherein in General Formula 6 above, one of $R^{12}$ to $R^{14}$ and $R^{16}$ to $R^{18}$ is $NR^{19}R^{20}$, wherein each of $R^{19}$ and $R^{20}$ independently represents an alkyl group or an aryl group, and these may bond to each other to form a ring.

11. The organic electroluminescence element according to claim 9, wherein in General Formula 6 above, $R^{13}$ and/or $R^{17}$ is $NR^{19}R^{20}$, wherein each of $R^{19}$ and $R^{20}$ independently represents an alkyl group or an aryl group, and these may bond to each other to form a ring.

12. The organic electroluminescence element according to claim 6, wherein the compound expressed by General Formula 5 above is expressed by General Formula 7 below:

General Formula 7

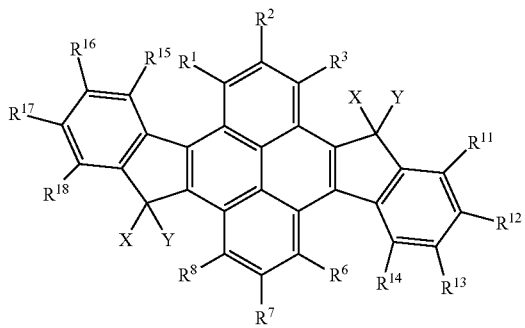

wherein X and Y represent each independently an alkyl group, an aryl group, or a silyl group; $R^1$ to $R^3$ and $R^6$ to $R^8$ represent each independently an alkyl group, an aryl group, a heteroaryl group, a fluorine atom, a hydrogen atom, or a deuterium atom; $R^{11}$ to $R^{18}$ independently represents an alkyl group, an alkoxy group, an alkylthio group, an aryl group, a heteroaryl group, an arylthio group, a fluorine atom, a hydrogen atom, a deuterium atom, a cyano group, or an amino group; and each pair of $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.

13. The organic electroluminescence element according to claim 12, wherein in General Formula 7 above, one of $R^{11}$ to $R^{13}$ and $R^{16}$ to $R^{18}$ is $NR^{19}R^{20}$, wherein each of $R^{19}$ and $R^{20}$ independently represents an alkyl group or an aryl group, and these may bond to each other to form a ring.

14. The organic electroluminescence element according to claim 12, wherein in General Formula 7 above, $R^{12}$ and/or $R^{17}$ is $NR^{19}R^{20}$, wherein each of $R^{19}$ and $R^{20}$ independently represents an alkyl group or an aryl group, and these may bond to each other to form a ring.

15. The organic electroluminescence element according to claim 1, wherein the compound expressed by General Formula 1 above includes in its molecule a group containing an alkyl group, a silyl group, or a fluorine atom.

16. The organic electroluminescence element according to claim 1, wherein the molecular weight of the compound expressed by General Formula 1 above is 1000 or less.

17. The organic electroluminescence element according to claim 1, wherein at least one organic layer that contains the compound expressed by General Formula 1 above is a light-emitting layer.

18. The organic electroluminescence element according to claim 17, wherein the compound expressed by General Formula 1 above is a light-emitting material.

19. The organic electroluminescence element according to claim 17, wherein said light-emitting layer includes an anthracene-based host material.

20. The organic electroluminescence element according to claim 19, wherein said anthracene-based host material is expressed by General Formula An-1 below:

General Formula An-1

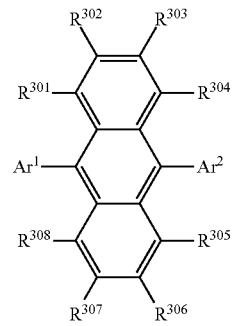

wherein $Ar^1$ and $Ar^2$ represent each independently an aryl group or a heteroaryl group; each of $R^{301}$ to $R^{308}$ independently represents a hydrogen atom or a substituent; and $R^{301}$ and $R^{302}$, $R^{302}$ and $R^{303}$, $R^{303}$ and $R^{304}$, $R^{305}$ and $R^{306}$, $R^{306}$ and $R^{307}$, and $R^{307}$ and $R^{308}$ may bond to each other to form a ring.

21. The organic electroluminescence element according to claim 20, wherein the compound expressed by General Formula An-1 above is a compound expressed by General Formula An-2 below:

General Formula An-2

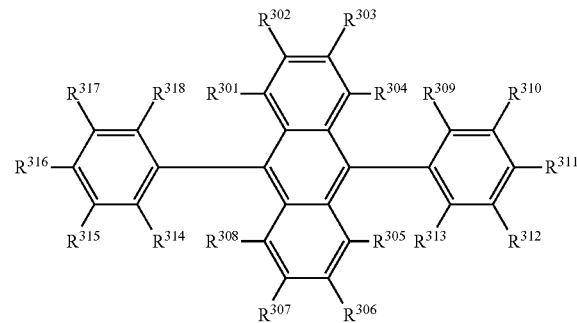

wherein each of $R^{301}$ to $R^{318}$ independently represents a hydrogen atom or a substituent; and each pair of $R^{301}$ and $R^{302}$, $R^{302}$ and $R^{303}$, $R^{303}$ and $R^{304}$, $R^{305}$ and $R^{306}$, $R^{306}$ and $R^{307}$, $R^{307}$ and $R^{308}$, $R^{309}$ and $R^{310}$, $R^{310}$ and $R^{311}$, $R^{311}$ and $R^{312}$, $R^{312}$ and $R^{313}$, $R^{314}$ and $R^{315}$, $R^{315}$ and $R^{316}$, $R^{316}$ and $R^{317}$, and $R^{317}$, and $R^{318}$ may bond to each other to form a ring.

22. The organic electroluminescence element according to claim 17, wherein said light-emitting layer is formed by a vacuum vapor deposition process.

23. The organic electroluminescence element according to claim 17, wherein said light-emitting layer is formed by a wet process.

24. A light-emitting device, display device, or illumination device which makes use of the organic electroluminescence element according to claim 1.

25. A material for an organic electroluminescence element expressed by General Formula 1 below:

General Formula 1

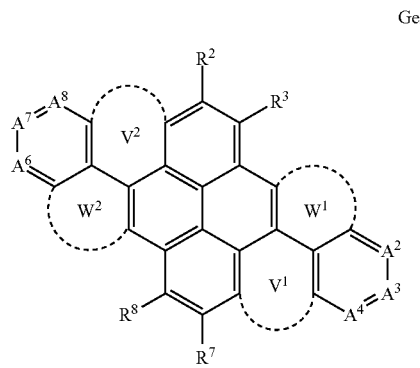

wherein either $V^1$ or $W^1$ forms a ring, either $V^2$ or $W^2$ also forms a ring, the ring formed by $V^1$ and $V^2$ is a six-membered ring, and the ring formed by $W^1$ and $W^2$ is a five-membered ring, wherein when both $V^1$ and $V^2$ form a six-membered ring, at least one of $V^1$ and $V^2$ has a linking group E that links the portion represented by a dotted line in General Formula 1, wherein E is $CR^xR^y$, $SiR^aR^b$, or O;
  each of $R^x$ and $R^y$ independently represents an alkyl group, an aryl group, or a silyl group;
  each of $R^a$ and $R^b$ independently represents an alkyl group or an aryl group;
  each of $A^2$ to $A^4$ and $A^6$ to $A^8$ independently represents $CR^Z$ or N, wherein two adjacent $CR^Z$ groups may together form a five- or six-membered ring, and $R^Z$ represents a hydrogen atom or a substituent; and
  $R^2$, $R^3$, $R^7$, and $R^8$ independently represents an alkyl group, an aryl group, a heteroaryl group, a fluorine atom, a hydrogen atom, or a deuterium atom.

26. The material for an organic electroluminescence element according to claim 25, wherein the material is expressed by General Formula 2 below:

General Formula 2

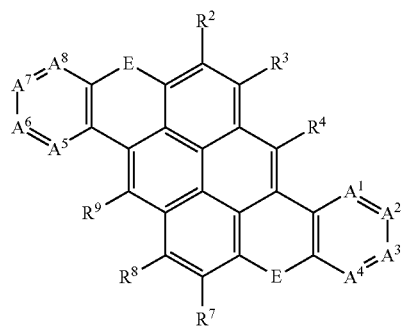

wherein $A^1$ to $A^8$ represent $CR^Z$ or N, and $R^Z$ represents a hydrogen atom or a substituent; E represents $CR^xR^y$, $SiR^aR^b$, or O; each of $R^x$ and $R^y$ independently represents an alkyl group, an aryl group, or a silyl group; each of $R^a$ and $R^b$ independently represents an alkyl group or an aryl group; and each of $R^2$ to $R^4$ and $R^7$ to $R^9$ independently represents, an alkyl group, an aryl group, a heteroaryl group, a fluorine atom, a hydrogen atom, or a deuterium atom.

27. The material for an organic electroluminescence element according to claim 25, wherein the material is expressed by General Formula 3 below:

General Formula 3

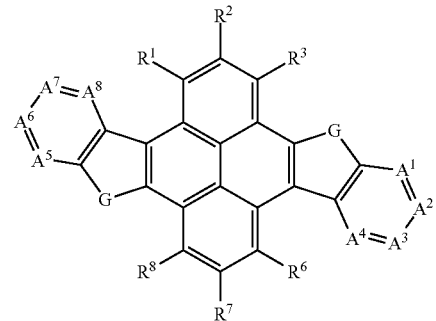

wherein $A^1$ to $A^8$ represent $CR^Z$ or N, and $R^Z$ represents a hydrogen atom or a substituent; G represents $CR^xR^y$, $SiR^aR^b$, $NR^c$, S, or O; each of $R^x$ and $R^y$ independently represents an alkyl group, an aryl group, or a silyl group; $R^a$, $R^b$, and $R^c$ represent each independently an alkyl group or an aryl group; and each of $R^1$ to $R^3$ and $R^6$ to $R^8$ independently represents an alkyl group, an aryl group, a heteroaryl group, a fluorine atom, a hydrogen atom, or a deuterium atom.

28. The material for an organic electroluminescence element according to claim 25, wherein the material is expressed by General Formula 6 below:

General Formula 6

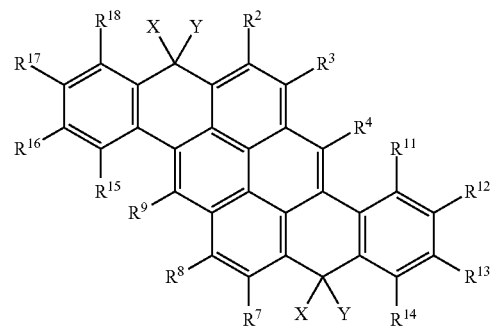

wherein each of X and Y independently represents an alkyl group, an aryl group, or a silyl group; each of $R^2$ to $R^4$ and $R^7$ to $R^9$ independently represents an alkyl group, an aryl group, a heteroaryl group, a fluorine atom, a hydrogen atom, or a deuterium atom; each of $R^{11}$ to $R^{18}$ independently represents an alkyl group, an alkoxy group, an alkylthio group, an aryl group, a heteroaryl group, an arylthio group, a fluorine atom, a hydrogen atom, a deuterium atom, a cyano group, or an amino group; and each pair of $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.

29. The material for an organic electroluminescence element according to claim 25, wherein the material is expressed by General Formula 7 below:

General Formula 7

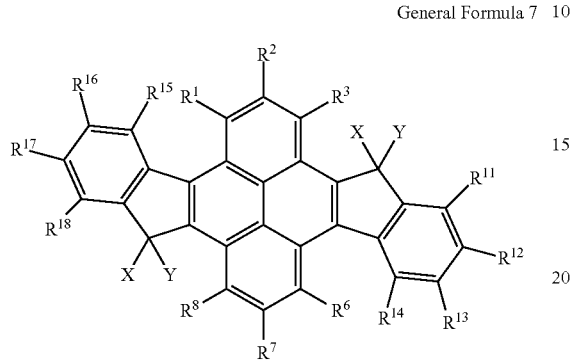

wherein each of X and Y independently represents an alkyl group, an aryl group, or a silyl group; $R^1$ to $R^3$ and $R^6$ to $R^8$ represent each independently an alkyl group, an aryl group, a heteroaryl group, a fluorine atom, a hydrogen atom, or a deuterium atom; each of $R^{11}$ to $R^{18}$ independently represents an alkyl group, an alkoxy group, an alkylthio group, an aryl group, a heteroaryl group, an arylthio group, a fluorine atom, a hydrogen atom, a deuterium atom, a cyano group, or an amino group; and each pair of $R^{11}$ and $R^{12}$, $R^{12}$ and $R^{13}$, $R^{13}$ and $R^{14}$, $R^{15}$ and $R^{16}$, $R^{16}$ and $R^{17}$, and $R^{17}$ and $R^{18}$ may bond to each other to form a ring.

30. A compound expressed by General Formula 1 below:

General Formula 1

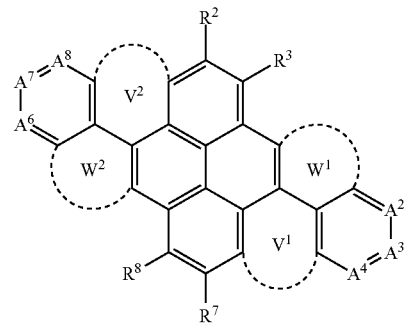

wherein either $V^1$ or $W^1$ forms a ring, either $V^2$ or $W^2$ also forms a ring, the ring formed by $V^1$ and $V^2$ is a six-membered ring, and the ring formed by $W^1$ and $W^2$ is a five-membered ring, wherein when both $V^1$ and $V^2$ form a six-membered ring, at least one of $V^1$ and $V^2$ has a linking group E that links the portion represented by a dotted line in General Formula 1, wherein E is $CR^xR^y$, $SiR^aR^b$, or O;

each of $R^x$ and $R^y$ independently represents an alkyl group, an aryl group, or a silyl group;

each of $R^a$ and $R^b$ independently represents an alkyl group or an aryl group;

$A^2$ to $A^4$ and $A^6$ to $A^8$ represent each independently $CR^Z$ or N, wherein two adjacent $CR^Z$ groups may together form a five- or six-membered ring, and $R^Z$ represents a hydrogen atom or a substituent; and $R^2$, $R^3$, $R^7$, and $R^8$ independently represents an alkyl group, an aryl group, a heteroaryl group, a fluorine atom, a hydrogen atom, or a deuterium atom.

* * * * *